US012588893B2

(12) United States Patent
Chiang et al.

(10) Patent No.: US 12,588,893 B2
(45) Date of Patent: Mar. 31, 2026

(54) TABLET ULTRASOUND SYSTEM

(71) Applicant: Teratech Corporation, Burlington, MA (US)

(72) Inventors: Alice M. Chiang, Wayland, MA (US); William M. Wong, Milton, MA (US); Noah Berger, Sudbury, MA (US)

(73) Assignee: Teratech Corporation, Burlington, MA (US)

( * ) Notice: Subject to any disclaimer, the term of this patent is extended or adjusted under 35 U.S.C. 154(b) by 0 days.

(21) Appl. No.: 15/025,058

(22) PCT Filed: Sep. 25, 2014

(86) PCT No.: PCT/US2014/057516
§ 371 (c)(1),
(2) Date: Mar. 25, 2016

(87) PCT Pub. No.: WO2015/048327
PCT Pub. Date: Apr. 2, 2015

(65) Prior Publication Data

US 2016/0228091 A1 Aug. 11, 2016

Related U.S. Application Data

(63) Continuation-in-part of application No. 14/037,106, filed on Sep. 25, 2013, now Pat. No. 9,877,699, and
(Continued)

(51) Int. Cl.
*A61B 8/00* (2006.01)
*A61B 8/08* (2006.01)
(Continued)

(52) U.S. Cl.
CPC .......... *A61B 8/4427* (2013.01); *A61B 8/0841* (2013.01); *A61B 8/0883* (2013.01);
(Continued)

(58) Field of Classification Search
CPC ..... A61B 8/4427; A61B 8/565; A61B 8/5207; A61B 8/469; A61B 8/468; A61B 8/465;
(Continued)

(56) References Cited

U.S. PATENT DOCUMENTS

| | | |
|---|---|---|
| 4,702,258 A | 10/1987 | Nicolas et al. |
| 4,727,376 A | 2/1988 | Prenat |

(Continued)

FOREIGN PATENT DOCUMENTS

| | | |
|---|---|---|
| CA | 2902224 A1 | 9/2014 |
| CN | 1759327 A | 4/2006 |

(Continued)

OTHER PUBLICATIONS

Esaote, MyLab Ultrasound Scanners, DICOM Conformance Statement, Document Version 6.3. May 21, 2010. 277 pages.

(Continued)

*Primary Examiner* — Sanjay Cattungal
(74) *Attorney, Agent, or Firm* — McCarter & English, LLP

(57) ABSTRACT

Exemplary embodiments provide systems and methods for portable medical ultrasound imaging. Preferred embodiments utilize a tablet touchscreen display operative to control imaging and display operations without the need for using traditional keyboards or controls. Certain embodiments provide ultrasound imaging system in which the scan head includes a beamformer circuit that performs far field sub array beamforming or includes a sparse array selecting circuit that actuates selected elements. Exemplary embodiments also provide an ultrasound engine circuit board including one or more multi-chip modules, and a portable medical ultrasound imaging system including an ultrasound engine circuit board with one or more multi-chip modules. Exemplary embodiments also provide methods for using a
(Continued)

hierarchical two-stage or three-stage beamforming system, three dimensional ultrasound images which can be generated in real-time.

43 Claims, 76 Drawing Sheets

Related U.S. Application Data a continuation-in-part of application No. PCT/US2013/033941, filed on Mar. 26, 2013, and a continuation-in-part of application No. 13/838,694, filed on Mar. 15, 2013, now Pat. No. 10,667,790, said application No. 14/037,106 is a continuation-in-part of application No. PCT/US2013/033941, filed on Mar. 26, 2013, and a continuation-in-part of application No. 13/838,694, filed on Mar. 15, 2013, now Pat. No. 10,667,790, said application No. PCT/US2013/033941 is a continuation-in-part of application No. 13/838,694, filed on Mar. 15, 2013, now Pat. No. 10,667,790.

(60) Provisional application No. 61/704,254, filed on Sep. 21, 2012, provisional application No. 61/615,627, filed on Mar. 26, 2012.

(51) Int. Cl.

| | |
|---|---|
| ***G01S 7/52*** | (2006.01) |
| ***G01S 15/89*** | (2006.01) |
| ***G06F 3/0488*** | (2022.01) |
| ***G06F 3/04883*** | (2022.01) |
| ***G16H 30/20*** | (2018.01) |
| ***G16H 30/40*** | (2018.01) |
| ***G16H 40/63*** | (2018.01) |
| ***G16H 40/67*** | (2018.01) |
| ***H01L 25/065*** | (2023.01) |
| *A61B 8/06* | (2006.01) |
| *A61B 8/13* | (2006.01) |

(52) U.S. Cl.

CPC .......... *A61B 8/0891* (2013.01); *A61B 8/4405* (2013.01); *A61B 8/4477* (2013.01); *A61B 8/4483* (2013.01); *A61B 8/461* (2013.01); *A61B 8/462* (2013.01); *A61B 8/463* (2013.01); *A61B 8/465* (2013.01); *A61B 8/467* (2013.01); *A61B 8/468* (2013.01); *A61B 8/469* (2013.01); *A61B 8/5207* (2013.01); *A61B 8/56* (2013.01); *A61B 8/565* (2013.01); *G01S 7/52019* (2013.01); *G01S 7/52023* (2013.01); *G01S 7/52074* (2013.01); *G01S 7/52082* (2013.01); *G01S 7/52084* (2013.01); *G01S 15/8925* (2013.01); *G06F 3/0488* (2013.01); *G06F 3/04883* (2013.01); *G16H 30/20* (2018.01); *G16H 30/40* (2018.01); *G16H 40/63* (2018.01); *G16H 40/67* (2018.01); *H01L 25/0657* (2013.01); *A61B 8/06* (2013.01); *A61B 8/08* (2013.01); *A61B 8/13* (2013.01); *A61B 8/4444* (2013.01); *A61B 8/54* (2013.01); *G01S 15/8979* (2013.01); *H01L 2224/32145* (2013.01); *H01L 2224/32245* (2013.01); *H01L 2224/48091* (2013.01); *H01L 2224/73265* (2013.01); *H01L 2225/0651* (2013.01); *H01L 2225/06575* (2013.01); *H01L 2924/181* (2013.01)

(58) Field of Classification Search

CPC ......... A61B 8/462; A61B 8/56; A61B 8/0891; A61B 8/0883; A61B 8/463; A61B 8/467; A61B 8/461; A61B 8/4483; A61B 8/4477; A61B 8/4405; A61B 8/0841; A61B 8/54; A61B 8/08; A61B 8/06; A61B 8/4444; A61B 8/13; G16H 30/20; G16H 40/63; G06F 19/321; G06F 3/04883; G06F 3/0488; H01L 25/0657; H01L 2225/06575; H01L 2225/0651; H01L 2924/181; H01L 2224/73265; H01L 2224/48091; H01L 2224/32245; H01L 2224/32145; G01S 15/8925; G01S 7/52023; G01S 7/52019; G01S 7/52082; G01S 7/52074; G01S 7/52084; G01S 15/8979

USPC .................................................. 600/437–469

See application file for complete search history.

(56) References Cited

U.S. PATENT DOCUMENTS

| | | | | |
|---|---|---|---|---|
| 4,991,604 | A | 2/1991 | Wurster et al. | |
| 5,170,791 | A | 12/1992 | Boos et al. | |
| 5,311,095 | A | 5/1994 | Smith et al. | |
| 5,381,794 | A | 1/1995 | Tei et al. | |
| 5,465,095 | A | 11/1995 | Bryant | |
| 5,487,388 | A | 1/1996 | Rello et al. | |
| 5,598,845 | A | 2/1997 | Chandraratna et al. | |
| 5,653,236 | A | 8/1997 | Miller | |
| 5,690,114 | A | 11/1997 | Chiang et al. | |
| 5,722,411 | A | 3/1998 | Suzuki et al. | |
| 5,735,797 | A | 4/1998 | Muzilla et al. | |
| 5,844,140 | A | 12/1998 | Seale | |
| 5,904,652 | A | 5/1999 | Gilbert et al. | |
| 5,957,846 | A | 9/1999 | Chiang et al. | |
| 5,964,709 | A | 10/1999 | Chiang et al. | |
| 6,059,727 | A | 5/2000 | Fowlkes et al. | |
| 6,063,030 | A * | 5/2000 | Vara | G16H 40/63 600/440 |
| 6,095,980 | A | 8/2000 | Burns et al. | |
| 6,106,472 | A | 8/2000 | Chiang et al. | |
| 6,111,816 | A | 8/2000 | Chiang et al. | |
| 6,126,601 | A | 10/2000 | Gilling | |
| 6,126,608 | A | 10/2000 | Kemme et al. | |
| 6,131,459 | A | 10/2000 | Seale et al. | |
| 6,139,501 | A | 10/2000 | Roundhill et al. | |
| 6,146,331 | A | 11/2000 | Wong | |
| 6,238,344 | B1 | 5/2001 | Gamelsky et al. | |
| 6,248,073 | B1 | 6/2001 | Gilbert et al. | |
| 6,261,234 | B1 * | 7/2001 | Lin | A61B 8/445 600/463 |
| 6,371,918 | B1 | 4/2002 | Bunce | |
| 6,417,797 | B1 | 7/2002 | Cousins et al. | |
| 6,417,857 | B2 | 7/2002 | Finger et al. | |
| 6,425,865 | B1 | 7/2002 | Salcudean et al. | |
| 6,436,040 | B1 | 8/2002 | Collamore et al. | |
| 6,447,451 | B1 | 9/2002 | Wing et al. | |
| 6,450,958 | B1 | 9/2002 | Linkhart et al. | |
| 6,468,212 | B1 * | 10/2002 | Scott | A61B 8/463 600/440 |
| 6,500,122 | B1 | 12/2002 | Washburn et al. | |
| 6,500,126 | B1 | 12/2002 | Brock-Fisher | |
| 6,516,667 | B1 | 2/2003 | Broad et al. | |
| 6,519,632 | B1 | 2/2003 | Brackett et al. | |
| 6,520,912 | B1 | 2/2003 | Brooks et al. | |
| 6,530,887 | B1 | 3/2003 | Gilbert et al. | |
| 6,540,682 | B1 | 4/2003 | Leavitt et al. | |
| 6,558,326 | B2 | 5/2003 | Pelissier | |
| 6,569,102 | B2 | 5/2003 | Imran et al. | |
| 6,575,908 | B2 | 6/2003 | Barnes et al. | |
| 6,599,256 | B1 | 7/2003 | Acker et al. | |
| 6,603,494 | B1 | 8/2003 | Banks et al. | |
| 6,638,226 | B2 | 10/2003 | He et al. | |
| 6,648,825 | B1 | 11/2003 | Mesaros et al. | |
| 6,663,567 | B2 | 12/2003 | Ji et al. | |

(56) References Cited

U.S. PATENT DOCUMENTS 6,669,633 B2 12/2003 Brodsky et al.
6,682,483 B1 1/2004 Abend et al.
6,689,055 B1 2/2004 Mullen et al.
6,709,391 B2 3/2004 Mesaros et al.
6,719,698 B2 4/2004 Manor et al.
6,760,755 B1 7/2004 Brackett
6,761,689 B2 7/2004 Salgo et al.
6,980,419 B2 12/2005 Smith et al.
7,022,075 B2 4/2006 Grunwald et al.
7,115,093 B2 10/2006 Halmann et al.
7,223,242 B2 5/2007 He et al.
7,338,450 B2 3/2008 Kristoffersen et al.
7,352,570 B2 4/2008 Smith et al.
7,457,672 B2 11/2008 Katsman et al.
7,604,601 B2 10/2009 Altmann et al.
7,736,313 B2 6/2010 Luo et al.
7,736,314 B2 6/2010 Beach et al.
7,794,398 B2 9/2010 Salgo
7,927,280 B2 4/2011 Davidsen
8,012,092 B2 9/2011 Powers et al.
8,128,563 B2 3/2012 Kristoffersen
8,172,753 B2 5/2012 Halmann
8,214,011 B2 7/2012 Friedman et al.
8,235,903 B2 8/2012 Abraham
8,241,220 B2 8/2012 Wilser et al.
8,319,770 B2 11/2012 Friedman et al.
8,357,094 B2 1/2013 Mo et al.
8,394,023 B2 3/2013 Friedman et al.
8,409,095 B1 4/2013 Marquis
8,435,183 B2 5/2013 Barnes et al.
8,659,507 B2 2/2014 Roncalez et al.
8,925,386 B2 1/2015 Oshiki
9,033,879 B2 5/2015 Urness et al.
9,072,471 B2 * 7/2015 Kato ........................ A61B 8/14
9,113,825 B2 8/2015 Chaggares et al.
9,163,980 B2 10/2015 Herzog et al.
9,173,639 B2 11/2015 Ichioka et al.
9,198,680 B2 12/2015 Fraser et al.
9,220,478 B2 12/2015 Smith et al.
9,301,730 B2 4/2016 Poland
9,314,225 B2 * 4/2016 Steen .................... G01S 7/5208
9,351,706 B2 5/2016 Rothberg et al.
9,386,964 B2 7/2016 Bagge
9,504,448 B2 11/2016 Cheng et al.
9,597,008 B2 3/2017 Henkel et al.
9,667,889 B2 5/2017 Rothberg
9,848,849 B2 12/2017 Pfeiffer et al.
9,877,699 B2 1/2018 Chiang et al.
9,962,143 B2 5/2018 Funakubo
9,983,905 B2 5/2018 Tobias
9,986,972 B2 6/2018 Halmann et al.
RE46,931 E 7/2018 McLaughlin et al.
10,426,430 B2 10/2019 Zagorchev et al.
10,667,790 B2 6/2020 Chiang et al.
10,856,847 B2 12/2020 Rothberg et al.
11,287,309 B2 3/2022 Schmid et al.
11,660,003 B2 5/2023 Schmid
11,865,287 B2 1/2024 Ignon et al.
2002/0087061 A1 7/2002 Lifshitz et al.
2002/0120193 A1 8/2002 Chiang et al.
2002/0154727 A1 10/2002 Ning
2002/0173721 A1 11/2002 Grunwald et al.
2003/0013959 A1 1/2003 Grunwald et al.
2003/0078501 A1 4/2003 Barnes et al.
2003/0088182 A1 5/2003 He et al.
2003/0097071 A1 5/2003 Halmann et al.
2003/0139664 A1 7/2003 Hunt et al.
2003/0195418 A1 * 10/2003 Barnes ................ G01S 7/52079
600/437
2003/0212327 A1 11/2003 Wang et al.
2004/0015079 A1 1/2004 Berger et al.
2004/0059220 A1 3/2004 Mourad et al.
2004/0138569 A1 7/2004 Grunwald et al.
2004/0147840 A1 7/2004 Duggirala et al.
2004/0150963 A1 8/2004 Holmberg et al.
2004/0152982 A1 8/2004 Hwang et al.
2004/0152986 A1 8/2004 Fidel et al.
2004/0158154 A1 8/2004 Hanafy et al.
2004/0193042 A1 9/2004 Scampini et al.
2005/0085730 A1 * 4/2005 Flesch ...................... A61B 8/12
600/459
2005/0101864 A1 5/2005 Zheng et al.
2005/0113690 A1 5/2005 Halmann et al.
2005/0119574 A1 6/2005 Maerfeld et al.
2005/0281444 A1 12/2005 Lundberg et al.
2006/0020204 A1 * 1/2006 Serra ..................... G01S 7/5208
600/437
2006/0020206 A1 1/2006 Serra et al.
2006/0058609 A1 3/2006 Olstad
2006/0173326 A1 8/2006 Thiele
2007/0139873 A1 6/2007 Thomas et al.
2007/0140424 A1 6/2007 Serceki
2007/0161905 A1 7/2007 Munrow
2007/0167709 A1 7/2007 Slayton et al.
2007/0211064 A1 9/2007 Buck et al.
2007/0265531 A1 11/2007 He et al.
2008/0055826 A1 3/2008 Smith et al.
2008/0108899 A1 5/2008 Halmann et al.
2008/0119731 A1 5/2008 Becerra et al.
2008/0146922 A1 6/2008 Steins et al.
2008/0161686 A1 7/2008 Halmann
2008/0161688 A1 7/2008 Poland et al.
2008/0172383 A1 7/2008 Lea et al.
2008/0208047 A1 8/2008 Delso
2008/0208061 A1 8/2008 Halmann
2008/0215982 A1 9/2008 Washburn et al.
2008/0249414 A1 10/2008 Yang et al.
2008/0253589 A1 10/2008 Trahms
2008/0319316 A1 12/2008 Powers et al.
2009/0012401 A1 1/2009 Steinbacher
2009/0043195 A1 2/2009 Poland
2009/0054781 A1 2/2009 Stonefield et al.
2009/0099453 A1 4/2009 Kristoffersen
2009/0125840 A1 5/2009 Squilla et al.
2009/0131793 A1 5/2009 Stonefield et al.
2009/0177086 A1 7/2009 Steen
2009/0198132 A1 8/2009 Pelissier et al.
2009/0275835 A1 11/2009 Hwang et al.
2010/0022890 A1 1/2010 Fukukita et al.
2010/0094132 A1 4/2010 Hansen et al.
2010/0145195 A1 6/2010 Hyun
2010/0160787 A1 6/2010 Gorzitze
2010/0174189 A1 7/2010 Abraham
2010/0179428 A1 * 7/2010 Pedersen .............. G09B 23/286
600/443
2010/0217123 A1 8/2010 Eran et al.
2010/0217128 A1 * 8/2010 Betts .................... A61B 8/4254
345/184
2010/0305444 A1 12/2010 Fujii et al.
2011/0050594 A1 3/2011 Kim et al.
2011/0099513 A1 4/2011 Ameline
2011/0112399 A1 5/2011 Willems et al.
2011/0125022 A1 5/2011 Lazebnik
2011/0202889 A1 * 8/2011 Ludwig ............... G06F 3/04815
715/856
2011/0218436 A1 9/2011 Dewey et al.
2011/0230764 A1 9/2011 Baba et al.
2011/0237948 A1 9/2011 Corn
2011/0313292 A1 12/2011 Kwak et al.
2012/0010508 A1 1/2012 Sokulin et al.
2012/0029303 A1 2/2012 Shaya
2012/0053463 A1 3/2012 Yoo
2012/0065513 A1 3/2012 Lee
2012/0078108 A1 3/2012 Kim et al.
2012/0089024 A1 4/2012 Hong
2012/0095342 A1 4/2012 Lee
2012/0101378 A1 4/2012 Lee
2012/0108962 A1 5/2012 Yoon
2012/0108964 A1 5/2012 Lee et al.
2012/0112605 A1 5/2012 Kim
2012/0130244 A1 5/2012 Kim
2012/0133601 A1 * 5/2012 Marshall ................ G16H 40/63
345/173
2012/0136252 A1 5/2012 Cho

(56) References Cited

U.S. PATENT DOCUMENTS

2012/0136254 A1 5/2012 Kim
2012/0157836 A1 6/2012 Kim
2012/0157844 A1 6/2012 Halmann
2012/0157847 A1 6/2012 Kim
2012/0157848 A1 6/2012 Kim
2012/0179037 A1 7/2012 Halmann
2012/0179038 A1 7/2012 Meurer et al.
2012/0184849 A1 7/2012 Sandstrom et al.
2012/0190984 A1 7/2012 Kim et al.
2012/0209107 A1 8/2012 Guo et al.
2012/0215108 A1 8/2012 Park et al.
2012/0220873 A1 8/2012 Hyun
2012/0232399 A1 9/2012 Lee
2012/0265027 A1 10/2012 Lee et al.
2012/0265074 A1 10/2012 Na et al.
2012/0283605 A1 11/2012 Lewis, Jr.
2012/0288172 A1 11/2012 Perrey et al.
2012/0289828 A1 11/2012 Jensen et al.
2012/0302883 A1 11/2012 Kong et al.
2012/0316444 A1 12/2012 Shim et al.
2013/0018265 A1 1/2013 Kim et al.
2013/0019193 A1 1/2013 Rhee et al.
2013/0072795 A1 3/2013 Mo et al.
2013/0072797 A1 3/2013 Lee
2013/0079627 A1 3/2013 Lee
2013/0144169 A1 6/2013 Lee et al.
2013/0144194 A1 6/2013 Ahn et al.
2013/0165783 A1 6/2013 Kim et al.
2013/0184578 A1 7/2013 Lee et al.
2013/0190624 A1 7/2013 Beger et al.
2013/0202169 A1 8/2013 Lee et al.
2013/0202174 A1 8/2013 Lee
2013/0218014 A1 8/2013 Shim et al.
2013/0218024 A1 8/2013 Boctor et al.
2013/0226001 A1* 8/2013 Steen .................... G01S 7/5208
600/447
2013/0226004 A1 8/2013 Lee
2013/0237811 A1 9/2013 Mihailescu et al.
2013/0237824 A1 9/2013 Kim
2013/0237828 A1 9/2013 Lee et al.
2013/0239052 A1* 9/2013 Moody .................. G06Q 50/02
715/810
2013/0245449 A1 9/2013 Barnes et al.
2013/0253316 A1 9/2013 Choi
2013/0253323 A1 9/2013 Kim
2013/0261434 A1 10/2013 Kim et al.
2013/0261448 A1 10/2013 Hyun et al.
2013/0261459 A1 10/2013 Na et al.
2013/0320485 A1 12/2013 Ching Tee et al.
2013/0324850 A1* 12/2013 Petruzzelli ............. A61B 8/465
600/407
2013/0328810 A1 12/2013 Li et al.
2013/0331694 A1 12/2013 Barnes et al.
2014/0005550 A1 1/2014 Lu et al.
2014/0009686 A1 1/2014 Segal
2014/0039277 A1 2/2014 Abraham
2014/0051984 A1 2/2014 Berger et al.
2014/0100440 A1 4/2014 Cheline et al.
2014/0107435 A1 4/2014 Sharf et al.
2014/0111451 A1 4/2014 Park et al.
2014/0114190 A1 4/2014 Chiang et al.
2014/0114194 A1 4/2014 Kanayama et al.
2014/0121524 A1 5/2014 Chiang et al.
2014/0164965 A1 6/2014 Lee et al.
2014/0180111 A1 6/2014 Gopinathan et al.
2014/0187934 A1 7/2014 Urness
2014/0187946 A1 7/2014 Miller et al.
2014/0194742 A1 7/2014 Sundaran Baby Sarojam et al.
2014/0200452 A1 7/2014 Chang et al.
2014/0200456 A1 7/2014 Owen
2014/0237811 A1 8/2014 Guercioni
2014/0243614 A1 8/2014 Rothberg et al.
2014/0243669 A1 8/2014 Halmann et al.
2014/0257104 A1 9/2014 Dunbar et al.
2014/0275976 A1 9/2014 Moro
2014/0296711 A1 10/2014 Lee
2014/0300720 A1 10/2014 Rothberg
2014/0378835 A1 12/2014 Satoh et al.
2015/0094587 A1 4/2015 Chen et al.
2015/0182197 A1 7/2015 Willems et al.
2015/0238168 A1 8/2015 Poland
2015/0265252 A1 9/2015 Chu et al.
2015/0366536 A1 12/2015 Courtney et al.
2016/0110875 A1 4/2016 Sugiyama et al.
2016/0135786 A1 5/2016 Mullen et al.
2016/0174937 A1 6/2016 Bakshi et al.
2016/0287214 A1 10/2016 Ralovich et al.
2017/0055951 A1 3/2017 Messina et al.
2017/0079551 A1 3/2017 Henkel et al.
2017/0095228 A1 4/2017 Richard et al.
2017/0095230 A1 4/2017 Richard et al.
2017/0095231 A1 4/2017 Richard et al.
2017/0143307 A1 5/2017 Tahmasebi Maraghoosh
2018/0168548 A1 6/2018 Chiang et al.
2018/0182096 A1 6/2018 Grady et al.
2019/0336101 A1 11/2019 Chiang et al.
2019/0365350 A1 12/2019 Chiang
2020/0268351 A1 8/2020 Chiang et al.
2025/0195037 A1 6/2025 Chiang et al.

FOREIGN PATENT DOCUMENTS

CN 101390778 A 3/2009
CN 101869484 A 10/2010
CN 102178547 A 9/2011
CN 102525556 A 7/2012
CN 102626324 A 8/2012
CN 102636787 A 8/2012
CN 101742968 B 1/2013
CN 102872542 A 1/2013
CN 102930170 A 2/2013
CN 102940507 A 2/2013
CN 102988043 A 3/2013
CN 101677805 B 5/2013
CN 103140175 A 6/2013
CN 103876781 A 6/2014
CN 105611877 A 5/2016
EP 1016875 A2 7/2000
EP 1239396 A2 9/2002
EP 1589878 B1 10/2009
EP 2422705 A1 2/2012
EP 2425784 A1 3/2012
EP 2453256 A2 5/2012
EP 2455753 A2 5/2012
EP 2468191 A1 6/2012
EP 2575628 A2 4/2013
EP 2599442 A1 6/2013
EP EP-2605035 A2 6/2013
EP 2637166 A2 9/2013
EP 2023820 B1 3/2019
EP 2967486 B1 7/2020
JP 62-97539 A 5/1987
JP 10-73658 A 3/1998
JP H11-508461 A 7/1999
JP 2003-190159 A 7/2003
JP 2004-530463 A 10/2004
JP 2005-137747 A 6/2005
JP 2005-526551 A 9/2005
JP 2006-68524 A 3/2006
JP 2008-18107 A 1/2008
JP 2008-515583 A 5/2008
JP 2008-536555 A 9/2008
JP 2009-45081 A 3/2009
JP 2009-119259 A 6/2009
JP 2009-523499 A 6/2009
JP 2009-525538 A 7/2009
JP 2009-183720 A 8/2009
JP 2009-240779 A 10/2009
JP 2010-131396 A 6/2010
JP 2010-220218 A 9/2010
JP 2011-72746 A 4/2011
JP 2011-87949 A 5/2011
JP 2011-104079 A 6/2011
JP 2011-200482 A 10/2011

(56) References Cited

FOREIGN PATENT DOCUMENTS

| | | | |
|---|---|---|---|
| JP | 2012-24133 | A | 2/2012 |
| JP | 2012101075 | A | 5/2012 |
| JP | 2013043082 | A | 3/2013 |
| JP | 2013-111203 | A | 6/2013 |
| JP | 2013-172959 | A | 9/2013 |
| JP | 2013-188328 | A | 9/2013 |
| JP | 2015-515312 | A | 5/2015 |
| JP | 2016-087020 | A | 5/2016 |
| KR | 20120043642 | A | 5/2012 |
| KR | 20120047785 | A | 5/2012 |
| KR | 20120071319 | A | 7/2012 |
| KR | 20120097324 | A | 9/2012 |
| KR | 20120117714 | A | 10/2012 |
| KR | 20120137206 | A | 12/2012 |
| KR | 20120138478 | A | 12/2012 |
| KR | 20130011793 | A | 1/2013 |
| KR | 20130012501 | A | 2/2013 |
| KR | 20130012844 | A | 2/2013 |
| KR | 20130020035 | A | 2/2013 |
| KR | 20130020054 | A | 2/2013 |
| KR | 20130020371 | A | 2/2013 |
| KR | 20130022249 | A | 3/2013 |
| KR | 20130026041 | A | 3/2013 |
| KR | 20130030663 | A | 3/2013 |
| KR | 20130036327 | A | 4/2013 |
| KR | KR-20130033717 | A | 4/2013 |
| KR | 101269459 | B1 | 5/2013 |
| KR | 20130043702 | A | 5/2013 |
| KR | 20130054013 | A | 5/2013 |
| KR | 20130056676 | A | 5/2013 |
| KR | 101273585 | B1 | 6/2013 |
| KR | 20130059307 | A | 6/2013 |
| KR | 20130060007 | A | 6/2013 |
| KR | 20130066821 | A | 6/2013 |
| KR | 20130074398 | A | 7/2013 |
| KR | 20130074399 | A | 7/2013 |
| KR | 20130075458 | A | 7/2013 |
| KR | 20130075465 | A | 7/2013 |
| KR | 20130075472 | A | 7/2013 |
| KR | 20130075477 | A | 7/2013 |
| KR | 20130075481 | A | 7/2013 |
| KR | 20130075486 | A | 7/2013 |
| KR | 20130076031 | A | 7/2013 |
| KR | 20130076042 | A | 7/2013 |
| KR | 20130076054 | A | 7/2013 |
| KR | 20130076064 | A | 7/2013 |
| KR | 20130076071 | A | 7/2013 |
| KR | 20130076404 | A | 7/2013 |
| KR | 20130076428 | A | 7/2013 |
| KR | 20130077118 | A | 7/2013 |
| KR | 20130077121 | A | 7/2013 |
| KR | 20130077406 | A | 7/2013 |
| KR | 20130078935 | A | 7/2013 |
| KR | 20130078972 | A | 7/2013 |
| KR | 20130080640 | A | 7/2013 |
| KR | 20130081067 | A | 7/2013 |
| KR | 20130081626 | A | 7/2013 |
| KR | 20130081684 | A | 7/2013 |
| KR | 20130082267 | A | 7/2013 |
| KR | 20130083725 | A | 7/2013 |
| KR | 20130084049 | A | 7/2013 |
| KR | 20130087291 | A | 8/2013 |
| KR | 20130087478 | | 8/2013 |
| KR | 20130088478 | A | 8/2013 |
| KR | 20130089037 | A | 8/2013 |
| KR | 20130090038 | A | 8/2013 |
| KR | 20130094671 | A | 8/2013 |
| KR | 20130095160 | A | 8/2013 |
| KR | 20130095236 | A | 8/2013 |
| KR | 20130095505 | A | 8/2013 |
| TW | I378255 | | 12/2012 |
| TW | I380014 | | 12/2012 |
| TW | I406684 | | 9/2013 |
| WO | 2000/31634 | A1 | 6/2000 |
| WO | 2002/068992 | A2 | 9/2002 |
| WO | 2003/027662 | A2 | 4/2003 |
| WO | 2003/075769 | A1 | 9/2003 |
| WO | 2005/058168 | A2 | 6/2005 |
| WO | WO-2005/053664 | A2 | 6/2005 |
| WO | 2006/030378 | A1 | 3/2006 |
| WO | WO-2006/040697 | A1 | 4/2006 |
| WO | 2006/111871 | A1 | 10/2006 |
| WO | 2006/111874 | A2 | 10/2006 |
| WO | 2006111872 | A2 | 10/2006 |
| WO | 2008/069021 | A1 | 6/2008 |
| WO | 2008/115312 | A2 | 9/2008 |
| WO | 2008146208 | A2 | 12/2008 |
| WO | 2009/129845 | A1 | 10/2009 |
| WO | 2010/020939 | A2 | 2/2010 |
| WO | 2010032151 | A1 | 3/2010 |
| WO | 2010/042282 | A1 | 4/2010 |
| WO | WO-2010/051587 | A1 | 5/2010 |
| WO | WO-2012091518 | A2 | 7/2012 |
| WO | 2012/101511 | A2 | 8/2012 |
| WO | WO-2012141550 | A2 | 10/2012 |
| WO | 2013/030746 | A1 | 3/2013 |
| WO | 2013/034175 | A1 | 3/2013 |
| WO | 2013/055707 | A1 | 4/2013 |
| WO | WO-2013095032 | A1 | 6/2013 |
| WO | WO-2013122320 | A1 | 8/2013 |
| WO | 2013/148730 | A2 | 10/2013 |
| WO | 2013/162244 | A1 | 10/2013 |
| WO | 2014/003404 | A1 | 1/2014 |
| WO | 2014/014965 | A1 | 1/2014 |
| WO | 2014035567 | A1 | 3/2014 |
| WO | 2014/134316 | A1 | 9/2014 |
| WO | 2015/048327 | A2 | 4/2015 |
| WO | 2015/114484 | A1 | 8/2015 |
| WO | 2016/001865 | A1 | 1/2016 |
| WO | 2016/083985 | A1 | 6/2016 |
| WO | 2017/013511 | A1 | 1/2017 |
| WO | 2017/222970 | A1 | 12/2017 |

OTHER PUBLICATIONS

Esaote, MyLab Ultrasound Scanners, DICOM Conformance Statement, Document Version 6.5. Jul. 19, 2011. 278 pages.

Esaote, MyLab Ultrasound Scanners, DICOM Conformance Statement, Document Version 6.6. Mar. 1, 2012. 278 pages.

Stolka et al., Needle guidance using handheld stereo vision and projection for ultrasound-based interventions. Med Image Comput Comput Assist Interv. 2014;17(Pt 2):684-91.

GE Healthcare Venue 40 Basic User Manual, Technical Publications Direction 5265930-100, Rev. 5. 288 pages (2008-2010).

NanoMaxx Ultrasound System—Sonosite—User Guide. 100 pages (2010).

Butrus, T. Khuri-Yakub, et al., "Capacitive Micromachined Ultrasonic Transducers for Medical Imaging and Therapy; CMUTS for Medical Imaging and Therapy," Journal of Micromechanics and Microengineering, Institute of Physics Publishing, vol. 21, No. 5, Apr. 28, 2013, p. 54004 (XP020190354).

International Search Report and Written Opinion of the International Searching Authority on International application No. PCT/US2013/0333941, issued Oct. 8, 2013.

International Preliminary Report on Patentability by the International Bureau of WIPO for International Application No. PCT/US2013/033941 dated Oct. 1, 2014. (24 pages).

Invitation to Pay Additional Fees including Communication Relating to the Results of the Partial International Search by the International Searching Authority for International Application No. PCT/US2014/057516 dated Jan. 13, 2015. (6 pages).

alibaba.com, Chison SonoTouch 10 B&W HAndled Ultrasound Tablet With CE FDA. Shaanxi Aipu Medical Instrument Co., Ltd. 6 pages, (2014).

Basoglu et al., Applications of a next-generation programmable ultrasound machine. Proceedings SPiE Medical Imaging. 1 page, Abstract 3031, May 7, 1997.

Basoglu et al., Computing requirements of modern medical diagnostic ultrasound machines. Parallel Computing. Sep. 1998;24(9-10):1407-1431.

(56) References Cited

OTHER PUBLICATIONS

Brattain et al. Machine learning for medical ultrasound: status, methods, and future opportunities. Abdominal Radiology. Apr. 1, 2018;43(4):786-99.

Chison Medical Imaging Co., Ltd., Premarket Notification [510(k)] Summary. SonoTouch Series Diagnostic Ultrasound System. 11 pages, Aug. 2, 2012.

Felix et al., Biplane ultrasound arrays with integrated multiplexing solution for enhanced diagnostic accuracy in endorectal and transvaginal imaging. IEEE Ultrasonics Symposium, Sep. 18, 2005;4:2251-2254.

Gray et al., Ultrasound-guided Regional Anesthesia, Current State of the Art. Anesthesiology. Feb. 2006;104:368-73.

Karadayi et al., Software-based Ultrasound Beamforming on Multi-core DSPs. IEEE International Ultrasonics. Oct. 18-21, 2011, 14 pages.

Soma, Access Systems, Introducing AxoTrack™ Needle visualization as you've never seen it. Retrieved online at: SomaAccessSystems.com, 6 pages.

Sono Touch, The Revolution is at Hand, catalog. Retrieved online at: www.sonatouch.com. 4 pages.

Sono Touch, The Revolution is at Hand, Sono Touch 20 Operation Manual. 68 pages.

Wygant et al., Beamforming and hardware design for a multichannel front-end integrated circuit for real-time 3D catheter-based ultrasonic imaging. Proceedings of SPiE. 2006;6147:61470A-1.

York et al., Ultrasound Processing and Computing: Review and Future Directions. Annu Rev Biomed Eng. 1999;1:559-588.

York, Architecture and Algorithms for a Fully Programmable Ultrasound System. A dissertation in partial fulfillment of the requirements for the Degree of Doctor of Philosophy, University of Washington. 141 pages, (1999).

Kang et al., Stereoscopic augmented reality for laparoscopic surgery. Surg Endosc. 2014;28(7):2227-2235.

Dickson, Wireless communication options for a mobile ultrasound system. Thesis Submitted to the Faculty of Worcester Polytechnic Institute. 2008. 252 pages.

Zhang et al., A software package for portable three-dimensional ultrasound imaging. 2nd IEEE International Symposium on Biomedical Imaging: Nano to Macro. 2004;1:539-42.

Lewandowski et al., Modular and scalable ultrasound platform with GPU processing. Conference Paper, Warsaw, Poland. 5 pages. (Oct. 2012).

Ultrasound Diagnostic System, Model: SonoTouch 20, Operator's Manual, Direction: CHUM-001a, Rev. 1.0, 98 pages, Oct. 13, 2012.

Dewaraja et al., GPU engine enhances ultrasound-detected brain motion calculations. OpenSystems Media. Retrieved online at: https://embeddedcomputing.com/application/healthcare/gpu-engine-enhances-ultrasound-detected-brain-motion-calculations. 5 pages, May 1, 2009.

U.S. Appl. No. 15/833,547, filed Dec. 6, 2017, U.S. Pat. No. 11,179,138, Issued.

U.S. Appl. No. 17/520,150, filed Nov. 5, 2021, 2022-0125407, Allowed.

U.S. Appl. No. 17/834,771, filed Jun. 7, 2022, 2022-0304661, Published.

U.S. Appl. No. 16/938,515, filed Jul. 24, 2020, 2021-0015456, Published.

U.S. Appl. No. 18/090,316, filed Dec. 28, 2022, 2023-0181160, Published.

Kasai et al., Real-Time Two-Dimensional Blood Flow Imaging Using an Autocorrelation Technique. IEEE Transactions on Sonics and Ultrasonics. May 1985;32(3):458-464.

Shenzhen Mindray Bio-Medical Electronics Co., Ltd., Digital Ultrasonic Diagnostic Imaging System. installation Manual. 32 pages, (2007).

* cited by examiner

FIG. 3A
FIG. 3AA
302
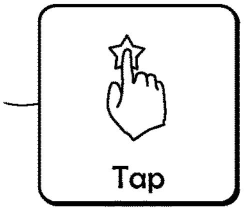
FIG. 3AG
314
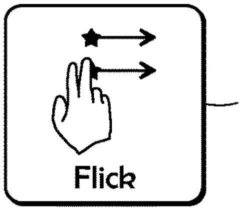
FIG. 3AB
304
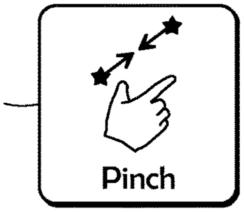
FIG. 3AH
316
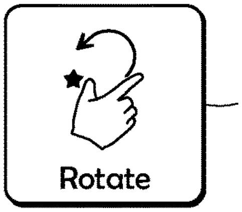
FIG. 3AC
306
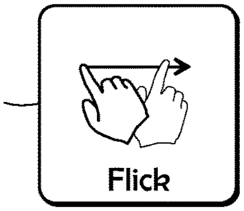
FIG. 3AI
318
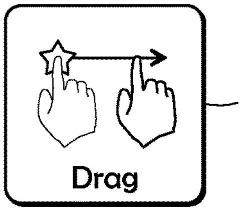
FIG. 3AD
308
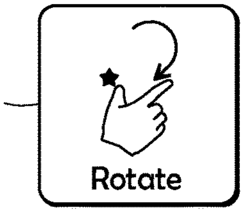
FIG. 3AJ
320
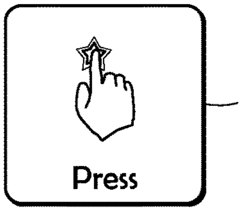
FIG. 3AE
310
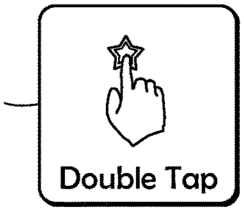
FIG. 3AK
322
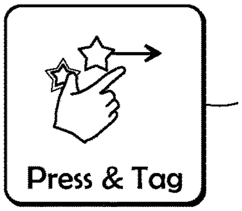
FIG. 3AF
312
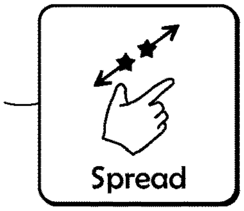
FIG. 3AL
324
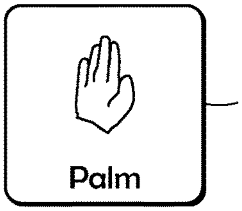

340

342 — Storing on a computer readable medium within a tablet ultrasound device, a touchscreen computer program responsive to a plurality of operations 344 — Selecting a first ultrasound display operation having a first plurality of touch gesture operations associated with the first display operation including a plurality of moving gestures 346 — Adjusting a beamforming operation associated with the first ultrasound display operation in response to at least one touchscreen gesture 348 — Updating a displayed image in response to the updated beamforming parameters selected by the touchscreen gesture 350 — Performing a second touch screen gesture to adjust a second characteristic of the first ultrasound display operation 352 — Displaying an updated first ultrasound display operation in response to the second gesture

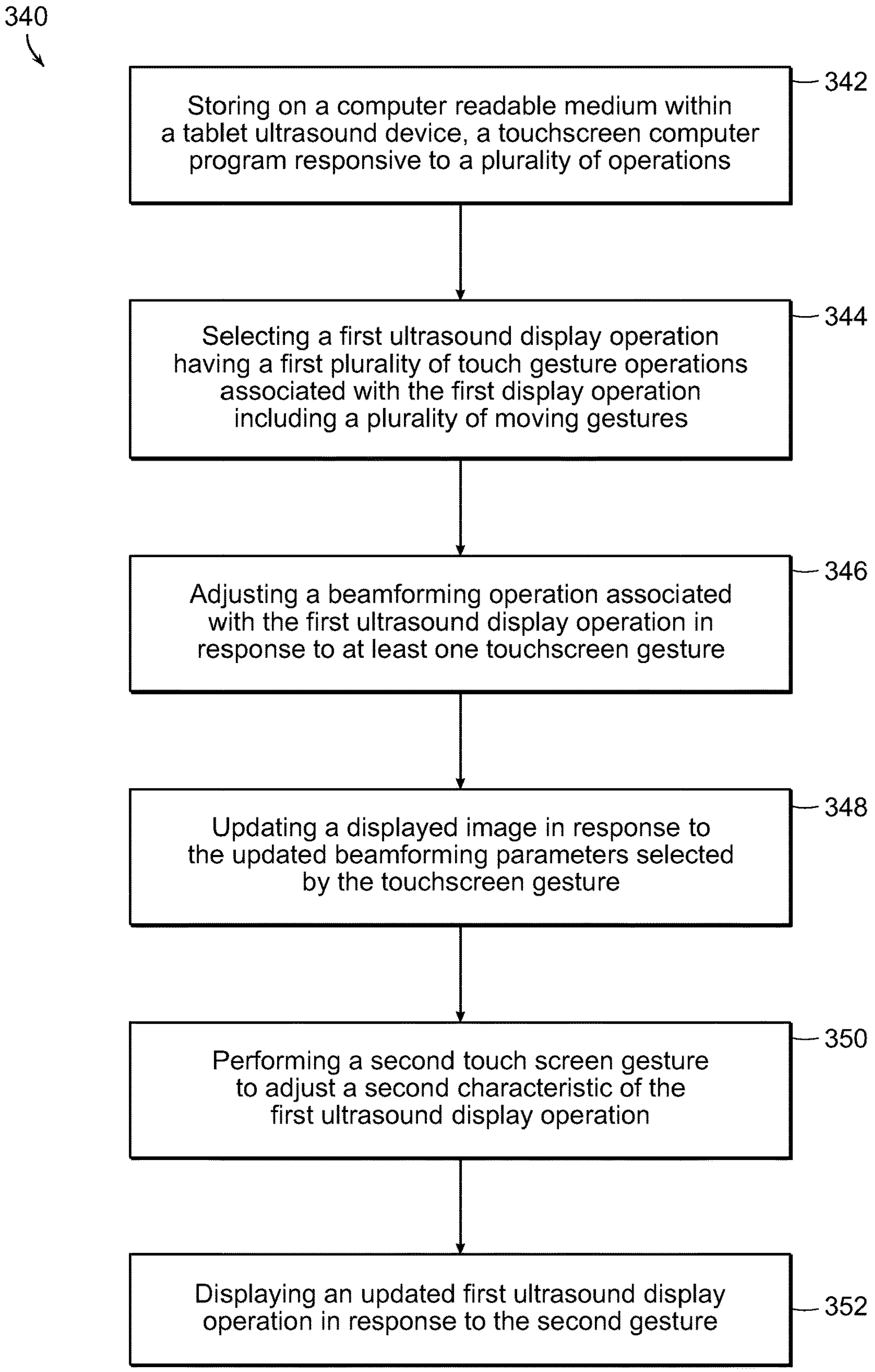

FIG. 3B

Ultrasound imaging probe assembly 978

Ultrasound reflector disc 964

980

Ultrasound transducer elements 960

Needle Guide 962

986

Needle 956

Needle guide mounting bracket 966

Ultrasound imaging probe assembly for imaging the patient body 982

Ultrasound transducer array 984

Cart
System
2100

Probe Connector
2118

2102
Touch Screen
Display

Tablet 2104

2106
Adjustable
Height device

2122
Base
Assembly

Cart Stand 2108

2124
Operator
Console

2110
Gel Holder

2120
Hot Probe
Holder

2112
Keyboard

2114
Storage Bin

2126
Wheels

LAPTOP PC

LAPTOP PC
OR DESKTOP PC

2604

2612

2610

2606

2608

2602

2600

800

LAPTOP PC

2604

WIRED AND/OR
WIRELESS NETWORK
FOR DATA/IMAGE
COMMUNICATION

PDA

2606

2610

2608

2802   HUB

2602

2804

2804

DESKTOP

2606

2804

2606

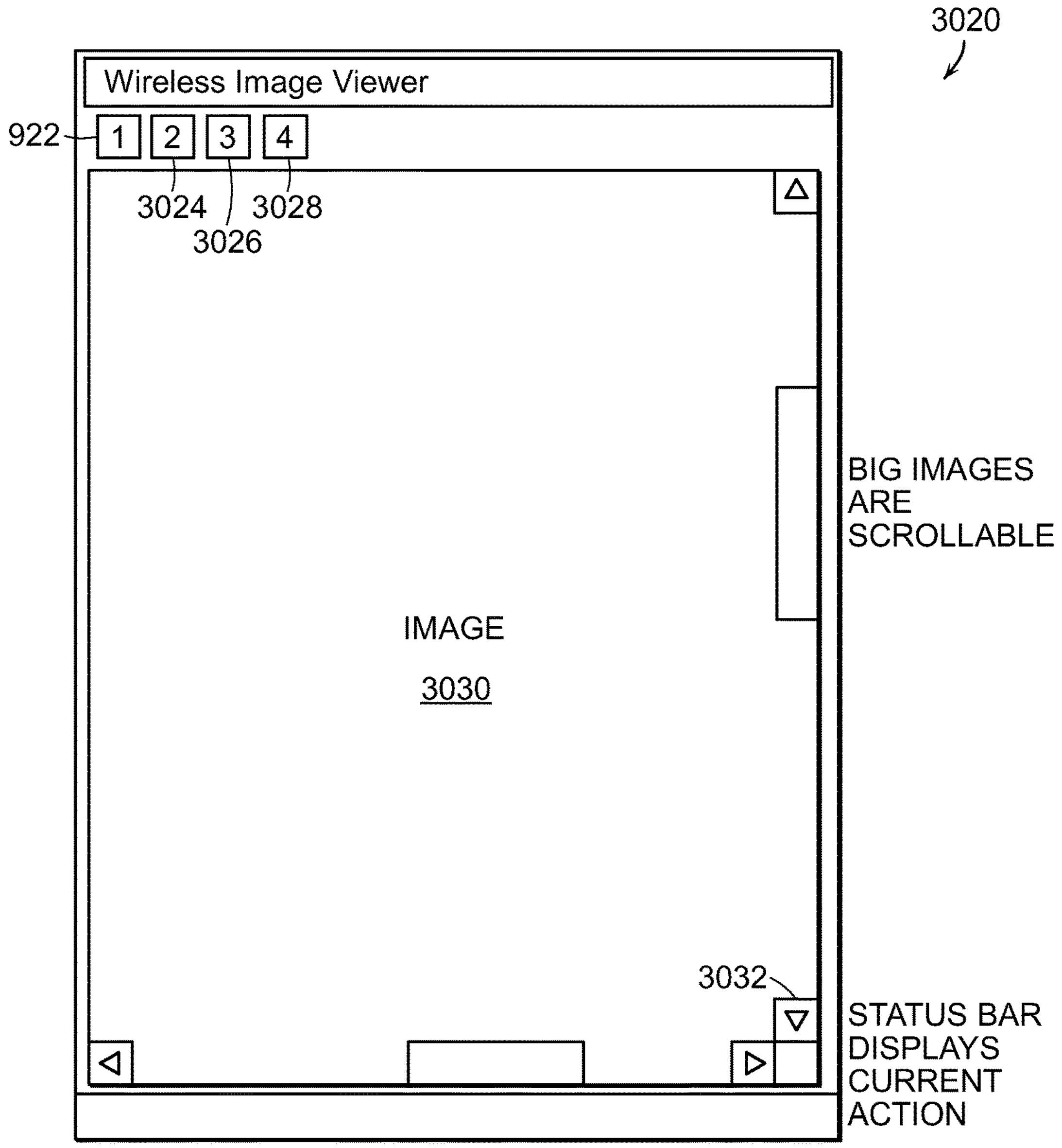

1 CONNECT BUTTON. INITIATES CONNECTION TO APPLICATION

2 DISCONNECT BUTTON. TERMINATES CONNECTION.

3 SELECT BUTTON. PROVIDES LIST OF PATIENTS AND IMAGES TO SELECT FROM. IMAGES CAN BE STORED LOCALLY OR REMOTELY. IF SELECTED IMAGE STORED REMOTELY INITIATES IMAGE TRANSMISSION. DISPLAYS SELECTED IMAGE.

4 OPTIONS BUTTON. ALLOWS TO CHANGE CONFIGURATION PARAMETERS SUCH AS IP ADDRESS.

FIG. 30

3506
Flexible Frequency 3502
2D Image Window 3504
2D Scan Image

3600
Tablet Display

3002
Flexible Frequency
Controls 3604
2D Image Window 3606
2D Image

3608
Scan Time
Sores Window

TABLET ULTRASOUND SYSTEM

CROSS REFERENCE TO RELATED APPLICATIONS

This patent application is a 35 U.S.C. § 371 national stage filing of International Application No. PCT/US2014/057516, filed on Sep. 25, 2014, which claims priority to U.S. application Ser. No. 14/037,106, filed Sep. 25, 2013, and is a continuation-in-part of International Application No. PCT/US2013/033941 filed Mar. 26, 2013, and also a continuation-in-part of U.S. application Ser. No. 13/838,694 filed Mar. 15, 2013, which claims priority to U.S. Application No. 61/615,627 filed Mar. 26, 2012 and U.S. Application No. 61/704,254 filed Sep. 21, 2012. The entire contents of these applications are incorporated herein by reference.

BACKGROUND

Medical ultrasound imaging has become an industry standard for many medical imaging applications. In recent years, there has been an increasing need for medical ultrasound imaging equipment that is portable to allow medical personnel to easily transport the equipment to and from hospital and/or field locations, and more user-friendly to accommodate medical personnel who may possess a range of skill levels.

Conventional medical ultrasound imaging equipment typically includes at least one ultrasound probe/transducer, a keyboard and/or a knob, a computer, and a display. In a typical mode of operation, the ultrasound probe/transducer generates ultrasound waves that can penetrate tissue to different depths based on frequency level, and receives ultrasound waves reflected back from the tissue. Further, medical personnel can enter system inputs to the computer via the keyboard and/or the knob, and view ultrasound images of tissue structures on the display.

However, conventional medical ultrasound imaging equipment that employ such keyboards and/or knobs can be bulky, and therefore may not be amenable to portable use in hospital and/or field locations. Moreover, because such keyboards and/or knobs typically have uneven surfaces, they can be difficult to keep clean in hospital and/or field environments, where maintenance of a sterile field can be crucial to patient health. Some conventional medical ultrasound imaging equipment have incorporated touchscreen technology to provide a partial user input interface. However, conventional medical ultrasound imaging equipment that employ such touchscreen technology generally provide only limited touchscreen functionality in conjunction with a traditional keyboard and/or knob, and can therefore not only be difficult to keep clean, but also complicated to use.

SUMMARY

In accordance with the present application, systems and methods of medical ultrasound imaging are disclosed. The presently disclosed systems and methods of medical ultrasound imaging employ medical ultrasound imaging equipment that includes a handheld housing in a tablet form factor, and a touchscreen display disposed on a front panel of the housing. The touchscreen display includes a multi-touch touchscreen that can recognize and distinguish one or more single, multiple, and/or simultaneous touches on a surface of the touchscreen display, thereby allowing the use of gestures, ranging from simple single point gestures to complex multipoint moving gestures, as user inputs to the medical ultrasound imaging equipment. The ultrasound tablet can include wireless transmission and reception circuitry to enable wireless connectivity to cellular networks for voice and data communication.

In accordance with one aspect, exemplary medical ultrasound imaging system includes a housing having a front panel and a rear panel rigidly mounted to each other in parallel planes, a touchscreen display, a computer having at least one processor and at least one memory, an ultrasound beamforming system, and a battery. The housing of the medical ultrasound imaging equipment is implemented in a tablet form factor. The touchscreen display is disposed on the front panel of the housing, and includes a multi-touch LCD touchscreen that can recognize and distinguish one or more single, multiple, and/or simultaneous touches or gestures on a surface of the touchscreen display. The computer, the ultrasound beamforming system or engine, and the battery are operatively disposed within the housing. The medical ultrasound imaging equipment can use a Firewire connection operatively connected between the computer and the ultrasound engine within the housing and a probe connector having a probe attach/detach lever to facilitate the connection of at least one ultrasound probe/transducer. In addition, the exemplary medical ultrasound imaging system includes an I/O port connector and a DC power input.

In an exemplary mode of operation, medical personnel can employ simple single point gestures and/or more complex multipoint gestures as user inputs to the multi-touch LCD touchscreen for controlling operational modes and/or functions of the exemplary medical ultrasound imaging equipment. Such single point/multipoint gestures can correspond to single and/or multipoint touch events that are mapped to one or more predetermined operations that can be performed by the computer and/or the ultrasound engine. Medical personnel can make such single point/multipoint gestures by various finger, palm, and/or stylus motions on the surface of the touchscreen display. The multi-touch LCD touchscreen receives the single point/multipoint gestures as user inputs, and provides the user inputs to the computer, which executes, using the processor, program instructions stored in the memory to carry out the predetermined operations associated with the single point/multipoint gestures, at least at some times, in conjunction with the ultrasound engine. Such single point/multipoint gestures on the surface of the touchscreen display can include, but are not limited to, a tap gesture, a pinch gesture, a flick gesture, a rotate gesture, a double tap gesture, a spread gesture, a drag gesture, a press gesture, a press and drag gesture, and a palm gesture. In contrast to existing ultrasound systems that rely on numerous control features operated by mechanical switching, keyboard elements, or touchpad trackball interface, preferred embodiments of the present invention employ a single on/off switch. All other operations have been implemented using touchscreen controls. Moreover, the preferred embodiments employ a capacitive touchscreen display that is sufficiently sensitive to detect touch gestures actuated by bare fingers of the user as well as gloved fingers of the user. Often medical personnel must wear sterilized plastic gloves during medical procedures. Consequently, it is highly desirable to provide a portable ultrasound device that can be used by gloved hands; however, this has previously prevented the use of touchscreen display control functions in ultrasound systems for many applications requiring sterile precautions. Preferred embodiments of the present invention provide control of all ultrasound imaging operations by gloved personnel on the touchscreen display using the programmed touch gestures.

In accordance with an exemplary aspect, at least one flick gesture may be employed to control the depth of tissue penetration of ultrasound waves generated by the ultrasound probe/transducer. For example, a single flick gesture in the "up" direction on the touchscreen display surface can increase the penetration depth by one (1) centimeter or any other suitable amount, and a single flick gesture in the "down" direction on the touchscreen display surface can decrease the penetration depth by one (1) centimeter or any other suitable amount. Further, a drag gesture in the "up" or "down" direction on the touchscreen display surface can increase or decrease the penetration depth in multiples of one (1) centimeter or any other suitable amount. Additional operational modes and/or functions controlled by specific single point/multipoint gestures on the touchscreen display surface can include, but are not limited to, freeze/store operations, 2-dimensional mode operations, gain control, color control, split screen control, PW imaging control, cine/time-series image clip scrolling control, zoom and pan control, full screen control, Doppler and 2-dimensional beam steering control, and/or body marking control. At least some of the operational modes and/or functions of the exemplary medical ultrasound imaging equipment can be controlled by one or more touch controls implemented on the touchscreen display in which beamforming parameters can be reset by moving touch gestures. Medical personnel can provide one or more specific single point/multipoint gestures as user inputs for specifying at least one selected subset of the touch controls to be implemented, as required and/or desired, on the touchscreen display. A larger number of touchscreen controls enable greater functionality when operating in full screen mode when a few or more virtual buttons or icons are available for use.

In accordance with another exemplary aspect, a press gesture can be employed inside a region of the touchscreen display, and, in response to the press gesture, a virtual window can be provided on the touchscreen display for displaying at least a magnified portion of an ultrasound image displayed on the touchscreen display. In accordance with still another exemplary aspect, a press and drag gesture can be employed inside the region of the touchscreen display, and, in response to the press and drag gesture, a predetermined feature of the ultrasound image can be traced. Further, a tap gesture can be employed inside the region of the touchscreen display, substantially simultaneously with a portion of the press and drag gesture, and, in response to the tap gesture, the tracing of the predetermined feature of the ultrasound image can be completed. These operations can operate in different regions of a single display format, so that a moving gesture within a region of interest within the image, for example, may perform a different function than the same gesture executed within the image but outside the region of interest.

By providing medical ultrasound imaging equipment with a multi-touch touchscreen, medical personnel can control the equipment using simple single point gestures and/or more complex multipoint gestures, without the need of a traditional keyboard or knob. Because the multi-touch touchscreen obviates the need for a traditional keyboard or knob, such medical ultrasound imaging equipment is easier to keep clean in hospital and/or field environments, provides an intuitive user friendly interface, while providing fully functional operations. Moreover, by providing such medical ultrasound imaging equipment in a tablet form factor, medical personnel can easily transport the equipment between hospital and/or field locations.

The system is operable to communicate with external and remote devices via a wireless communication network such as a 3G or 4G wireless cellular network. The system can thus provide voice and data transfer including over a wireless public access network for mobile device communication.

Certain exemplary embodiments provide a multi-chip module for an ultrasound engine of a portable medical ultrasound imaging system, in which a transmit/receive (TR) chip, a pre-amp/time gain compensation (TGC) chip and a beamformer chip are assembled in a vertically stacked configuration. The transmission circuit provides high voltage electrical driving pulses to the transducer elements to generate a transmit beam. As the transmit chip operates at voltages greater than 80V, a CMOS process utilizing a 1 micron design rule has been utilized for the transmit chip and a submicron design rule has been utilized for the low-voltage receiving circuits (less than 5V).

Preferred embodiments of the present invention utilize a submicron process to provide integrated circuits with sub-circuits operating at a plurality of voltages, for example, 2.5V, 5V and 60V or higher. These features can be used in conjunction with a bi-plane transducer probe in accordance with certain preferred embodiments of the invention.

Thus, a single IC chip can be utilized that incorporates high voltage transmission, low voltage amplifier/TGC and low voltage beamforming circuits in a single chip. Using a 0.25 micron design rule, this mixed signal circuit can accommodate beamforming of 32 transducer channels in a chip area less than 0.7×0.7 (0.49) $cm^2$. Thus, 128 channels can be processed using four 32 channel chips in a total circuit board area of less than 1.5×1.5 (2.25) $cm^2$.

The term "multi-chip module," as used herein, refers to an electronic package in which multiple integrated circuits (IC) are packaged with a unifying substrate, facilitating their use as a single component, i.e., as a higher processing capacity IC packaged in a much smaller volume. Each IC can comprise a circuit fabricated in a thinned semiconductor wafer. Exemplary embodiments also provide an ultrasound engine including one or more such multi-chip modules, and a portable medical ultrasound imaging system including an ultrasound engine circuit board with one or more multi-chip modules. Exemplary embodiments also provide methods for fabricating and assembling multi-chip modules as taught herein. Vertically stacking the TR chip, the pre-amp/TGC chip, and the beamformer chip on a circuit board minimizes the packaging size (e.g., the length and width) and the footprint occupied by the chips on the circuit board.

The TR chip, the pre-amp/TGC chip, and the beamformer chip in a multi-chip module may each include multiple channels (for example, 8 channels per chip to 64 channels per chip). In certain embodiments, the high-voltage TR chip, the pre-amp/TGC chip, and the sample-interpolate receive beamformer chip may each include 8, 16, 32, 64 channels. In a preferred embodiment, each circuit in a two layer beamformer module has 32 beamformer receive channels to provide a 64 channel receiving beamformer. A second 64 channel two layer module can be used to form a 128 channel handheld tablet ultrasound device having an overall thickness of less than 2 cm. A transmit multi-chip beamformer can also be used having the same or similar channel density in each layer.

Exemplary numbers of chips vertically integrated in a multi-chip module may include, but are not limited to, two, three, four, five, six, seven, eight, and the like. In one embodiment of an ultrasound device, a single multi-chip module is provided on a circuit board of an ultrasound engine that performs ultrasound-specific operations. In other embodiments, a plurality of multi-chip modules are provided on a circuit board of an ultrasound engine. The plurality of multi-chip modules may be stacked vertically on top of one another on the circuit board of the ultrasound engine to further minimize the packaging size and the footprint of the circuit board.

Providing one or more multi-chip modules on a circuit board of an ultrasound engine achieves a high channel count while minimizing the overall packaging size and footprint. For example, a 128-channel ultrasound engine circuit board can be assembled, using multi-chip modules, within exemplary planar dimensions of about 10 cm×about 10 cm, which is a significant improvement over the much larger space requirements of conventional ultrasound circuits. A single circuit board of an ultrasound engine including one or more multi-chip modules may have 16 to 128 channels in some embodiments. In certain embodiments, a single circuit board of an ultrasound engine including one or more multi-chip modules may have 16, 32, 64, 128 or 192 channels, and the like.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 3A illustrates exemplary single point and multipoint gestures that can be employed as user inputs to the medical ultrasound imaging system in accordance with preferred embodiments of the invention;

FIG. 3B illustrates a process flow diagram for operating a tablet ultrasound system in accordance with preferred embodiments of the invention;

FIG. 30 illustrates an image viewer in communication with a personal computer, in accordance with an embodiment of the present invention;

FIG. 48 is a block diagram illustrating the structure of the physical shared memory, according to one embodiment of the present invention;

FIG. 51 illustrates a main screen display of a graphical user interface in accordance with one embodiment of the present invention;

DETAILED DESCRIPTION

Systems and methods of medical ultrasound imaging are disclosed. The presently disclosed systems and methods of medical ultrasound imaging employ medical ultrasound imaging equipment that includes housing in a tablet form factor, and a touchscreen display disposed on a front panel of the housing. The touchscreen display includes a multi-touch touchscreen that can recognize and distinguish one or more single, multiple, and/or simultaneous touches on a surface of the touchscreen display, thereby allowing the use of gestures, ranging from simple single point gestures to complex multipoint gestures, as user inputs to the medical ultrasound imaging equipment. Further details regarding tablet ultrasound systems and operations are described in U.S. application Ser. No. 10/997,062 filed on Nov. 11, 2004, Ser. No. 10/386,360 filed Mar. 11, 2003 and U.S. Pat. No. 6,969,352, the entire contents of these patents and applications are incorporated herein by reference.

Figure 1:
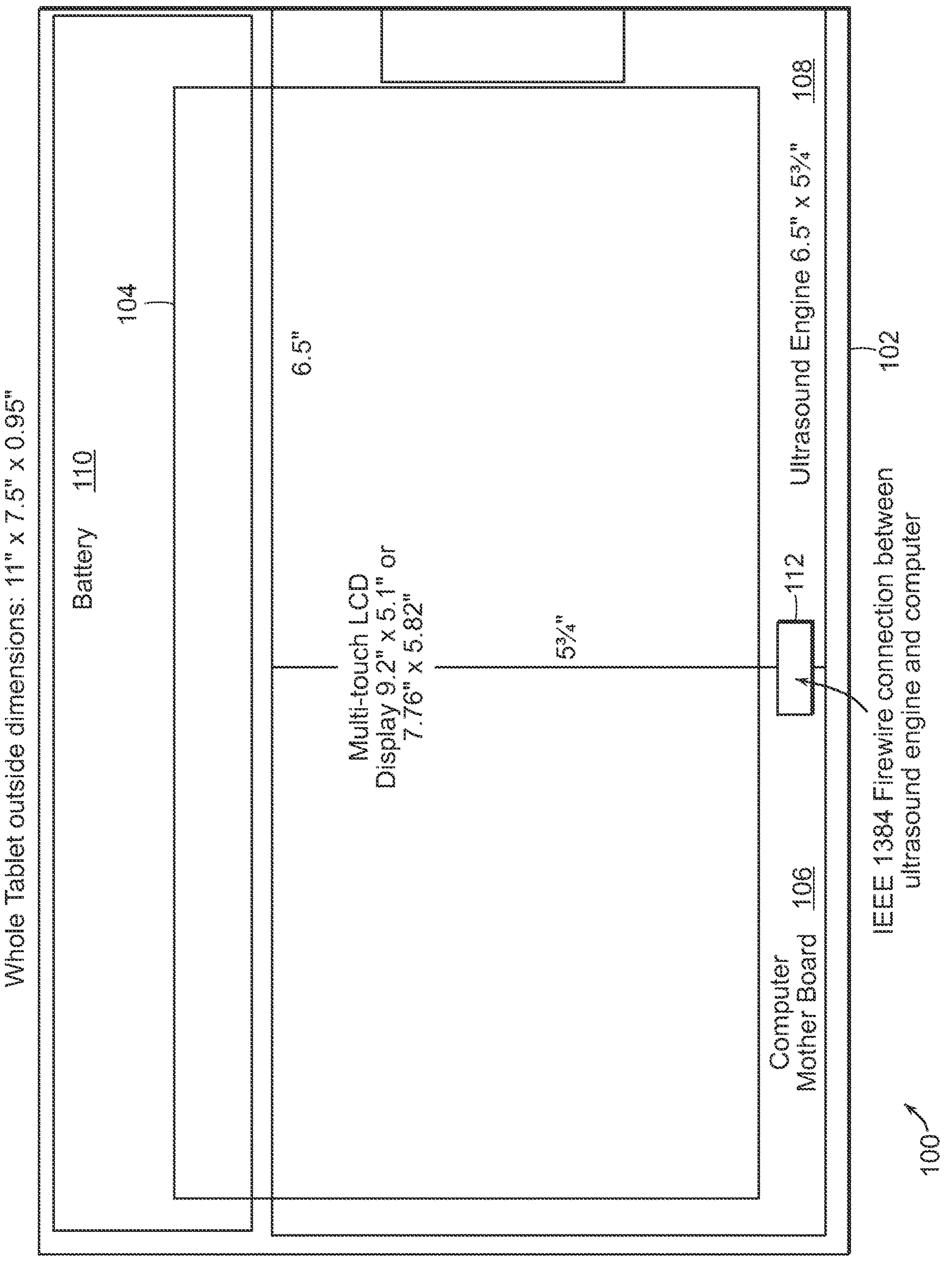
FIG. 1 is a plan view of exemplary medical ultrasound imaging equipment, in accordance with an exemplary embodiment of the present application.

FIG. 1 depicts an illustrative embodiment of exemplary medical ultrasound imaging equipment 100, in accordance with the present application. As shown in FIG. 1, the medical ultrasound imaging equipment 100 includes a housing 102, a touchscreen display 104, a computer having at least one processor and at least one memory implemented on a computer motherboard 106, an ultrasound engine 108, and a battery 110. For example, the housing 102 can be implemented in a tablet form factor, or any other suitable form factor. The housing 102 has a front panel 101 and a rear panel 103. The touchscreen display 104 is disposed on the front panel 101 of the housing 102, and includes a multi-touch LCD touchscreen that can recognize and distinguish one or more multiple and/or simultaneous touches on a surface 105 of the touchscreen display 104. The computer motherboard 106, the ultrasound engine 108, and the battery 110 are operatively disposed within the housing 102. The medical ultrasound imaging equipment 100 further includes a Firewire connection 112 (see also FIG. 2A) operatively connected between the computer motherboard 106 and the ultrasound engine 108 within the housing 102, and a probe connector 114 having a probe attach/detach lever 115 (see also FIGS. 2A and 2B) to facilitate the connection of at least one ultrasound probe/transducer. The transducer probe housing can include circuit components including a transducer array, transmit and receive circuitry, as well as beamformer and beamformer control circuits in certain preferred embodiments. In addition, the medical ultrasound imaging equipment 100 has one or more I/O port connectors 116 (see FIG. 2A), which can include, but are not limited to, one or more USB connectors, one or more SD cards, one or more network ports, one or more mini display ports, and a DC power input.

In an exemplary mode of operation, medical personnel (also referred to herein as the "user" or "users") can employ simple single point gestures and/or more complex multipoint gestures as user inputs to the multi-touch LCD touchscreen of the touchscreen display 104 for controlling one or more operational modes and/or functions of the medical ultrasound imaging equipment 100. Such a gesture is defined herein as a movement, a stroke, or a position of at least one finger, a stylus, and/or a palm on the surface 105 of the touchscreen display 104. For example, such single point/multipoint gestures can include static or dynamic gestures, continuous or segmented gestures, and/or any other suitable gestures. A single point gesture is defined herein as a gesture that can be performed with a single touch contact point on the touchscreen display 104 by a single finger, a stylus, or a palm. A multipoint gesture is defined herein as a gesture that can be performed with multiple touch contact points on the touchscreen display 104 by multiple fingers, or any suitable combination of at least one finger, a stylus, and a palm. A static gesture is defined herein as a gesture that does not involve the movement of at least one finger, a stylus, or a palm on the surface 105 of the touchscreen display 104. A dynamic gesture is defined herein as a gesture that involves the movement of at least one finger, a stylus, or a palm, such as the movement caused by dragging one or more fingers across the surface 105 of the touchscreen display 104. A continuous gesture is defined herein as a gesture that can be performed in a single movement or stroke of at least one finger, a stylus, or a palm on the surface 105 of the touchscreen display 104. A segmented gesture is defined herein as a gesture that can be performed in multiple movements or stokes of at least one finger, a stylus, or a palm on the surface 105 of the touchscreen display 104.

Such single point/multipoint gestures performed on the surface 105 of the touchscreen display 104 can correspond to single or multipoint touch events, which are mapped to one or more predetermined operations that can be performed by the computer and/or the ultrasound engine 108. Users can make such single point/multipoint gestures by various single finger, multi-finger, stylus, and/or palm motions on the surface 105 of the touchscreen display 104. The multi-touch LCD touchscreen receives the single point/multipoint gestures as user inputs, and provides the user inputs to the processor, which executes program instructions stored in the memory to carry out the predetermined operations associated with the single point/multipoint gestures, at least at some times, in conjunction with the ultrasound engine 108. As shown in FIG. 3A, such single point/multipoint gestures on the surface 105 of the touchscreen display 104 can include, but are not limited to, a tap gesture 302, a pinch gesture 304, a flick gesture 306, 314, a rotate gesture 308, 316, a double tap gesture 310, a spread gesture 312, a drag gesture 318, a press gesture 320, a press and drag gesture 322, and/or a palm gesture 324. For example, such single point/multipoint gestures can be stored in at least one gesture library in the memory implemented on the computer motherboard 106. The computer program operative to control system operations can be stored on a computer readable medium and can optionally be implemented using a touch processor connected to an image processor and a control processor connected to the system beamformer. Thus beamformer delays associated with both transmission and reception can be adjusted in response to both static and moving touch gestures.

In accordance with the illustrative embodiment of FIG. 1, at least one flick gesture 306 or 314 may be employed by a user of the medical ultrasound imaging equipment 100 to control the depth of tissue penetration of ultrasound waves generated by the ultrasound probe/transducer. For example, a dynamic, continuous, flick gesture 306 or 314 in the "up" direction, or any other suitable direction, on the surface 105 of the touchscreen display 104 can increase the penetration depth by one (1) centimeter, or any other suitable amount. Further, a dynamic, continuous, flick gesture 306 or 314 in the "down" direction, or any other suitable direction, on the surface 105 of the touchscreen display 104 can decrease the penetration depth by one (1) centimeter, or any other suitable amount. Moreover, a dynamic, continuous, drag gesture 318 in the "up" or "down" direction, or any other suitable direction, on the surface 105 of the touchscreen display 104 can increase or decrease the penetration depth in multiple centimeters, or any other suitable amounts.

Additional operational modes and/or functions controlled by specific single point/multipoint gestures on the surface 105 of the touchscreen display 104 can include, but are not limited to, freeze/store operations, 2-dimensional mode operations, gain control, color control, split screen control, PW imaging control, cine/time-series image clip scrolling control, zoom and pan control, full screen display, Doppler and 2-dimensional beam steering control, and/or body marking control. At least some of the operational modes and/or functions of the medical ultrasound imaging equipment 100 can be controlled by one or more touch controls implemented on the touchscreen display 104. Further, users can provide one or more specific single point/multipoint gestures as user inputs for specifying at least one selected subset of the touch controls to be implemented, as required and/or desired, on the touchscreen display 104. Associated with each imaging mode is a plurality of preset scan parameters that are displayed as icons or are delectable from a menu so that the scan parameters are automatically selected for that mode.

Shown in FIG. 3B is a process sequence in which ultrasound beamforming and imaging operations 340 are controlled in response to touch gestures entered on a touchscreen. Various static and moving touch gestures have been programmed into the system such that the data processor is operable to control beamforming and image processing operations 342 within the tablet device. A user can select 344 a first display operation having a first plurality of touch gestures associated therewith. Using a static or moving gesture the user can perform one of the plurality of gestures operable to control the imaging operation and can specifically select one of a plurality of gestures that can adjust beamforming parameters 346 being used to generate image data associated with the first display operation. The displayed image is updated and displayed 348 response to the updated beamforming procedure. The user can further elect to perform a different gesture having a different velocity characteristic (direction or speed or both) to adjust 350 a second characteristic of the first ultrasound display operation. The displayed image is then updated 352 based on the second gesture, which can modify imaging processing parameters or beamforming parameters. Examples of this process are described in further detail herein where changes in velocity and direction of different gestures can be associated with distinct imaging parameters of a selected display operation.

Ultrasound images of flow or tissue movement, whether color flow or spectral Doppler, are essentially obtained from measurements of movement. In ultrasound scanners, a series of pulses is transmitted to detect movement of blood. Echoes from stationary targets are the same from pulse to pulse. Echoes from moving scatterers exhibit slight differences in the time for the signal to be returned to the scanner.

Figure 3C:
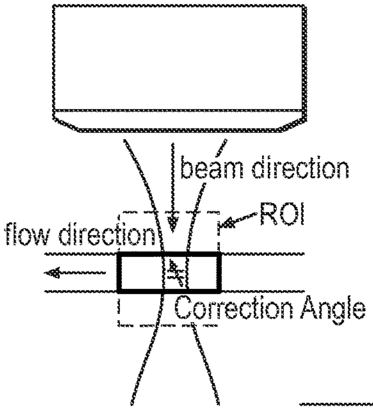
FIG. 3C-3K illustrates details of touchscreen gestures to adjust beamforming and display operation.
Figure 3D:
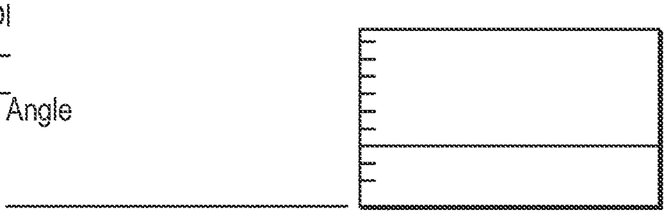
Figure 3E:
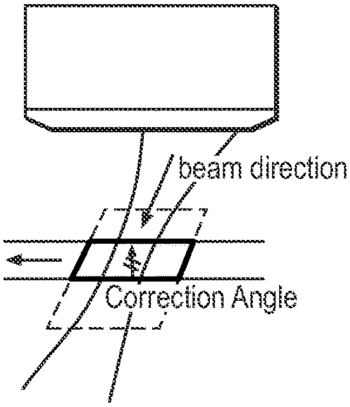
Figure 3F:
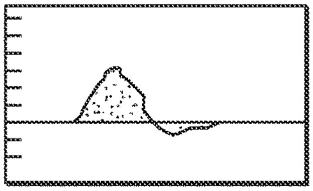
Figure 3G:
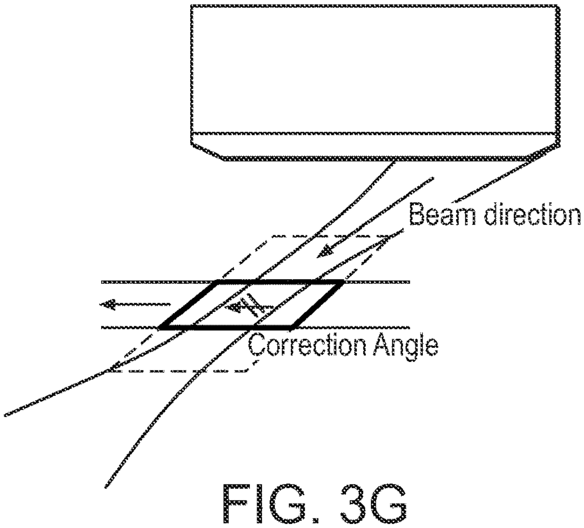
Figure 3H:
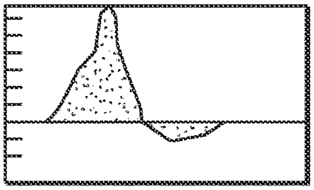

As can be seen from FIG. 3C-3H, there has to be motion in the direction of the beam; if the flow is perpendicular to the beam, there is no relative motion from pulse to pulse receive, there is no flow detected. These differences can be measured as a direct time difference or, more usually, in terms of a phase shift from which the 'Doppler frequency' is obtained. They are then processed to produce either a color flow display or a Doppler sonogram. In FIG. 3C-3D, the flow direction is perpendicular to the beam direction, no flow is measured by Pulse Wave spectral Doppler. In FIG. 3G-3H when the ultrasound beam is steered to an angle that is better aligned to the flow, a weak flow is shown in the color flow map, and in addition flow is measured by Pulse Wave Doppler. In FIG. 3H, when the ultrasound beam is steered to an angle much better aligned to the flow direction in response to a moving, the color flow map is stronger, in addition when the correction angle of the PWD is placed aligned to the flow, a strong flow is measured by the PWD.

Figure 3I:
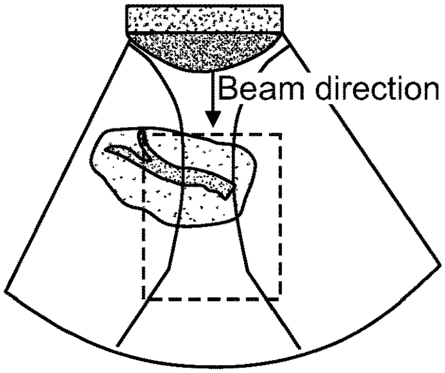
Figure 3J:
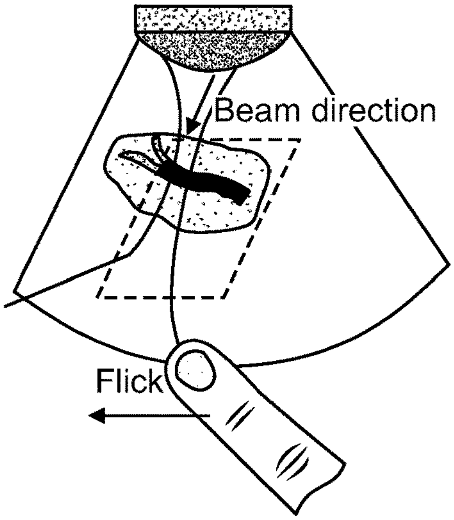

In this tablet ultrasound system, an ROI, region of interest, is also used to define the direction in response to a moving gesture of the ultrasound transmit beam. A liver image with a branch of renal flow in color flow mode is shown in FIG. 3I since the ROI is straight down from the transducer, the flow direction is almost normal to the ultrasound beam, so very week renal flow is detected. Hence, the color flow mode is used to image a renal flow in liver. As can be seen, the beam is almost normal to the flow and very weak flow is detected. A flick gesture with the finger outside of the ROI is used to steer the beam. As can be seen in FIG. 3J, the ROI is steered by resetting beamforming parameters so that the beam direction is more aligned to the flow direction, a much stronger flow within the ROI is detected. In FIG. 3J, a flick gesture with the finger outside of the ROI is used to steer the ultrasound beam into the direction more aligned to the flow direction. Stronger flow within the ROI can be seen. A panning gesture with the finger inside the ROI will move the ROI box into a position that covers the entire renal region, i.e., panning allows a translation movement of the ROI box such that the box covers the entire target area.

Figure 3K:
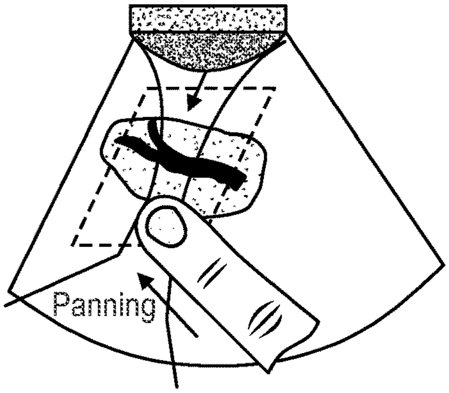

FIG. 3K demonstrates a panning gesture. With the finger inside the ROI, it can move the ROI box to any place within the image plane. In the above embodiment, it is easy to differentiate a "flick" gesture with a finger outside an "ROI" box is intended for steering a beam, and a "drag-and-move, panning" gesture with a finger inside the "ROI" is intended for moving the ROI box. However, there are applications in which no ROI as a reference region, then it is easy to see that it is difficult to differentiate a "flick" or a "panning" gesture, in this case, the touch-screen program needs to track the initial velocity or acceleration of the finger to determine it is a "flick" gesture or a "drag-and-move" gesture. Thus, the touch engine that receives data from the touchscreen sensor device is programmed to discriminate between velocity thresholds that indicate different gestures. Thus, the time, speed and direction associated with different moving gestures can have preset thresholds. Two and three finger static and moving gestures can have separate thresholds to differentiate these control operations. Note that preset displayed icons or virtual buttons can have distinct static pressure or time duration thresholds. When operated in full screen mode, the touchscreen processor, which is preferably operating on the systems central processing unit that performs other imaging operations such as scan conversion, switches off the static icons.

Figure 4A:
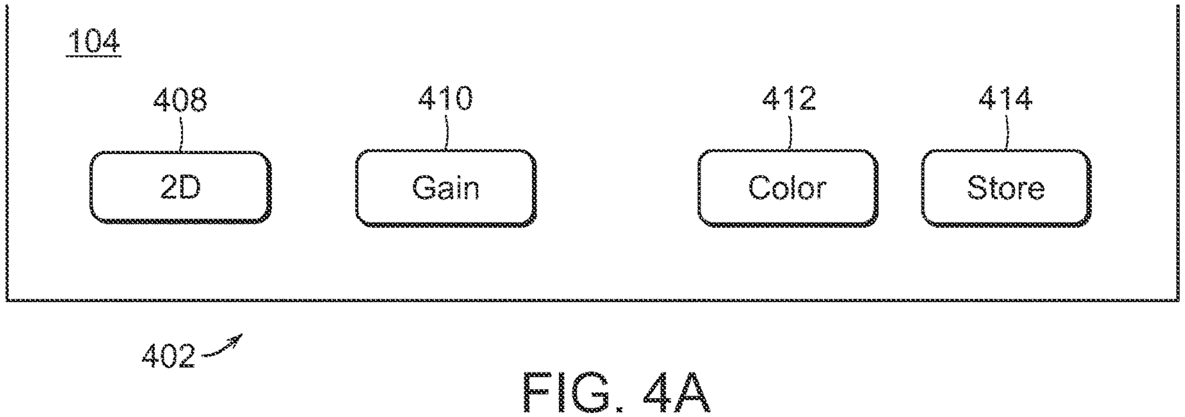
FIGS. 4A-4C illustrates exemplary subsets of touch controls that can be implemented on the medical ultrasound imaging system in accordance with preferred embodiments of the invention.
Figure 4B:
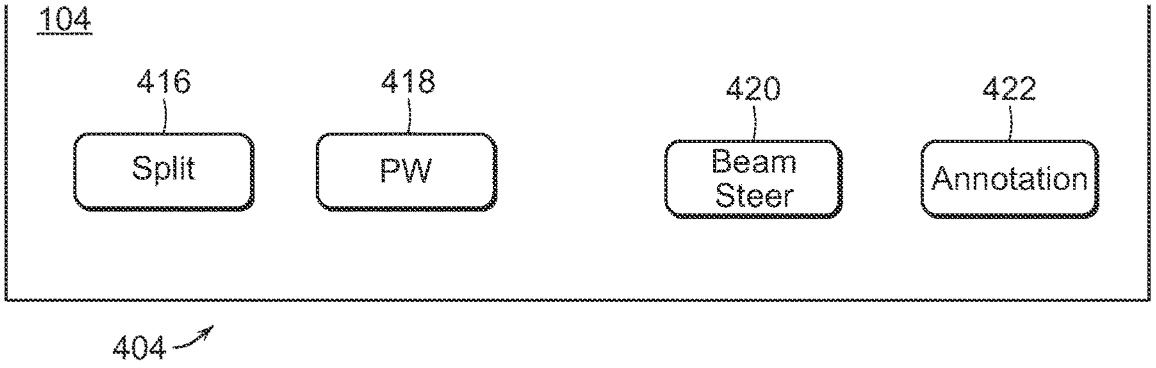
Figure 4C:
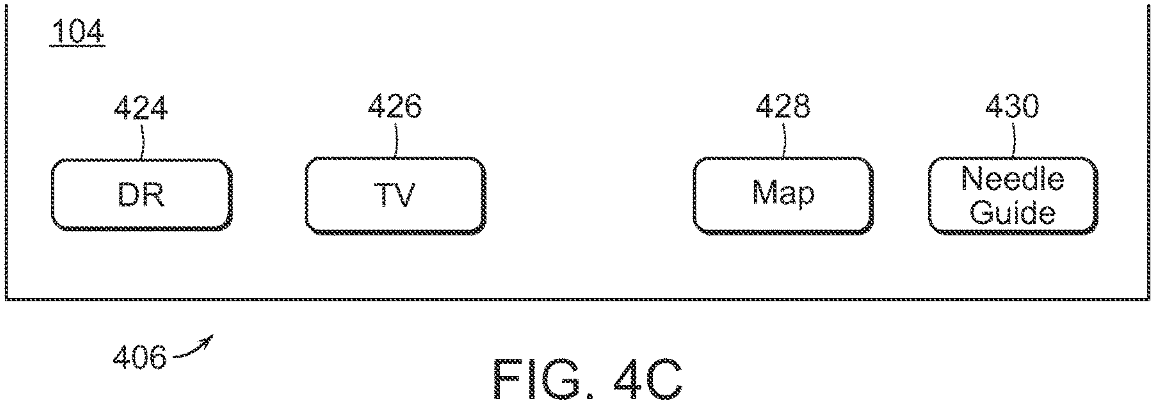

FIGS. 4A-4C depict exemplary subsets 402, 404, 406 of touch controls that can be implemented by users of the medical ultrasound imaging equipment 100 on the touchscreen display 104. It is noted that any other suitable subset(s) of touch controls can be implemented, as required and/or desired, on the touchscreen display 104. As shown in FIG. 4A, the subset 402 includes a touch control 408 for performing 2-dimensional (2D) mode operations, a touch control 410 for performing gain control operations, a touch control 412 for performing color control operations, and a touch control 414 for performing image/clip freeze/store operations. For example, a user can employ the press gesture 320 to actuate the touch control 408, returning the medical ultrasound imaging equipment 100 to 2D mode. Further, the user can employ the press gesture 320 against one side of the touch control 410 to decrease a gain level, and employ the press gesture 320 against another side of the touch control 410 to increase the gain level. Moreover, the user can employ the drag gesture 318 on the touch control 412 to identify ranges of densities on a 2D image, using a predetermined color code. In addition, the user can employ the press gesture 320 to actuate the touch control 414 to freeze/store a still image or to acquire a cine image clip.

As shown in FIG. 4B, the subset 404 includes a touch control 416 for performing split screen control operations, a touch control 418 for performing PW imaging control operations, a touch control 420 for performing Doppler and 2-dimensional beam steering control operations, and a touch control 422 for performing annotation operations. For example, a user can employ the press gesture 320 against the touch control 416, allowing the user to toggle between opposing sides of the split touchscreen display 104 by alternately employing the tap gesture 302 on each side of the split screen. Further, the user can employ the press gesture 320 to actuate the touch control 418 and enter the PW mode, which allows (1) user control of the angle correction, (2) movement (e.g., "up" or "down") of a baseline that can be displayed on the touchscreen display 104 by employing the press and drag gesture 322, and/or (3) an increase or a decrease of scale by employing the tap gesture 302 on a scale bar that can be displayed on the touchscreen display 104. Moreover, the user can employ the press gesture 320 against one side of the touch control 420 to perform 2D beam steering to the "left" or any other suitable direction in increments of five (5) or any other suitable increment, and employ the press gesture 320 against another side of the touch control 420 to perform 2D beam steering to the "right" or any other suitable direction in increments of five (5) or any other suitable increment. In addition, the user can employ the tap gesture 302 on the touch control 422, allowing the user to enter annotation information via a pop-up keyboard that can be displayed on the touchscreen display 104.

As shown in FIG. 4C, the subset 406 includes a touch control 424 for performing dynamic range operations, a touch control 426 for performing Teravision™ software operations, a touch control 428 for performing map operations, and a touch control 430 for performing needle guide operations. For example, a user can employ the press gesture 320 and/or the press and drag gesture 322 against the touch control 424 to control or set the dynamic range. Further, the user can employ the tap gesture 302 on the touch control 426 to choose a desired level of the Teravision™ software to be executed from the memory by the processor on the computer motherboard 106. Moreover, the user can employ the tap gesture 302 on the touch control 428 to perform a desired map operation. In addition, the user can employ the press gesture 320 against the touch control 430 to perform a desired needle guide operation.

In accordance with the present application, various measurements and/or tracings of objects (such as organs, tissues, etc.) displayed as ultrasound images on the touchscreen display 104 of the medical ultrasound imaging equipment 100 (see FIG. 1) can be performed, using single point/multipoint gestures on the surface 105 of the touchscreen display 104. The user can perform such measurements and/or tracings of objects directly on an original ultrasound image of the displayed object, on a magnified version of the ultrasound image of the displayed object, and/or on a magnified portion of the ultrasound image within a virtual window 506 (see FIGS. 5C and 5D) on the touchscreen display 104.

Figure 5A:
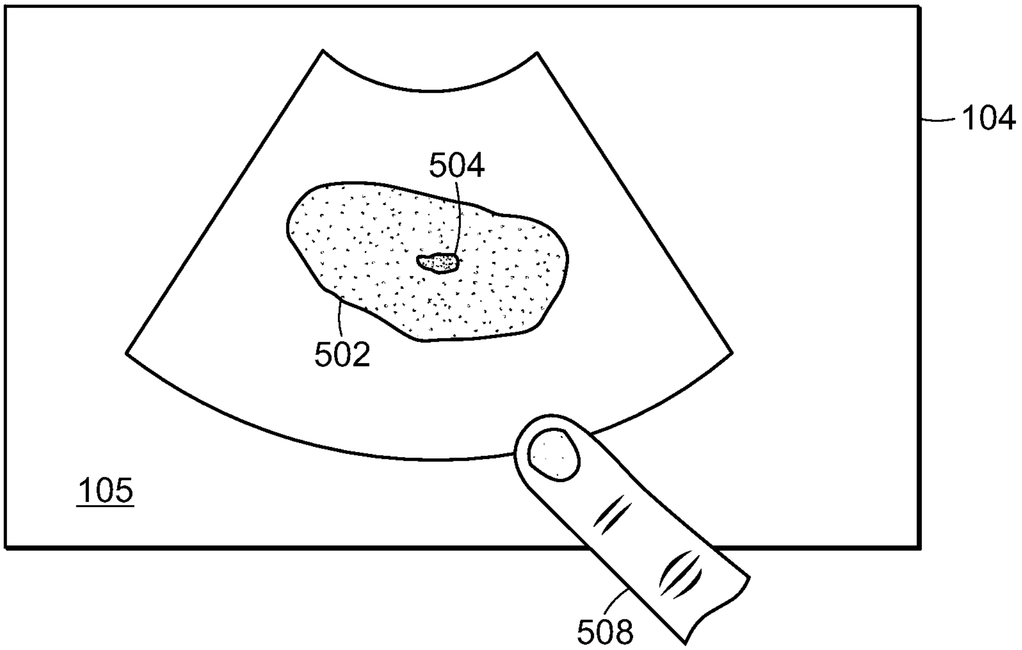
FIGS. 5A and 5B are exemplary representations of a liver with a cystic lesion on a touchscreen display of the medical ultrasound imaging system in accordance with preferred embodiments of the invention.
Figure 5B:
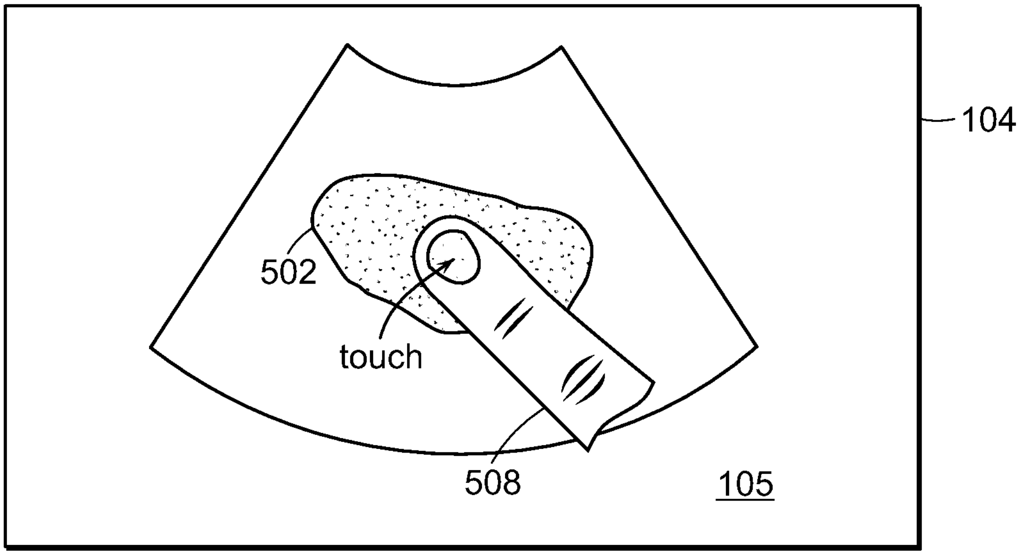
Figure 5C:
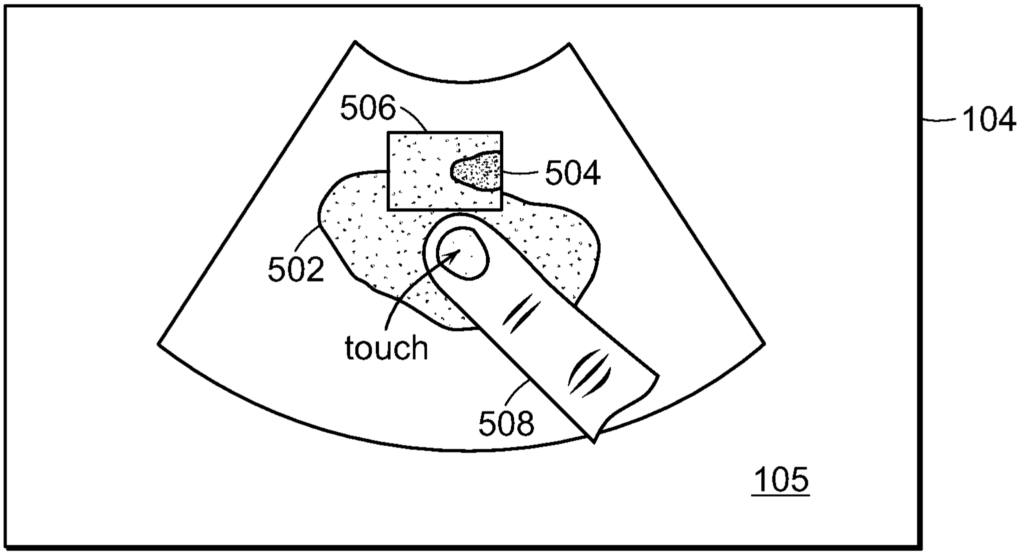
FIGS. 5C and 5D are exemplary representations of the liver and cystic lesion on the touchscreen display of FIGS. 5A and 5B, including a virtual window that corresponds to a magnified portion of the liver.
Figure 5D:
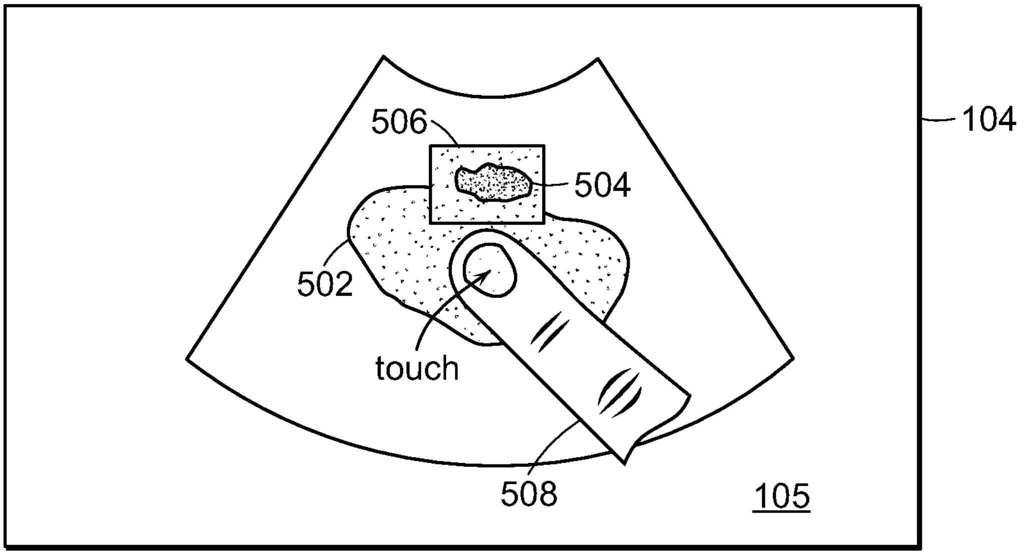

FIGS. 5A and 5B depict an original ultrasound image of an exemplary object, namely, a liver 502 with a cystic lesion 504, displayed on the touchscreen display 104 of the medical ultrasound imaging equipment 100 (see FIG. 1). It is noted that such an ultrasound image can be generated by the medical ultrasound imaging equipment 100 in response to penetration of the liver tissue by ultrasound waves generated by an ultrasound probe/transducer operatively connected to the equipment 100. Measurements and/or tracings of the liver 502 with the cystic lesion 504 can be performed directly on the original ultrasound image displayed on the touchscreen display 104 (see FIGS. 5A and 5B), or on a magnified version of the ultrasound image. For example, the user can obtain such a magnified version of the ultrasound image using a spread gesture (see, e.g., the spread gesture 312; FIG. 3) by placing two (2) fingers on the surface 105 of the touchscreen display 104, and spreading them apart to magnify the original ultrasound image. Such measurements and/or tracings of the liver 502 and cystic lesion 504 can also be performed on a magnified portion of the ultrasound image within the virtual window 506 (see FIGS. 5C and 5D) on the touchscreen display 104.

For example, using his or her finger (see, e.g., a finger 508; FIGS. 5A-5D), the user can obtain the virtual window 506 by employing a press gesture (see, e.g., the press gesture 320; FIG. 3) against the surface 105 of the touchscreen display 104 (see FIG. 5B) in the vicinity of a region of interest, such as the region corresponding to the cystic lesion 504. In response to the press gesture, the virtual window 506 (see FIGS. 5C and 5D) is displayed on the touchscreen display 104, possibly at least partially superimposed on the original ultrasound image, thereby providing the user with a view of a magnified portion of the liver 502 in the vicinity of the cystic lesion 504. For example, the virtual window 506 of FIG. 5C can provide a view of a magnified portion of the ultrasound image of the cystic lesion 504, which is covered by the finger 508 pressed against the surface 105 of the touchscreen display 104. To re-position the magnified cystic lesion 504 within the virtual window 506, the user can employ a press and drag gesture (see, e.g., the press and drag gesture 322; FIG. 3) against the surface 105 of the touchscreen display 104 (see FIG. 5D), thereby moving the image of the cystic lesion 504 to a desired position within the virtual window 506. In one embodiment, the medical ultrasound imaging equipment 100 can be configured to allow the user to select a level of magnification within the virtual window 506 to be 2 times larger, 4 times larger, or any other suitable number of times larger than the original ultrasound image. The user can remove the virtual window 506 from the touchscreen display 104 by lifting his or her finger (see, e.g., the finger 508; FIGS. 5A-5D) from the surface 105 of the touchscreen display 104.

Figure 6A:
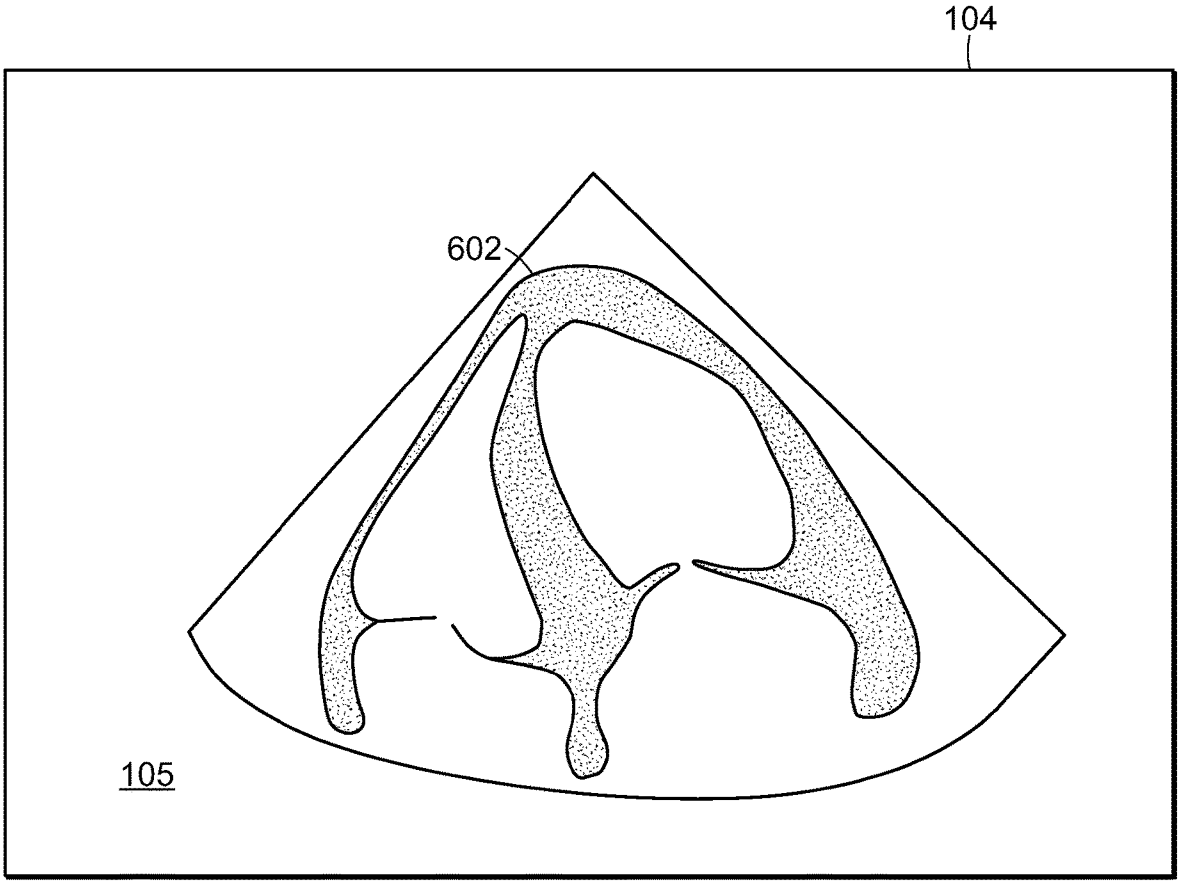
FIG. 6A is an exemplary representation of an apical four (4) chamber view of a heart on the touchscreen display of the medical ultrasound imaging system.
Figure 6B:
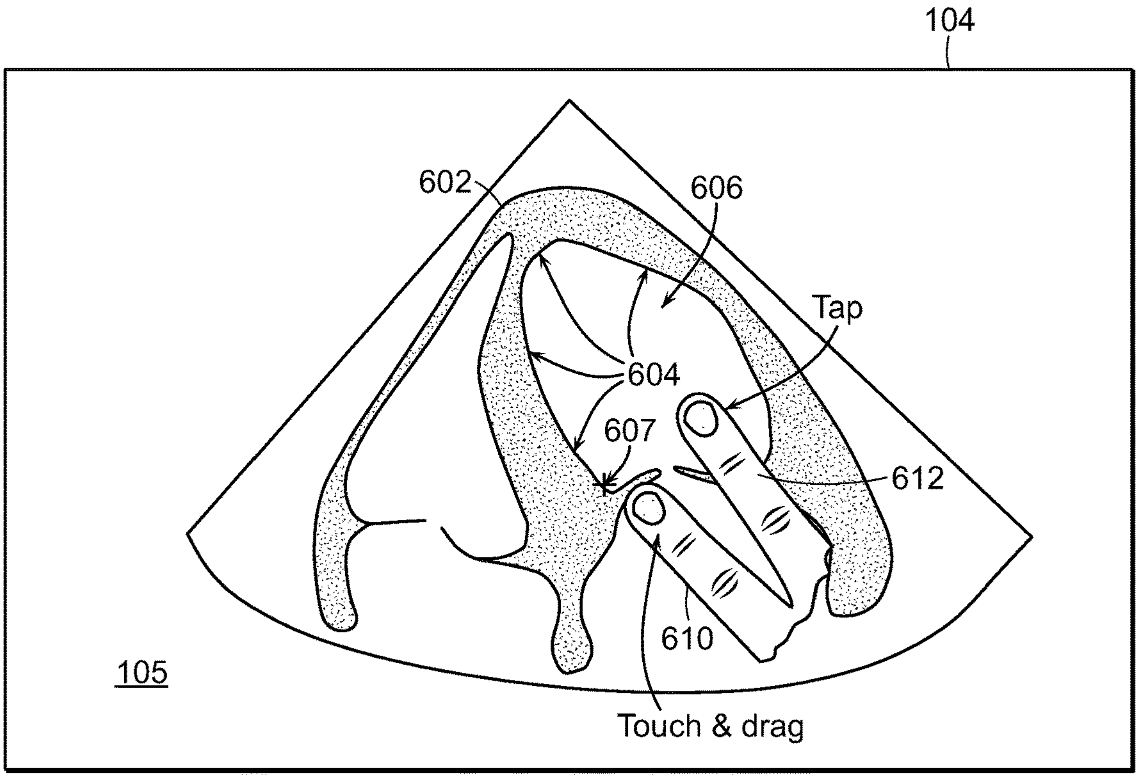
FIGS. 6B-6E illustrates an exemplary manual tracing of an endocardial border of a left ventricle of the heart on the touchscreen display of FIG. 6A.

FIG. 6A depicts an ultrasound image of another exemplary object, namely, an apical four (4) chamber view of a heart 602, displayed on the touchscreen display 104 of the medical ultrasound imaging equipment 100 (see FIG. 1). It is noted that such an ultrasound image can be generated by the medical ultrasound imaging equipment 100 in response to penetration of the heart tissue by ultrasound waves generated by an ultrasound probe/transducer operatively connected to the equipment 100. Measurements and/or tracings of the heart 602 can be performed directly on the original ultrasound image displayed on the touchscreen display 104 (see FIGS. 6A-6E), or on a magnified version of the ultrasound image. For example, using his or her fingers (see, e.g., fingers 610, 612; FIGS. 6B-6E), the user can perform a manual tracing of an endocardial border 604 (see FIG. 6B) of a left ventricle 606 (see FIGS. 6B-6E) of the heart 602 by employing one or more multi-finger gestures on the surface 105 of the touchscreen display 104. In one embodiment, using his or her fingers (see, e.g., the fingers 610, 612; FIGS. 6B-6E), the user can obtain a cursor 607 (see FIG. 6B) by employing a double tap gesture (see, e.g., the double tap gesture 310; FIG. 3A) on the surface 105 of the touchscreen display 104, and can move the cursor 607 by employing a drag gesture (see, e.g., the drag gesture 318; FIG. 3A) using one finger, such as the finger 610, thereby moving the cursor 607 to a desired location on the touchscreen display 104. The systems and methods described herein can be used for the quantitative measurement of heart wall motion and specifically for the measurement of ventricular dysynchrony as described in detail in U.S. application Ser. No. 10/817,316 filed on Apr. 2, 2004, the entire contents of which is incorporated herein by reference.

Figure 6C:
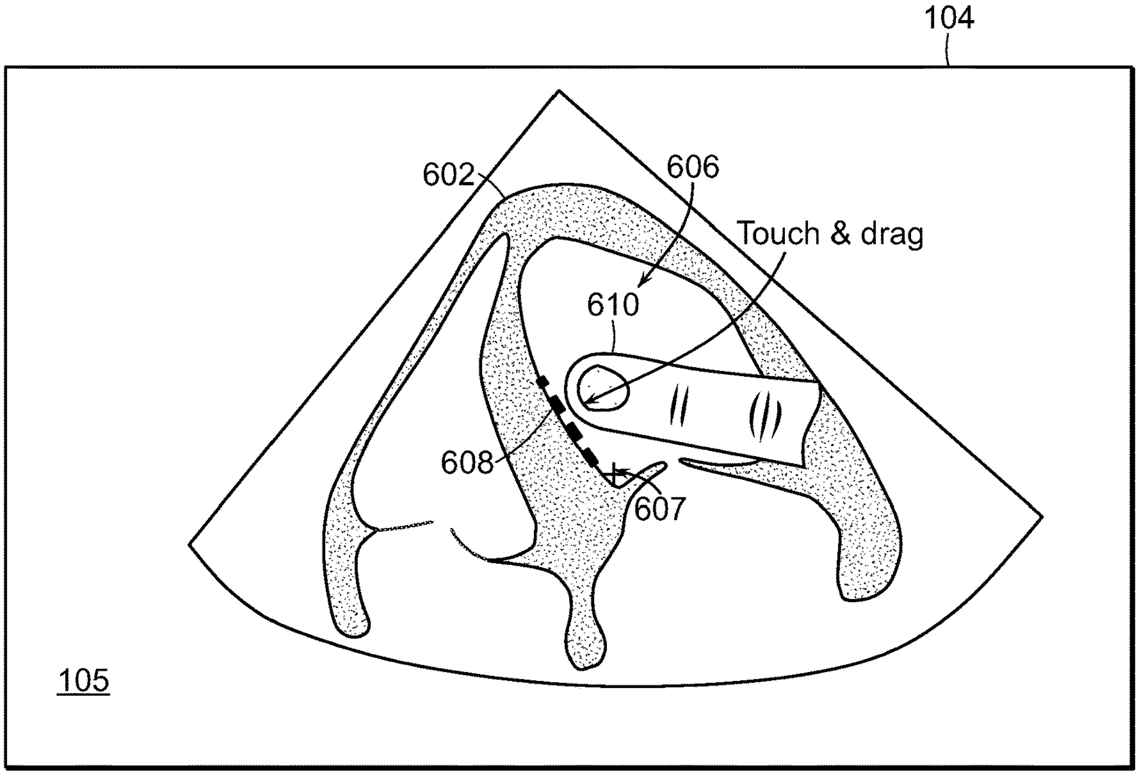
Figure 6D:
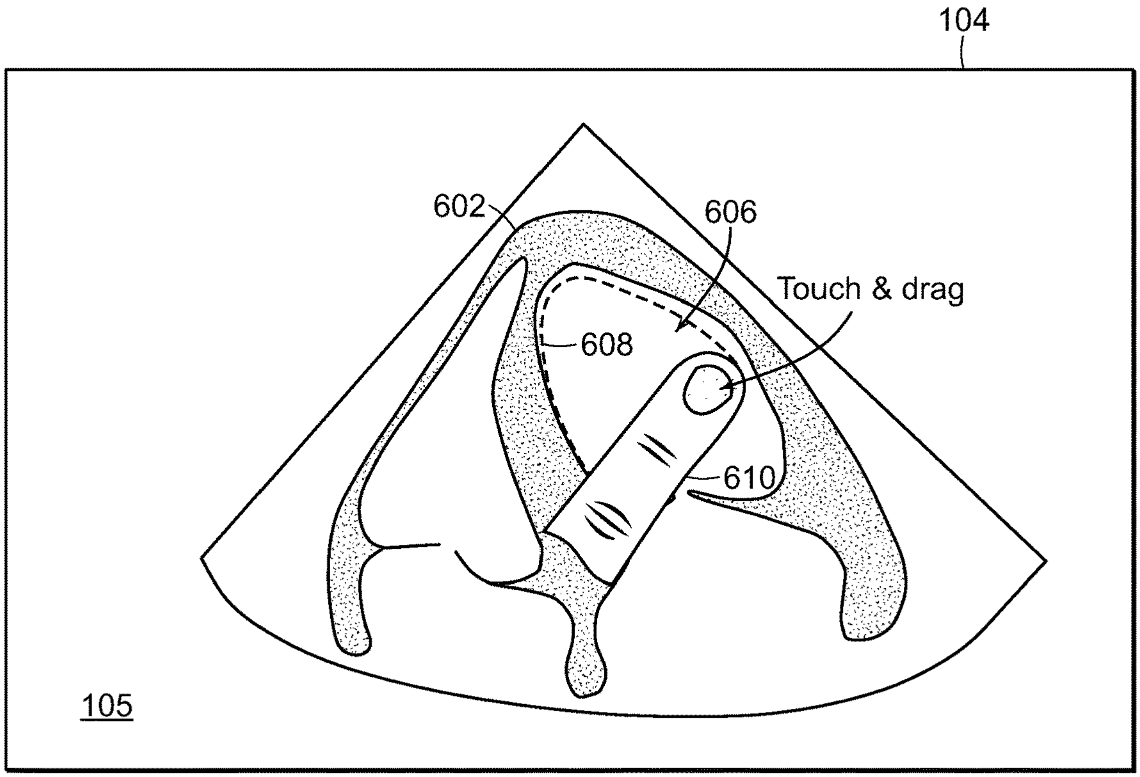
Figure 6E:
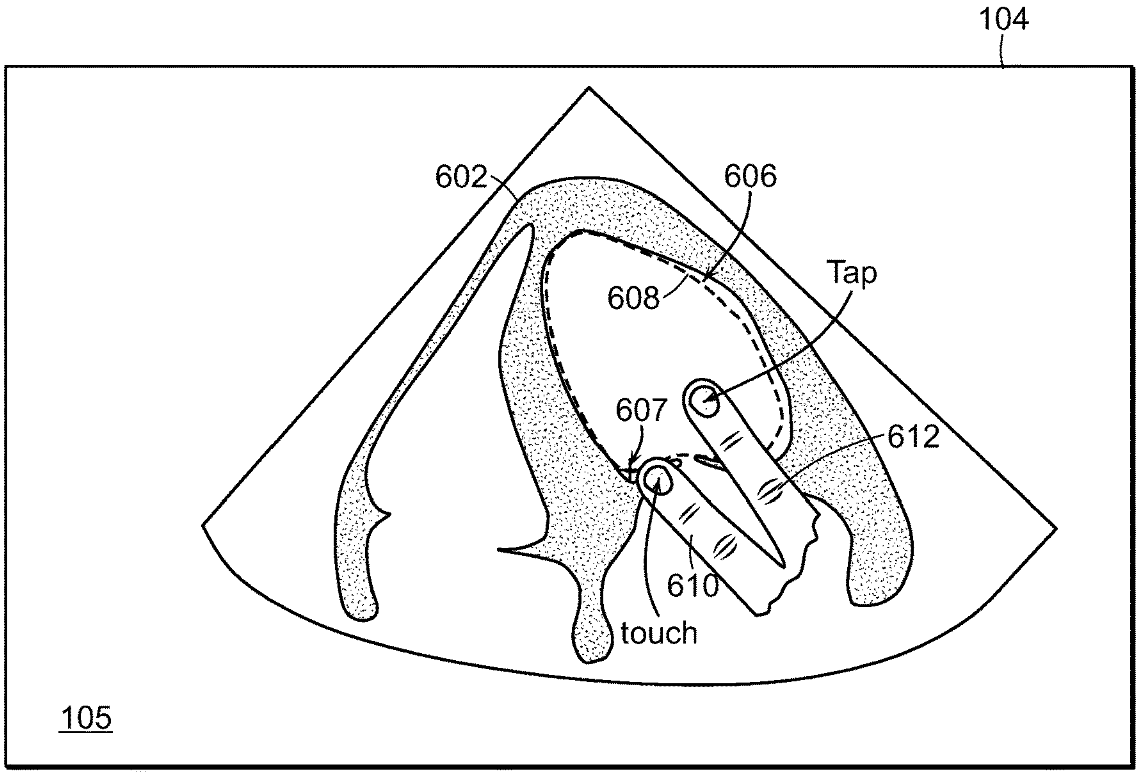

Once the cursor 607 is at the desired location on the touchscreen display 104, as determined by the location of the finger 610, the user can fix the cursor 607 at that location by employing a tap gesture (see, e.g., the tap gesture 302; see FIG. 3) using another finger, such as the finger 612. To perform a manual tracing of the endocardial border 604 (see FIG. 6B), the user can employ a press and drag gesture (see, e.g., the press and drag gesture 322; FIG. 3) using the finger 610, as illustrated in FIGS. 6C and 6D. Such a manual tracing of the endocardial border 604 can be highlighted on the touchscreen display 104 in any suitable fashion, such as by a dashed line 608 (see FIGS. 6C-6E). The manual tracing of the endocardial border 604 can continue until the finger 610 arrives at any suitable location on the touchscreen display 104, or until the finger 610 returns to the location of the cursor 607, as illustrated in FIG. 6E. Once the finger 610 is at the location of the cursor 607, or at any other suitable location, the user can complete the manual tracing operation by employing a tap gesture (see, e.g., the tap gesture 302; see FIG. 3) using the finger 612. It is noted that such a manual tracing operation can be employed to trace any other suitable feature(s) and/or waveform(s), such as a pulsed wave Doppler (PWD) waveform. In one embodiment, the medical ultrasound imaging equipment 100 can be configured to perform any suitable calculation(s) and/or measurement(s) relating to such feature(s) and/or waveform(s), based at least in part on a manual tracing(s) of the respective feature(s)/waveform(s).

Figure 7C:
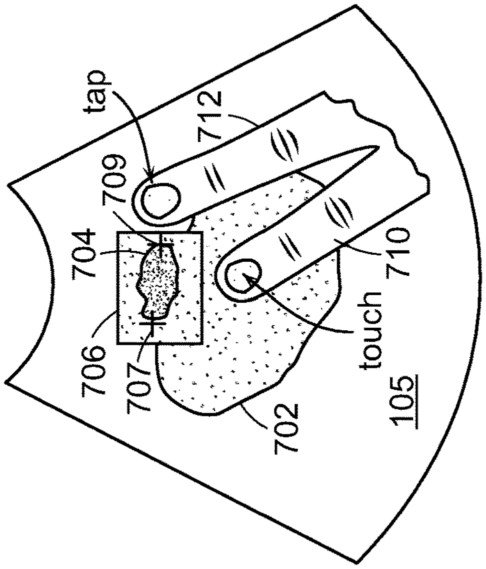
FIGS. 7A-7C illustrates an exemplary measurement of the size of the cystic lesion on the liver within the virtual window of FIGS. 5C and 5D.
Figure 7B:
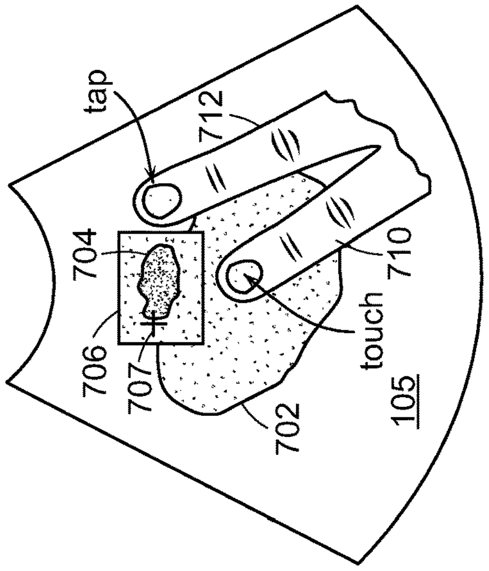
Figure 7A:
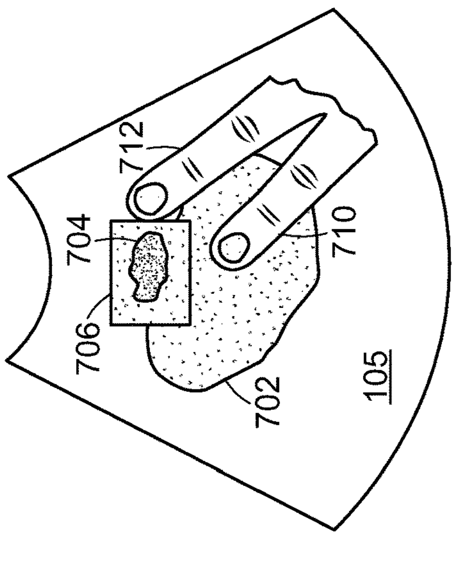

As described above, the user can perform measurements and/or tracings of objects on a magnified portion of an original ultrasound image of a displayed object within a virtual window on the touchscreen display 104. FIGS. 7A-7C depict an original ultrasound image of an exemplary object, namely, a liver 702 with a cystic lesion 704, displayed on the touchscreen display 104 of the medical ultrasound imaging equipment 100 (see FIG. 1). FIGS. 7A-7C further depict a virtual window 706 that provides a view of a magnified portion of the ultrasound image of the cystic lesion 704, which is covered by one of the user's fingers, such as a finger 710, pressed against the surface 105 of the touchscreen display 104. Using his or her fingers (see, e.g., fingers 710, 712; FIGS. 7A-7C), the user can perform a size measurement of the cystic lesion 704 within the virtual window 706 by employing one or more multi-finger gestures on the surface 105 of the touchscreen display 104.

For example, using his or her fingers (see, e.g., the fingers 710, 712; FIGS. 7A-7C), the user can obtain a first cursor 707 (see FIGS. 7B, 7C) by employing a double tap gesture (see, e.g., the double tap gesture 310; FIG. 3) on the surface 105, and can move the first cursor 707 by employing a drag gesture (see, e.g., the drag gesture 318; FIG. 3) using one finger, such as the finger 710, thereby moving the first cursor 707 to a desired location. Once the first cursor 707 is at the desired location, as determined by the location of the finger 710, the user can fix the first cursor 707 at that location by employing a tap gesture (see, e.g., the tap gesture 302; see FIG. 3) using another finger, such as the finger 712. Similarly, the user can obtain a second cursor 709 (see FIG. 7C) by employing a double tap gesture (see, e.g., the double tap gesture 310; FIG. 3) on the surface 105, and can move the second cursor 709 by employing a drag gesture (see, e.g., the drag gesture 318; FIG. 3) using the finger 710, thereby moving the second cursor 709 to a desired location. Once the second cursor 709 is at the desired location, as determined by the location of the finger 710, the user can fix the second cursor 709 at that location by employing a tap gesture (see, e.g., the tap gesture 302; see FIG. 3) using the finger 712. In one embodiment, the medical ultrasound imaging equipment 100 can be configured to perform any suitable size calculation(s) and/or measurement(s) relating to the cystic lesion 704, based at least in part on the locations of the first and second cursors 707, 709.

Figure 8C:
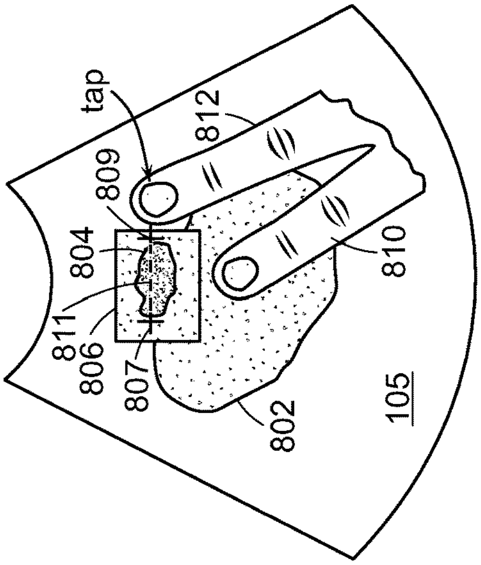
FIGS. 8A-8C illustrates an exemplary caliper measurement of the cystic lesion on the liver within the virtual window of FIGS. 5C and 5D.
Figure 8B:
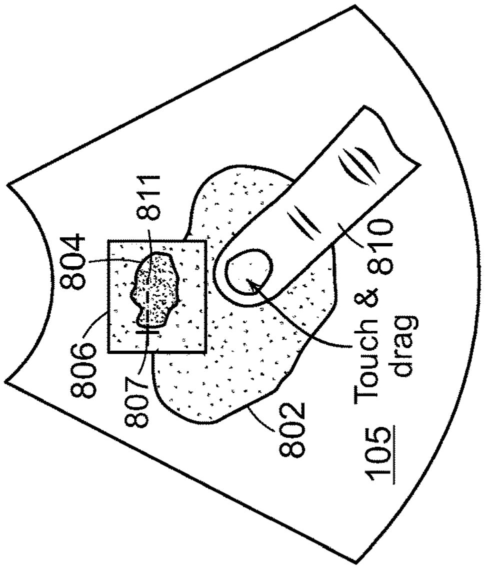
Figure 8A:
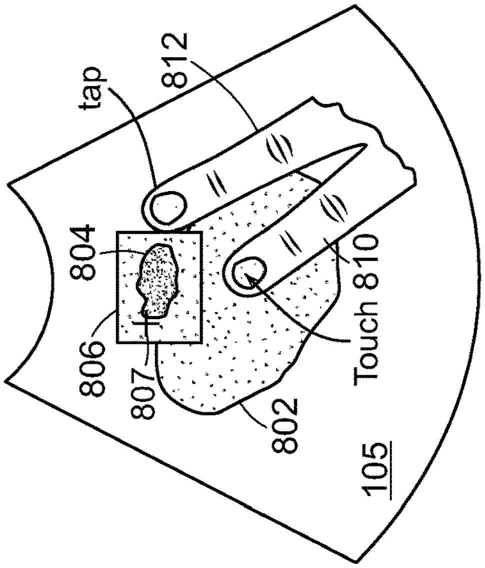

FIGS. 8A-8C depict an original ultrasound image of an exemplary object, namely, a liver 802 with a cystic lesion 804, displayed on the touchscreen display 104 of the medical ultrasound imaging equipment 100 (see FIG. 1). FIGS. 8*a*-8*c* further depict a virtual window 806 that provides a view of a magnified portion of the ultrasound image of the cystic lesion 804, which is covered by one of the user's fingers, such as a finger 810, pressed against the surface 105 of the touchscreen display 104. Using his or her fingers (see, e.g., fingers 810, 812; FIGS. 8A-8C), the user can perform a caliper measurement of the cystic lesion 804 within the virtual window 806 by employing one or more multi-finger gestures on the surface 105 of the touchscreen display 104.

For example, using his or her fingers (see, e.g., the fingers 810, 812; FIGS. 8A-8C), the user can obtain a first cursor 807 (see FIGS. 8B, 8C) by employing a double tap gesture (see, e.g., the double tap gesture 310; FIG. 3) on the surface 105, and can move the cursor 807 by employing a drag gesture (see, e.g., the drag gesture 318; FIG. 3) using one finger, such as the finger 810, thereby moving the cursor 807 to a desired location. Once the cursor 807 is at the desired location, as determined by the location of the finger 810, the user can fix the cursor 807 at that location by employing a tap gesture (see, e.g., the tap gesture 302; see FIG. 3) using another finger, such as the finger 812. The user can then employ a press and drag gesture (see, e.g., the press and drag gesture 322; FIG. 3) to obtain a connecting line 811 (see FIGS. 8B, 8C), and to extend the connecting line 811 from the first cursor 807 across the cystic lesion 804 to a desired location on another side of the cystic lesion 804. Once the connecting line 811 is extended across the cystic lesion 804 to the desired location on the other side of the cystic lesion 804, the user can employ a tap gesture (see, e.g., the tap gesture 302; see FIG. 3) using the finger 812 to obtain and fix a second cursor 809 (see FIG. 8C) at that desired location. In one embodiment, the medical ultrasound imaging equipment 100 can be configured to perform any suitable caliper calculation(s) and/or measurement(s) relating to the cystic lesion 804, based at least in part on the connecting line 811 extending between the locations of the first and second cursors 807, 809.

Figure 9A:
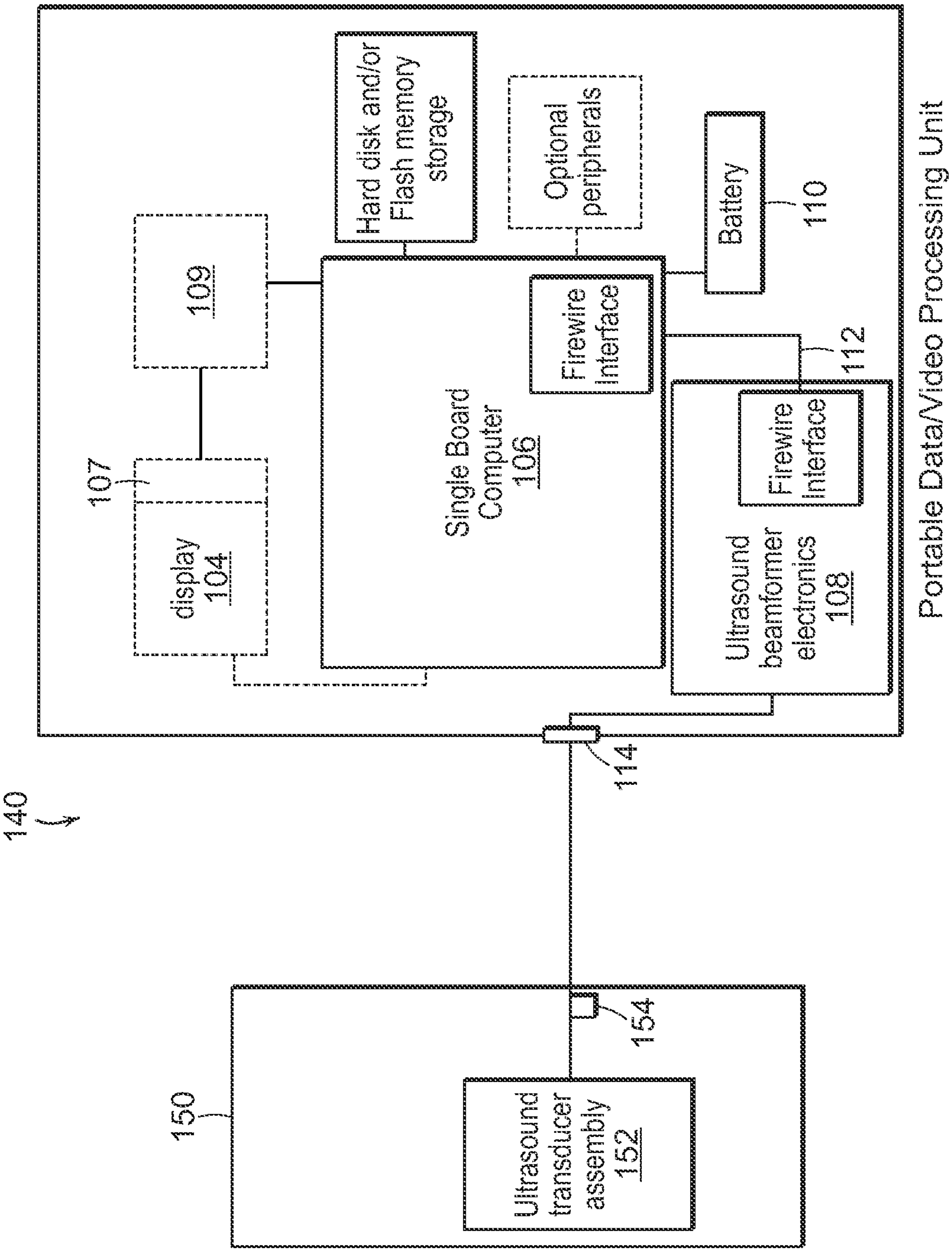
FIG. 9A illustrates one of a plurality of transducer arrays attached to the processor housing.

FIG. 9A shows a system 140 in which a transducer housing 150 with an array of transducer elements 152 can be attached at connector 114 to housing 102. Each probe 150 can have a probe identification circuit 154 that uniquely identifies the probe that is attached. When the user inserts a different probe with a different array, the system identifies the probe operating parameters. Note that preferred embodiments can include a display 104 having a touch sensor 107 which can be connected to a touch processor 109 that analyzes touchscreen data from the sensor 107 and transmits commands to both image processing operations and to a beamformer control processor (1116, 1124). In a preferred embodiment, the touch processor can include a computer readable medium that stores instructions to operate an ultrasound touchscreen engine that is operable to control display and imaging operations described herein.

Figure 9B:
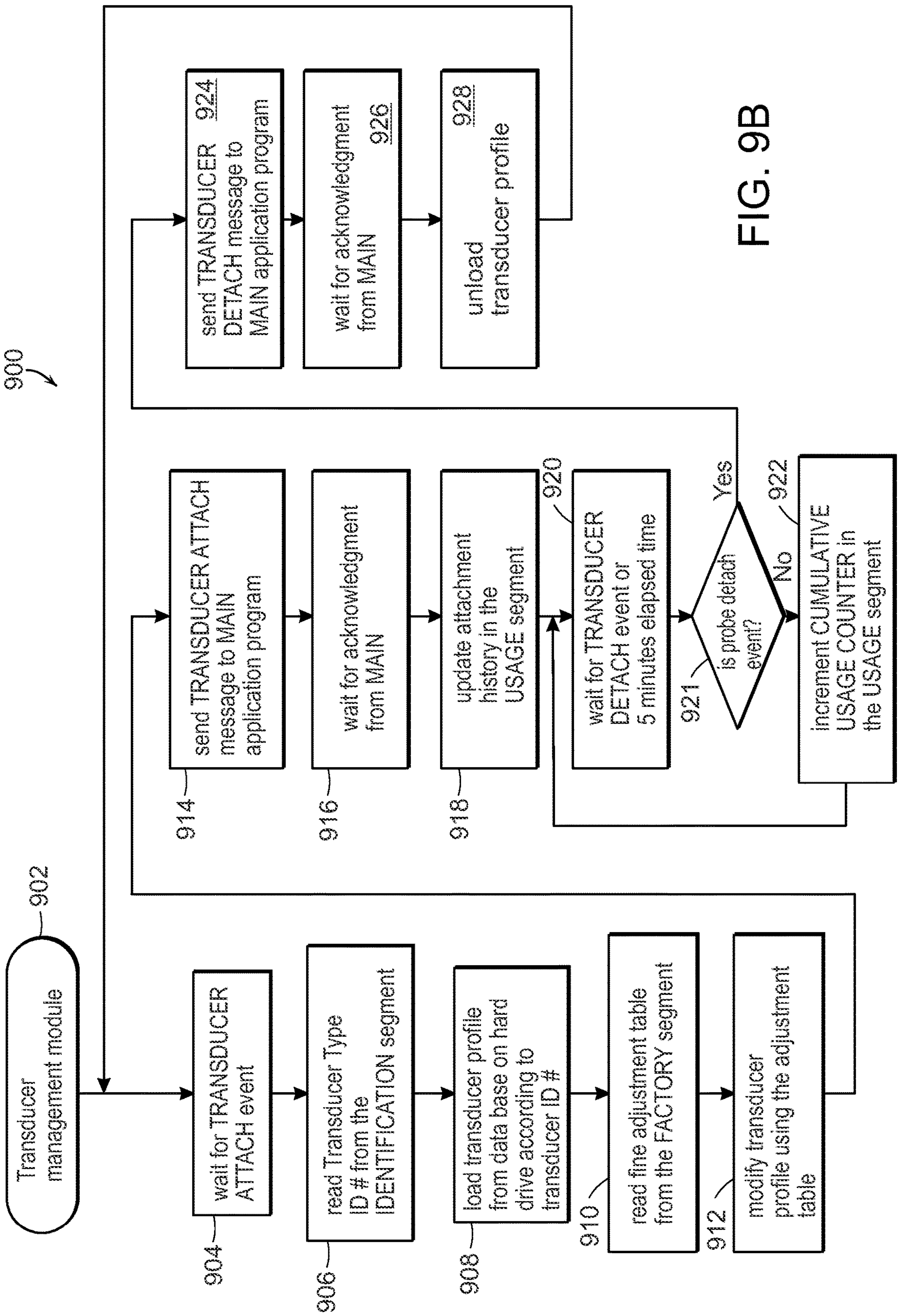
FIG. 9B shows a software flowchart of a transducer management module within an ultrasound application program, in accordance with an exemplary embodiment.

FIG. 9B shows a software flowchart 900 of a typical transducer management module 902 within the ultrasound application program. When a TRANSDUCER ATTACH 904 event is detected, the Transducer Management Software Module 902 first reads the Transducer type ID 906 and hardware revision information from the IDENTIFICATION Segment. The information is used to fetch the particular set of transducer profile data 908 from the hard disk and load it into the memory of the application program. The software then reads the adjustment data from the FACTORY Segment 910 and applies the adjustments to the profile data just loaded into memory 912. The software module then sends a TRANSDUCER ATTACH Message 914 to the main ultrasound application program, which uses the transducer profile already loaded. After acknowledgment 916, an ultrasound imaging sequence is performed and the USAGE segment is updated 918. The Transducer Management Software Module then waits for either a TRANSDUCER DETACH event 920, or the elapse of 5 minutes. If a TRANSDUCER DETACH event is detected 921, a message 924 is sent and acknowledged 926, the transducer profile data set is removed 928 from memory and the module goes back to wait for another TRANSDUCER ATTACH event. If a 5 minutes time period expires without detecting a TRANSDUCER DETACH event, the software module increments a Cumulative Usage Counter in the USAGE Segment 922, and waits for another 5 minutes period or a TRANSDUCER DETACH event. The cumulative usage is recorded in memory for maintenance and replacement records.

There are many types of ultrasound transducers. They differ by geometry, number of elements, and frequency response. For example, a linear array with center frequency of 10 to 15 MHz is better suited for breast imaging, and a curved array with center frequency of 3 to 5 MHz is better suited for abdominal imaging.

It is often necessary to use different types of transducers for the same or different ultrasound scanning sessions. For ultrasound systems with only one transducer connection, the operator will change the transducer prior to the start of a new scanning session.

In some applications, it is necessary to switch among different types of transducers during one ultrasound scanning session. In this case, it is more convenient to have multiple transducers connected to the same ultrasound system, and the operator can quickly switch among these connected transducers by hitting a button on the operator console, without having to physically detach and re-attach the transducers, which takes a longer time. Preferred embodiments of the invention can include a multiplexor within the tablet housing that can select between a plurality of probe connector ports within the tablet housing, or alternatively, the tablet housing can be connected to an external multiplexor that can be mounted on a cart as described herein.

Figure 9C:
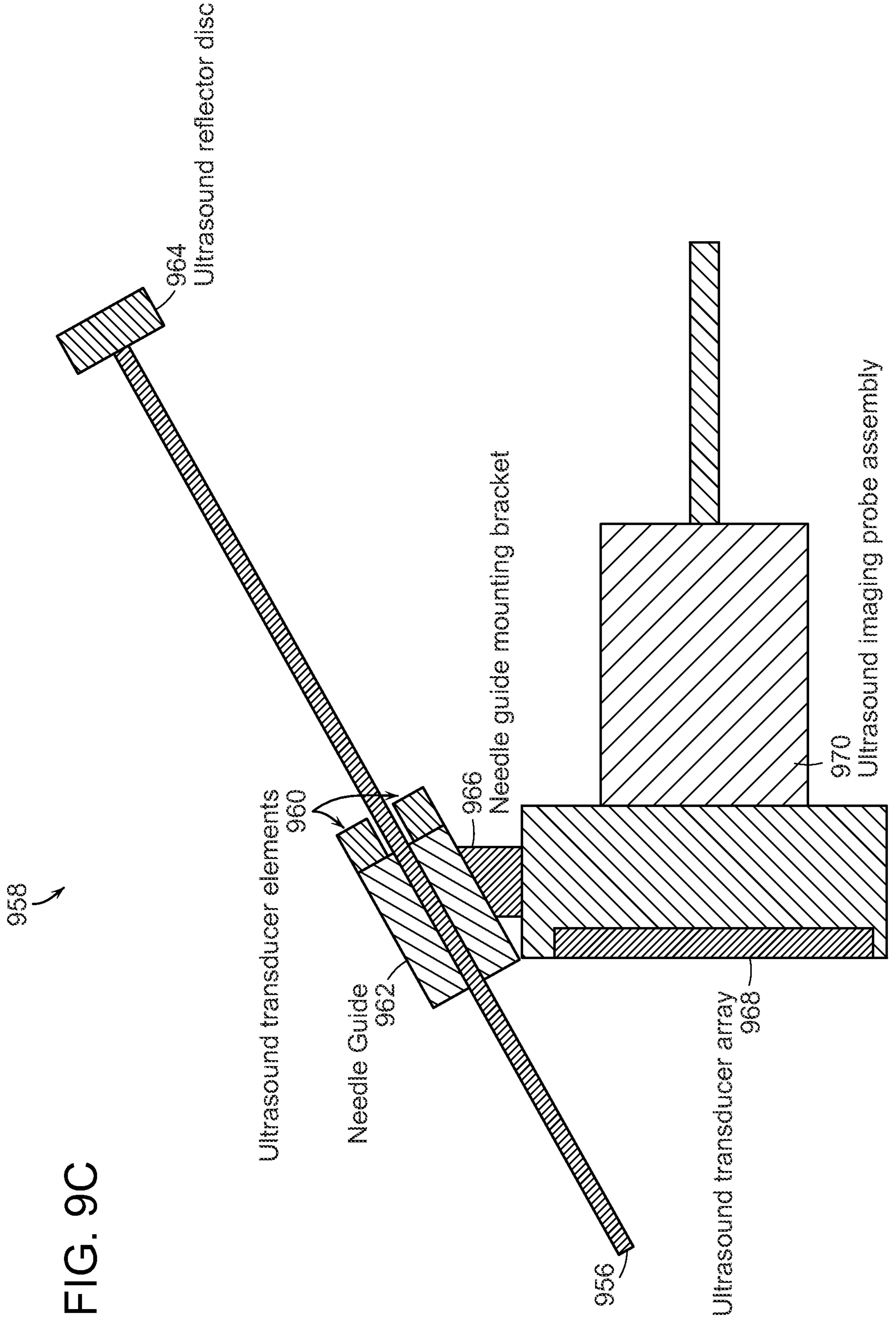
FIG. 9C shows a perspective view of a needle sensing positioning system with exemplary embodiments.

FIG. 9C is a perspective view of an exemplary needle sensing positioning system using ultrasound transducers without the requirement of any active electronics in the sensor assembly. The sensor transducer may include a passive ultrasound transducer element. The elements may be used in a similar way as a typical transducer probe, utilizing the ultrasound engine electronics. The system 958 includes the addition of ultrasound transducer elements 960, added to a needle guide 962, that is represented in FIG. 9C but that may be any suitable form factor. The ultrasound transducer element 960, and needle guide 962, may be mounted using a needle guide mounting bracket 966, to an ultrasound transducer probe acoustic handle or an ultrasound imagining probe assembly 970. The needle with a disc mounted on the exposed end, the ultrasound reflector disc 964, is reflective to ultrasonic waves.

The ultrasound transducer element 960, on the needle guide 962, may be connected to the ultrasound engine. The connection may be made through a separate cable to a dedicated probe connector on the engine, similar to a sharing the pencil CW probe connector. In an alternate embodiment, a small short cable may be plugged into the larger image transducer probe handle or a split cable connecting to the same probe connector at the engine. In another alternate embodiment the connection may be made via an electrical connector between the image probe handle and the needle guide without a cable in between. In an alternate embodiment the ultrasound transducer elements on the needle guide may be connected to the ultrasound engine by enclosing the needle guide and transducer elements in the same mechanical enclosure of the imagining probe handle.

Figure 9D:
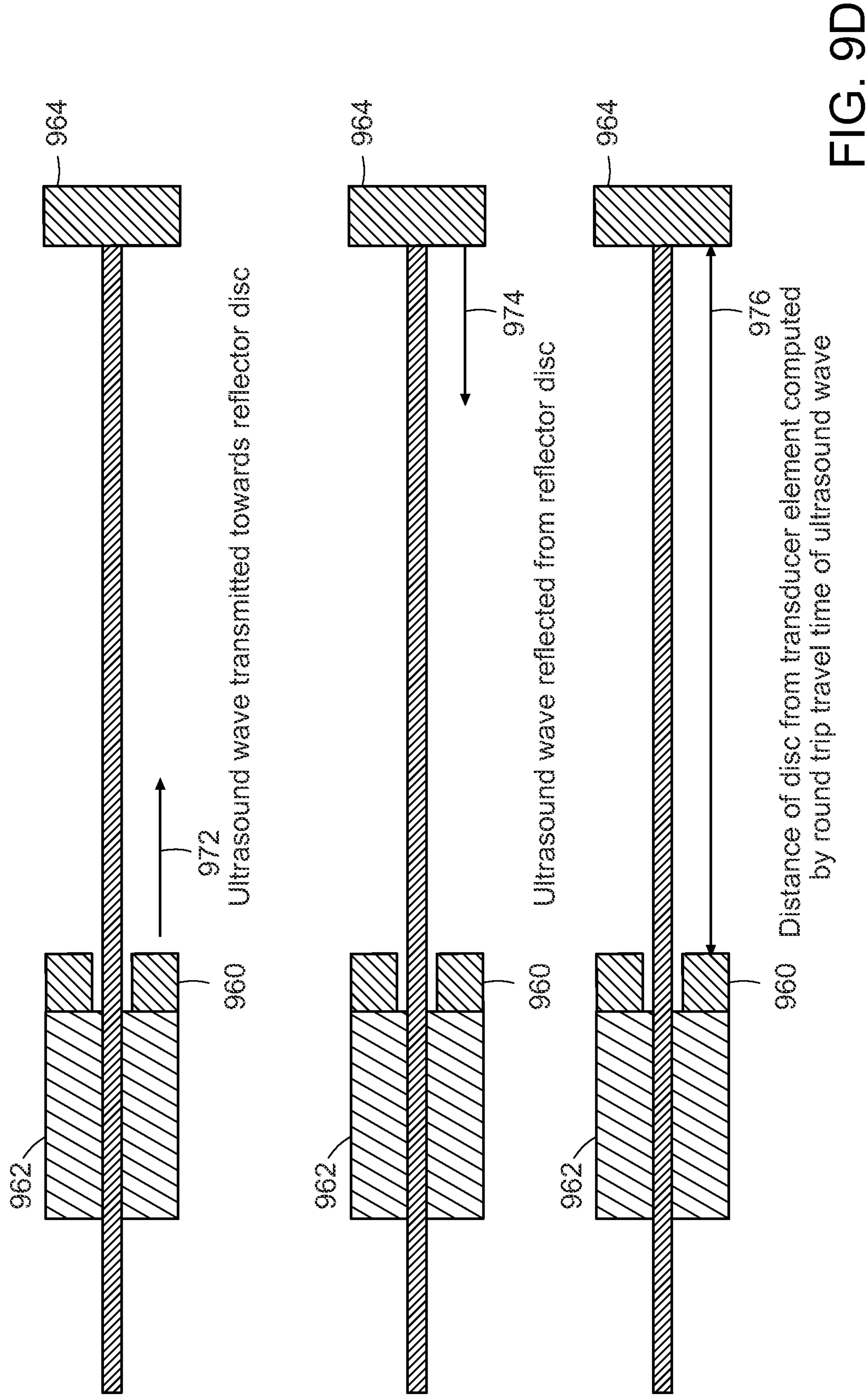
FIG. 9D shows a perspective view of a needle guide with exemplary embodiments.

FIG. 9D is a perspective view of a needle guide 962, positioned with transducer elements 960 and the ultrasound reflector disc 964. The position of the reflector disc 964 is located by transmitting ultrasonic wave 972, from the transducer element 960 on the needle guide 962. The ultrasound wave 972 travels through the air towards reflector disc 964 and is reflected by the reflector disc 964. The reflected ultrasound wave 974, reaches the transducer element 960 on the needle guide 962. The distance 976, between the reflector disc 964, and the transducer element 960 is calculated from the time elapsed and the speed of sound in the air.

Figure 9E:
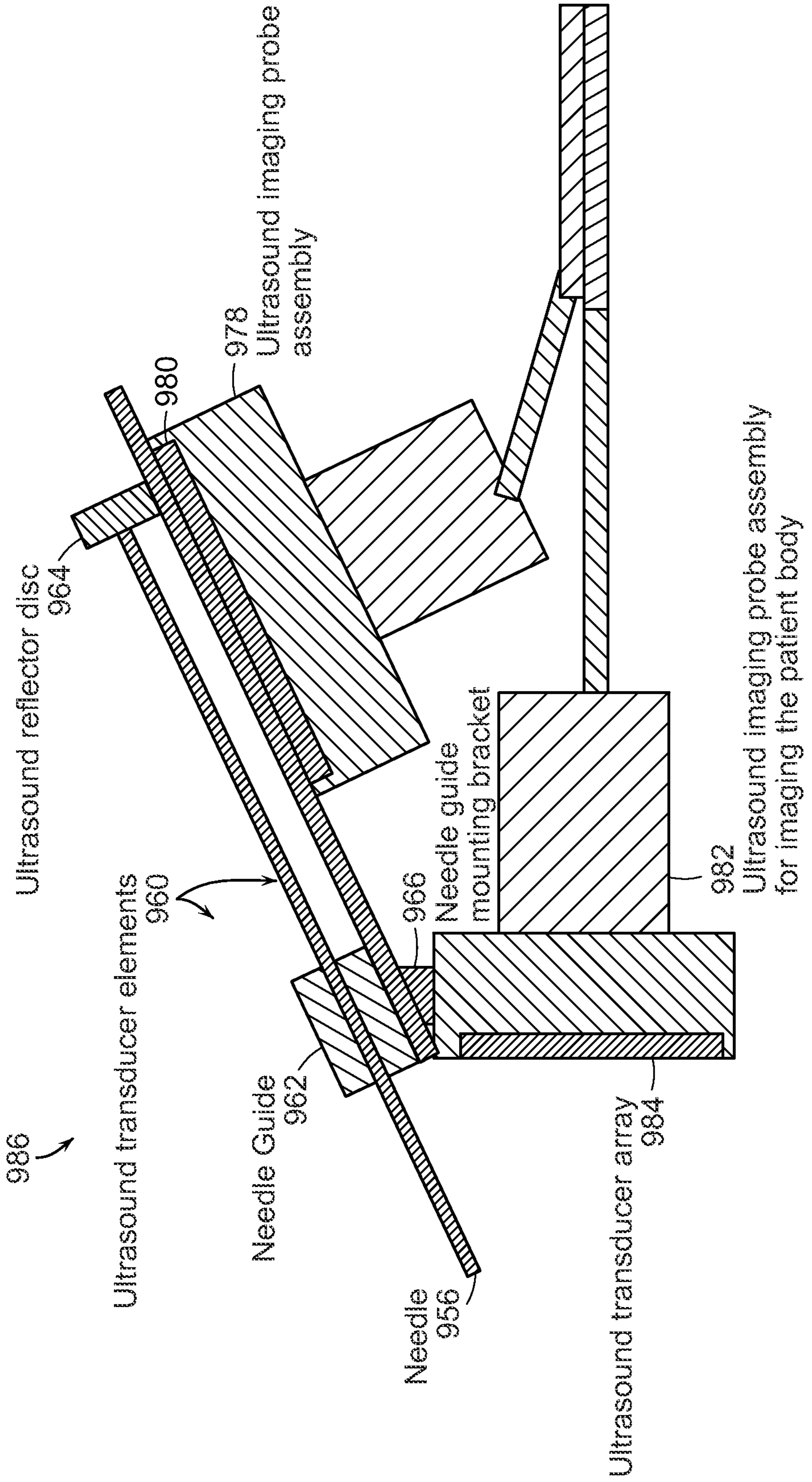
FIG. 9E shows a perspective view of a needle sensing positioning system with exemplary embodiments.

FIG. 9E is a perspective view of an alternate embodiment of the exemplary needle sensing positioning system using ultrasound transducers without the requirement of any active electronics in the sensor assembly. The sensor transducer may include a passive ultrasound transducer element. The elements may be used in a similar way as a typical transducer probe, utilizing the ultrasound engine electronics.

The system 986 includes needle guide 962 that may be mounted to a needle guide mounting bracket 966 that may be coupled to an ultrasound imaging probe assembly for imaging the patient's body 982, or alterative suitable form factors. The ultrasound reflector disc 964 may be mounted at the exposed end of the needle 956. In this embodiment a linear ultrasound acoustic array 978, is mounted parallel to the direction of movement of the needle 956. The linear ultrasound acoustic array 978 includes an ultrasound transducer array 980 positioned parallel to the needle 956. In this embodiment an ultrasound imagining probe assembly 982, is positioned for imagining the patient body. The ultrasound imaging probe assembly for imaging the patient body 982 is configured with an ultrasound transducer array 984.

In this embodiment, the position of the ultrasound reflector disc 964 can be detected by using the ultrasound transducer array 980 coupled to an ultrasound imaging probe assembly for imaging 978. The position of the reflector disc 964 is located by transmitting ultrasonic wave 972, from the transducer element 980 on the ultrasound imaging probe assembly for imaging 978. The ultrasound wave 972 travels through the air towards reflector disc 964 and is reflected by the reflector disc 964. The reflected ultrasound wave 974, reaches the transducer element 980 on the ultrasound imaging probe assembly for imaging 978. The distance 976, between the reflector disc 964, and the transducer element 980 is calculated from the time elapsed and the speed of sound in the air. In an alternate embodiment an alternate algorithm may be used to sequentially scan the polarity of elements in the transducer array and analyze the reflections produced per transducer array element. In an alternate embodiment a plurality of scans may occur prior to forming an ultrasound image.

Figure 9F:
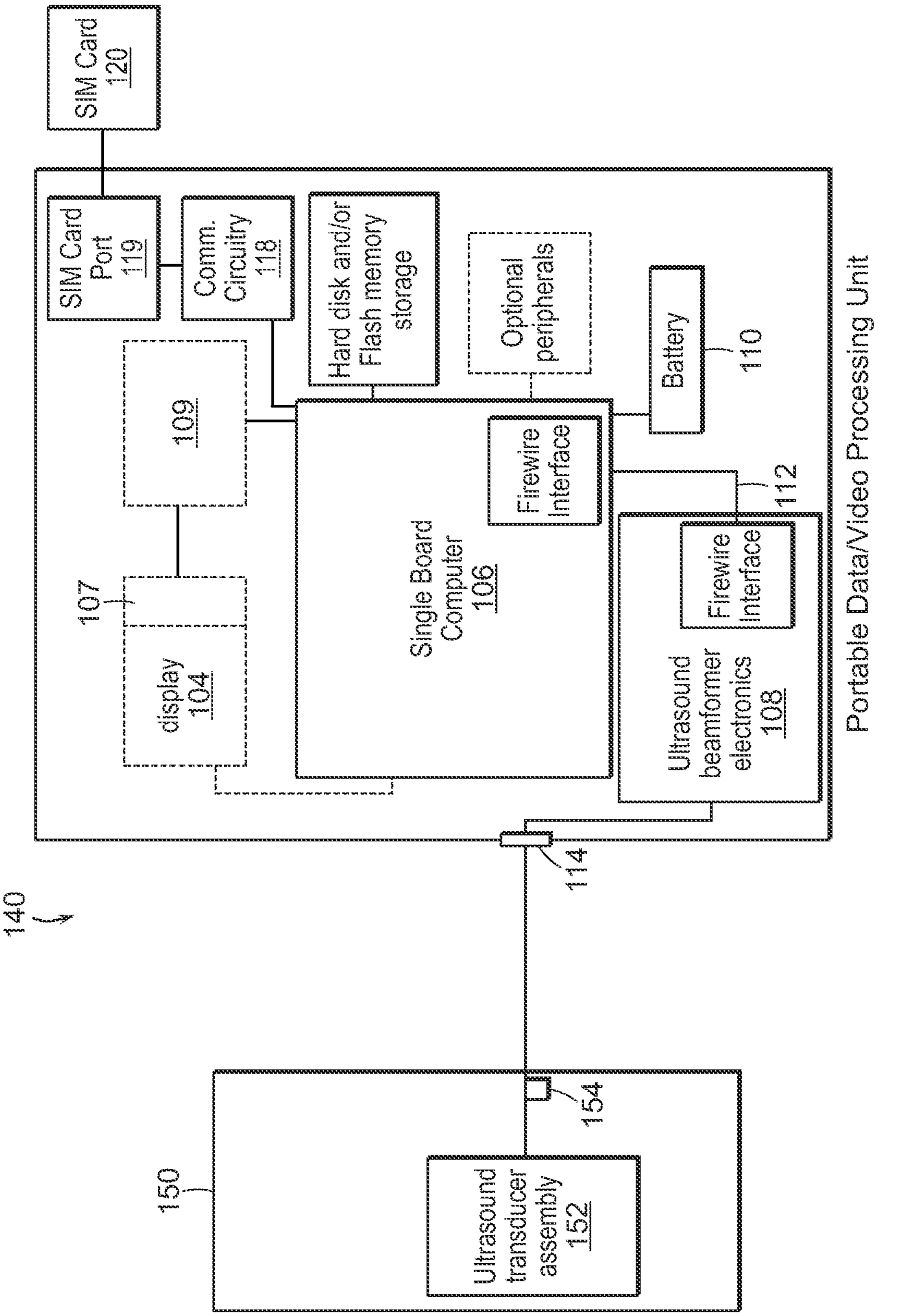
FIG. 9F illustrates an exemplary system configured to receive a subscriber identification module (SIM) card for wireless communication.

FIG. 9F illustrates a system 140 similar to that shown in FIG. 9A and configured to receive a subscriber identification module (SIM) card for wireless communication. In this particular embodiment, communication circuitry 118 is connected to the computing circuitry 106, and a SIM card port 119 is configured to receive a SIM card 120 and connect the SIM card 120 to the communication circuitry 118 via a number of conductive contacts. In some embodiments, the ultrasound device may be configured with a SIM card port 119 capable of receiving a standard SIM card, mini SIM card, micro SIM card, nano SIM card, embedded SIM card, or other similar wireless identification/authorization card or circuit. The system incorporates a SIM card interface circuit 118 such as those available from NXP Semiconductors N.V. of Eindhoven, The Netherlands, which can include EMI filtering and ESD protection features. The identification card incorporates an identification circuit, typically an integrated circuit embedded in a plastic card or substrate that includes a memory device that stores the international mobile subscriber identity (IMSI) and a key that identifies and authenticates subscribers to a mobile wireless network such as a 3G or 4G communications network.

Figure 10A:
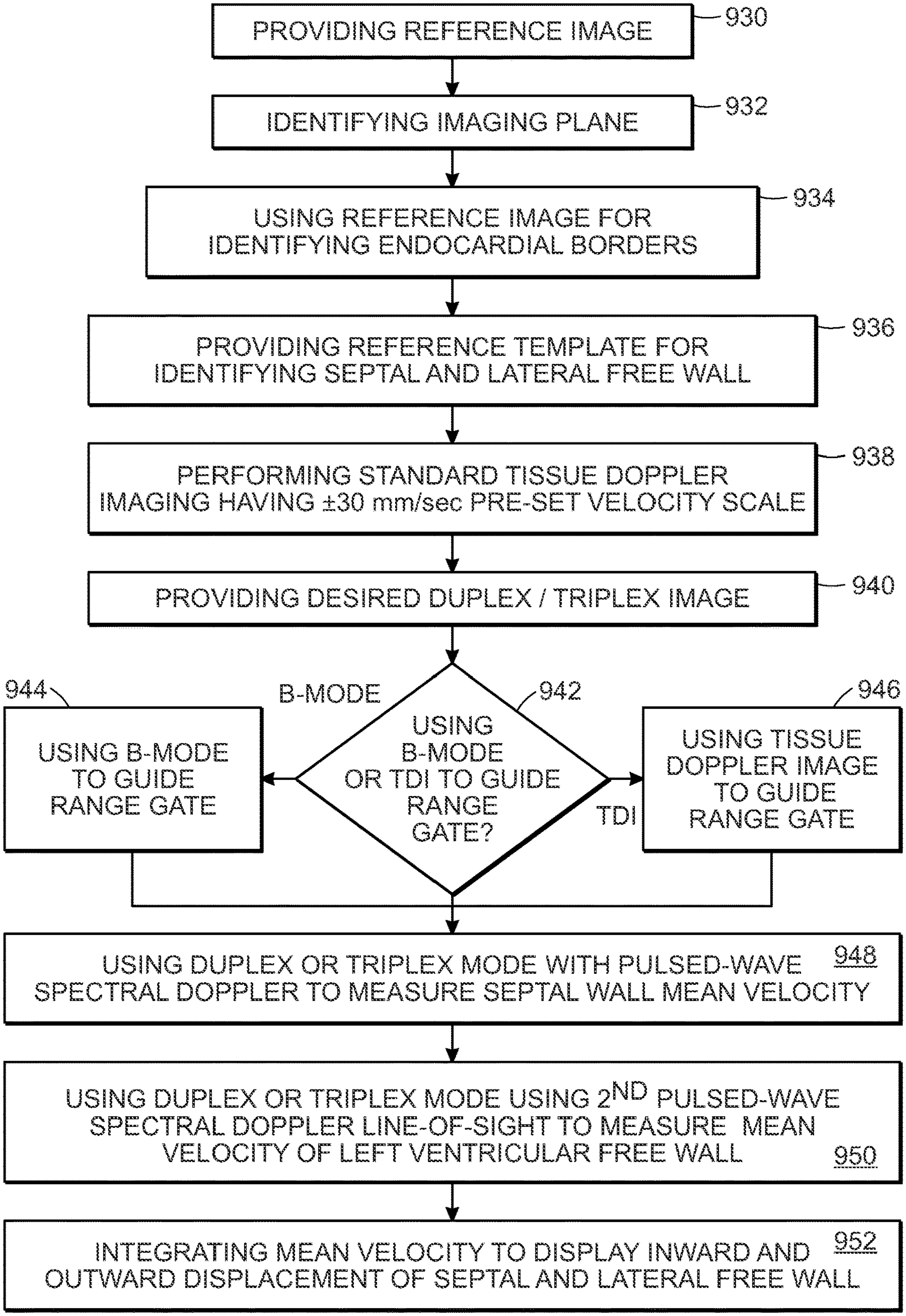
FIG. 10A shows an exemplary method of measuring heart wall motion.

FIG. 10A illustrates an exemplary method for monitoring the synchrony of a heart in accordance with exemplary embodiments. In the method, a reference template is loaded into memory and used to guide a user in identifying an imaging plane (per step 930). Next a user identifies a desired imaging plane (per step 932). Typically an apical 4-chamber view of the heart is used; however, other views may be used without departing from the spirit of the invention.

At times, identification of endocardial borders may be difficult, and when such difficulties are encountered tissue Doppler imaging of the same view may be employed (per step 934). A reference template for identifying the septal and lateral free wall is provided (per step 936). Next, standard tissue Doppler imaging (TDI) with pre-set velocity scales of, say, ±30 cm/sec may be used (per step 938).

Then, a reference of the desired triplex image may be provided (per step 940). Either B-mode or TDI may be used to guide the range gate (per step 942). B-mode can be used for guiding the range gate (per step 944) or TDI for guiding the range gate (per step 946). Using TDI or B-mode for guiding the range gate also allows the use of a direction correction angle for allowing the Spectral Doppler to display the radial mean velocity of the septal wall. A first pulsed-wave spectral Doppler is then used to measure the septal wall mean velocity using duplex or triplex mode (per step 948). The software used to process the data and calculate dysychrony can utilize a location (e.g. a center point) to automatically set an angle between dated locations on a heart wall to assist in simplifying the setting of parameters.

A second range-gate position is also guided using a duplex image or a TDI (per step 950), and a directional correction angle may be used if desired. After step 950, the mean velocity of the septal wall and lateral free wall are being tracked by the system. Time integration of the Spectral Doppler mean velocities 952 at regions of interest (e.g., the septum wall and the left ventricular free wall) then provides the displacement of the septal and left free wall, respectively.

The above method steps may be utilized in conjunction with a high pass filtering means, analog or digital, known in the relevant arts for removing any baseline disturbance present in collected signals. In addition, the disclosed method employs multiple simultaneous PW Spectral Doppler lines for tracking movement of the interventricular septum and the left ventricular fee wall. In additional, a multiple gate structure may be employed along each spectral line, thus allowing quantitative measurement of regional wall motion. Averaging over multiple gates may allow measurement of global wall movement.

Figure 10B:
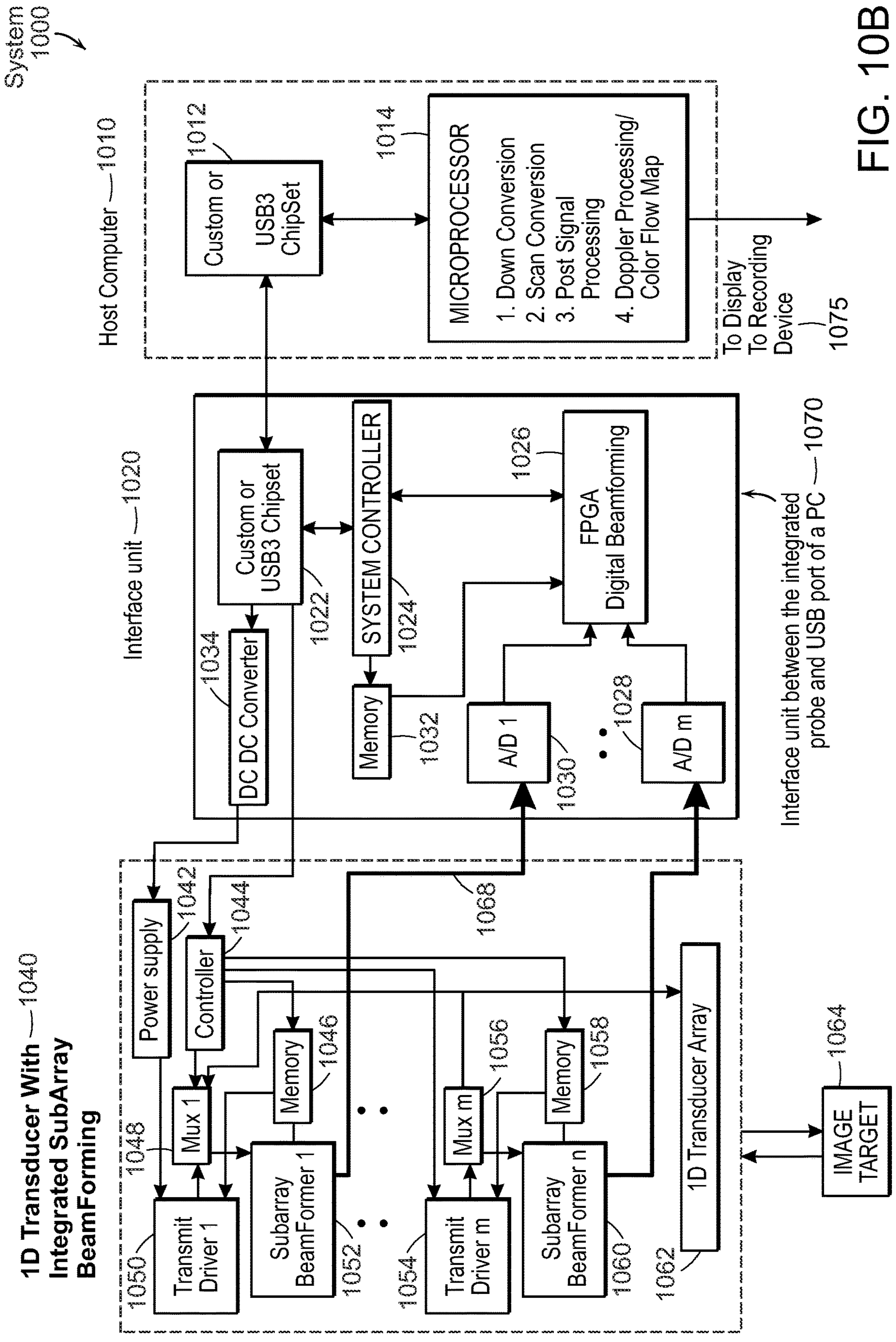
FIG. 10B shows a schematic block diagram for an integrated ultrasound probe with exemplary embodiments.

FIG. 10B is a detailed schematic block diagram for an exemplary embodiment of the integrated ultrasound probe 1040 can be connected to any PC 1010 through an Interface unit 1020. The ultra sound probe 1040 is configured to transmit ultrasound waves to and reduce reflected ultrasound waves from on ore more image targets 1064. The transducer 1040 can be coupled to the interface unit 1020 using one or more cables 1066, 1068. The interface unit 1020 can be positioned between the integrated ultrasound probe 1040 and the host computer 1010. The two stage beam forming system 1040 and 1020 can be connected to any PC through a USB connection 1022, 1012.

The ultrasound probe 1040, can include sub-arrays/apertures 1052 consisting of neighboring elements with an aperture smaller than that of the whole array. Returned echoes are received by the 1D transducer array 1062 and transmitted to the controller 1044. The controller initiates formation of a coarse beam by transmitting the signals to memory 1058, 1046. The memory 1058, 1046 transmits a signal to a transmit Driver 1 1050, and Transmit Driver m 1054. Transmit Driver 1 1050 and Transmit Driver m 1054 then send the signal to mux1 1048 and mux m 1056, respectively. The signal is transmitted to sub-array beamformer 1 1052 and sub-array beamformer n 1060.

The outputs of each coarse beam forming operation can include further processing through a second stage beam forming in the interface unit 1020 to convert the beam forming output to digital representation. The coarse beam forming operations can be coherently summed to form a fine beam output for the array. The signals can be transmitted from the ultrasound probe 1040 sub-array beam former 1

1052 and sub-array beam former n 1060 to the A/D convertors 1030 and 1028 within the interface unit 1020. Within the interface unit 1020 there are A/D converters 1028, 1030 for converting the first stage beam forming output to digital representation. The digital conversion can be received from the A/D convertors 1030, 1028 by a customer ASIC such as a FPGA 1026 to complete the second stage beam forming. The FPGA Digital beam forming 1026 can transmit information to the system controller 1024. The system controller can transmit information to a memory 1032 which may send a signal back to the FPGA Digital Beam forming 1026. Alternatively, the system controller 1024 may transmit information to the custom USB3 Chipset 1022. The USB3 Chipset 1022 may then transmit information to a DC-DC convertor 1034. In turn, the DC-DC convertor 1034 may transmit power from the interface unit 1020 to the ultrasound probe 1040. Within the ultrasound probe 1040 a power supply 1042 may receive the power signal and interface with the transmit driver 1 1050 to provide the power to the front end integration probe.

The Interface unit 1020 custom or USB3 Chipset 1022 may be used to provide a communication link between the interface unit 10220 and the host computer 1010. The custom or USB3 Chipset 1022 transmits a signal to the host computer's 1010 custom or USB3 Chipset 1012. The custom or the USB3 Chipset 1012 then interfaces with the microprocessor 1014. The microprocessor 1014 then may display information or send information to a device 1075.

In an alternate embodiment, a narrow band beamformer can be used. For example, an individual analog phase shifter is applied to each of the received echoes. The phase shifted outputs within each sub-array are then summed to form a coarse beam. The A/D converters can be used to digitize each of the coarse beams; a digital beam former is then used to form the fine beam.

In another embodiment, forming a 64 element linear array may use eight adjacent elements to form a coarse beam output. Such arrangement may utilize eight output analog cables connecting the outputs of the integrated probe to the interface units. The coarse beams may be sent through the cable to the corresponding A/D convertors located in the interface unit. The digital delay is used to form a fine beam output. Eight A/D convertors may be required to form the digital representation.

In another embodiment, forming a 128 element array may use sixteen sub-array beam forming circuits. Each circuit may form a coarse beam from an adjacent eight element array provided in the first stage output to the interface unit. Such arrangement may utilize sixteen output analog cables connecting the outputs of the integrated probe to the interface units to digitize the output. A PC microprocessor or a DSP may be used to perform the down conversion, basebanding, scan conversion and post image processing functions. The microprocessor or DSP can also be used to perform all the Doppler processing functions.

Figure 10C:
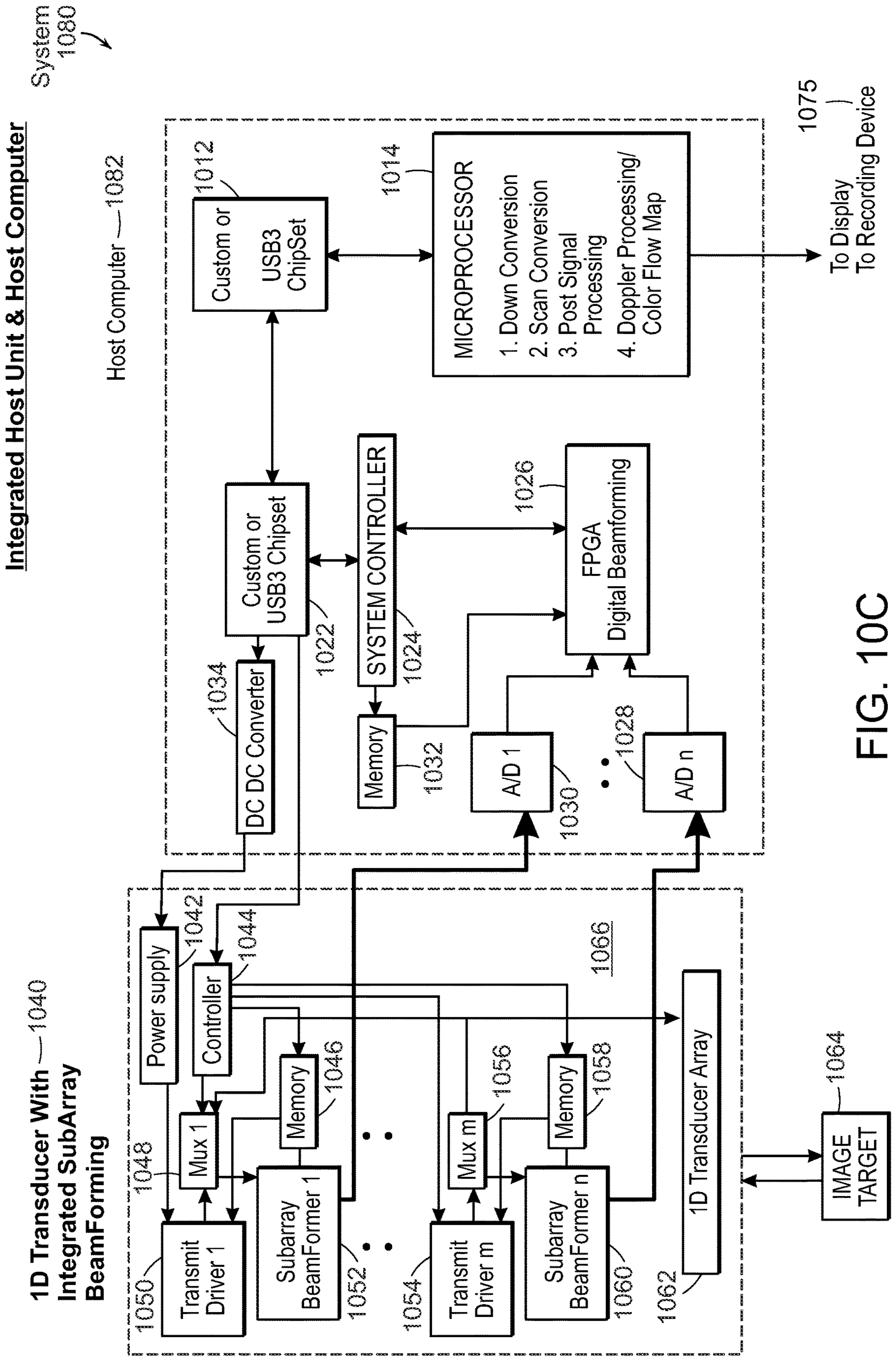
FIG. 10C shows an alternative schematic block diagram for an integrated ultrasound probe with exemplary embodiments.

FIG. 10C is a detailed schematic block diagram for an exemplary embodiment of the integrated ultrasound probe 1040 with the first sub array beamforming circuit, and the second stage beamforming circuits are integrated inside the host computer 1082. The back end computer with the second stage beamforming circuit may be a PDA, tablet or mobile device housing. The ultra sound probe 1040 is configured to transmit ultrasound waves to and reduce reflected ultrasound waves from on ore more image targets 1064. The transducer 1040 is coupled to the host computer 1082 using one or more cables 1066, 1068. Note that A/D circuit elements can also be placed in the transducer probe housing.

The ultrasound probe 1040 includes subarray/apertures 1052 consisting of neighboring elements with an aperture smaller than that of the whole array. Returned echoes are received by the 1D transducer array 1062 and transmitted to the controller 1044. The controller initiates formation of a coarse beam by transmitting the signals to memory 1058, 1046. The memory 1058, 1046 transmits a signal to a transmit Driver 1 1050, and Transmit Driver m 1054. Transmit Driver 1 1050 and Transmit Driver m 1054 then send the signal to mux1 1048 and mux m 1056, respectively. The signal is transmitted to subarray beamformer 1 1052 and subarray beamformer n 1060.

The outputs of each coarse beam forming operation then go through a second stage beam forming in the interface unit 1020 to convert the beam forming output to digital representation. The coarse beamforming operations are coherently summed to form a fine beam output for the array. The signals are transmitted from the ultrasound probe 1040 subarray beamformer 1 1052 and subarray beamformer n 1060 to the A/D convertors 1030 and 1028 within the host computer 1082. Within the host computer 1082 there are A/D converters 1028, 1030 for converting the first stage beamforming output to digital representation. The digital conversion is received from the A/D convertors 1030, 1028 by a customer ASIC such as a FPGA 1026 to complete the second stage beamforming. The FPGA Digital beamforming 1026 transmits information to the system controller 1024. The system controller transmits information to a memory 1032 which may send a signal back to the FPGA Digital Beam forming 1026. Alternatively, the system controller 1024 may transmit information to the custom USB3 Chip set 1022. The USB3 Chipset 1022 may then transmit information to a DC-DC convertor 1034. In turn, the DC-DC convertor 1034 may transmit power from the interface unit 1020 to the ultrasound probe 1040. Within the ultrasound probe 1040 a power supply 1042 may receive the power signal and interface with the transmit driver 1 1050 to provide the power to the front end integration probe. The power supply can include a battery to enable wireless operation of the transducer assembly. A wireless transceiver can be integrated into controller circuit or a separate communications circuit to enable wireless transfer of image data and control signals.

The host computer's 1082 custom or USB3 Chipset 1022 may be used to provide a communication link between the custom or USB3 Chipset 1012 to transmits a signal to the microprocessor 1014. The microprocessor 1014 then may display information or send information to a device 1075.

Figure 2A:
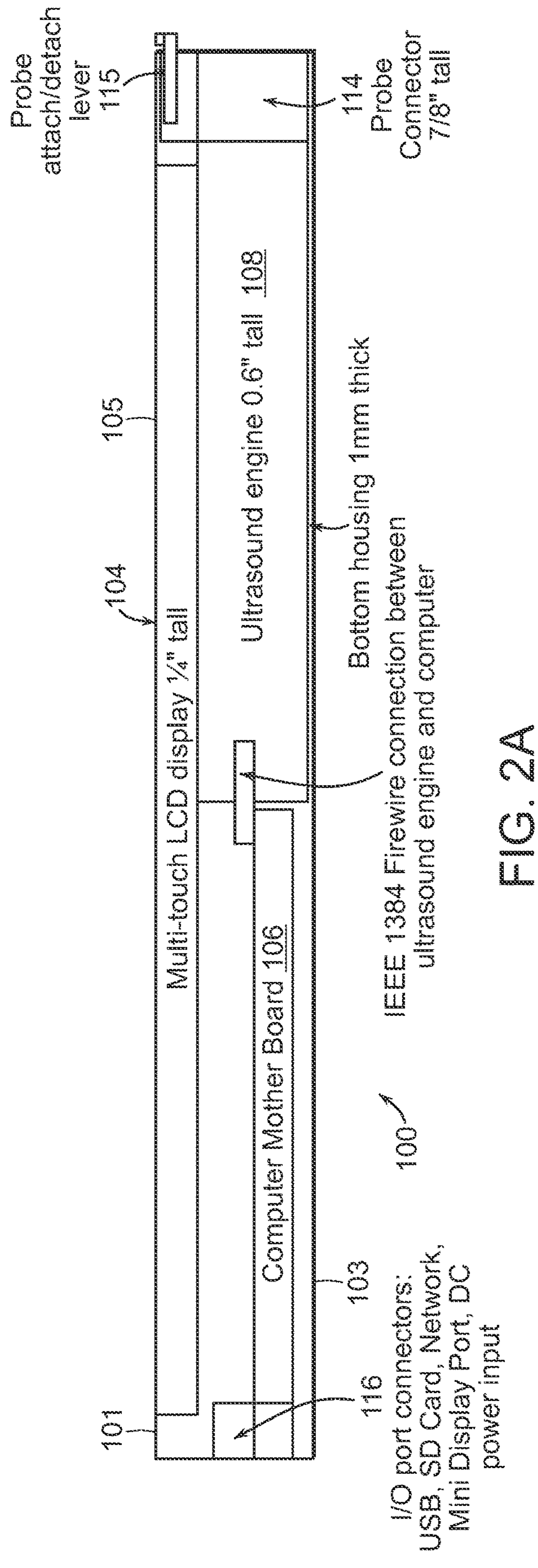
FIGS. 2A and 2B are side views of the medical ultrasound imaging system in accordance with preferred embodiments of the invention.
Figure 2B:
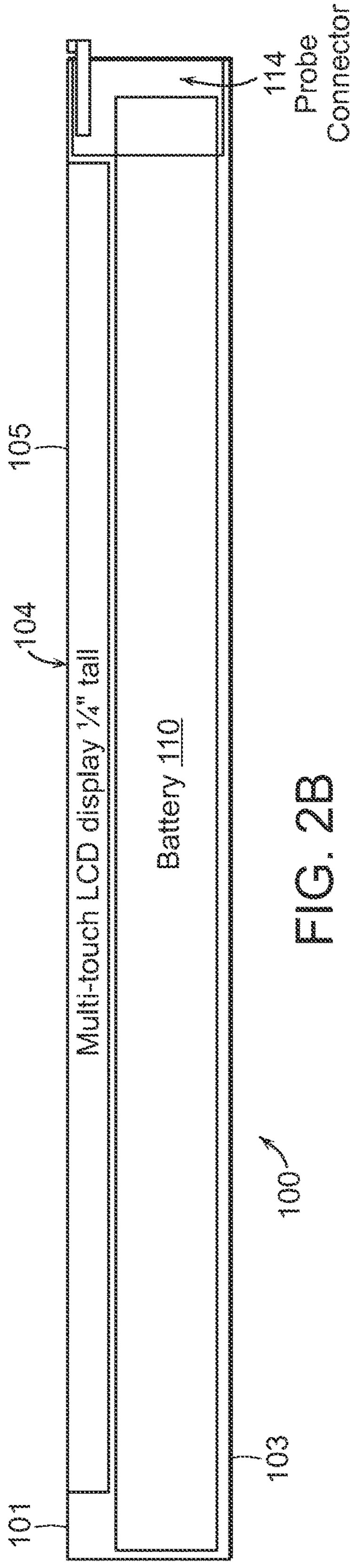
Figure 11:
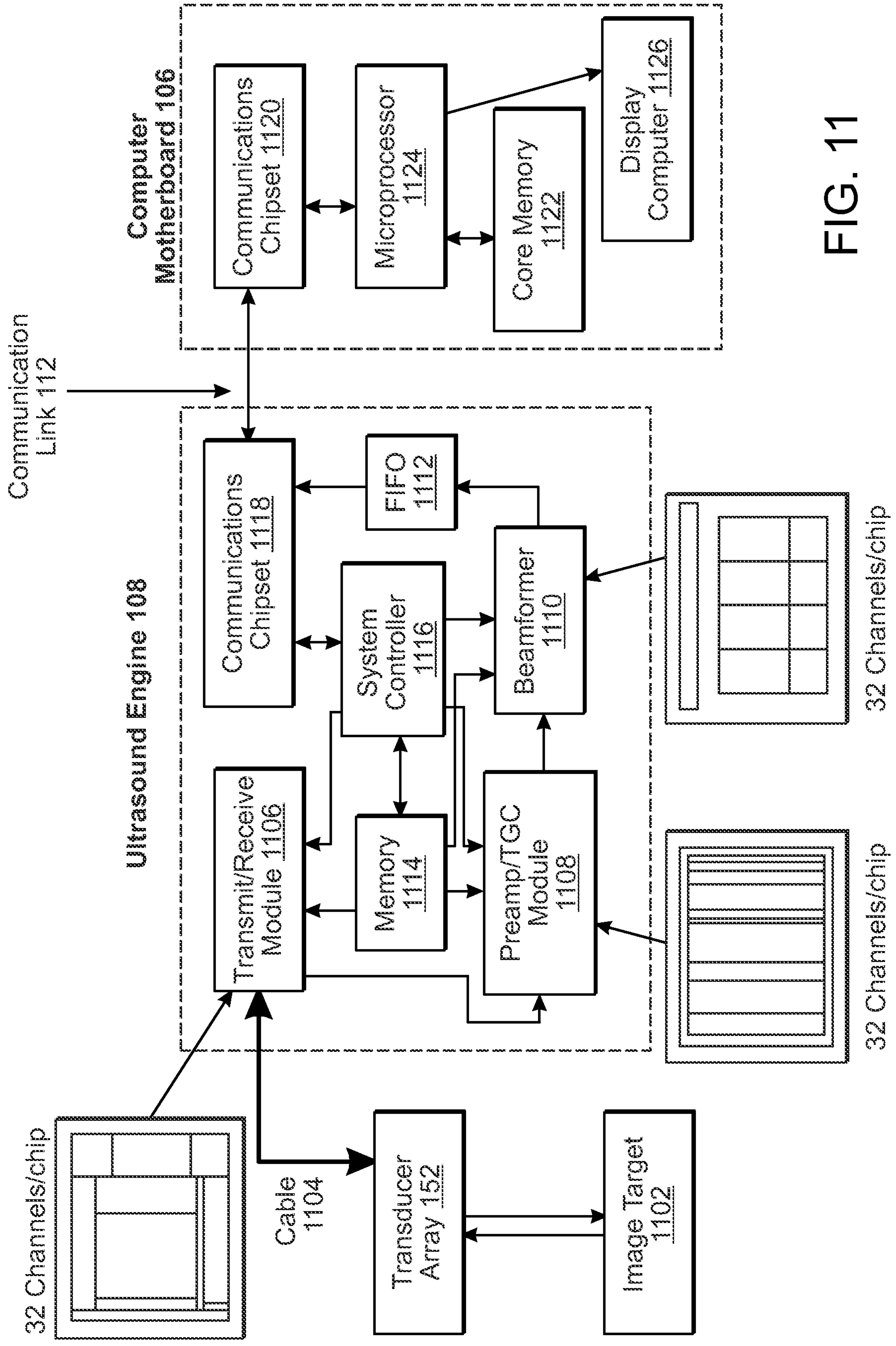
FIG. 11 is a detailed schematic block diagram of an exemplary embodiment of an ultrasound engine (i.e., the front-end ultrasound specific circuitry) and an exemplary embodiment of a computer motherboard (i.e., the host computer) of the exemplary ultrasound device.

FIG. 11 is a detailed schematic block diagram of an exemplary embodiment of the ultrasound engine 108 (i.e., the front-end ultrasound specific circuitry) and an exemplary embodiment of the computer motherboard 106 (i.e., the host computer) of the ultrasound device illustrated in FIGS. 1 and 2A. The components of the ultrasound engine 108 and/or the computer motherboard 106 may be implemented in application-specific integrated circuits (ASICs). Exemplary ASICs have a high channel count and can pack 32 or more channels per chip in some exemplary embodiments. One of ordinary skill in the art will recognize that the ultrasound engine 108 and the computer motherboard 106 may include more or fewer modules than those shown. For example, the ultrasound engine 108 and the computer motherboard 106 may include the modules shown in FIG. 17.

A transducer array 152 is configured to transmit ultrasound waves to and receive reflected ultrasound waves from one or more image targets 1102. The transducer array 152 is coupled to the ultrasound engine 108 using one or more cables 1104.

The ultrasound engine 108 includes a high-voltage transmit/receive (TR) module 1106 for applying drive signals to the transducer array 152 and for receiving return echo signals from the transducer array 152. The ultrasound engine 108 includes a pre-amp/time gain compensation (TGC) module 1108 for amplifying the return echo signals and applying suitable TGC functions to the signals. The ultrasound engine 108 includes a sampled-data beamformer 1110 that the delay coefficients used in each channel after the return echo signals have been amplified and processed by the pre-amp/TGC module 1108.

In some exemplary embodiments, the high-voltage TR module 1106, the pre-amp/TGC module 1108, and the sample-interpolate receive beamformer 1110 may each be a silicon chip having 8 to 64 channels per chip, but exemplary embodiments are not limited to this range. In certain embodiments, the high-voltage TR module 1106, the pre-amp/TGC module 1108, and the sample-interpolate receive beamformer 1110 may each be a silicon chip having 8, 16, 32, 64 channels, and the like. As illustrated in FIG. 11, an exemplary TR module 1106, an exemplary pre-amp/TGC module 1108 and an exemplary beamformer 1110 may each take the form of a silicon chip including 32 channels.

The ultrasound engine 108 includes a first-in first-out (FIFO) buffer module 1112 which is used for buffering the processed data output by the beamformer 1110. The ultrasound engine 108 also includes a memory 1114 for storing program instructions and data, and a system controller 1116 for controlling the operations of the ultrasound engine modules.

The ultrasound engine 108 interfaces with the computer motherboard 106 over a communications link 112 which can follow a standard high-speed communications protocol, such as the Fire Wire (IEEE 1394 Standards Serial Interface) or fast (e.g., 200-400 Mbits/second or faster) Universal Serial Bus (USB 2.0 USB 3.0), protocol. The standard communication link to the computer motherboard operates at least at 400 Mbits/second or higher, preferably at 800 Mbits/second or higher. Alternatively, the link 112 can be a wireless connection such as an infrared (IR) link. The ultrasound engine 108 includes a communications chipset 1118 (e.g., a Fire Wire chipset) to establish and maintain the communications link 112.

Similarly, the computer motherboard 106 also includes a communications chipset 1120 (e.g., a Fire Wire chipset) to establish and maintain the communications link 112. The computer motherboard 106 includes a core computer-readable memory 1122 for storing data and/or computer-executable instructions for performing ultrasound imaging operations. The memory 1122 forms the main memory for the computer and, in an exemplary embodiment, may store about 4 GB of DDR3 memory. The computer motherboard 106 also includes a microprocessor 1124 for executing computer-executable instructions stored on the core computer-readable memory 1122 for performing ultrasound imaging processing operations. An exemplary microprocessor 1124 may be an off-the-shelf commercial computer processor, such as an Intel Core-i5 processor. Another exemplary microprocessor 1124 may be a digital signal processor (DSP) based processor, such as one or more DaVinci™ processors from Texas Instruments. The computer motherboard 106 also includes a display controller 1126 for controlling a display device that may be used to display ultrasound data, scans and maps.

Exemplary operations performed by the microprocessor 1124 include, but are not limited to, down conversion (for generating I, Q samples from received ultrasound data), scan conversion (for converting ultrasound data into a display format of a display device), Doppler processing (for determining and/or imaging movement and/or flow information from the ultrasound data), Color Flow processing (for generating, using autocorrelation in one embodiment, a color-coded map of Doppler shifts superimposed on a B-mode ultrasound image), Power Doppler processing (for determining power Doppler data and/or generating a power Doppler map), Spectral Doppler processing (for determining spectral Doppler data and/or generating a spectral Doppler map), and post signal processing. These operations are described in further detail in WO 03/079038 A2, filed Mar. 11, 2003, titled "Ultrasound Probe with Integrated Electronics," the entire contents of which are expressly incorporated herein by reference.

To achieve a smaller and lighter portable ultrasound devices, the ultrasound engine 108 includes reduction in overall packaging size and footprint of a circuit board providing the ultrasound engine 108. To this end, exemplary embodiments provide a small and light portable ultrasound device that minimizes overall packaging size and footprint while providing a high channel count. In some embodiments, a high channel count circuit board of an exemplary ultrasound engine may include one or more multi-chip modules in which each chip provides multiple channels, for example, 32 channels. The term "multi-chip module," as used herein, refers to an electronic package in which multiple integrated circuits (IC) are packaged into a unifying substrate, facilitating their use as a single component, i.e., as a larger IC. A multi-chip module may be used in an exemplary circuit board to enable two or more active IC components integrated on a High Density Interconnection (HDI) substrate to reduce the overall packaging size. In an exemplary embodiment, a multi-chip module may be assembled by vertically stacking a transmit/receive (TR) silicon chip, an amplifier silicon chip and a beamformer silicon chip of an ultrasound engine. A single circuit board of the ultrasound engine may include one or more of these multi-chip modules to provide a high channel count, while minimizing the overall packaging size and footprint of the circuit board.

Figure 12:
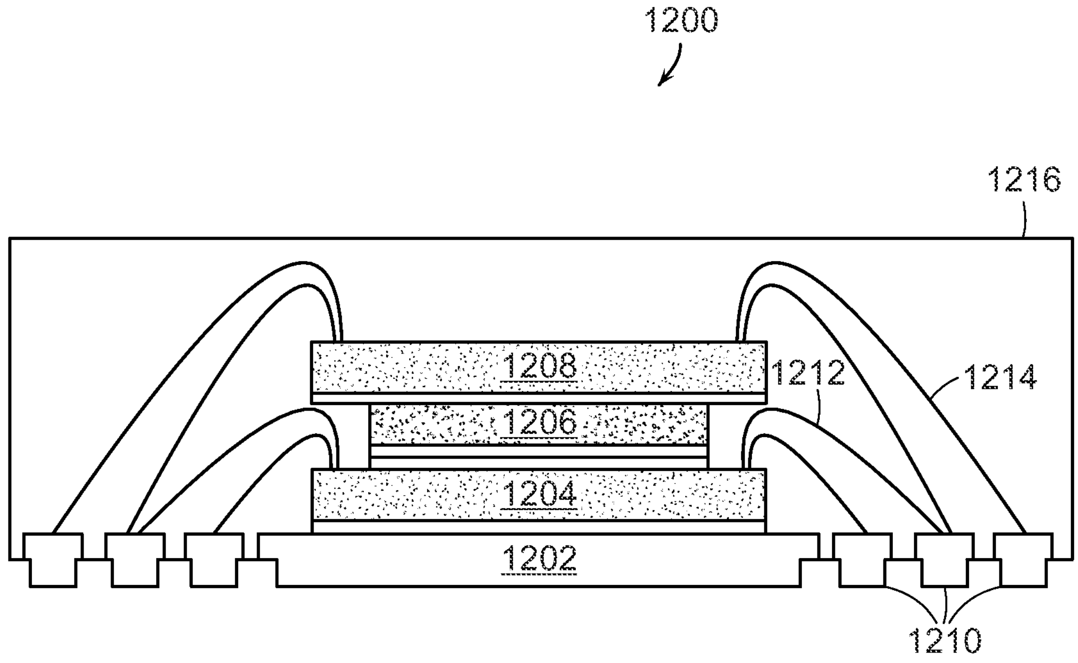
FIG. 12 depicts a schematic side view of a circuit board including a multi-chip module assembled in a vertically stacked configuration.

FIG. 12 depicts a schematic side view of a portion of a circuit board 1200 including a multi-chip module assembled in a vertically stacked configuration. Two or more layers of active electronic integrated circuit components are integrated vertically into a single circuit. The IC layers are oriented in spaced planes that extend substantially parallel to one another in a vertically stacked configuration. In FIG. 12, the circuit board includes an HDI substrate 1202 for supporting the multi-chip module. A first integrated circuit chip 1204 including, for example, a first beamformer device is coupled to the substrate 1202 using any suitable coupling mechanism, for example, epoxy application and curing. A first spacer layer 1206 is coupled to the surface of the first integrated circuit chip 1204 opposite to the substrate 1202 using, for example, epoxy application and curing. A second integrated circuit chip 1208 having, for example, a second beamformer device is coupled to the surface of the first spacer layer 1206 opposite to the first integrated circuit chip 1204 using, for example, epoxy application and curing. A metal frame 1210 is provided for mechanical and/or electrical connection among the integrated circuit chips. An exemplary metal frame 1210 may take the form of a leadframe. The first integrated circuit chip 1204 may be coupled to the metal frame 1210 using wiring 1212. The second integrated circuit chip 1208 may be coupled to the same metal frame 1210 using wiring 1214. A packaging 1216 is provided to encapsulate the multi-chip module assembly and to maintain the multiple integrated circuit chips in substantially parallel arrangement with respect to one another.

As illustrated in FIG. 12, the vertical three-dimensional stacking of the first integrated circuit chip 1204, the first spacer layer 1206 and the second integrated circuit chip 1208 provides high-density functionality on the circuit board while minimizing overall packaging size and footprint (as compared to an ultrasound engine circuit board that does not employ a vertically stacked multi-chip module). One of ordinary skill in the art will recognize that an exemplary multi-chip module is not limited to two stacked integrated circuit chips. Exemplary numbers of chips vertically integrated in a multi-chip module may include, but are not limited to, two, three, four, five, six, seven, eight, and the like.

In one embodiment of an ultrasound engine circuit board, a single multi-chip module as illustrated in FIG. 12 is provided. In other embodiments, a plurality of multi-chip modules also illustrated in FIG. 12. In an exemplary embodiment, a plurality of multi-chip modules (for example, two multi-chip modules) may be stacked vertically on top of one another on a circuit board of an ultrasound engine to further minimize the packaging size and footprint of the circuit board.

In addition to the need for reducing the footprint, there is also a need for decreasing the overall package height in multi-chip modules. Exemplary embodiments may employ wafer thinning to sub-hundreds micron to reduce the package height in multi-chip modules.

Any suitable technique can be used to assemble a multi-chip module on a substrate. Exemplary assembly techniques include, but are not limited to, laminated MCM (MCM-L) in which the substrate is a multi-layer laminated printed circuit board, deposited MCM (MCM-D) in which the multi-chip modules are deposited on the base substrate using thin film technology, and ceramic substrate MCM (MCM-C) in which several conductive layers are deposited on a ceramic substrate and embedded in glass layers that layers are co-fired at high temperatures (HTCC) or low temperatures (LTCC).

Figure 13:
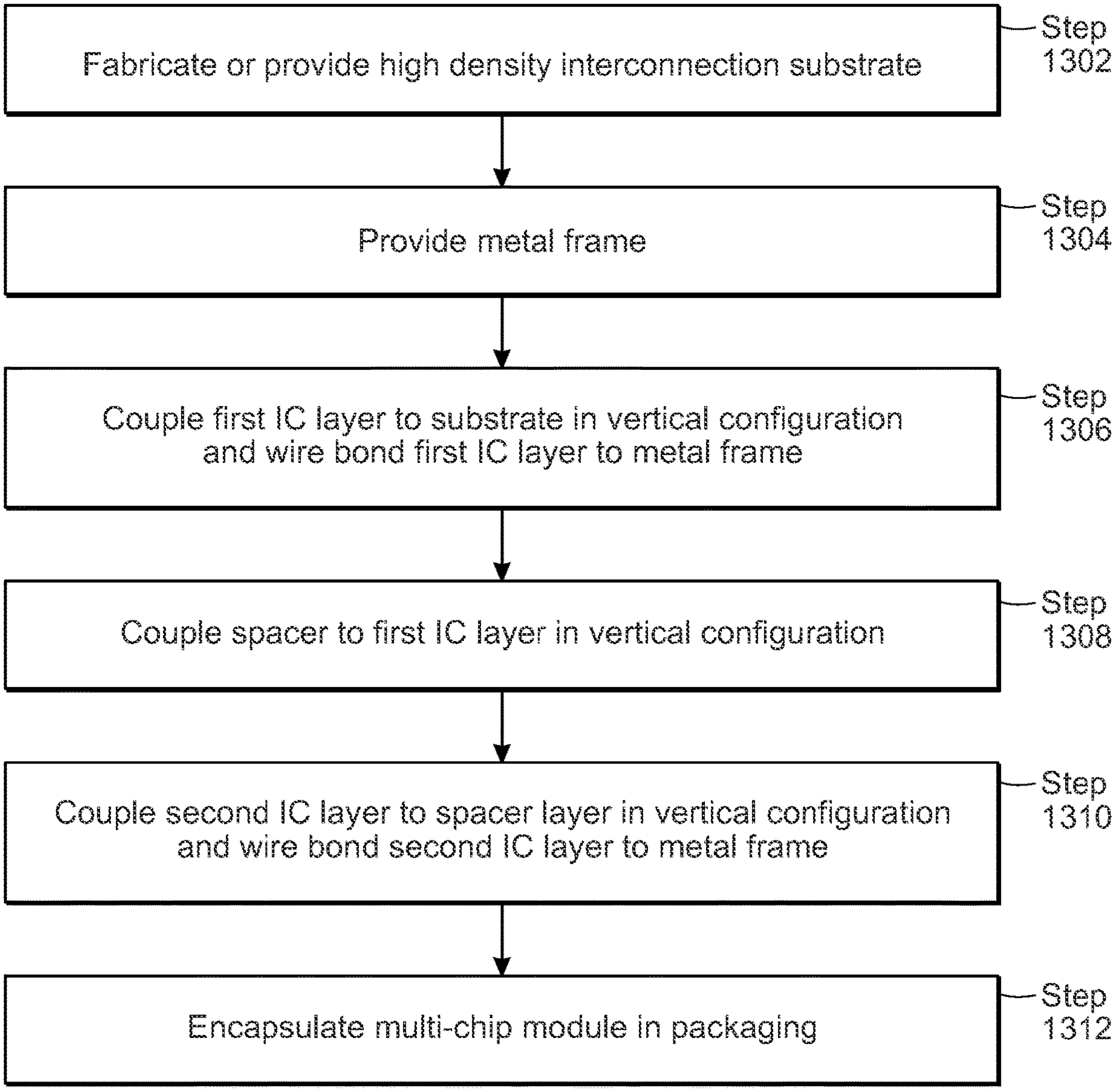
FIG. 13 is a flowchart of an exemplary method for fabricating a circuit board including a multi-chip module assembled in a vertically stacked configuration.

FIG. 13 is a flowchart of an exemplary method for fabricating a circuit board including a multi-chip module assembled in a vertically stacked configuration. In step 1302, a HDI substrate is fabricated or provided. In step 1304, a metal frame (e.g., leadframe) is provided. In step 1306, a first IC layer is coupled or bonded to the substrate using, for example, epoxy application and curing. The first IC layer is wire bonded to the metal frame. In step 1308, a spacer layer is coupled to the first IC layer using, for example, epoxy application and curing, so that the layers are stacked vertically and extend substantially parallel to each other. In step 1310, a second IC layer is coupled to the spacer layer using, for example, epoxy application and curing, so that all of the layers are stacked vertically and extend substantially parallel to one another. The second IC layer is wire bonded to the metal frame. In step 1312, a packaging is used to encapsulate the multi-chip module assembly.

Exemplary chip layers in a multi-chip module may be coupled to each other using any suitable technique. For example, in the embodiment illustrated in FIG. 12, spacer layers may be provided between chip layers to spacedly separate the chip layers. Passive silicon layers, die attach paste layers and/or die attach film layers may be used as the spacer layers. Exemplary spacer techniques that may be used in fabricating a multi-chip module is further described in Toh C H et al., "Die Attach Adhesives for 3D Same-Sized Dies Stacked Packages," the 58th Electronic Components and Technology Conference (ECTC2008), pp. 1538-43, Florida, US (27-30 May 2008), the entire contents of which are expressly incorporated herein by reference.

Important requirements for the die attach (DA) paste or film is excellent adhesion to the passivation materials of adjacent dies. Also, a uniform bond-link thickness (BLT) is required for a large die application. In addition, high cohesive strength at high temperatures and low moisture absorption are preferred for reliability.

Figure 14A:
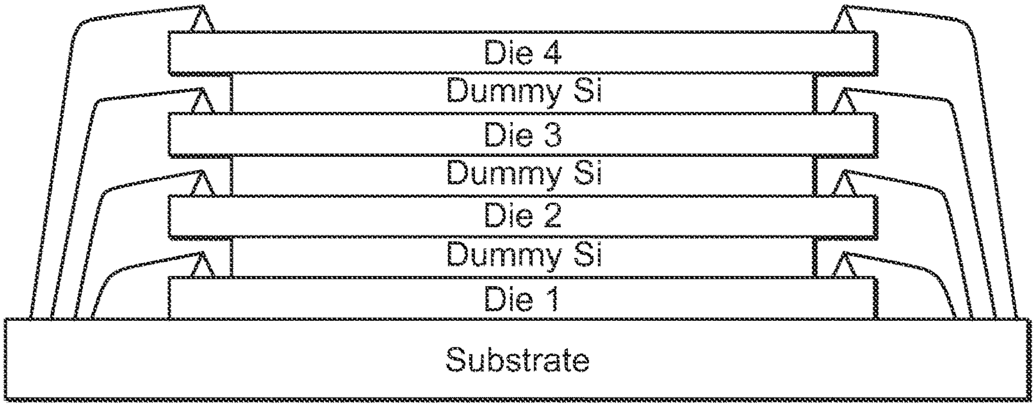
FIG. 14A is a schematic side view of a multi-chip module including four vertically stacked dies in which the dies are spacedly separated from one another by passive silicon layers with a 2-in-1 dicing die attach film (D-DAF)
Figure 14B:
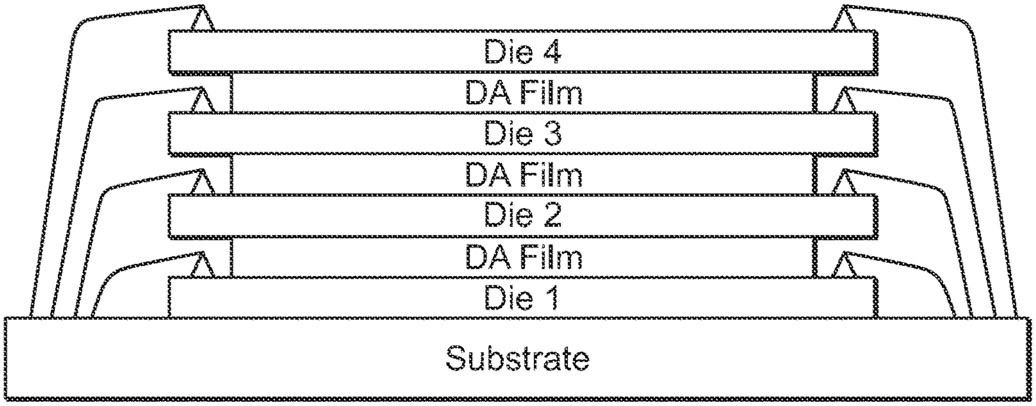
FIG. 14B is a schematic side view of a multi-chip module including four vertically stacked dies in which the dies are spacedly separated from one another by DA film-based adhesives acting as die-to-die spacers.
Figure 14C:
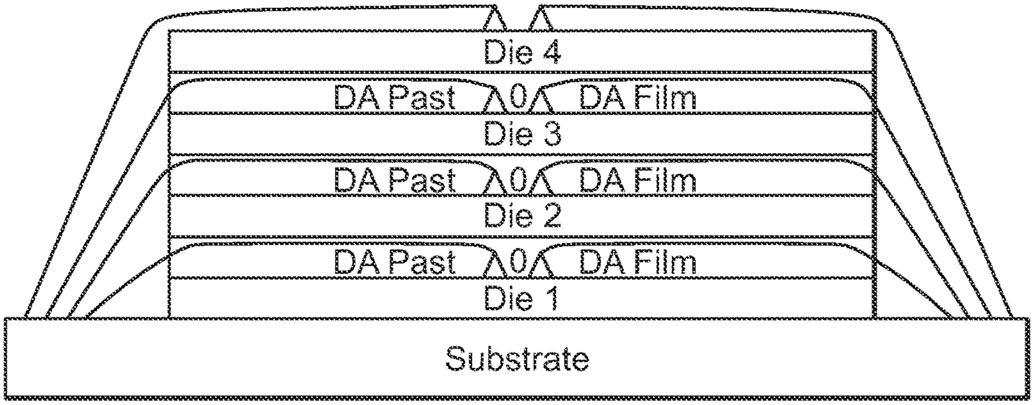
FIG. 14C is a schematic side view of a multi-chip module including four vertically stacked dies in which the dies are spacedly separated from one another by DA paste or film-based adhesives acting as die-to-die spacers.

FIGS. 14A-14C are schematic side views of exemplary multi-chip modules, including vertically stacked dies, that may be used in accordance with exemplary embodiments. Both peripheral and center pads wire bond (WB) packages are illustrated and may be used in wire bonding exemplary chip layers in a multi-chip module. FIG. 14A is a schematic side view of a multi-chip module including four vertically stacked dies in which the dies are spacedly separated from one another by passive silicon layers with a 2-in-1 dicing die attach film (D-DAF). FIG. 14B is a schematic side view of a multi-chip module including four vertically stacked dies in which the dies are spacedly separated from one another by DA film-based adhesives acting as die-to-die spacers. FIG. 14C is a schematic side view of a multi-chip module including four vertically stacked dies in which the dies are spacedly separated from one another by DA paste or film-based adhesives acting as die-to-die spacers. The DA paste or film-based adhesives may have wire penetrating capability in some exemplary embodiments. In the exemplary multi-chip module of FIG. 14C, film-over wire (FOW) is used to allow long wire bonding and center bond pads stacked die packages. FOW employs a die-attach film with wire penetrating capability that allows the same or similar-sized wire-bonded dies to be stacked directly on top of one another without passive silicon spacers. This solves the problem of stacking same or similar-sized dies directly on top of each other, which otherwise poses a challenge as there is no or insufficient clearance for the bond wires of the lower dies.

The DA material illustrated in FIGS. 14B and 14C preferably maintain a bond-line thickness (BLT) with little to no voiding and bleed out through the assembly process. Upon assembly, the DA materials sandwiched between the dies maintain an excellent adhesion to the dies. The material properties of the DA materials are tailored to maintain high cohesive strength for high temperature reliability stressing without bulk fracture. The material properties of the DA materials are tailored to also minimize or preferably eliminate moisture accumulation that may cause package reliability failures (e.g., popcorning whereby interfacial or bulk fractures occur as a result of pressure build-up from moisture in the package).

Figure 15:
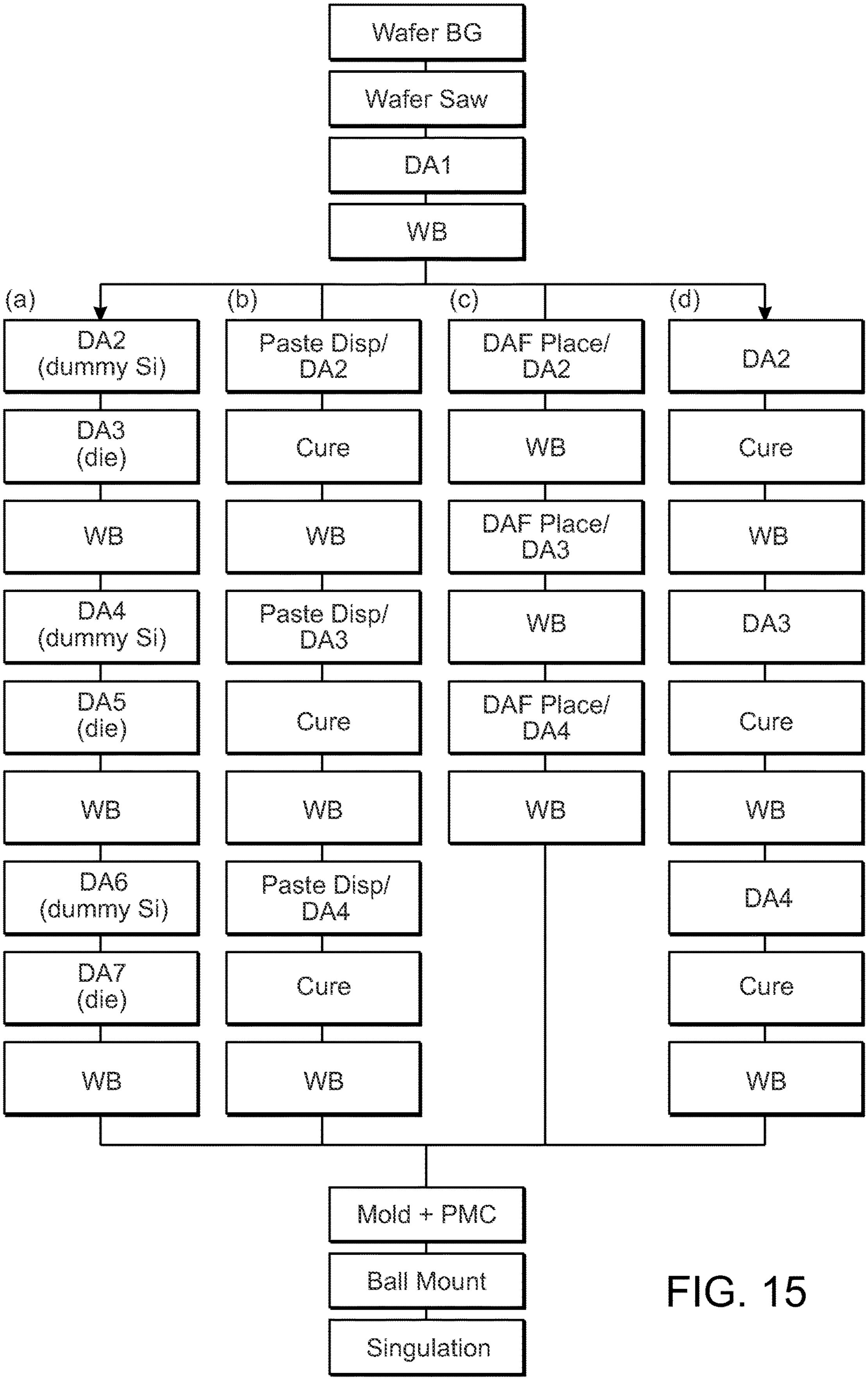
FIG. 15 is a flowchart of another exemplary method of die-to-die stacking using (a) passive silicon layers with a 2-in-1 dicing die attach film (D-DAF), (b) DA paste, (c) thick DA-film, and (d) film-over wire (FOW) including a 2-in-1 D-DAF.

FIG. 15 is a flowchart of certain exemplary methods of die-to-die stacking using (a) passive silicon layers with a 2-in-1 dicing die attach film (D-DAF), (b) DA paste, (c) thick DA-film, and (d) film-over wire (FOW) that employs a die-attach film with wire penetrating capability that allows the same or similar-sized wire-bonded dies to be stacked directly on top of one another without passive silicon spacers. Each method performs backgrinding of wafers to reduce the wafer thickness to enable stacking and high density packaging of integrated circuits. The wafers are sawed to separate the individual dies. A first die is bonded to a substrate of a multi-chip module using, for example, epoxy application and curing in an oven. Wire bonding is used to couple the first die to a metal frame.

In method (A), a first passive silicon layer is bonded to the first die in a stacked manner using a dicing die-attach film (D-DAF). A second die is bonded to the first passive layer in a stacked manner using D-DAF. Wire bonding is used to couple the second die to the metal frame. A second passive silicon layer is bonded to the second die in a stacked manner using D-DAF. A third die is bonded to the second passive layer in a stacked manner using D-DAF. Wire bonding is used to couple the third die to the metal frame. A third passive silicon layer is bonded to the third die in a stacked manner using D-DAF. A fourth die is bonded to the third passive layer in a stacked manner using D-DAF. Wire bonding is used to couple the fourth die to the metal frame.

In method (B), die attach (DA) paste dispensing and curing is repeated for multi-thin die stack application. DA paste is dispensed onto a first die, and a second die is provided on the DA paste and cured to the first die. Wire bonding is used to couple the second die to the metal frame. DA paste is dispensed onto the second die, and a third die is provided on the DA paste and cured to the second die. Wire bonding is used to couple the third die to the metal frame. DA paste is dispensed onto the third die, and a fourth die is provided on the DA paste and cured to the third die. Wire bonding is used to couple the fourth die to the metal frame.

In method (C), die attach films (DAF) are cut and pressed to a bottom die and a top die is then placed and thermal compressed onto the DAF. For example, a DAF is pressed to the first die and a second die is thermal compressed onto the DAF. Wire bonding is used to couple the second die to the metal frame. Similarly, a DAF is pressed to the second die and a third die is thermal compressed onto the DAF. Wire bonding is used to couple the third die to the metal frame. A DAF is pressed to the third die and a fourth die is thermal compressed onto the DAF. Wire bonding is used to couple the fourth die to the metal frame.

In method (D), film-over wire (FOW) employs a die-attach film with wire penetrating capability that allows the same or similar-sized wire-bonded dies to be stacked directly on top of one another without passive silicon spacers. A second die is bonded and cured to the first die in a stacked manner. Film-over wire bonding is used to couple the second die to the metal frame. A third die is bonded and cured to the first die in a stacked manner. Film-over wire bonding is used to couple the third die to the metal frame. A fourth die is bonded and cured to the first die in a stacked manner. Film-over wire bonding is used to couple the fourth die to the metal frame.

After the above-described steps are completed, in each method (a)-(d), wafer molding and post-mold curing (PMC) are performed. Subsequently, ball mount and singulation are performed.

Further details on the above-described die attachment techniques are provided in TOH C H et al., “Die Attach Adhesives for 3D Same-Sized Dies Stacked Packages,” the 58th Electronic Components and Technology Conference (ECTC2008), pp. 1538-43, Florida, US (27-30 May 2008), the entire contents of which are expressly incorporated herein by reference.

Figure 16:
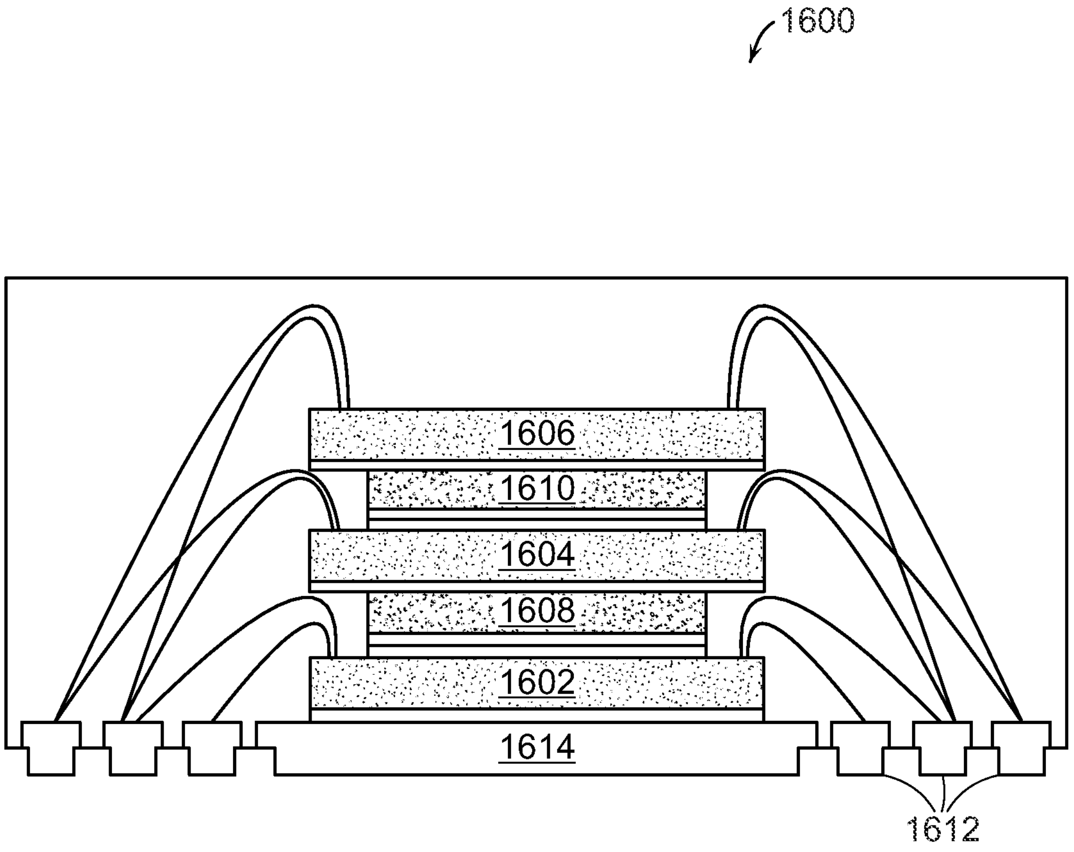
FIG. 16 is a schematic side view of a multi-chip module including an ultrasound transmit/receive IC chip, an amplifier IC chip and an ultrasound beamformer IC chip vertically integrated in a vertically stacked configuration.

FIG. 16 is a schematic side view of a multi-chip module 1600 including a TR chip 1602, an amplifier chip 1604 and a beamformer chip 1606 vertically integrated in a vertically stacked configuration on a substrate 1614. Any suitable technique illustrated in FIGS. 12-15 may be used to fabricate the multi-chip module. One of ordinary skill in the art will recognize that the particular order in which the chips are stacked may be different in other embodiments. First and second spacer layers 1608, 1610 are provided to spacedly separate the chips 1602, 1604, 1606. Each chip is coupled to a metal frame (e.g., a leadframe) 1612. In certain exemplary embodiments, heat transfer and heat sink mechanisms may be provided in the multi-chip module to sustain high temperature reliability stressing without bulk failure. Other components of FIG. 16 are described with reference to FIGS. 12 and 14.

In this exemplary embodiment, each multi-chip module may handle the complete transmit, receive, TGC amplification and beam forming operations for a large number of channels, for example, 32 channels. By vertically integrating the three silicon chips into a single multi-chip module, the space and footprint required for the printed circuit board is further reduced. A plurality of multi-chip modules may be provided on a single ultrasound engine circuit board to further increase the number of channels while minimizing the packaging size and footprint. For example, a 128 channel ultrasound engine circuit board 108 can be fabricated within exemplary planar dimensions of about 10 cm×about 10 cm, which is a significant improvement of the space requirements of conventional ultrasound circuits. A single circuit board of an ultrasound engine including one or more multi-chip modules may have 16 to 128 channels in preferred embodiments. In certain embodiments, a single circuit board of an ultrasound engine including one or more multi-chip modules may have 16, 32, 64, 128 channels, and the like.

Figure 17:
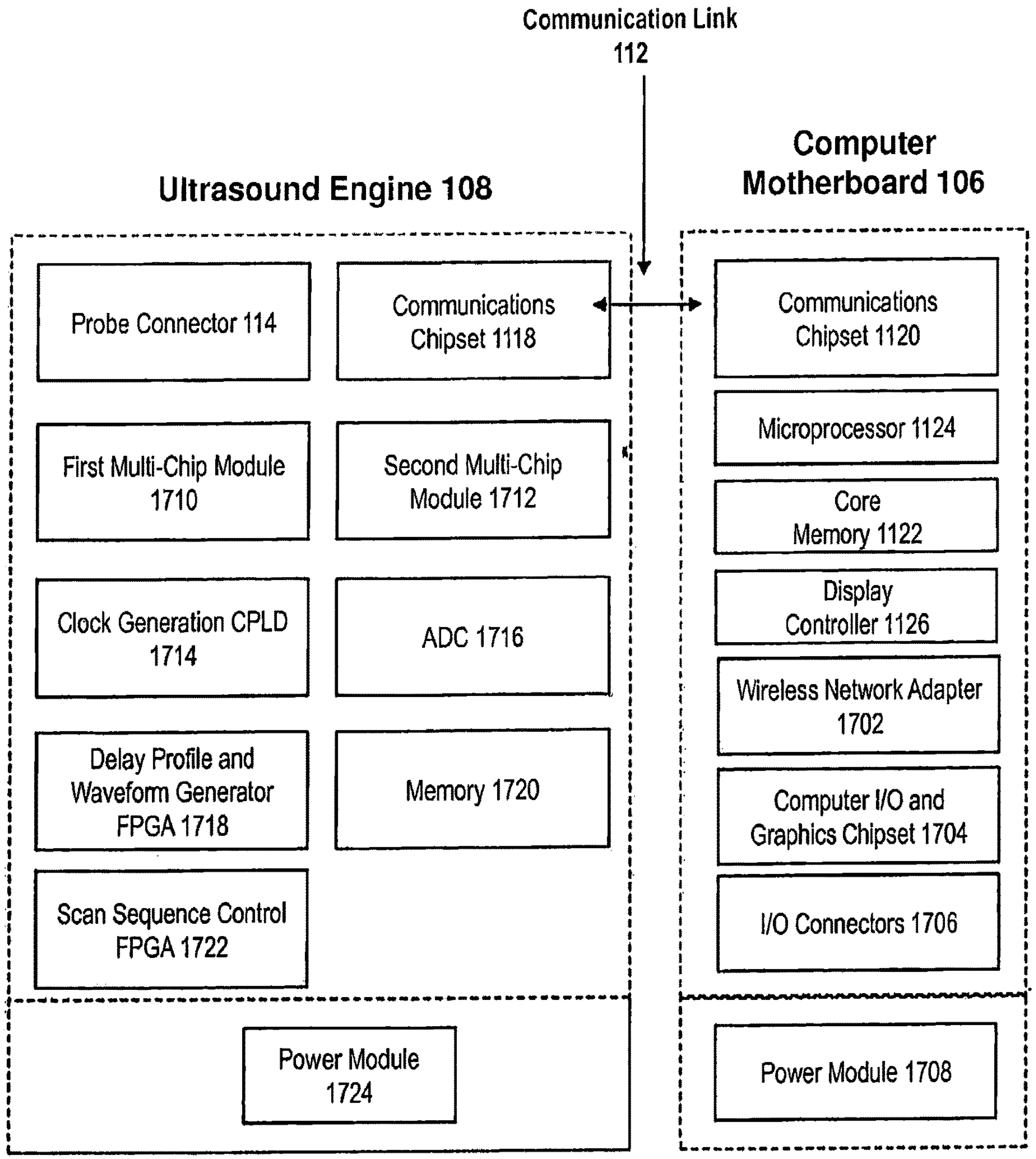
FIG. 17 is a detailed schematic block diagram of an exemplary embodiment of an ultrasound engine (i.e., the front-end ultrasound specific circuitry) and an exemplary embodiment of a computer motherboard (i.e., the host computer) provided as a single board complete ultrasound system.

FIG. 17 is a detailed schematic block diagram of an exemplary embodiment of the ultrasound engine 108 (i.e., the front-end ultrasound specific circuitry) and an exemplary embodiment of the computer motherboard 106 (i.e., the host computer) provided as a single board complete ultrasound system. An exemplary single board ultrasound system as illustrated in FIG. 17 may have exemplary planar dimensions of about 25 cm×about 18 cm, although other dimensions are possible. The single board complete ultrasound system of FIG. 17 may be implemented in the ultrasound device illustrated in FIGS. 1, 2A, 2B, and 9A, and may be used to perform the operations depicted in FIGS. 3-8, 9B, and 10.

The ultrasound engine 108 includes a probe connector 114 to facilitate the connection of at least one ultrasound probe/transducer. In the ultrasound engine 108, a TR module, an amplifier module and a beamformer module may be vertically stacked to form a multi-chip module as shown in FIG. 16, thereby minimizing the overall packaging size and footprint of the ultrasound engine 108. The ultrasound engine 108 may include a first multi-chip module 1710 and a second multi-chip module 1712, each including a TR chip, an ultrasound pulser and receiver, an amplifier chip including a time-gain control amplifier, and a sample-data beamformer chip vertically integrated in a stacked configuration as shown in FIG. 16. The first and second multi-chip modules 1710, 1712 may be stacked vertically on top of each other to further minimize the area required on the circuit board. Alternatively, the first and second multi-chip modules 1710, 1712 may be disposed horizontally on the circuit board. In an exemplary embodiment, the TR chip, the amplifier chip and the beamformer chip is each a 32-channel chip, and each multi-chip module 1710, 1712 has 32 channels. One of ordinary skill in the art will recognize that exemplary ultrasound engines 108 may include, but are not limited to, one, two, three, four, five, six, seven, eight multi-chip modules. Note that in a preferred embodiment the system can be configured with a first beamformer in the transducer housing and a second beamformer in the tablet housing.

The ASICs and the multi-chip module configuration enable a 128-channel complete ultrasound system to be implemented on a small single board in a size of a tablet computer format. An exemplary 128-channel ultrasound engine 108, for example, can be accommodated within exemplary planar dimensions of about 10 cm×about 10 cm, which is a significant improvement of the space requirements of conventional ultrasound circuits. An exemplary 128-channel ultrasound engine 108 can also be accommodated within an exemplary area of about 100 $cm^2$.

The ultrasound engine 108 also includes a clock generation complex programmable logic device (CPLD) 1714 for generating timing clocks for performing an ultrasound scan using the transducer array. The ultrasound engine 108 includes an analog-to-digital converter (ADC) 1716 for converting analog ultrasound signals received from the transducer array to digital RF formed beams. The ultrasound engine 108 also includes one or more delay profile and waveform generator field programmable gate arrays (FPGA) 1718 for managing the receive delay profiles and generating the transmit waveforms. The ultrasound engine 108 includes a memory 1720 for storing the delay profiles for ultrasound scanning. An exemplary memory 1720 may be a single DDR3 memory chip. The ultrasound engine 108 includes a scan sequence control field programmable gate array (FPGA) 1722 configured to manage the ultrasound scan sequence, transmit/receiving timing, storing and fetching of profiles to/from the memory 1720, and buffering and moving of digital RF data streams to the computer motherboard 106 via a high-speed serial interface 112. The high-speed serial interface 112 may include Fire Wire or other serial or parallel bus interface between the computer motherboard 106 and the ultrasound engine 108. The ultrasound engine 108 includes a communications chipset 1118 (e.g., a Fire Wire chipset) to establish and maintain the communications link 112.

A power module 1724 is provided to supply power to the ultrasound engine 108, manage a battery charging environment and perform power management operations. The power module 1724 may generate regulated, low noise power for the ultrasound circuitry and may generate high voltages for the ultrasound transmit pulser in the TR module.

The computer motherboard 106 includes a core computer-readable memory 1122 for storing data and/or computer-executable instructions for performing ultrasound imaging operations. The memory 1122 forms the main memory for the computer and, in an exemplary embodiment, may store about 4 Gb of DDR3 memory. The memory 1122 may include a solid state hard drive (SSD) for storing an operating system, computer-executable instructions, programs and image data. An exemplary SSD may have a capacity of about 128 GB.

The computer motherboard 106 also includes a microprocessor 1124 for executing computer-executable instructions stored on the core computer-readable memory 1122 for performing ultrasound imaging processing operations. Exemplary operations include, but are not limited to, down conversion, scan conversion, Doppler processing, Color Flow processing, Power Doppler processing, Spectral Doppler processing, and post signal processing. An exemplary microprocessor 1124 may be an off-the-shelf commercial computer processor, such as an Intel Core-i5 processor. Another exemplary microprocessor 1124 may be a digital signal processor (DSP) based processor, such as DaVinci™ processors from Texas Instruments.

The computer motherboard 106 includes an input/output (I/O) and graphics chipset 1704 which includes a co-processor configured to control I/O and graphic peripherals such as USB ports, video display ports and the like. The computer motherboard 106 includes a wireless network adapter 1702 configured to provide a wireless network connection. An exemplary adapter 1702 supports 802.11g and 802.11n standards. The computer motherboard 106 includes a display controller 1126 configured to interface the computer motherboard 106 to the display 104. The computer motherboard 106 includes a communications chipset 1120 (e.g., a Fire Wire chipset or interface) configured to provide a fast data communication between the computer motherboard 106 and the ultrasound engine 108. An exemplary communications chipset 1120 may be an IEEE 1394b 800 Mbit/sec interface. Other serial or parallel interfaces 1706 may alternatively be provided, such as USB3, Thunder-Bolt, PCIe, and the like. A power module 1708 is provided to supply power to the computer motherboard 106, manage a battery charging environment and perform power management operations.

An exemplary computer motherboard 106 may be accommodated within exemplary planar dimensions of about 12 cm×about 10 cm. An exemplary computer motherboard 106 can be accommodated within an exemplary area of about 120 $cm^2$.

Figure 18:
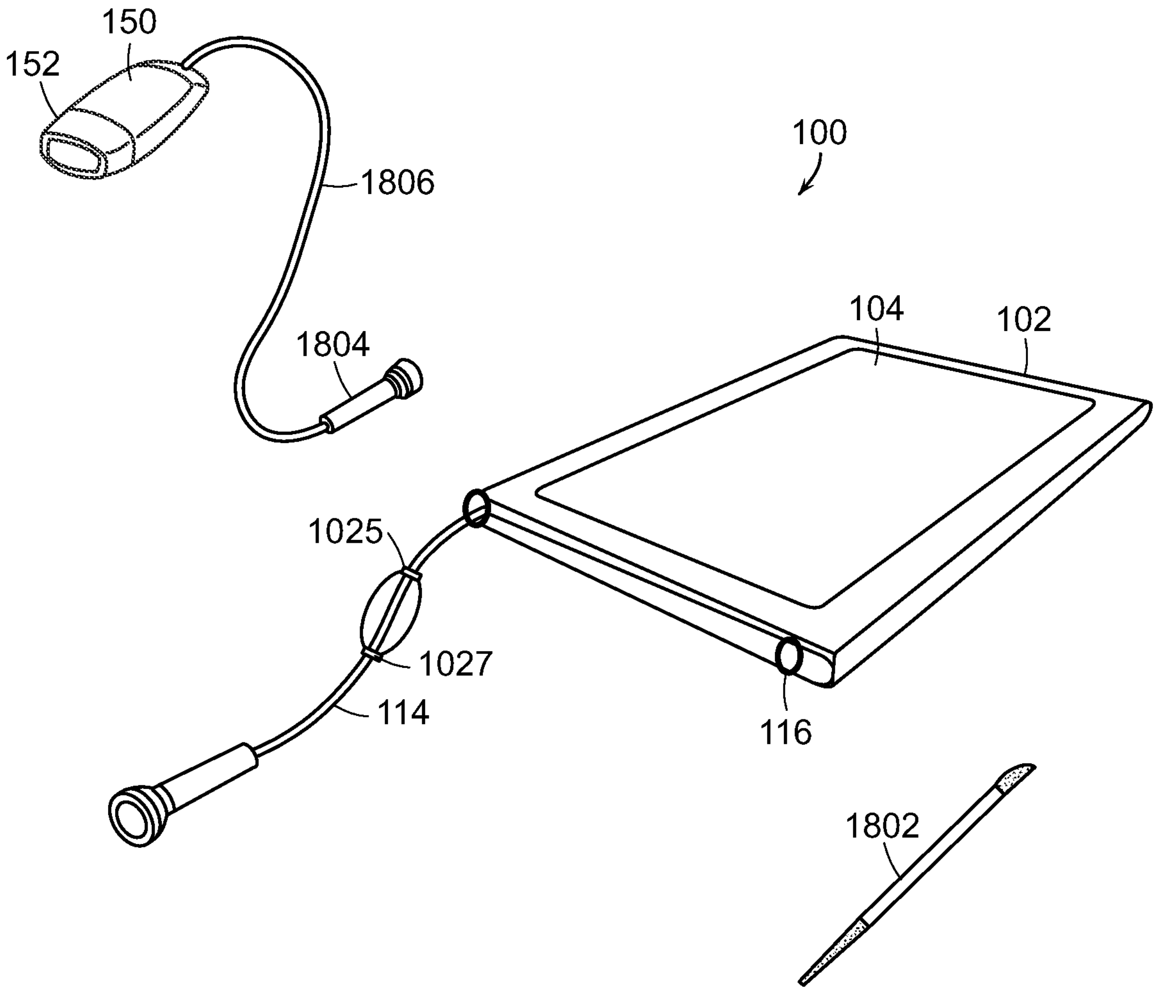
FIG. 18 is a perspective view of an exemplary portable ultrasound system provided in accordance with exemplary embodiments.

FIG. 18 is a perspective view of an exemplary portable ultrasound system 100 provided in accordance with exemplary embodiments. The system 100 includes a housing 102 that is in a tablet form factor as illustrated in FIG. 18, but that may be in any other suitable form factor. An exemplary housing 102 may have a thickness below 2 cm and preferably between 0.5 and 1.5 cm. A front panel of the housing 102 includes a multi-touch LCD touchscreen display 104 that is configured to recognize and distinguish one or more multiple and/or simultaneous touches on a surface of the touchscreen display 104. The surface of the display 104 may be touched using one or more of a user's fingers, a user's hand or an optional stylus 1802. The housing 102 includes one or more I/O port connectors 116 which may include, but are not limited to, one or more USB connectors, one or more SD cards, one or more network mini display ports, and a DC power input. The embodiment of housing 102 in FIG. 18 can also be configured within a palm-carried form factor having dimensions of 150 mm×100 mm×15 mm (a volume of 225000 $mm^3$) or less. The housing 102 can have a weight of less than 200 g. Optionally, cabling between the transducer array and the display housing can include interface circuitry 1020 as described herein. The interface circuitry 1020 can include, for example, beamforming circuitry and/or A/D circuitry in a pod that dangles from the tablet. Separate connectors 1025, 1027 can be used to connect the dangling pod to the transducer probe cable. The connector 1027 can include probe identification circuitry as described herein. The unit 102 can include a camera, a microphone and a speaker as well as wireless telephone circuitry for voice and data communications as well as voice activated software that can be used to control the ultrasound imaging operations described herein.

The housing 102 includes or is coupled to a probe connector 114 to facilitate connection of at least one ultrasound probe/transducer 150. The ultrasound probe 150 includes a transducer housing including one or more transducer arrays 152. The ultrasound probe 150 is couplable to the probe connector 114 using a housing connector 1804 provided along a flexible cable 1806. One of ordinary skill in the art will recognize that the ultrasound probe 150 may be coupled to the housing 102 using any other suitable mechanism, for example, an interface housing that includes circuitry for performing ultrasound-specific operations like beamforming. Other exemplary embodiments of ultrasound systems are described in further detail in WO 03/079038 A2, filed Mar. 11, 2003, titled "Ultrasound Probe with Integrated Electronics," the entire contents of which is expressly incorporated herein by reference. Preferred embodiments can employ a wireless connection between the hand-held transducer probe 150 and the display housing. Beamformer electronics can be incorporated into probe housing 150 to provide beamforming of subarrays in a 1D or 2D transducer array as described herein. The display housing can be sized to be held in the palm of the user's hand and can include wireless network connectivity to public access networks such as the internet.

Figure 19:
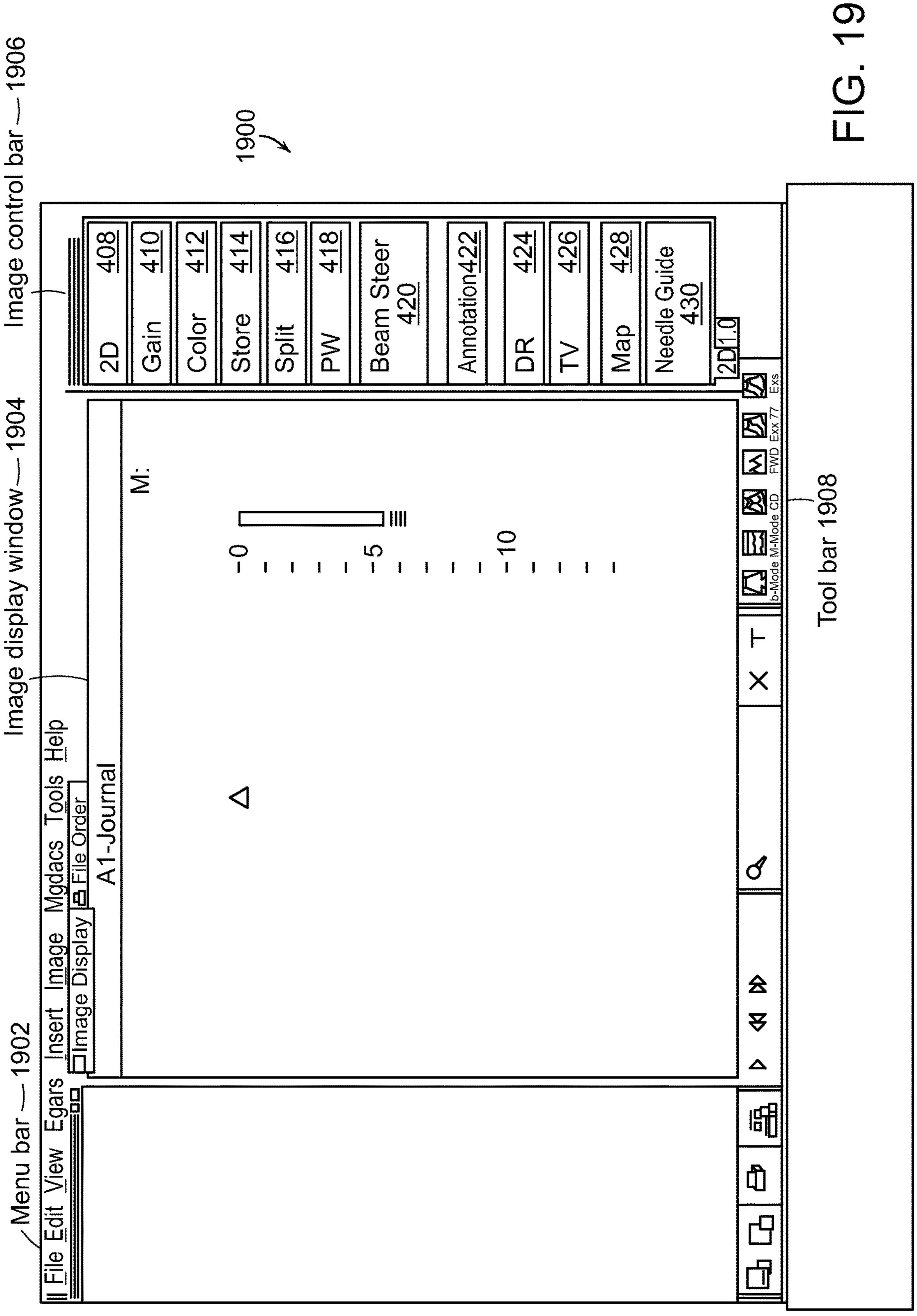
FIG. 19 illustrates an exemplary view of a main graphical user interface (GUI) rendered on a touchscreen display of the exemplary portable ultrasound system of FIG. 18.

FIG. 19 illustrates an exemplary view of a main graphical user interface (GUI) 1900 rendered on the touchscreen display 104 of the portable ultrasound system 100 of FIG. 18. The main GUI 1900 may be displayed when the ultrasound system 100 is started. To assist a user in navigating the main GUI 1900, the GUI may be considered as including four exemplary work areas: a menu bar 1902, an image display window 1904, an image control bar 1906, and a tool bar 1908. Additional GUI components may be provided on the main GUI 1900 to, for example, enable a user to close, resize and exit the GUI and/or windows in the GUI.

The menu bar 1902 enables a user to select ultrasound data, images and/or videos for display in the image display window 1904. The menu bar 1902 may include, for example, GUI components for selecting one or more files in a patient folder directory and an image folder directory. The image display window 1904 displays ultrasound data, images and/or videos and may, optionally, provide patient information. The tool bar 1908 provides functionalities associated with an image or video display including, but not limited to, a save button for saving the current image and/or video to a file, a save Loop button that saves a maximum allowed number of previous frames as a Cine loop, a print button for printing the current image, a freeze image button for freezing an image, a playback toolbar for controlling aspects of playback of a Cine loop, and the like. Exemplary GUI functionalities that may be provided in the main GUI 1900 are described in further detail in WO 03/079038 A2, filed Mar. 11, 2003, titled "Ultrasound Probe with Integrated Electronics," the entire contents of which are expressly incorporated herein by reference.

The image control bar 1906 includes touch controls that may be operated by touch and touch gestures applied by a user directly to the surface of the display 104. Exemplary touch controls may include, but are not limited to, a 2D touch control 408, a gain touch control 410, a color touch control 412, a storage touch control 414, a split touch control 416, a PW imaging touch control 418, a beamsteering touch control 20, an annotation touch control 422, a dynamic range operations touch control 424, a Teravision™ touch control 426, a map operations touch control 428, and a needle guide touch control 428. These exemplary touch controls are described in further detail in connection with FIGS. 4*a*-4*c*.

Figure 20A:
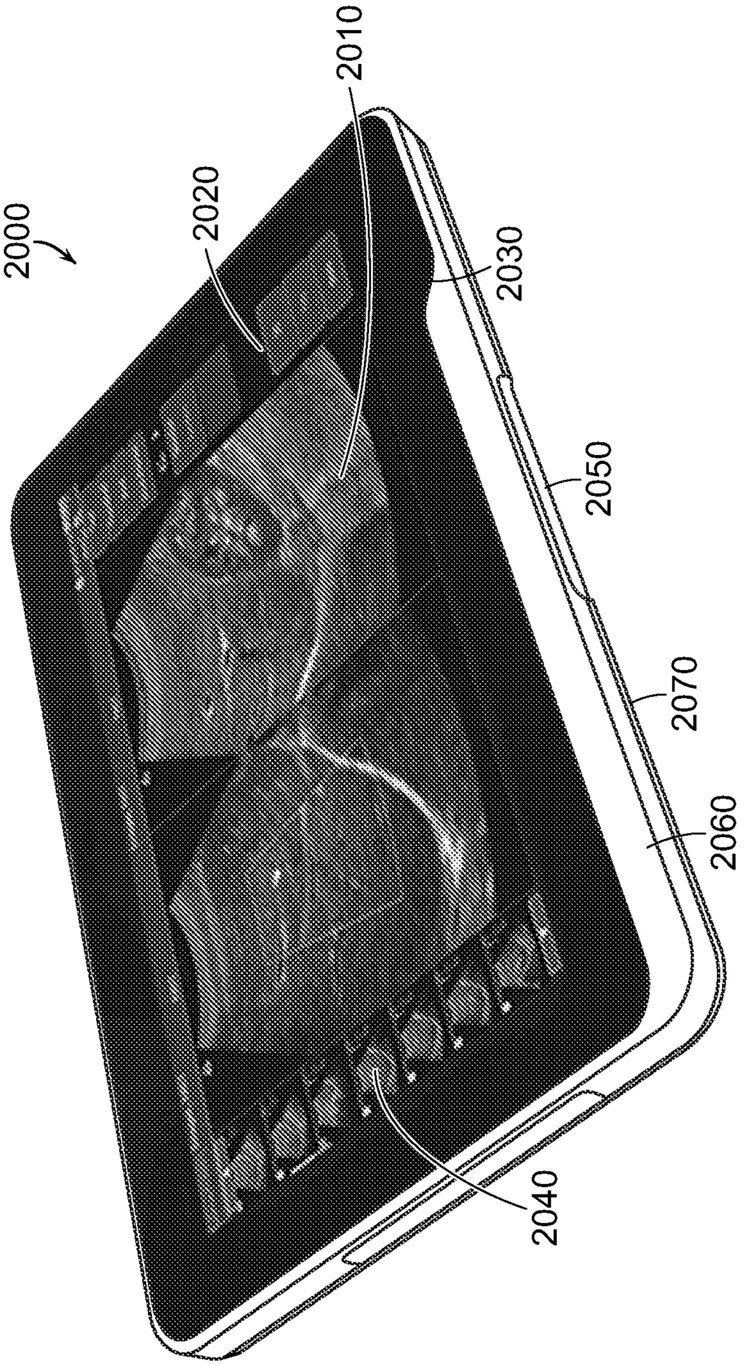
FIG. 20A is a top view of the medical ultrasound imaging system in accordance with another preferred embodiment of the invention.

FIG. 20A depicts an illustrative embodiment of exemplary medical ultrasound imaging equipment 2000, implemented in the form factor of a tablet in accordance with one embodiment of the invention. The table may have the dimensions of 12.5"×1.25"×8.75" or 31.7 cm×3.175 cm×22.22 cm but it may also be in any other suitable form factor having a volume of less than 2500 $cm^3$ and a weight of less than 8 lbs. As shown in FIG. 20A, the medical ultrasound imaging equipment 2000, includes a housing 2030, a touchscreen display 2010, wherein ultrasound images 2010, and ultra sound data 2040, can be displayed and ultrasound controls 2020, are configured to be controlled by a touchscreen display 2010. The housing 2030, may have a front panel 2060 and a rear panel 2070. The touchscreen display 2010, forms the front panel 2060, and includes a multi-touch LCD touchscreen that can recognize and distinguish one or more multiple and or simultaneous touches of the user on the touchscreen display 2010. The front panel can include a single button, switch or touch sensitive actuator to turn on the power of the device. In a preferred embodiment, all other manual controls of the tablet are performed by touchscreen gestures. The touchscreen display 2010 may have a capacitive multi-touch and AVAH LCD screen. For example, the capacitive multi-touch and AVAH LCD screen may enable a user to view the image from multi angles without losing resolution. In another embodiment, the user may utilize a stylus for data input on the touchscreen. The tablet can include an integrated foldable stand that permits a user to swivel the stand from a storage position that conforms to the tablet form factor so that the device can lay flat on the rear panel, or alternatively, the user can swivel the stand to enable the tablet to stand at an upright position at one of a plurality of oblique angles relative to a support surface.

Capacitive touchscreen module comprises an insulator for example glass, coated with a transparent conductor, such as indium tin oxide. The manufacturing process may include a bonding process among glass, x-sensor film, y-sensor film and a liquid crystal material. The tablet is configured to allow a user to perform multi-touch gestures such as pinching and stretching while wearing a dry or a wet glove. The surface of the screen registers the electrical conductor making contact with the screen. The contact distorts the screens electrostatic field resulting in measureable changes in capacitance. A processor then interprets the change in the electrostatic field. Increasing levels of responsiveness are enabled by reducing the layers and by producing touchscreens with "in-cell" technology. "In-cell" technology eliminates layers by placing the capacitors inside the display. Applying "in-cell" technology reduces the visible distance between the user's finger and the touchscreen target, thereby creating a more directive contact with the content displayed and enabling taps and gestures to have an increase in responsiveness.

Figure 20B:
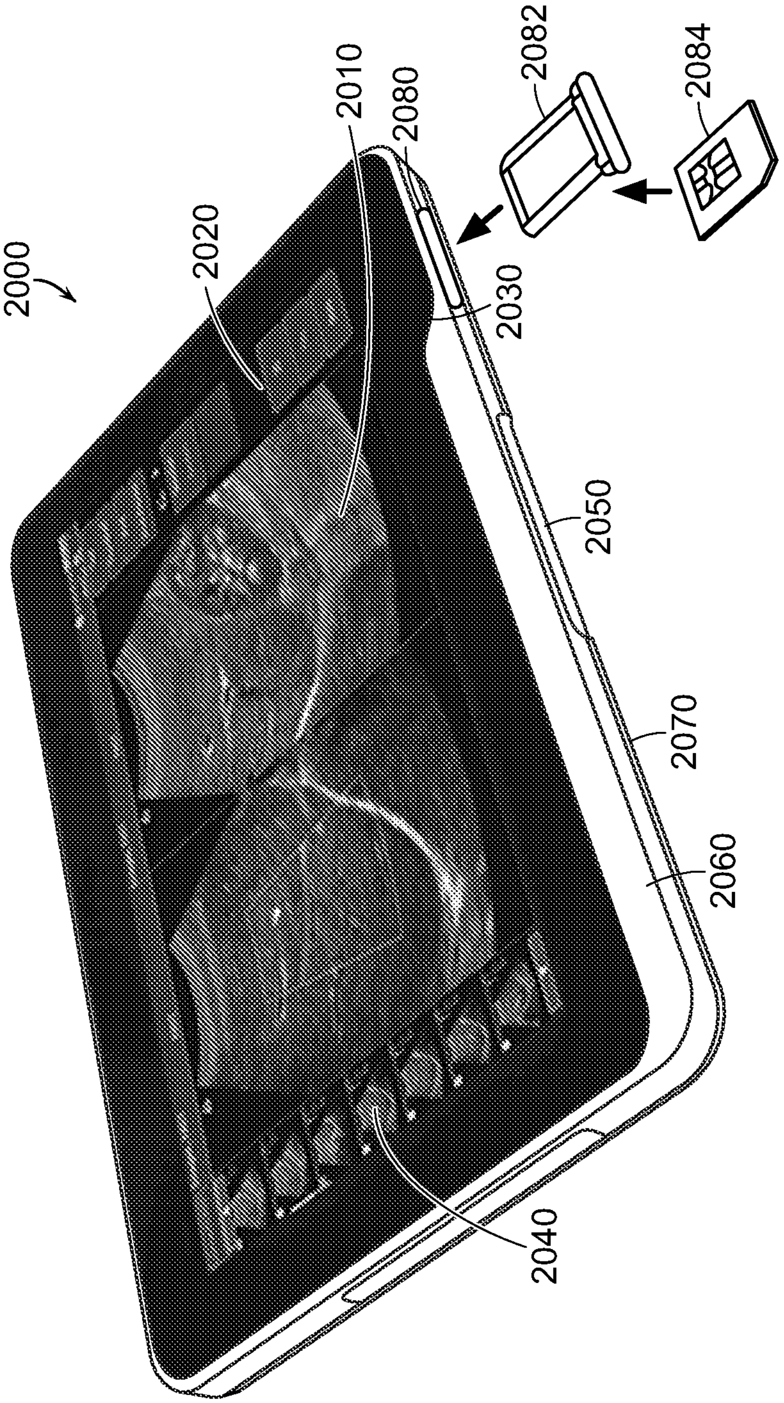
FIG. 20B is a top view of the medical ultrasound imaging system configured to receive a wireless SIM card, in accordance with another embodiment of the invention.

FIG. 20B depicts an illustrative embodiment of exemplary medical ultrasound imaging equipment 2000, implemented in the form factor of a tablet in accordance with one embodiment of the invention and configured to receive a wireless SIM card. In this particular embodiment, the ultrasound imaging equipment/device 2000 includes a SIM card port 2080 which is configured to receive a SIM card 2084 and connect the SIM card circuit to wireless communication circuitry within the device. The SIM card port 2080, in this embodiment, includes metal contacts within that connect the ID circuit of the SIM card 2084 to the circuitry of the device 2000. In this particular example, a SIM card tray 2082 is configured to receive the SIM card 2084 and connect it to the SIM card port 2080. In some embodiments, the SIM card port 2080 and/or the SIM card tray 2082 may be configured to receive a standard SIM card, mini SIM card, micro SIM card, nano SIM card, or other similar wireless identification/authorization card or circuit.

Figure 21:
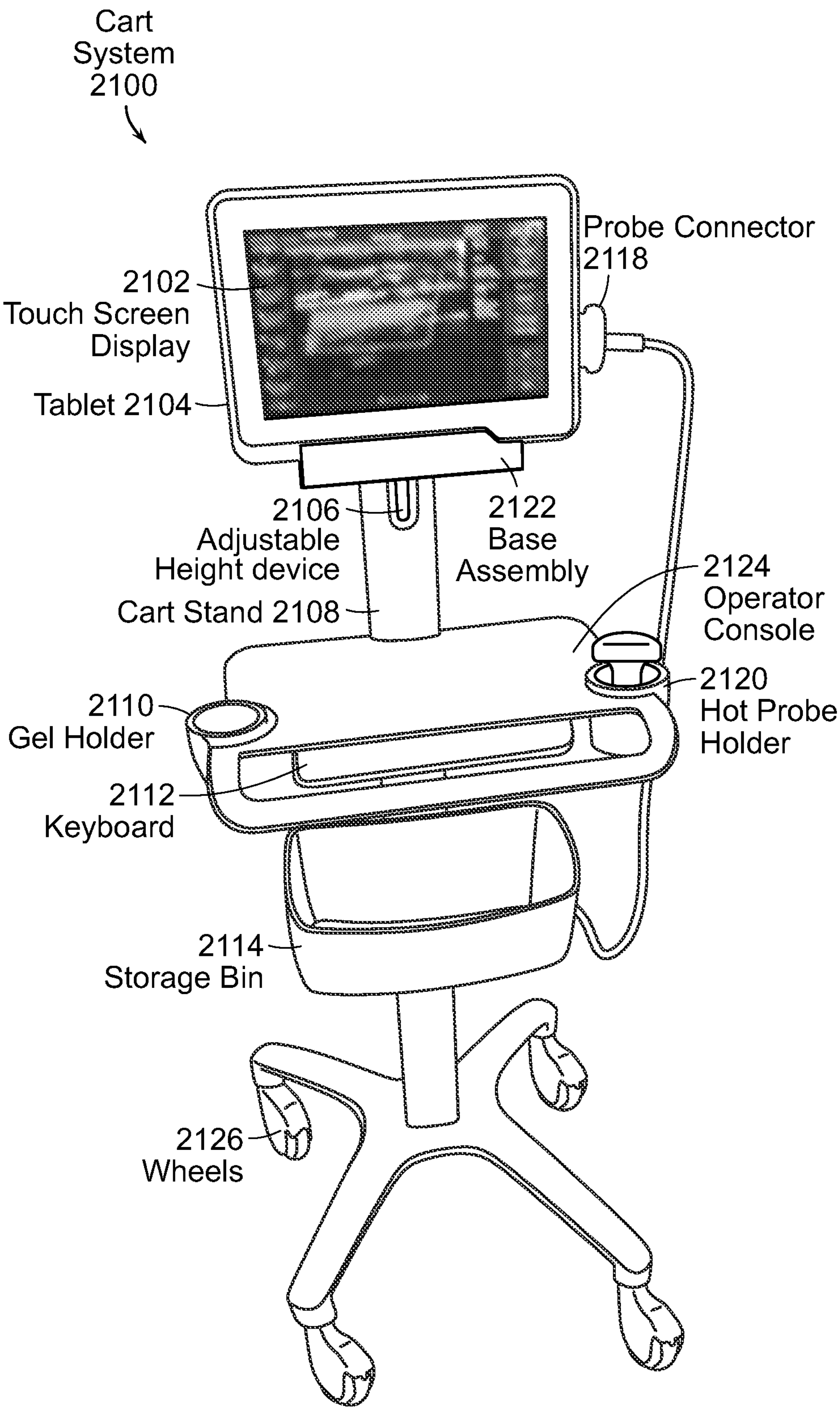
FIG. 21 illustrates a preferred cart system for a tablet ultrasound system in accordance with preferred embodiment 9 of the invention.

FIG. 21 illustrates a preferred cart system for a modular ultrasound imaging system in accordance with one embodiment of the invention. The cart system 2100 uses a base assembly 2122 including a docking bay that receives the tablet. The cart configuration 2100 is configured to dock tablet 2104, including a touchscreen display 2102, to a cart 2108, which can include a full operator console 2124. After the tablet 2104, is docked to the cart stand 2108, the system forms a full feature roll about system. The full feature roll about system may include, an adjustable height device 2106, a gel holder 2110, and a storage bin 2114, a plurality of wheels 2116, a hot probe holder 2120, and the operator console 2124. The control devices may include a keyboard 2112 on the operator console 2124 that may also have other peripherals added such as a printer or a video interface or other control devices.

Figure 22:
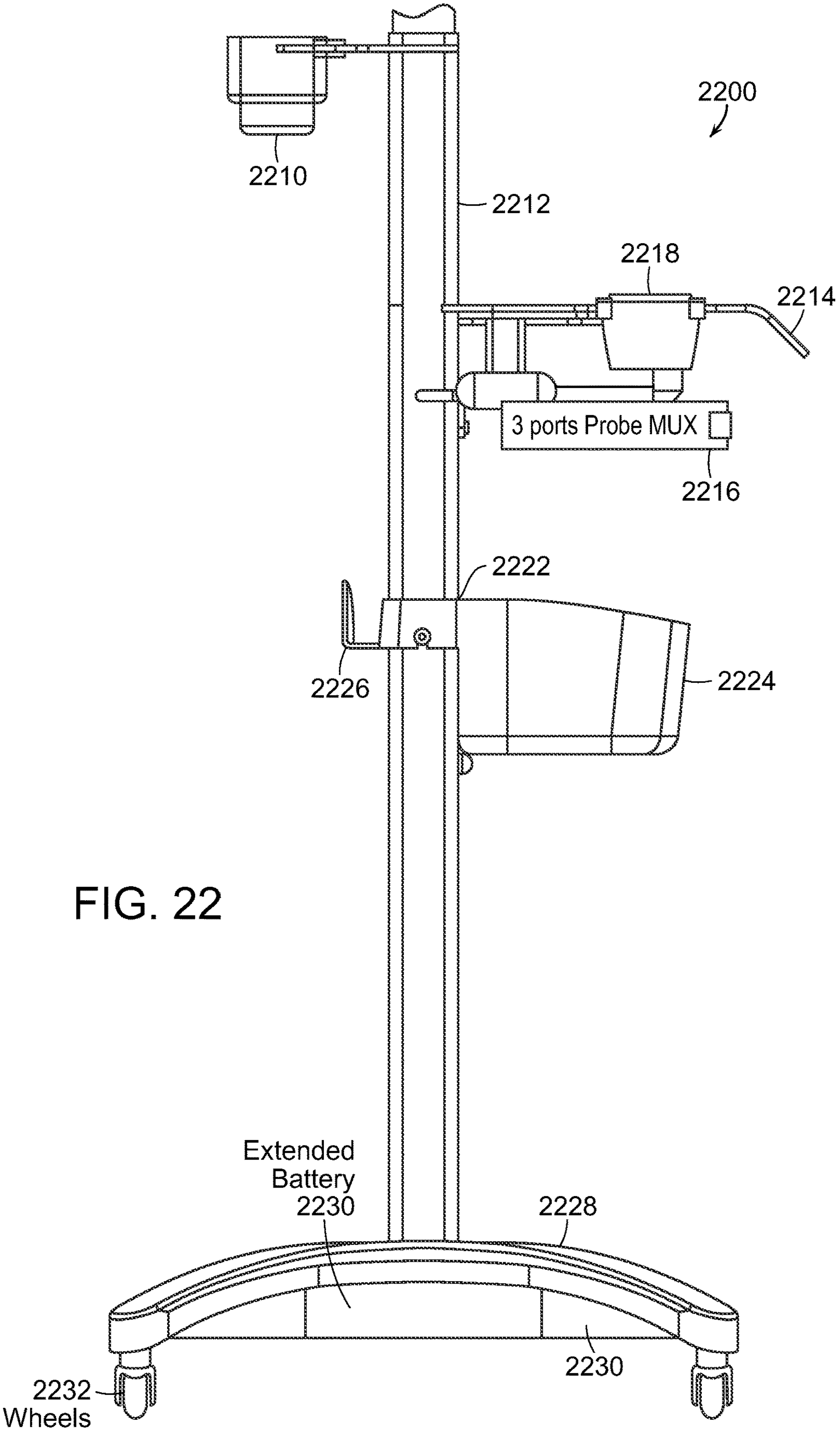
FIG. 22 illustrates preferred cart system for a modular ultrasound imaging system in accordance with preferred embodiments of the invention.

FIG. 22 illustrate a preferred cart system, for use in embodiments with a modular ultrasound imaging system in accordance with one embodiment of the invention. The cart system 2200 may be configured with a vertical support member 2212, coupled to a horizontal support member 2028. An auxiliary device connector 2018, having a position for auxiliary device attachment 2014, may be configured to connect to the vertical support member 2212. A 3 port Probe MUX connection device 2016 may also be configured to connect to the tablet. A storage bin 2224 can be configured to attach by a storage bin attachment mechanism 2222, to vertical support member 2212. The cart system may also include a cord management system 2226, configured to attach to the vertical support member. The cart assembly 2200 includes the support beam 2212 mounted on a base 2228 having wheels 2232 and a battery 2230 that provides power for extended operation of the tablet. The assembly can also include an accessory holder 2224 mounted with height adjustment device 2226. Holders 2210, 2218 can be mounted on beam 2212 or on console panel 2214. The multiport probe multiplex device 2216 connects to the tablet to provide simultaneous connection of several transducer probes which the user can select in sequence with the displayed virtual switch. A moving touch gesture, such as a three finger flick on the displayed image or touching of a displayed virtual button or icon can switch between connected probes.

Figure 23A:
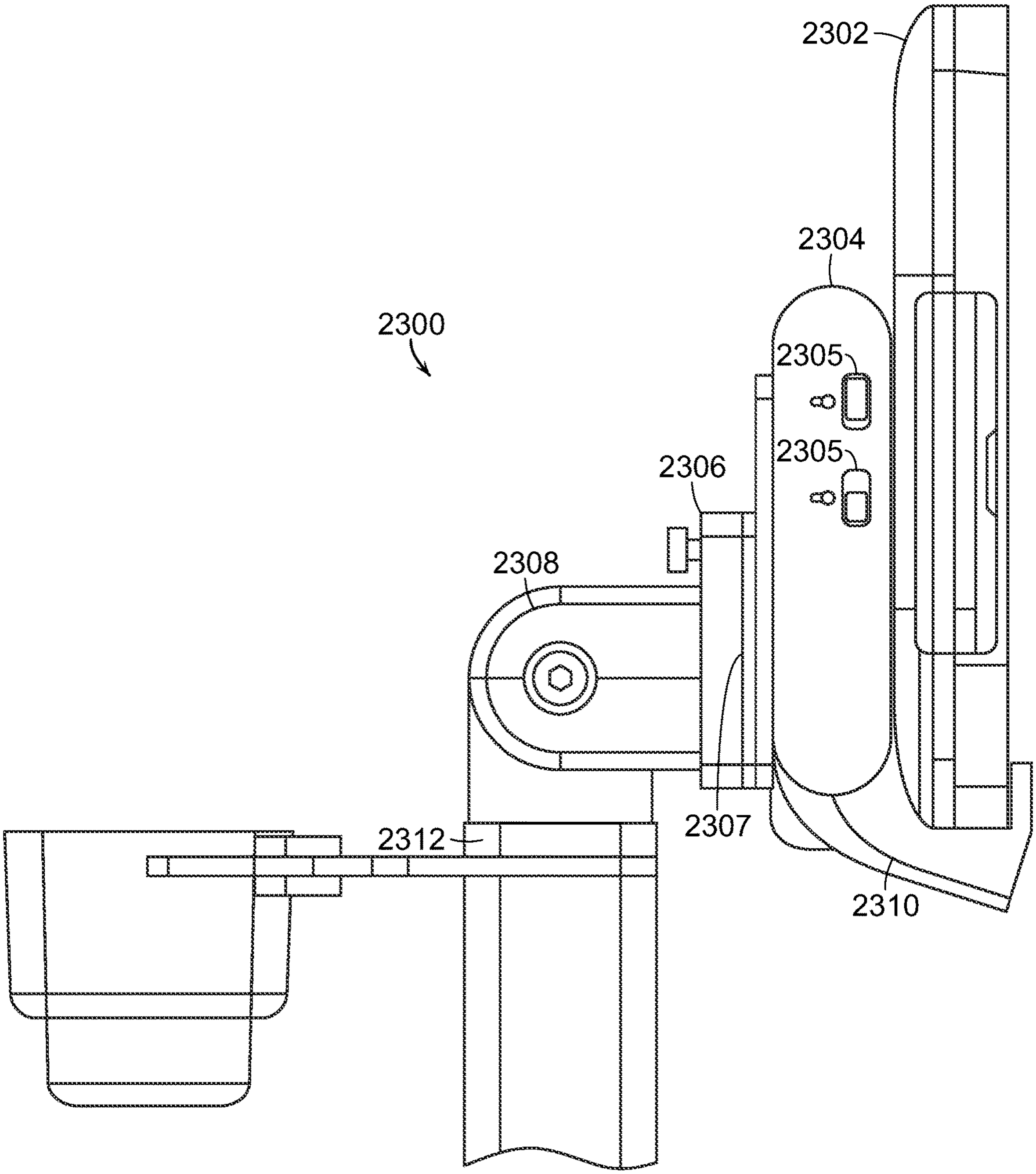
FIG. 23A illustrates preferred cart system for a modular ultrasound imaging system in accordance with preferred embodiments of the invention.

FIG. 23A illustrates preferred cart mount system for a modular ultrasound imaging system in accordance with one embodiment of the invention. Arrangement 2300 depicts the tablet 2302, coupled to the docking station 2304. The docking station 2304 is affixed to the attachment mechanism 2306. The attachment mechanism 2306 may include a hinged member 2308, allowing for the user display to tilted into a user desired position. The attachment mechanism 2306 is attached to the vertical member 2312. A tablet 2302 as described herein can be mounted on the base docking unit 2304 which is mounted to a mount assembly 2306 on top of beam 2212. The base unit 2304 includes cradle 2310, electrical connectors 2305 and a port 2307 to connect to the system 2302 to battery 2230 and multiplexor device 2216.

Figure 23B:
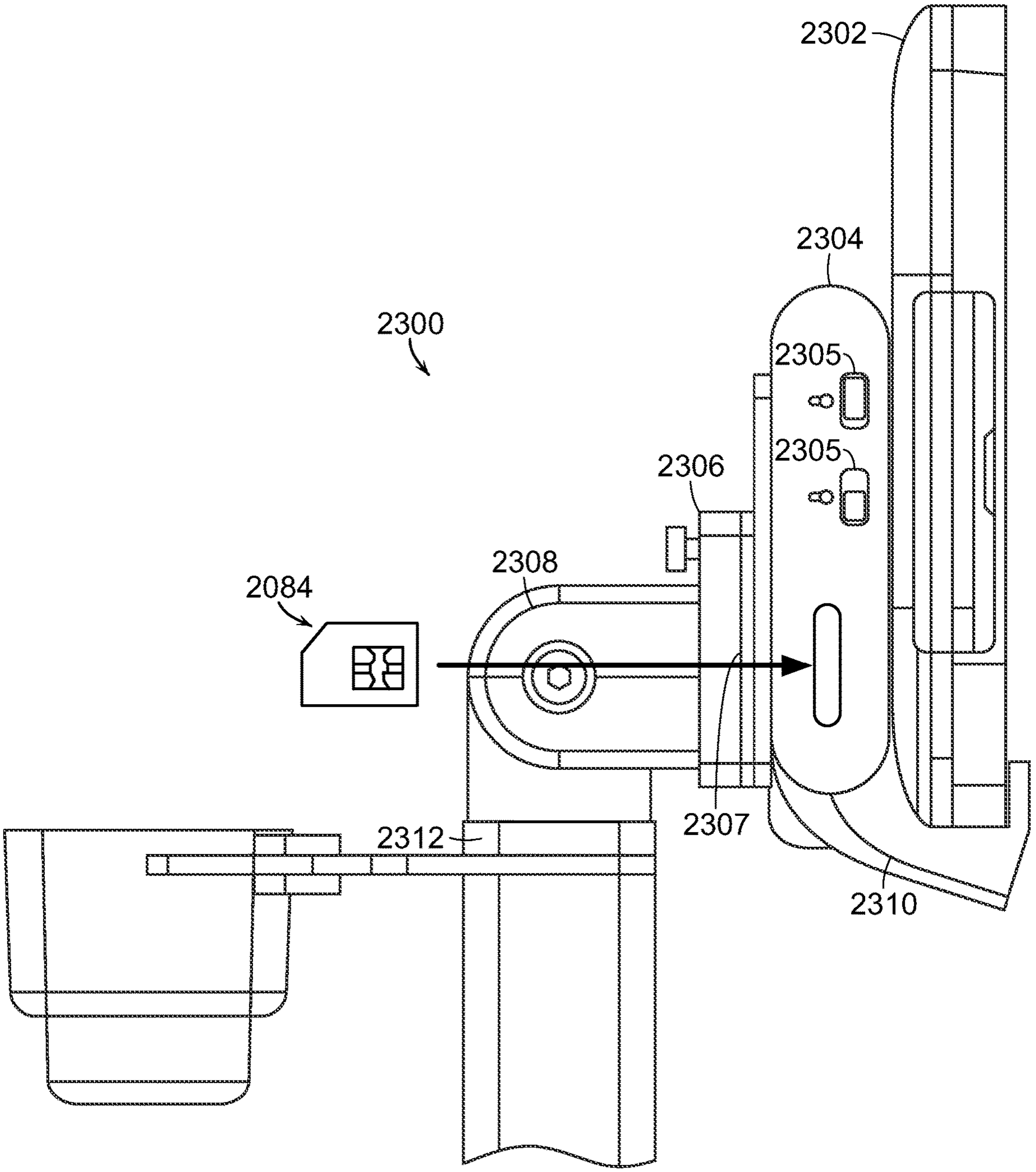
FIG. 23B illustrates an alternative cart system for a modular ultrasound imaging system configured to receive a wireless SIM card, in accordance with another embodiment of the invention.

FIG. 23B illustrates a cart mount system for a modular ultrasound imaging system configured to receive a wireless SIM card, in accordance with an embodiment of the present invention. In this particular embodiment, the docking station 2304 includes a SIM card port 2080 which is configured to receive a SIM card 2084 and connect the SIM card circuit to wireless communication circuitry located either within the docking station 2304 or the tablet 2302. In this particular example, a SIM card 2084 may be inserted directly into the SIM card port 2080, while in other examples a SIM card tray (such as the one shown in FIG. 20B) may be used to connect the SIM card 2084 to the metal contacts within the SIM card port 2080. In some embodiments, the SIM card port 2080 and/or the SIM card tray 2082 may be configured to receive a standard SIM card, mini SIM card, micro SIM card, nano SIM card, or other similar wireless identification/authorization card or circuit.

Preferred embodiments can also employ a near field communication (NFC) device located in the tablet, handle or stand, in the transducer probe or in the cart to transmit information or data. Such NFC devices enable transmission of patient identification information, for example.

Figure 24:
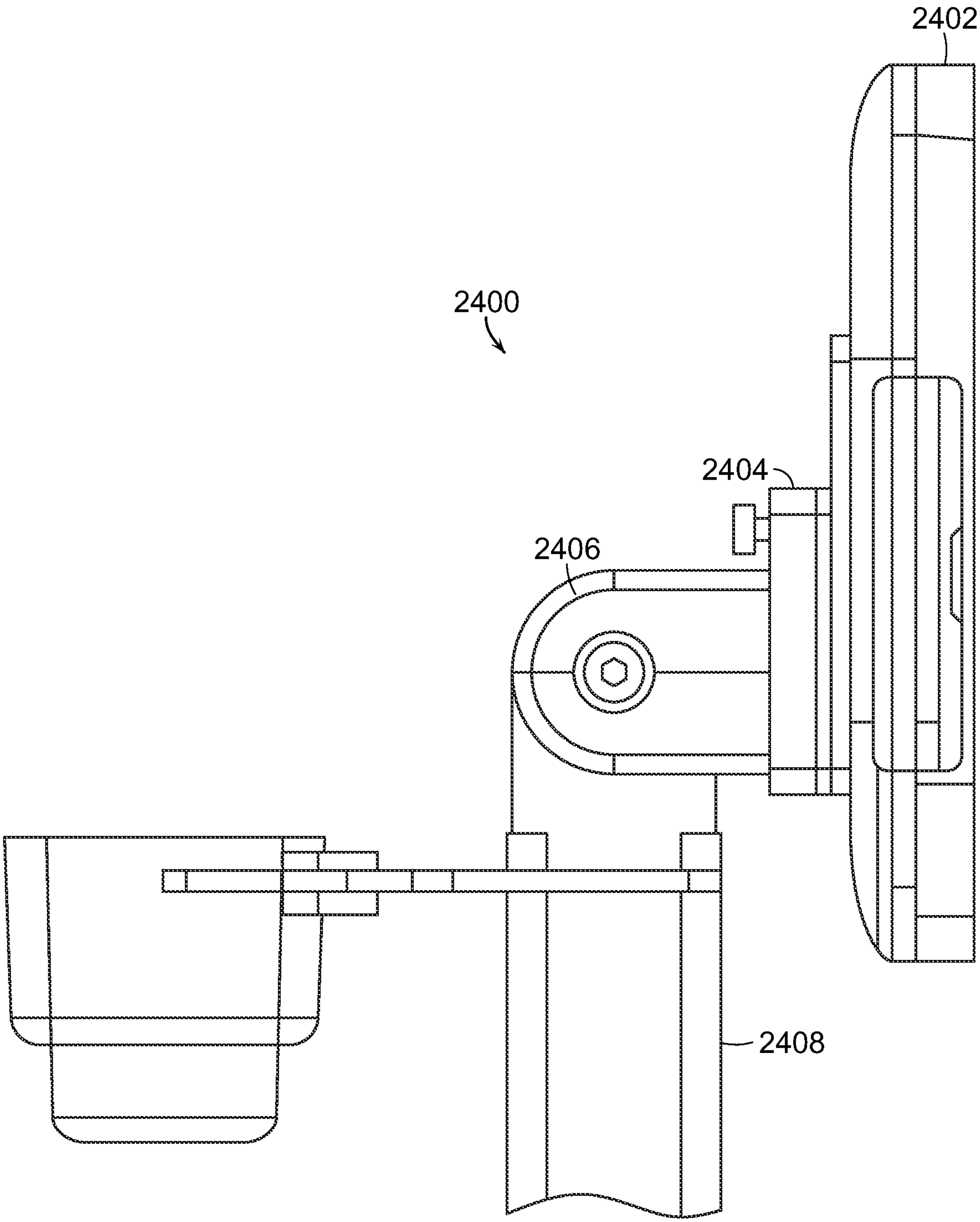
FIG. 24 illustrates preferred cart system for a modular ultrasound imaging system in accordance with preferred embodiments of the invention.

FIG. 24 illustrates preferred cart system 2400 modular ultrasound imaging system in accordance with one embodiment of the invention in which tablet 2402 is connected on mounting assembly 2406 with connector 2404. Arrangement 2400 depicts the tablet 2402, coupled to the vertical support member 2408, via attachment mechanism 2404 without the docking element 2304. Attachment mechanism 2404 may include a hinged member 2406 for display adjustment.

Figure 25A:
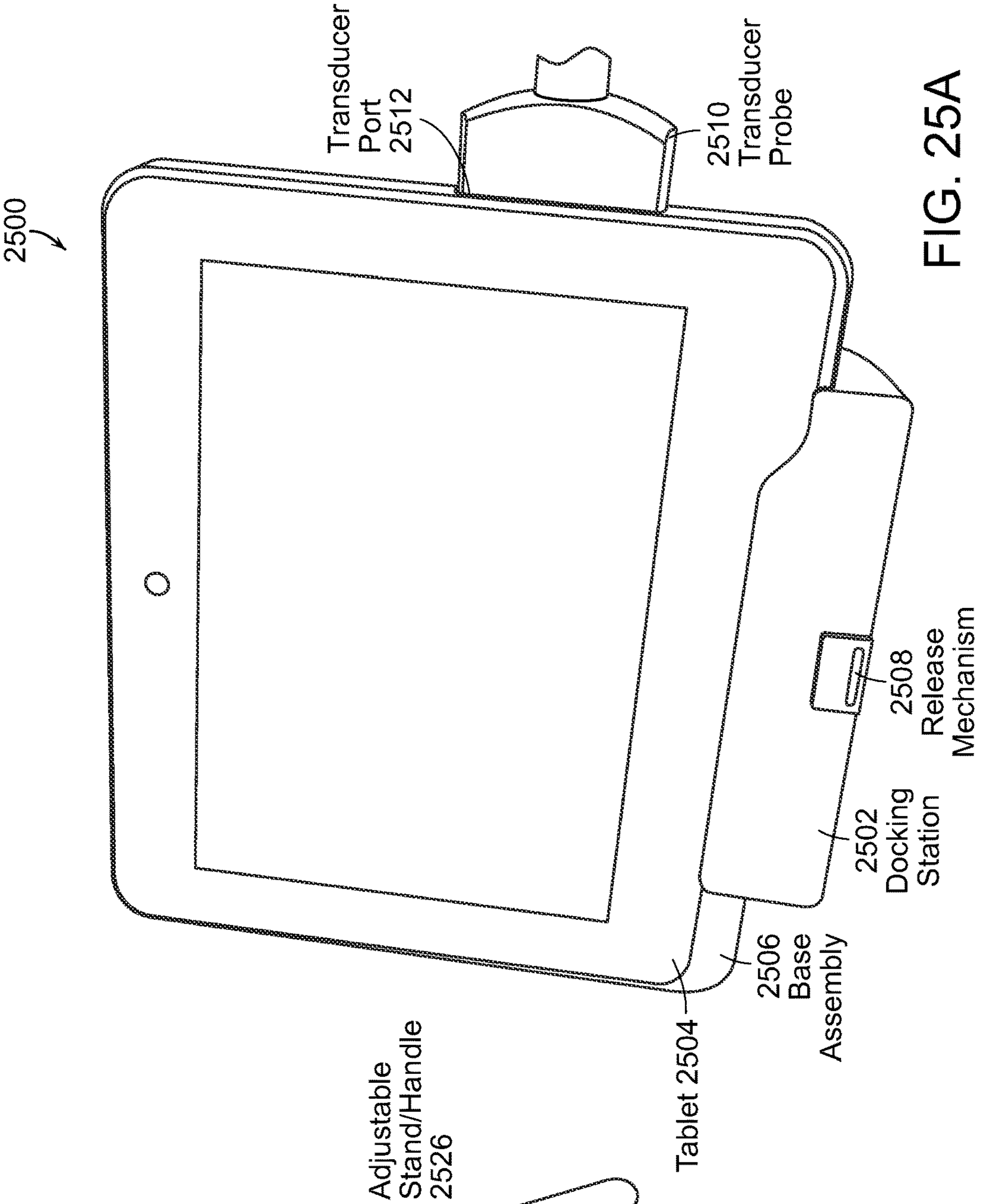
FIGS. 25A-25B illustrate a multifunction docking base for tablet ultrasound device.
Figure 25B:
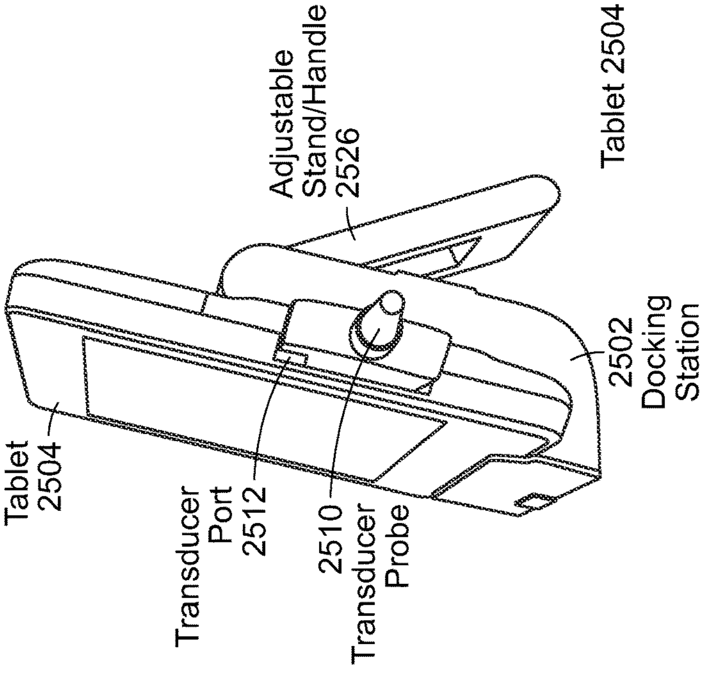

FIGS. 25A and 25B illustrate a multi-function docking station. FIG. 25A illustrates docking station 2502, and tablet 2504, having a base assembly 2506, that mates to the docking station 2502. The tablet 2504, and the docking station 2502, may be electrically connected. The tablet 2504 may be released from docking station 2502, by engaging the release mechanism 2508. The docking station 2502 may contain a transducer port 2512, for connection of a transducer probe 2510. The docking station 2502 can contain 3 USB 3.0 ports, a LAN port, a headphone jack and a power connector for charging. FIG. 25B illustrates a side view of the tablet 2504, and docking station 2502, having a stand in accordance with the preferred embodiments of the present invention. The docking station may include an adjustable stand/handle 2526. The adjustable stand/handle 2526 may be tilted for multiple viewing angles. The adjustable stand/handle 2526 may be flipped up for transport purposes. The side view also illustrates a transducer port 2512, and a transducer probe connector 2510.

The US data therefore, is transmitted to a user computing device 2604 via the standard interface 112, relieving the need for specialized components to be employed in the user computing device 2604. The user computing device 2604 therefore provides an ultrasonic application server which may be integrated with an external application, as will be described further below. The ultrasonic application server running on the user computer device 2604, therefore, receives the US data, and makes it available to be invoked by an external application for further processing. The external application may be either local, and therefore running on the user computer device 2604, or remote, and accessing the ultrasonic application server remotely.

In particular embodiments, the external application is operable to process 2 dimensional and 3 dimensional radiation therapy data, fetal image data, cardiac image data, and image guided surgery data. Such applications are employed in the medical field by operators such as surgeons to provide visual feedback about medical information. For example, fetal image data is used to view a fetus in utero. By employing multidimensional data to provide a visual image, conditions such as birth defects, treatable ailments, gender, size, and others can be determined. Similarly, radiation therapy data may be employed to simultaneously display information about the direction and intensity of radiation treatment, and a visual image of the treatment area. Such visual image data may also be employed in image guided surgery, to indicate the location of a surgical instrument. Such information is particularly useful in contexts such as brain surgery, where it may not be possible to expose the afflicted area.

Figure 25C:
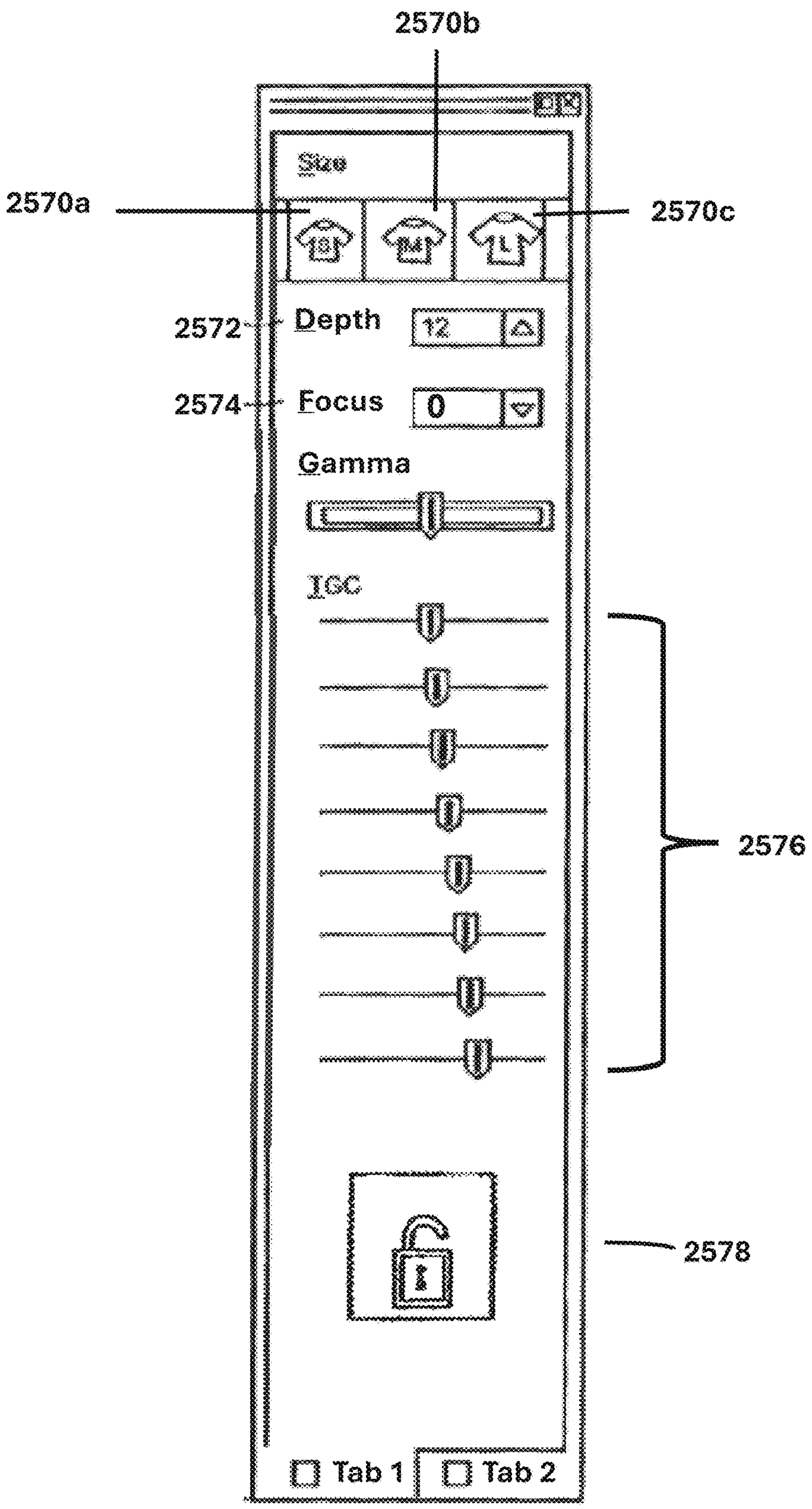
FIG. 25C shows a graphical user interface (GUI) for use with an ultrasonic imaging system as defined herein.

The ultrasonic application server also includes a graphical user interface for manipulating operations without accessing the external application. Referring to FIG. 25C, a control bar 2578 of a top level GUI screen is shown. The control bar allows manipulation of tools affecting image settings of the display via image control presets. The image settings are controlled for each of three sizes small 2570*a*, medium 2570*b*, and large 2570*c*. For each size, the image settings within that size may be controlled, including depth 2572, focus 2574, and time gain compensation 2576. Each of these settings may be saved under a user defined name for later recall. The user clicks on a save button and is prompted to enter a file name. Each of the three sets of image settings corresponding to the size settings 2570*a*, 2570*b*, and 2570*c* is then stored corresponding to the file name, and may be recalled by the user at a later time.

Those skilled in the art should readily appreciate that the programs defining the operations and methods defined herein are deliverable to a user computing device and a remote computing device in many forms, including but not limited to a) information permanently stored on non-writeable storage media such as ROM devices, b) information alterably stored on writeable storage media such as floppy disks, magnetic tapes, CDs, RAM devices, and other magnetic and optical media, or c) information conveyed to a computer through communication media, for example using baseband signaling or broadband signaling techniques, as in an electronic network such as the Internet or telephone modem lines. The operations and methods may be implemented in a software executable by a processor or as a set of instructions embedded in a carrier wave. Alternatively, the operations and methods may be embodied in whole or in part using hardware components, such as Application Specific Integrated Circuits (ASICs), state machines, controllers or other hardware components or devices, or a combination of hardware, software, and firmware components.

Figure 26A:
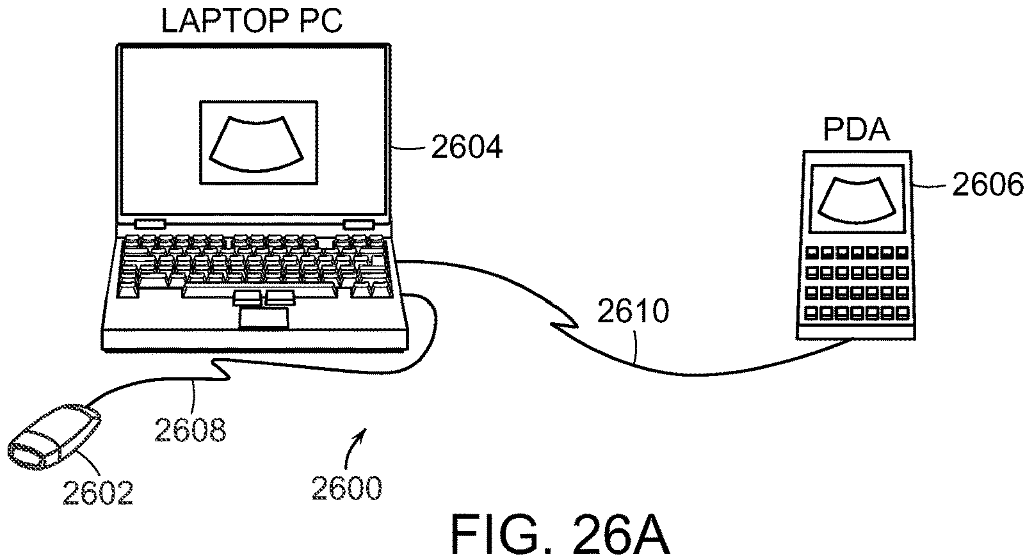
FIG. 26A illustrates an integrated probe system, configured in accordance with an embodiment of the present invention.

Referring to FIG. 26A, the integrated probe system 2600 includes the front end probe 2602, the host computer 2604, and a portable information device such as a personal digital assistant (PDA) 2606. The PDA 2606, such as a Palm Pilot device, or other hand-held computing device is a remote display and/or recording device 2606. In the embodiment shown, the front end probe 2602 is connected to the host computer 2604 by the communication link 2608 that is a wired link. The host computer 2604, a computing device, is connected to the PDA 2606 by a communication link or interface 2610 that is wireless link 2610.

In that the integrated ultrasound probe system 2600 in the embodiment described has a Windows®-based host computer 2604, the system can leverage the extensive selection of software available for the Windows® operating system. One potentially useful application is electronically connecting ultrasound systems allowing physicians to send and receive messages, diagnostic images, instructions, reports or even remotely controlling the front-end probe 2602 using the system.

The connections through the communication links or interfaces 2608 and 2610 can be either wired through an Ethernet or wireless through a wireless communication link such as, but not limited to, IEEE 802.11a, IEEE 802.11b, Hyperlink or HomeRF. FIG. 26A shows a wired link for the communication link 2608 and a wireless link for the communication link 2610. It is recognized that other wired embodiments or protocols can be used.

The wireless communication link 2610 can use various different protocols, such as, an RF link which may be implemented using all or parts of a specialized protocol, such as the IEEE 1394 protocol stack or Bluetooth system protocol stack. IEEE 1394 is a preferred interface for high bandwidth applications such as high quality digital video editing of ultrasonic imaging data. The Bluetooth protocol uses a combination of circuit and packet switching. Slots can be reserved for synchronous packets. Bluetooth can support an asynchronous data channel, up to three simultaneous synchronous channels, or a channel which simultaneously supports asynchronous data and synchronous voice. Each synchronous channel support a 64 kb/s synchronous (voice) channel in each direction. The asynchronous channel can support maximal 723.2 kb/s asymmetric, or 433.9 kb/s symmetric.

The Bluetooth system consists of a radio unit, a link control unit, and a support unit for link management and host terminal interface functions. The link controller carries out the baseband protocols and other low-level link routines.

The Bluetooth system provides a point-to-point connection (only two Bluetooth units involved), or a point-to-multipoint connection. In the point-to-multipoint connection, the channel is shared among several Bluetooth units. Two or more units sharing the same channel form a piconet. One Bluetooth unit acts as the master of the piconet, whereas the other units act as slaves. Up to seven slaves can be active in a piconet.

The Bluetooth link controller has two major states: STANDBY and CONNECTION, in addition, there are seven substates, page, page scan, inquiry, inquiry scan, master response, slave response, and inquiry response. The substates are interim states that are used to add new slaves to a piconet.

The link may also be implemented using, but not limited to, Home RF, or the IEEE 802.11 wireless LAN specification. For more information on the IEEE 802.11 Wireless LAN specification, see the IEEE standard for Wireless LAN incorporated herein by reference. IEEE standards can be found on the World Wide Web at the Universal Resource Locator (URL) www.ieee.org. For example, hardware supporting IEEE standard 802.11b provides a communications link between two personal computers at 2 and 11 Mbps. The frequency bands allocated for transmission and reception of the signals is approximately 2.4 GHz. In comparison, IEEE standard 802.11a provides 54 Mbps communications. The frequency allocation for this standard is around 5 GHz. Recently, vendors, such as Proxim, have manufactured PC Cards and access points (basestations) that use a proprietary data-doubling, chipset, technology to achieve 108 Mbps communications. The chip that provides the data doubling (the AR5000) is manufactured by Atheros Communications. As with any radio system, the actual data rate maintained between two computers is related to the physical distance between the transmitter and receiver.

The wireless link 2610 can also take on other forms, such as, an infrared communications link as defined by the Infrared Data Association (IrDA). Depending on the type of communication desired (i.e., Bluetooth, Infrared, RFID, or NFC device, etc.) the host computer 5 and the remote display and/or recording device 9 each has the desired communication port.

Figure 26B:
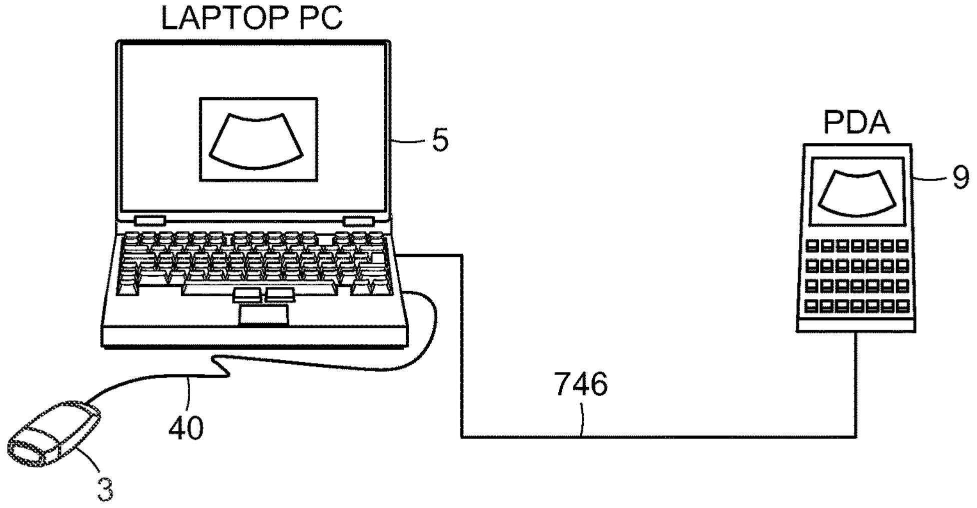
FIG. 26B illustrates a wireless communication link between the probe and host computer, in accordance with an embodiment of the present invention.

FIG. 26B shows the communication link 2608 between the probe 3 and the host computer 5 as a wireless link. The communication link 2610 between the host computer 2604 and the PDA 2606 is shown as a wired link.

Figure 26C:
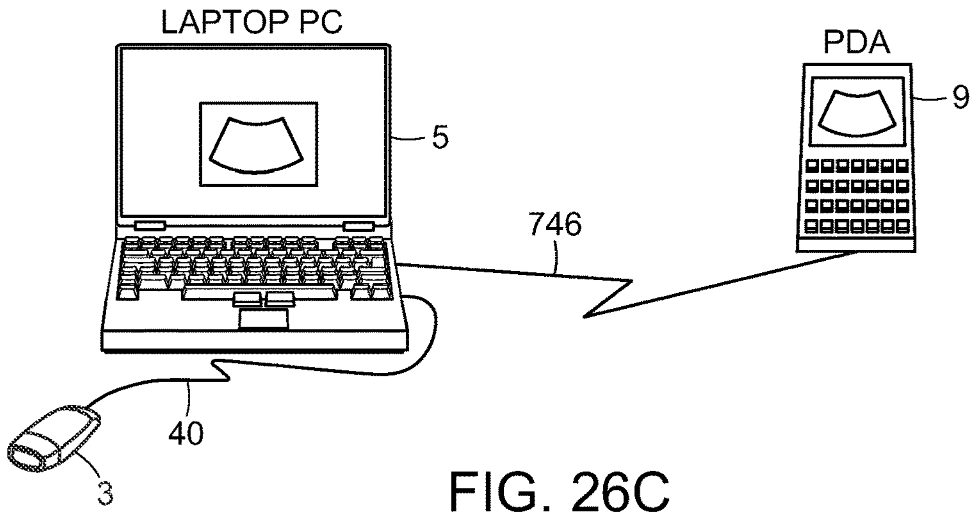
FIG. 26C illustrates a wireless ultrasound system, in accordance with an embodiment of the present invention.

The integrated probe system 2600 of FIG. 26C has wireless links for both the communication link 2608 between the probe 2602 and the host computer 2604 and the communication link 2610 between the host computer 2604 and the PDA 2606. It is recognized that wired and wireless links can both be used together or in the alternative, can be exclusively wired links or wireless links in a system 2600.

Figure 27:
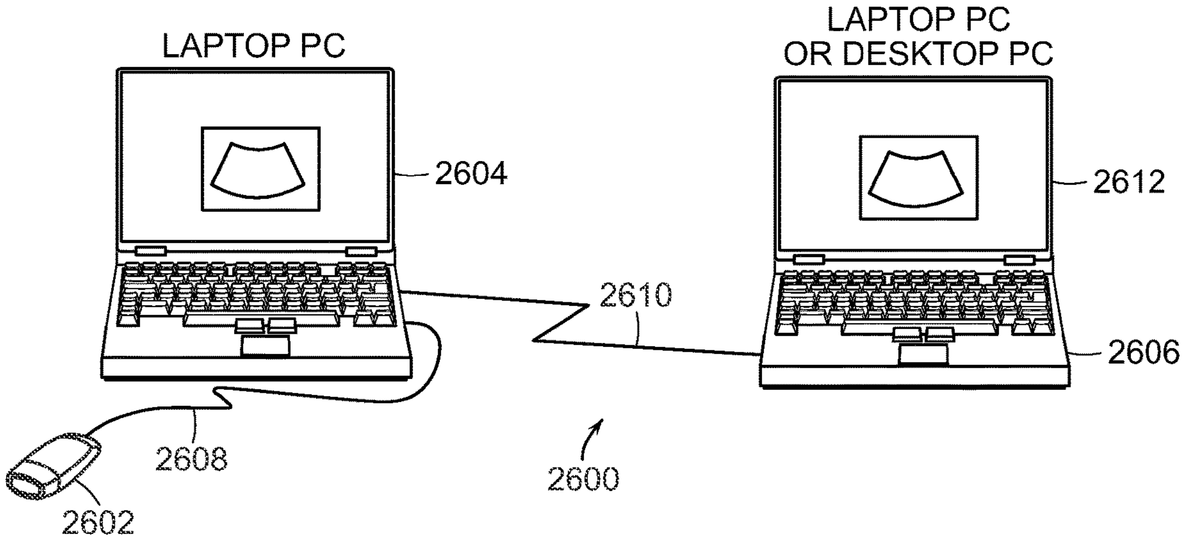
FIG. 27 illustrates an alternative wireless ultrasound system, in accordance with an embodiment of the present invention.

The remote display and/or recording device 2606 of the integrated probe system 2600 of FIG. 27 is a remote computing system 2612. The remote computing system 2612 in addition to having remote display and/or recording capability can also remotely control the probe 2602. The communication link 2610 is shown as a wireless link. The communication link 2608 between the probe 2602 and the host computer 2604 is shown as a wired link.

An example of a remote control system includes using a wearable computer (such as the one manufactured by Xybernaut Corporation), a pair of high-speed, wireless PC Cards (such as those provided by Proxim) and the ultrasound program and the probe 2602. A portable-networked ultrasound system can be configured weighing less than 2.5 pounds. Using a program similar to Microsoft® NetMeeting, a real-time connection between a remote PC and the wearable computer can be established. The remote host can monitor all interactions with the wearable computer, including real-time ultrasound imaging (at display rates up to approximately 4 frames per second). NetMeeting can also be used to "take control" of the wearable computer and manage the ultrasound session from the remote personal computer in real time. In addition, images and iterative executable software instructions that are archived to the hard disk on the wearable computer can be transferred at 108 Mbps to the host computer. With this technology, real time ultrasound diagnoses can be performed and relayed to a remote sight at speeds that rival a hardwired 100 million bits per second (Mbps) local area network (LAN).

Figure 28:
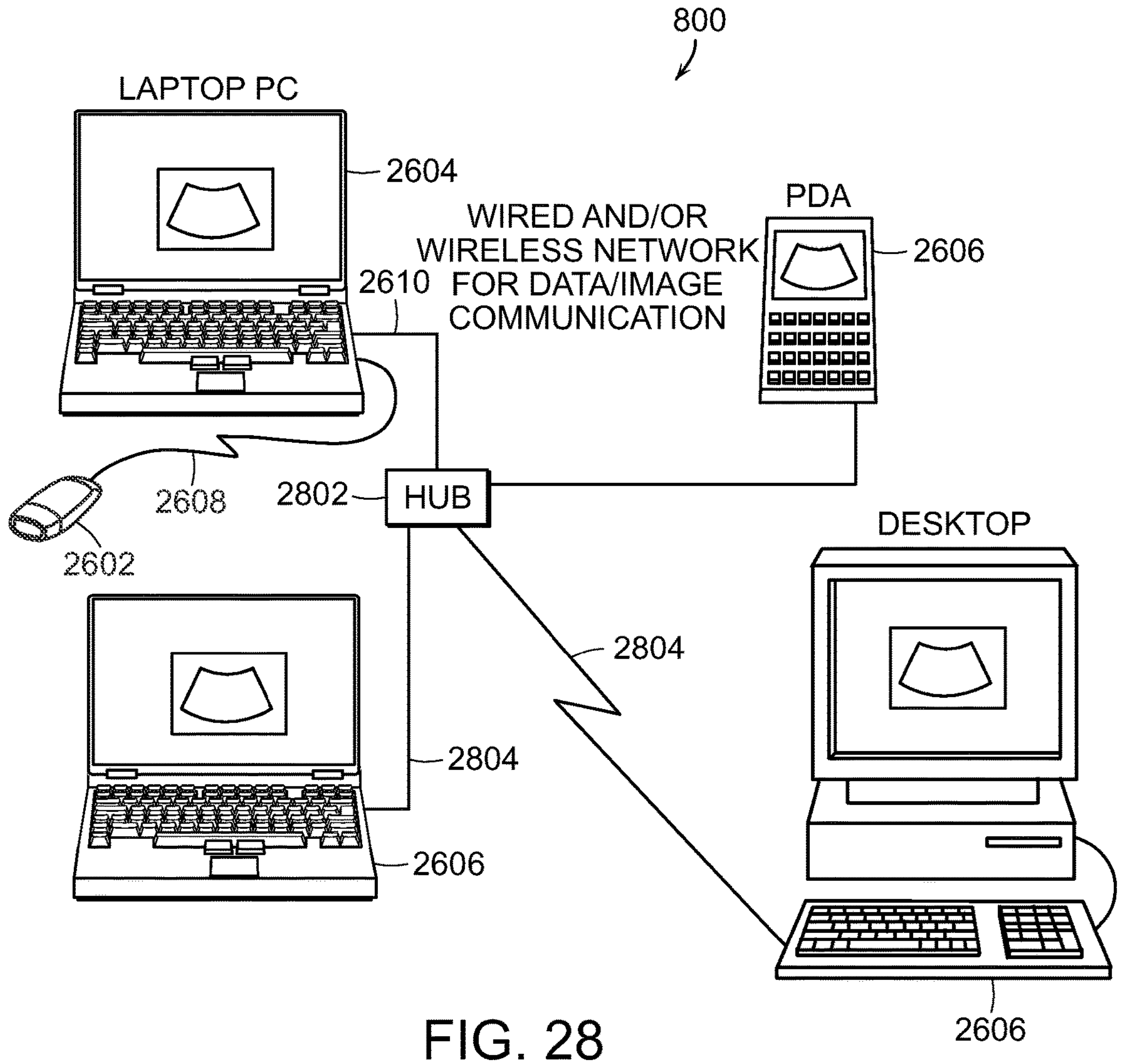
FIG. 28 illustrates an alternate integrated probe system, configured in accordance with another embodiment of the present invention.

FIG. 28 illustrates an integrated probe system 2800 that has a hub 2802 for connecting a plurality of remote devices 2606 to the host computer 2604. The communication link 2804 from the hub 2802 to the remote devices are shown both as wireless and wired links. It is recognized that a completely wired network such as a LAN or Ethernet can be used. In the alternative, with a wireless transceiver and port in each of the computers (remote device) 2606, a wireless Network/Communication system can readily be established. With the recent advent of high-speed wireless standards, such as IEEE 802.11a, the communications between the remote and local machines can rival that of a wired, 100 Mbps local area network (LAN). Another alternative is using a Bluetooth system to form a piconet.

The increasing use of combined audio-visual and computer data is leading to greater need for multimedia networking capabilities and solutions are beginning to emerge that are included in preferred embodiments of the present invention. Standardization of multimedia networking is underway, and IEEE 1394 is emerging as the leading contender, capable of interfacing with a number of audio-visual (AV), computer and other digital consumer electronics and providing transmission bandwidth of up to 400 Mbps.

Preferred embodiments use IEEE 1394 technology which uses a wireless solution for the transmission of 1394 protocols over IEEE 802.11, the emerging standard for wireless data transmission in the corporate environment and increasingly in the home as well. In a preferred embodiment IEEE 1394 is implemented as a Protocol Adaptation Layer (PAL) on top of the 802.11 radio hardware and Ethernet protocols, bringing together a convergence of these important technologies. This protocol adaptation layer enables the PC to function as a wireless 1394 device. The engineering goal is for real delivered IEEE 1394 bandwidth sufficient for the transmission of a single high-definition MPEG2 video stream (or multiple standard-definition MPEG2 video streams) from one room in a facility to another.

Preferred embodiments of the present invention include the use of wireless transmission of IEEE 1394 at 2.4 GHz using Wi-LAN's Wideband Orthogonal Frequency Division Multiplexing (W-OFDM) technology. This development establishes W-OFDM, the most bandwidth-efficient wireless transmission technology, as one of the technologies capable of providing data rates necessary for in-home multimedia networking.

The Wireless IEEE 1394 system includes an MPEG-2 data stream generator, which feeds a multiple transport stream into a Set Top Box (STB) such as provided by Philips Semiconductors. The STB converts this signal to an IEEE 1394 data stream and applies it to the W-OFDM radio system such as provided by Wi-LAN™. The radio transmitter then sends the IEEE 1394 data stream over the air to the corresponding W-OFDM receiver in the host computer, for example. On the receive side, the IEEE 1394 signal is demodulated and sent to two STBs, which display the content of the different MPEG-2 data streams on two separate TV monitors. Using IEEE 1394 as the interface for the wired part of the network optimizes the entire system for transmission of isochronous information (voice, live video) and provides an ideal interface to multimedia devices in the facility. W-OFDM technology is inherently immune to the effects of multipath Like all modulation schemes, OFDM encodes data inside a radio frequency (RF) signal. Radio communications are often obstructed by occurring noise, stray and reflected signals. By sending high-speed signals concurrently on different frequencies, OFDM technology offers robust communications. OFDM-enabled systems are highly tolerant to noise and multipath, making wide-area and in-home multi-point coverage possible. Additionally, as these systems are very efficient in use of bandwidth, many more high-speed channels are possible within a frequency band. W-OFDM is a cost-effective variation of OFDM that allows much larger throughputs than conventional OFDM by using a broad frequency band. W-OFDM further processes the signal to maximize the range. These improvements to conventional OFDM result in the dramatically increased transmission speeds.

OFDM technology is becoming increasingly more visible as American and European standardization committees are choosing it as the only technology capable of providing reliable wireless high data rate connections. European terrestrial digital video broadcasting uses OFDM and the IEEE 802.11 working group recently selected OFDM in its proposed 6 to 54 Mbps wireless LAN standard. The European Telecommunications Standards Institute is considering W-OFDM for the ETSI BRAN standard. Detailed information on Wi-LAN™ can be found on the Web at http://www.wi-lan.com/Philips Semiconductors, a division of Royal Philips Electronics, headquartered in Eindhoven, The Netherlands. Additional information on Philips Semiconductors can be obtained by accessing its home page at http://www.semiconductors.philips.com/.

Further, NEC Corporation's wireless transmission technology based on the IEEE 1394 high-speed serial bus capable of 400 megabits (Mbps), at transmission ranges of up to 7 meters through interior walls and up to 12 meters by line-of-sight may also be used in preferred embodiments. This embodiment uses 60 GHz millimeter wavelength transmissions, which does not require any kind of license, with the amplitude shift keying (ASK) modulation scheme and the development of a low cost transceiver. This embodiment incorporates an echo detection function in NEC's PD72880

400 Mbps long-distance transmission physical layer device, to prevent the influence of signal reflections, a significant obstacle to stable operation of IEEE 1394 over a wireless connection.

Wireless IEEE 1394 can play an important role in bridging the PC to clusters of interconnected IEEE 1394 devices, which can be in another room in the facility. Three example applications are sourcing video or audio stream from a PC, providing internet content and connectivity to a IEEE 1394 cluster, and provide command, control and configuration capabilities to the cluster. In the first embodiment, the PC may provide data to someone in another room in a facility. In the second embodiment, the PC may provide an avenue for 1394 enabled devices to access the Internet. In the third embodiment, the PC plays the role of orchestrating activities in the 1394 clusters and routing data within the clusters and over bridges—though the actual data does not flow through the PC.

Figure 29:
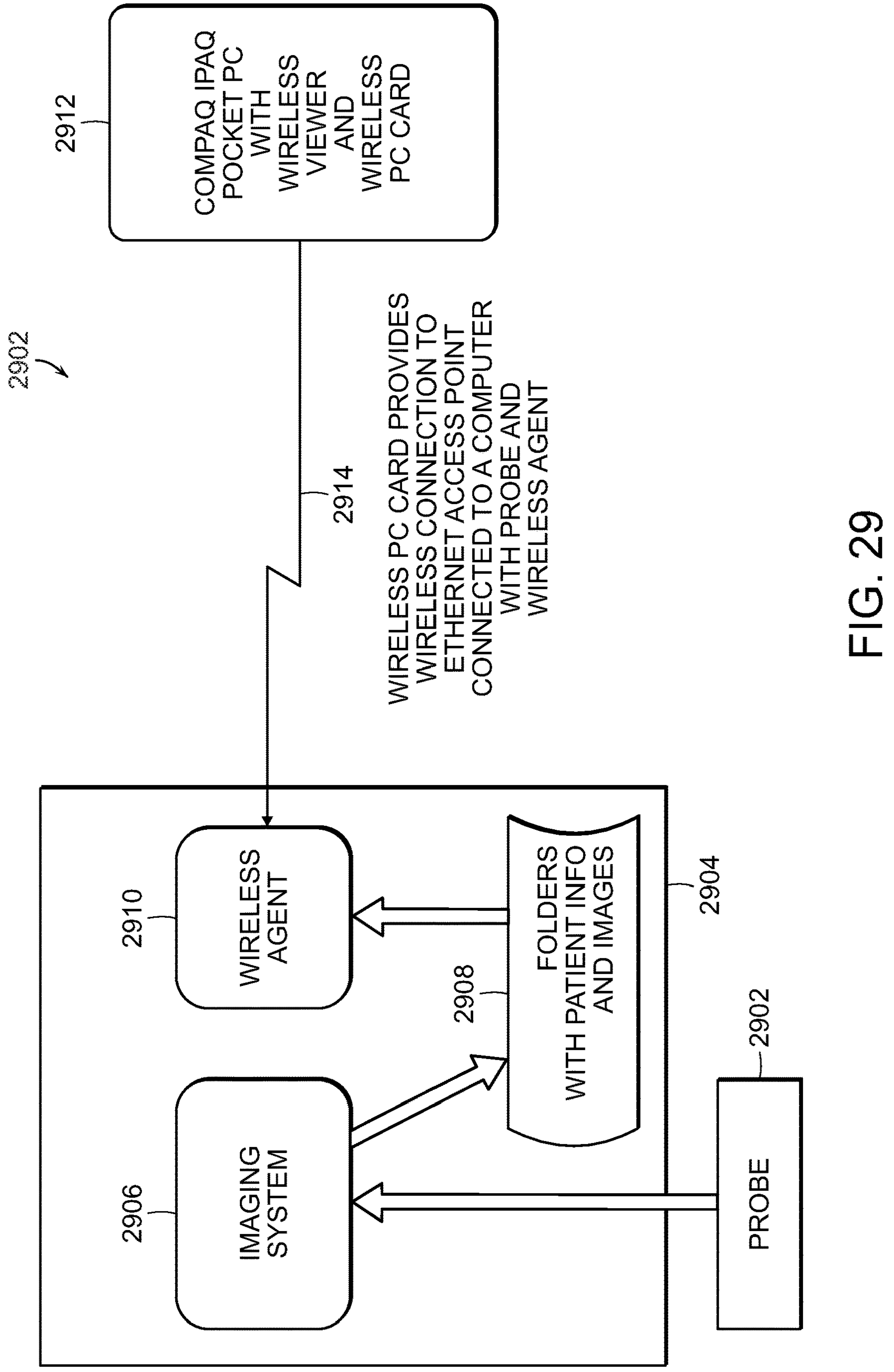
FIG. 29 illustrates the provision of wireless access to the images created by an ultrasound imaging system, in accordance with an embodiment of the present invention.

FIG. 29 is a diagram showing the provision of wireless access to the images created by a preferred embodiment ultrasound imaging system and the associated architecture. The imaging system 2906 exports patient information and images to files in corresponding folders. Executable software instructions have all functionality required to implement the ultrasonic imaging methods described hereinbefore.

The wireless agent 2910 serves to detect patient directories and image files and opens a port for wireless clients to get connection thereto. Upon establishing a connection it sends back to the client list of patients and corresponding images. For example, the wireless agent 2910 may include data interface circuitry which may include a first port such as a RF interface port.

The wireless viewer 2912 residing on a handheld side can establish connection to the wireless agent 2910 and retrieve patient and image information. Upon user selection of the patient and image it initiates file transmission from the wireless agent. Upon receiving an image the Viewer 2912 displays this image along with patient information. The image gets stored on the handheld for future use. The handheld user can view images retrieved in previous sessions or can request new image transmission.

Figure 33:
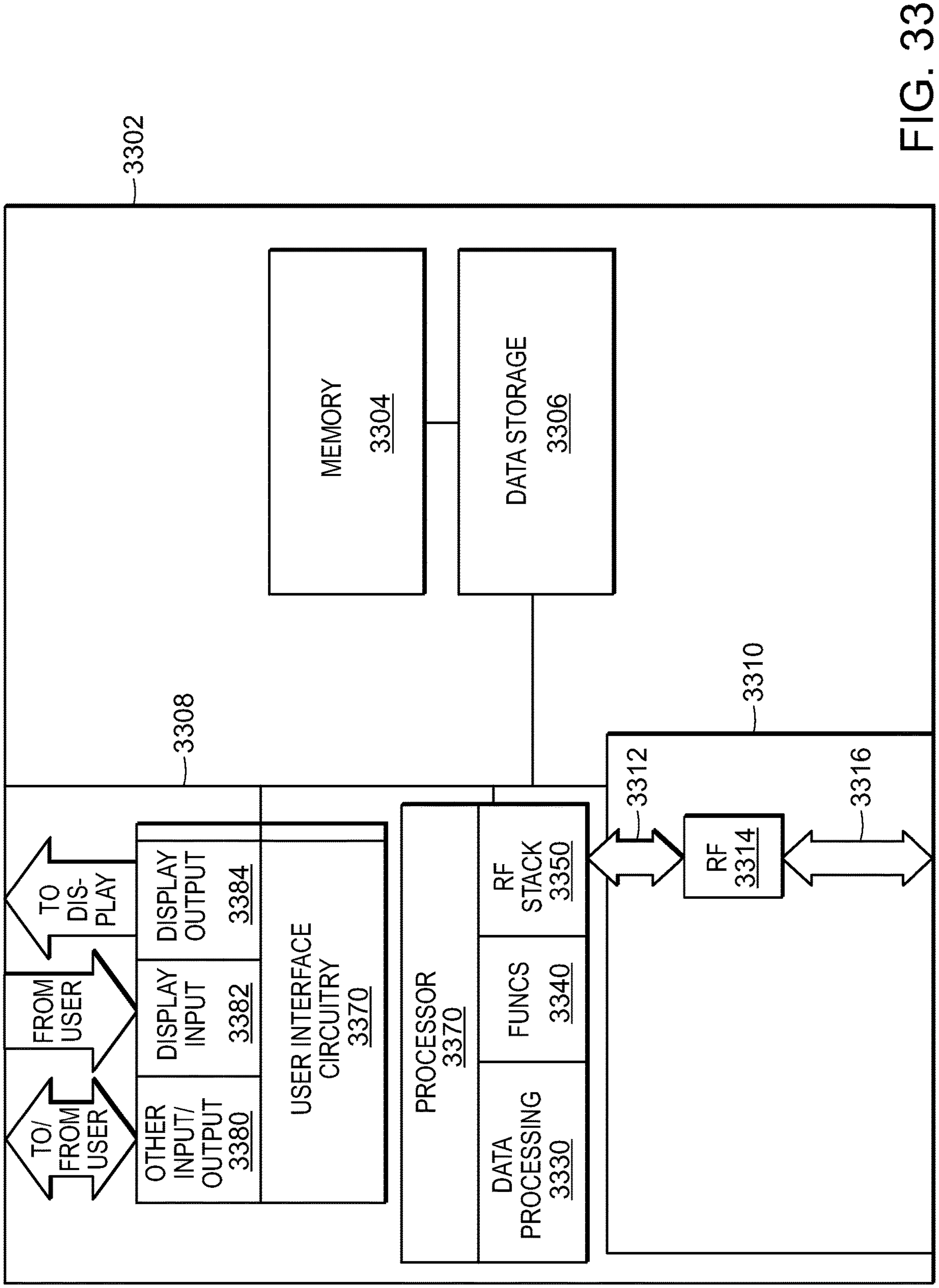
FIG. 33 illustrates data processing and storage systems for wireless operations.

FIG. 33 is a block diagram illustrating a portable information device such as a personal digital assistant (PDA) or any computing device according to an exemplary embodiment of the present invention. The link interface or data interface circuitry 3310 illustrates, but is not limited to, one link interface for establishing a wireless link to another device. The wireless link is preferable an RF link, defined by IEEE 1394 communications specifications. However, the wireless link can take on other forms, such as the infrared communications link as defined by the Infrared Data Association (IrDA). The PDA includes a processor 3360 that is capable of executing an RF stack 3350 that communicates with a data interface circuitry 3310 through bus 3308. The processor 3360 is also connected through bus 3308 to user interface circuitry 3370, data storage 3306 and memory 3304.

The data interface circuitry 3310 includes a port such as the RF interface port. The RF link interface may include a first connection 3312 which includes radio-frequency (RF) circuitry 3314 for converting signals into radio-frequency output and for accepting radio-frequency input. The RF circuitry 3314 can send and receive RF data communications via a transceiver that establishes communication port 1026. RF communication signals received by the RF circuitry 3314 are converted into electrical signals and relayed to the RF stack 3350 in processor 3360 via bus 3308. The radio interface 3314, 3316 and the link between the laptop PC (host computer) and the PDA may be implemented by, without limitation, IEEE 1394 specifications.

Similarly, the PC host computer has a RF stack and circuitry to be able to communicate to the remotely located image viewer. In a preferred embodiment, the remote image viewer may be used to monitor and/or control the ultrasonic imaging operations not just display the resultant imaging data.

The current market offers a lot of different options related to wireless connectivity. In a preferred embodiment, spread-spectrum technology Wireless LAN is used. Among wireless LAN solutions the most advanced is the 802.11b standard. Many manufacturers offer 802.11b compliant equipment. Compatibility with the selected handheld is the major criteria in a specified class of wireless connectivity options.

The handheld market offers various handheld devices as well. For imaging purposes it is very important to have high quality screen and enough processing power to display an image. Considering these factors, in a preferred embodiment, a Compaq iPAQ is used, in particular a Compaq iPAQ 3870 is used. A wireless PC card compatible with the handheld is used such as Compaq's Wireless PC Card WL110 and corresponding Wireless Access Point.

FIG. 30 illustrates the image viewer 3020 in communication with the personal computer in a preferred embodiment or the probe in an alternate embodiment. The image viewer has user interface buttons 3022, 3024, 3026, 3028 that allow the user to interface with the ultrasonic imaging system computer or probe in accordance with preferred embodiments of the present invention. In a preferred embodiment, a communicating interface such as button 3022 allows the user to initiate a connection with the ultrasonic imaging application. Similarly, button 3024 is used to terminate an established connection with the ultrasonic imaging application. A button 3026 functions as a selection button that is used to provide a list of patients and corresponding images that are selectable. These images are either stored locally or remotely. If selected, the image that may be stored remotely is transmitted to the viewer. The selected image is displayed on the viewer 3030.

Additional communication interface buttons such as button 3028 functions as an options button which may, but is not limited to, allow changing configuration parameters such as an internet protocol (IP) address.

Figure 31:
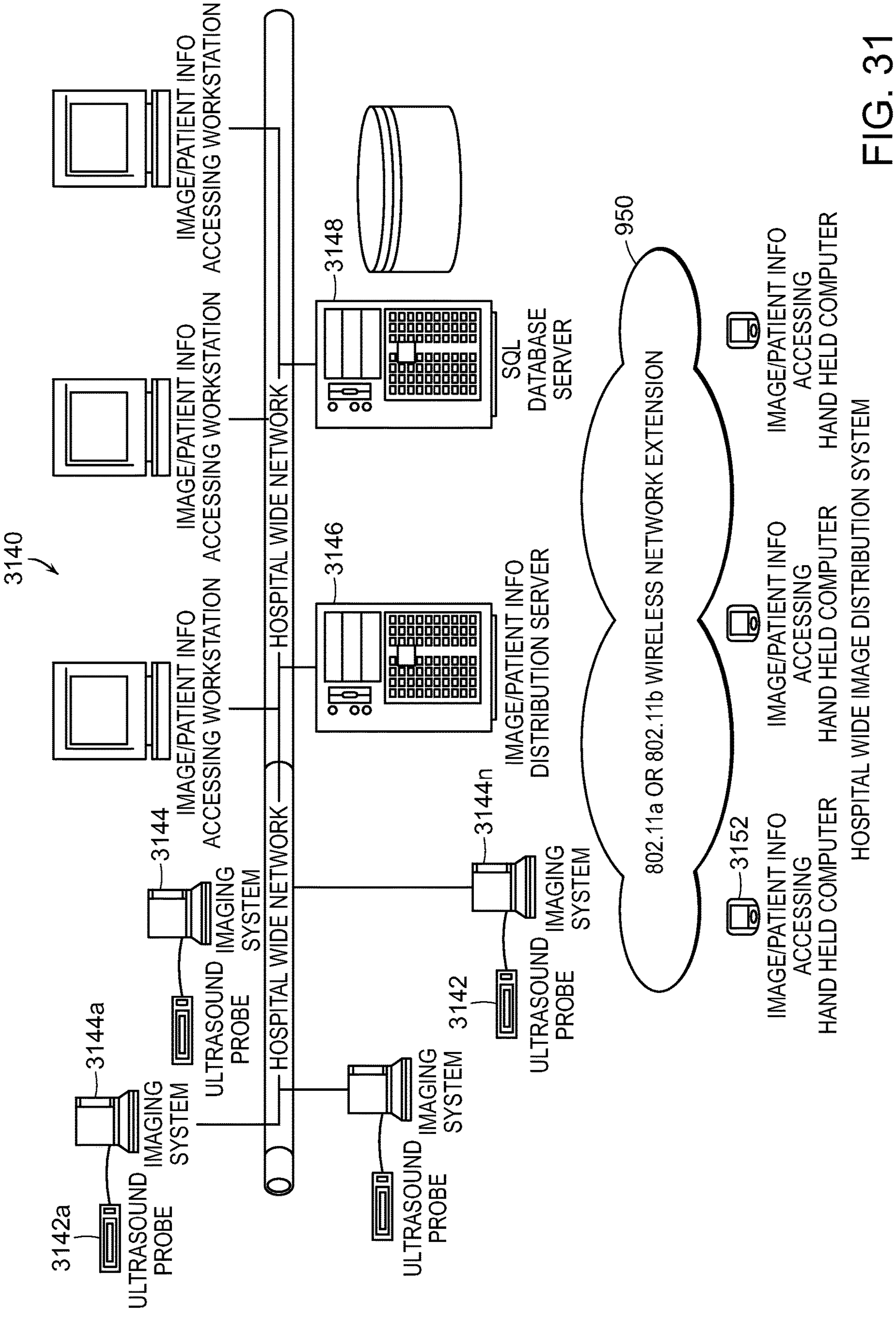
FIG. 31 illustrates an exemplary ultrasound image collection and distribution system.

FIG. 31 is a diagram illustrating a preferred embodiment ultrasound image collection and distribution system including four major software components. The main hardware element of the system is ultrasound probe 3142*a* . . . *n*. The probe in communication with the laptop computer 3144*a* . . . *n* allows generation of the ultrasound images and related patient information and submits images and information to an image/patient information distribution server 3146. The distribution server utilizes an SQL database server 3148 to store and retrieve images and related patient information. The SQL server provides distributed database management. Multiple workstations can manipulate data stored on the server, and the server coordinates operations and performs resource-intensive calculations.

Image viewing software or executable instructions may be implemented in two different embodiments. In a first embodiment, a full stationary version of the Image Viewer as described in FIG. 30 may reside on a workstation or laptop computer equipped with high bandwidth network connection. In a second embodiment, a light weight version of the Image Viewer may reside on a small PocketPC handheld 952 equipped with IEEE 802.11b and/or IEEE 802.11a compliant network card. The PocketPC image viewer implements only limited functionality allowing basic image viewing operations. The wireless network protocols 3150 such as IEEE 802.11 may be used to transmit information to a handheld or other computing devices 3152 in communication with a hospital network.

This preferred embodiment describes the ultrasound imaging system to cover hospital wide image collecting and retrieving needs. It also provides instant access to non-image patient related information. In order to provide inter-hospital information exchange, image distribution servers have the ability to maintain connectivity with each other across wide area networks.

Figure 32:
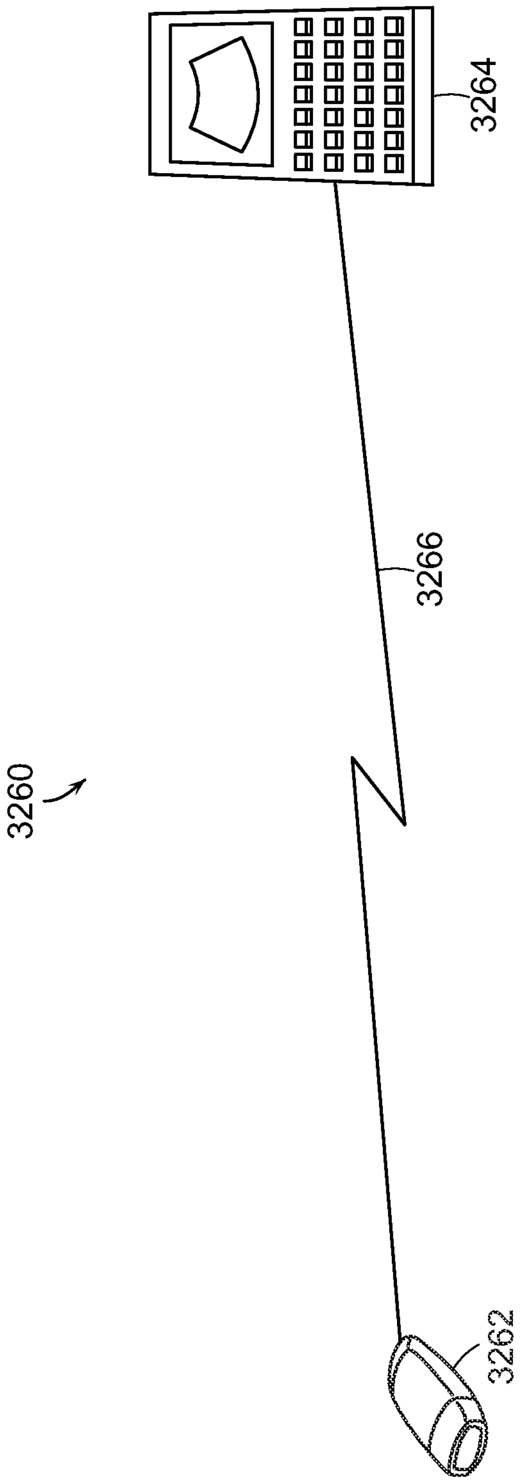
FIG. 32 illustrates an ultrasound imaging system with a wireless communication link between the remote computing device and the probe, in accordance with an embodiment of the present invention.

In another preferred embodiment, the probe may directly communicate with a remote computing device such as a PDA 3264 using a wireless communication link 3266, as shown in FIG. 32. The communication link may use the IEEE 1394 protocol. The probe and the PDA both have an RF stack and circuitry described with respect to FIG. 33 to communicate using wireless protocols. The probe includes a transducer array, beamforming circuitry, transmit/receive module, a system controller and digital communication control circuitry. Post processing of the ultrasonic image data including scan conversion is provided in the PDA.

Figure 34:
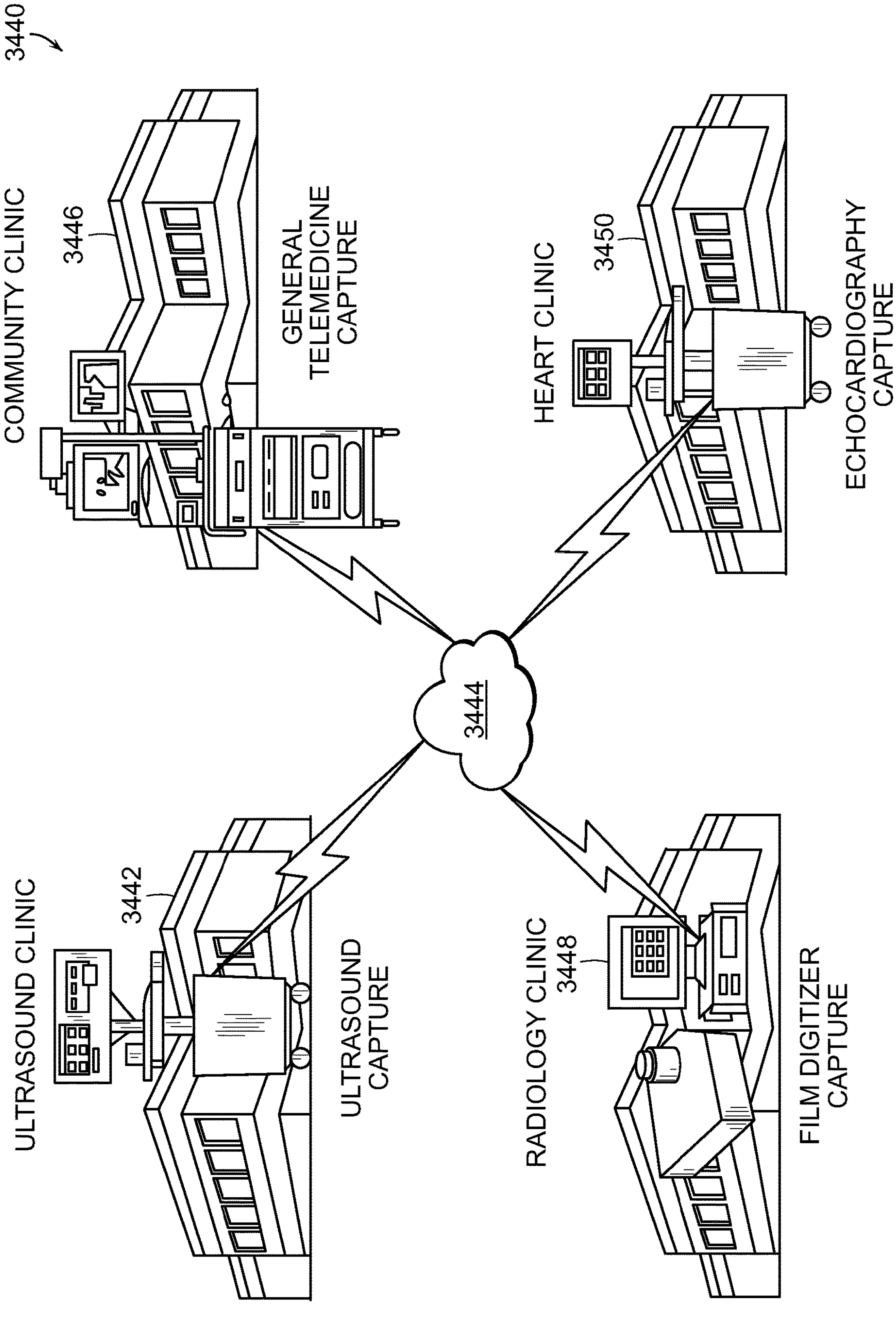
FIG. 34 is a schematic diagram illustrating an imaging and telemedicine system integrating an ultrasound system, in accordance with an embodiment of the present invention.

FIG. 34 is a schematic diagram 3440 illustrating an imaging and telemedicine system integrating the ultrasound system in accordance with a preferred embodiment of the present invention. Preferred embodiments of the system output the real-time RE digital data or the front-end data.

As will be appreciated, the various wireless connections described herein, such as the connection 3444 between clinics 3442, 3446, 3448, and 3450; as well as the connections shown in FIGS. 26A-29 and FIGS. 31-32, may include 3G, 4G, GSM, CDMA, CDMA 2000, W-CDMA, or any other suitable wireless connection using any number of communication protocols. Thus, preferred embodiments enable connection to cellular base stations for transmission of voice and data including streaming ultrasound video images. The touchscreen display is operative to enable the user to select one of a plurality of addresses that are displayed using a pull down menu for transmission of ultrasound images. The user touch operates displayed icons to select the data for transmission from stored files or images being generated simultaneously for transmission. In some cases, the ultrasound imaging device may be configured to initiate a wireless connection with a remote computer or other electronic device in response to a command from the user performed via the touch sensitive UI of the ultrasound imaging screen. For example, during, before, or after performing an ultrasound procedure a user may initiate a wireless connection with a hospital or doctor in order to transmit ultrasound imaging data. The data may be transmitted in real time as it is being generated, or already-generated data may be transmitted. An audio and/or video connection may also be initiated over the same wireless network such that the user of the ultrasound imaging device may be in contact with a hospital or doctor while performing the procedure. The options described herein may be navigated and/or selected via the touchscreen UI provided on the ultrasound imaging screen. In some embodiments, all or portions of the touchscreen may be provided to the user via the wireless network using, for example, JavaScript or some other browser-based technologies, Portions of the UI may be executed on the device or remotely, and various device-side and/or server-side techniques may be implemented to provide the various UI features described herein.

In a preferred embodiment, the ultrasound imaging system provides an elastographic image of a tissue's elastic properties both in-vitro and in-vivo. Ultrasound elastography is an imaging technique whereby local axial tissue strains are estimated from differential ultrasonic speckle displacements. These displacements are generated by a weak, quasi-static stress field. The resultant strain image is called an elastogram. Most pathological changes are associated with changes in tissue stiffness. Palpation is an effective method for lesion detection and evaluation. Many cancers (breast, prostate) are isoechoic, and hence difficult to detect by ultrasound alone.

Elastography uses the principle by which a small compression (strain) of the tissue results in a small compression of the signal (similar to frequency modulation.) Ultrasound elastography conveys new and clinically important tissue information. The tradeoffs among engineering and elastographic image parameters are now reasonably well understood. Elastography can operate in hypoechoic areas, for example, shadows. Reliable small elastic contrast exists among normal soft-tissue components, good carrier-to-noise ratio (CNR) allows its visualization. Pathology generally exhibits large elastic contrast. Areas that can benefit from the elastography include breast, prostate, vasculature, small parts and treatment monitoring.

Currently, breast cancer is the most frequent cancer in women. Every ninth woman in the U.S. is affected during her lifetime. It is well known that palpation of the breast is a very helpful mean to detect conspicuous lesions. Although a lot of effort is put into screening methods for breast cancer, in the majority of cases the patient herself is the first who notices palpable changes in her breast during self-examination. Although it can support the diagnostics of breast tissue, there is still a need for an imaging modality that can provide a direct measure of material parameters related to tissue elasticity such as Young's modulus. Concerning breast imaging, the elasticity tensor can be reconstructed three-dimensionally using magnetic resonance imaging. A semi-quantitative measure of elasticity with ultrasound has recently become a real-time imaging modality. As described hereinbefore, the strain imaging or elastography method is helpful to describe mechanical properties of tissue in vivo. Elastography compares ultrasonic radio frequency (RF) data of an object before and after the application of a slight compression step. Time delays between the pre- and post-compression RF signals can be estimated and converted to mechanical displacement in the axial direction. The derivative of axial displacement leads to axial strain as a semi-quantitative measure of elastic properties.

The quality of strain images or elastograms is limited by noise due to signal decorrelation in the time delay estimation. One method to minimize this source of error is to apply motor-driven compression plates and to use multi-compression averaging. Another method is to correct for lateral displacements by interpolating A-lines two-dimensionally. For breast imaging, initial clinical results have been published, which indicate that ultrasound elastography has the potential for improving differential diagnosis of benign and malignant breast lesions. Preferred embodiments of the present invention ultrasound systems can be used for ultrasound elastography and provide elastograms which can be used to diagnose benign and malignant lesions.

In accordance with a preferred embodiment, when the suspect lesion is found, a slight compression can be applied to the breast and a palpation performed with the transducer including both compression and relaxation. Usually the system is able to store the last two compression cycles in a cine-buffer of the ultrasound system, including approximately 80 images. In the conventional B-mode it is only possible to record demodulated echo data, i.e., gray-scaled imaged data. In order to acquire RF data for elastography at the same time, a color-mode window of 20×40 mm, i.e., 20 mm depth and 40 mm width can be used. The RF data from the color-mode window, which is usually used to calculate flow parameters, can be recorded as IQ-data (base-band data). Prior to the off-line calculation of strain images, the limited bandwidth of color-mode RF data is compensated for. The ultrasound system is reprogrammed to use broadband transmit pulses and broadband receive filter for the color-mode. After performing time delay estimation on every two successive frames of an IQ-data series, a series of time-delay images or axial displacement images is obtained, respectively.

The purpose of imaging elastic tissue properties using ultrasound elastography is to support the detection, localization and differential diagnosis of lesions. Strain imaging is a semi-quantitative method. Therefore, it is definitely possible to evaluate elastograms qualitatively. A qualitative method for the evaluation of ultrasound elastograms uses a gray-scaled colormap. The appearance (visualization, brightness, margin) and size of each lesion on the elastogram in comparison to the B-mode image, in order to distinguish breast tissues is used. However, the results of a qualitative image analysis depend on the choice of the colormap and image scaling, respectively.

Figure 35:
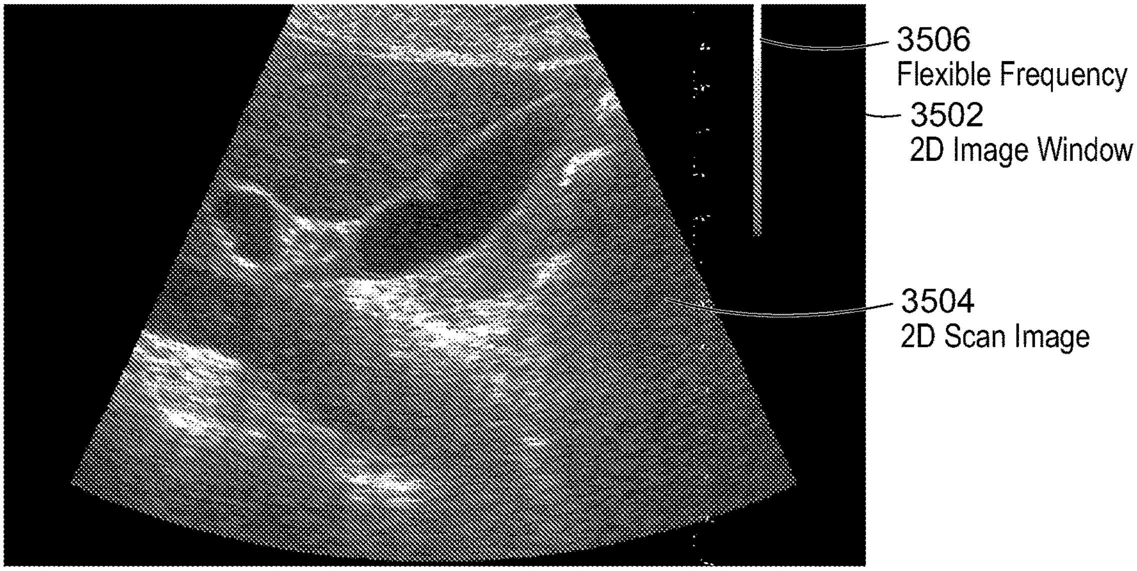
FIG. 35 illustrates a 2D imaging mode of operation with a modular ultrasound imaging system in accordance with one embodiment of the invention.

FIG. 35 illustrates a 2D imaging mode of operation with a modular ultrasound imaging system in accordance with one embodiment of the invention. The touchscreen of table 2504 may display images obtained by 2-dimensional transducer probe using a 256 digital beamformer channels. The 2-dimensional image window 3502 depicts a 2-dimensional image scan 3504. The 2-dimensional image may be obtained using flexible frequency scans 3506, wherein the control parameters are represented on the tablet.

Figure 36:
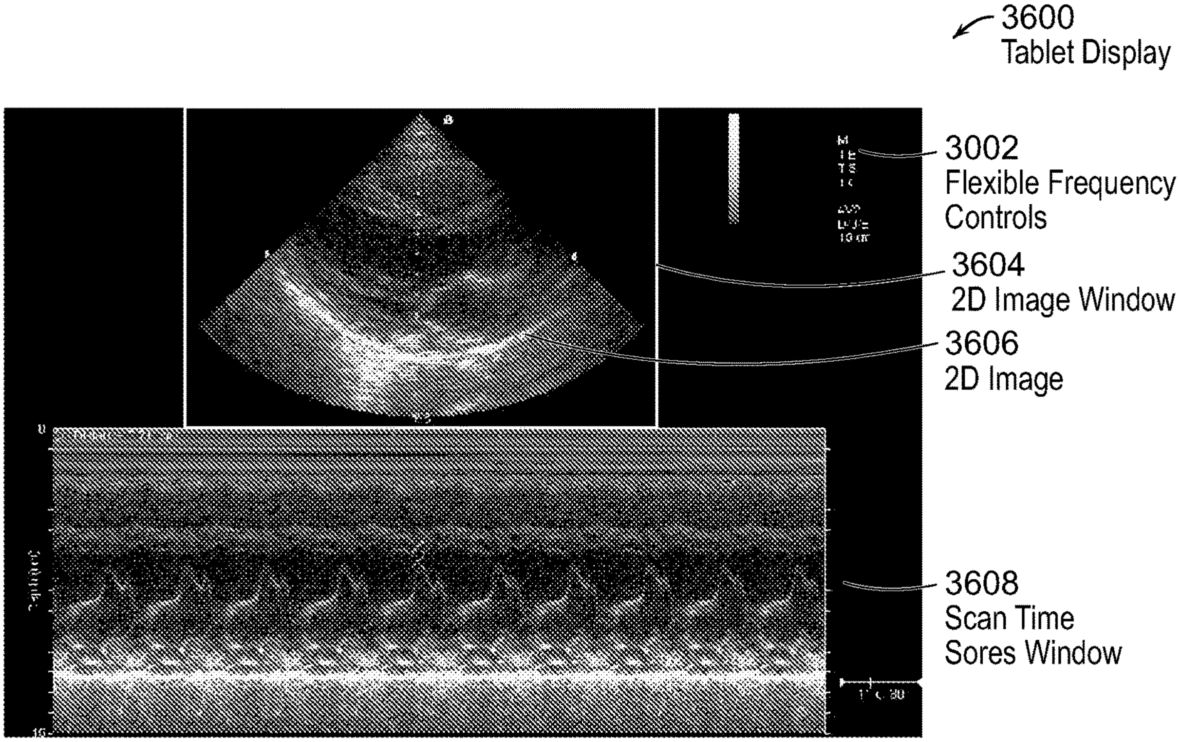
FIG. 36 illustrates a motion mode of operation with a modular ultrasound imaging system in accordance with one embodiment of the invention.

FIG. 36 illustrates a motion mode of operation with a modular ultrasound imaging system in accordance with one embodiment of the invention. The touchscreen display of tablet 3600, may display images obtained by a motion mode of operation. The touchscreen display of tablet 3600, may simultaneously display 2-dimensional 3606, and motion mode imaging 3608. The touchscreen display of tablet 3600, may display a 2-dimensional image window 3604, with a 2-dimensional image 3606. Flexible frequency controls 3602 displayed with the graphical user interface can be used to adjust the frequency from 2 MHz to 12 MHz.

Figure 37:
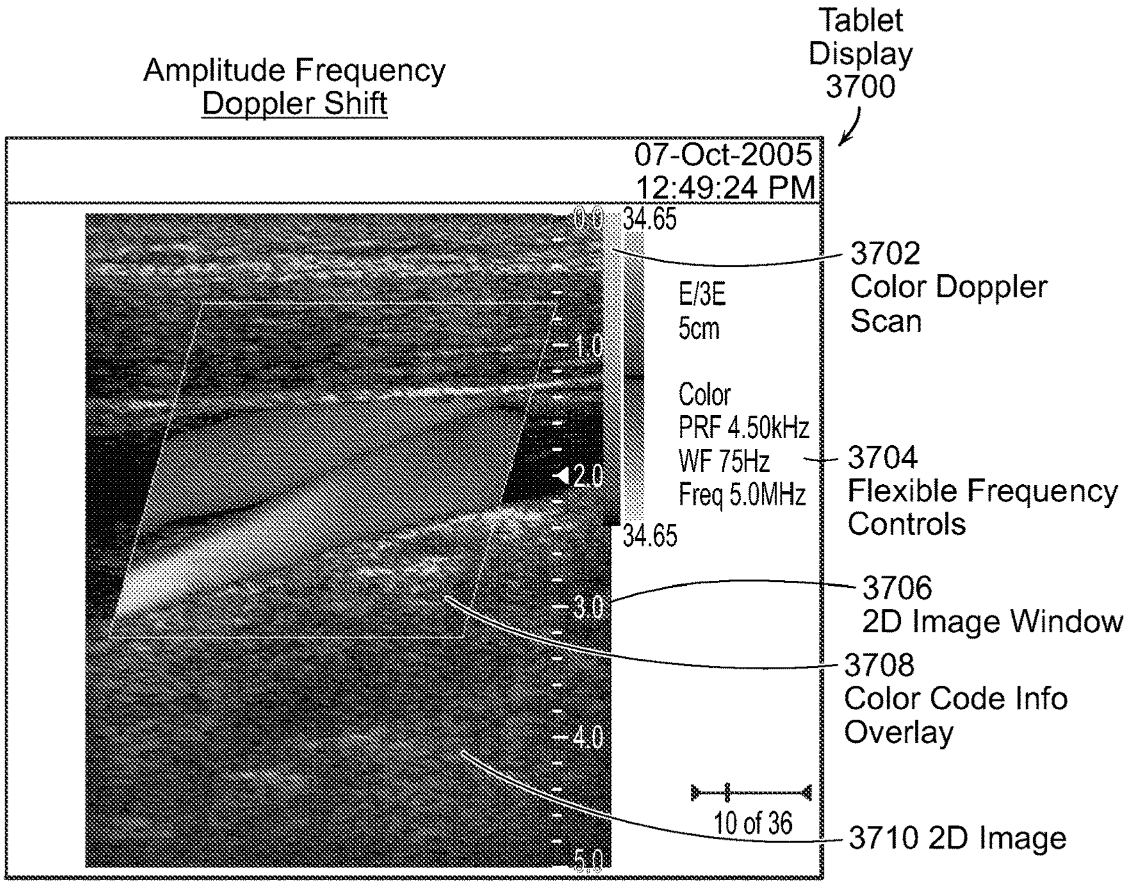
FIG. 37 illustrates a color Doppler mode of operation with a modular ultrasound imaging system in accordance with one embodiment of the invention.

FIG. 37 illustrates a color Doppler mode of operation with a modular ultrasound imaging system in accordance with one embodiment of the invention. The touchscreen display of tablet 3700 displays images obtained by color Doppler mode of operation. A 2-dimensional image window 3706 is used as the base display. The color coded information 3708, is overlaid on the 2-dimensional image 3710. Ultrasound-based imaging of red blood cells are derived from the received echo of the transmitted signal. The primary characteristics of the echo signal are the frequency and the amplitude. Amplitude depends on the amount of moving blood within the volume sampled by the ultrasound beam. A high frame rate or high resolution can be adjusted with the display to control the quality of the scan. Higher frequencies may be generated by rapid flow and can be displayed in lighter colors, while lower frequencies are displayed in darker colors. Flexible frequency controls 3704, and color Doppler scan information 3702, may be displayed on the tablet display 3700.

Figure 38:
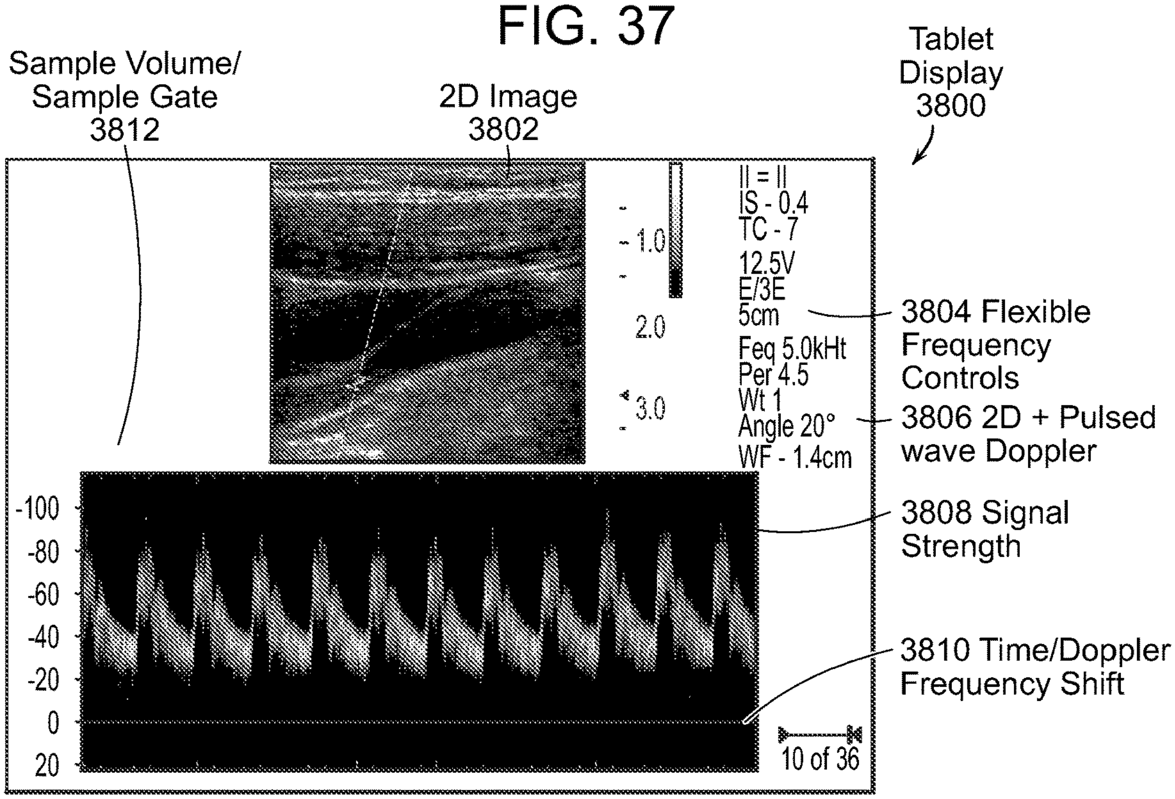
FIG. 38 illustrates a pulsed-wave Doppler mode of operation with a modular ultrasound imaging system in accordance with one embodiment of the invention.

FIG. 38 illustrates a Pulsed wave Doppler mode of operation with a modular ultrasound imaging system in accordance with one embodiment of the invention. The touchscreen display of tablet 3800, may display images obtained by pulsed wave Doppler mode of operation. Pulsed wave Doppler scans produce a series of pulses used to analyse the motion of blood flow in a small region along a desired ultrasound cursor called the sample volume or sample gate 3812. The tablet display 3800 may depict a 2-dimensional image 3802, wherein the sample volume/sample gate 3812 is overlaid. The tablet display 3800 may use a mixed mode of operation 3806, to depict a 2-dimensional image 3802, and a time/doppler frequency shift 3810. The time/doppler frequency shift 3810 can be converted into velocity and flow if an appropriate angle between the beam and blood flow is known. Shades of gray 3808, in the time/doppler frequency shift 3810, may represent the strength of signal. The thickness of the spectral signal may be indicative of laminar or turbulent flow. The tablet display 3800 can depict adjustable frequency controls 3804.

Figure 39:
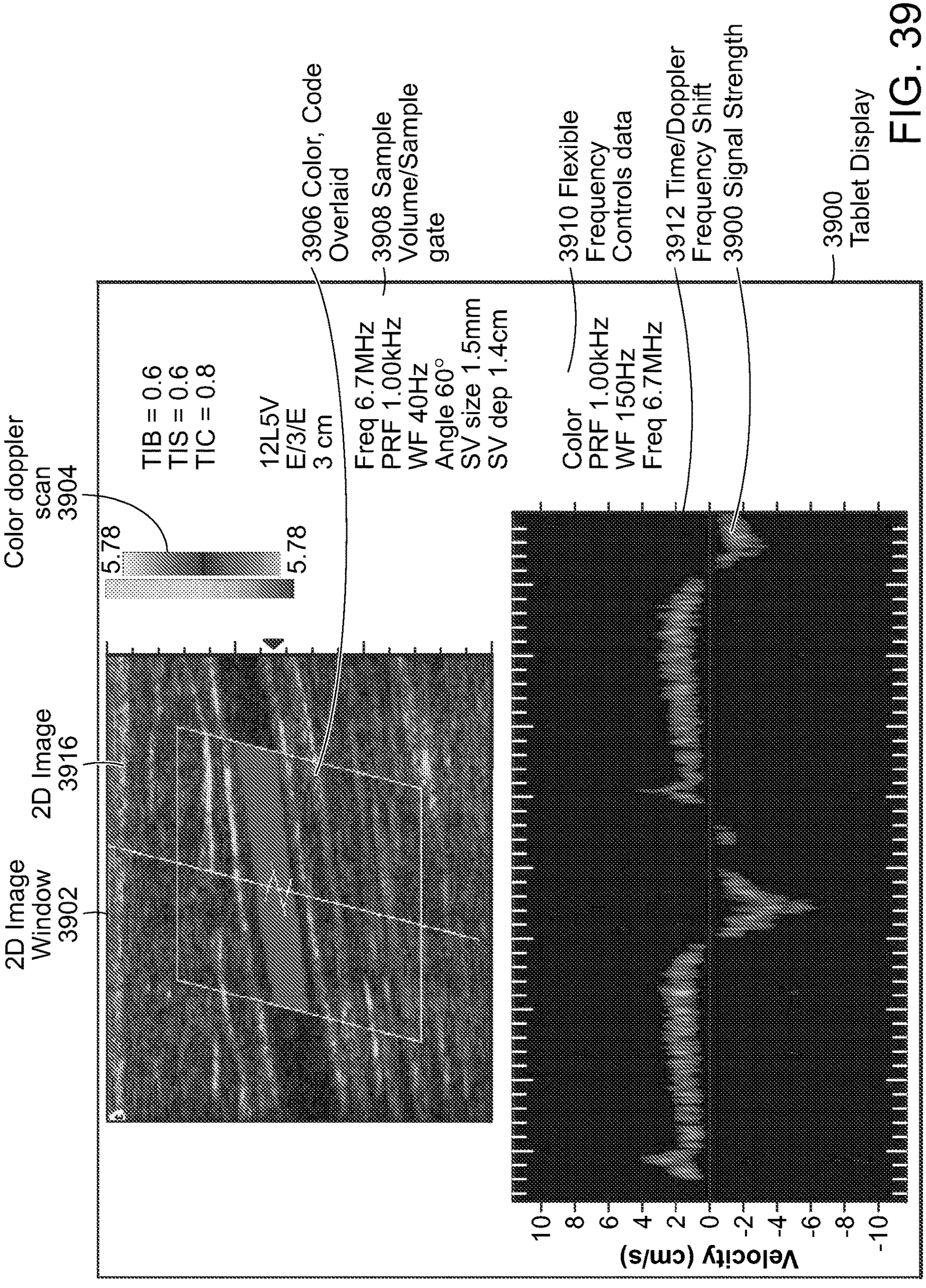
FIG. 39 illustrates a Triplex scan mode of operation with a modular ultrasound imaging system in accordance with one embodiment of the invention.

FIG. 39 illustrates a triplex scan mode of operation with a modular ultrasound imaging system in accordance with one embodiment of the invention. The tablet display 3900 may include a 2-dimensional window 3902, capable of displaying 2-dimensional images alone or in combination with the color Doppler or directional Doppler features. The touchscreen display of tablet 3900, may display images obtained by color Doppler mode of operation. A 2-dimensional image window 3902 is used as the base display. The color coded information 3904, is overlaid 3906, on the 2-dimensional image 3916. The pulsed wave Doppler feature may be used alone or in combination with 2-dimensional imaging or the color Doppler imaging. The tablet display 3900 may include a pulsed wave Doppler scan represented by a sample volume/sample gate 3908, overlaid over 2 dimensional images 3916, or the color code overlaid 3906, either alone or in combination. The tablet display 3900 may depict a split screen representing the time/doppler frequency shift 3912. The time/doppler frequency shift 3912 can be converted into velocity and flow if an appropriate angle between the insolating beam and blood flow is known. Shades of gray 3914, in the time/doppler frequency shift 3912, may represent the strength of signal. The thickness of the spectral signal may be indicative of laminar or turbulent flow. The tablet display 3900 also may depict flexible frequency controls 3910.

Figure 40:
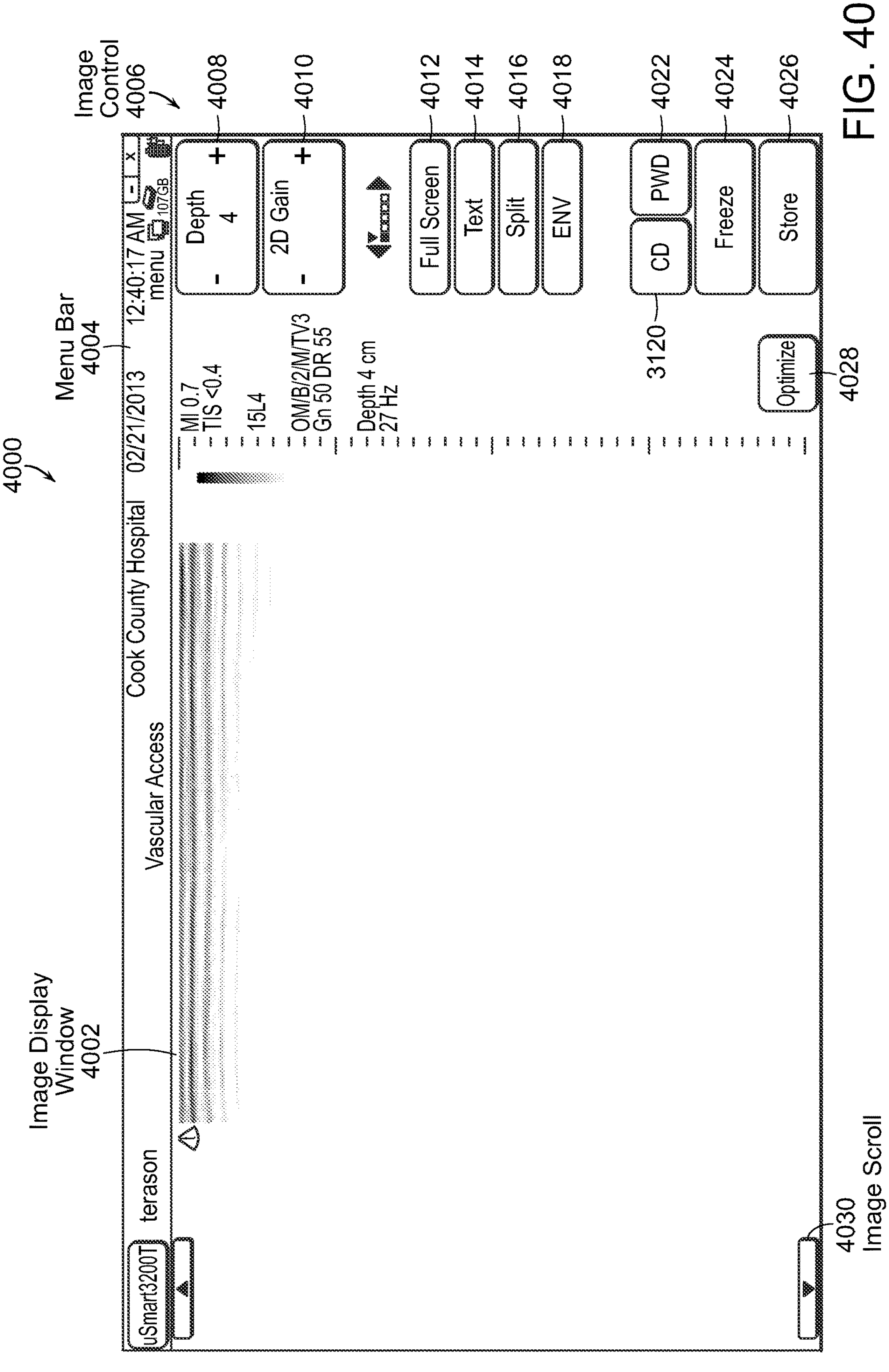
FIG. 40 illustrates a GUI Home Screen interface for a user mode of operation with a modular ultrasound imaging system in accordance with one embodiment of the invention.

FIG. 40 illustrates a GUI home screen interface 4000, for a user mode of operation, with a modular ultrasound imaging system in accordance with one embodiment of the invention. The screen interface for a user mode of operation 4000 may be displayed when the ultrasound system is started. To assist a user in navigating the GUI home screen 4000, the home screen may be considered as including three exemplary work areas: a menu bar 4004, an image display window 4002, and an image control bar 4006. Additional GUI components may be provided on the main GUI home screen 4000, to enable a user to close, resize and exit the GUI home screen and/or windows in the GUI home screen.

The menu bar 4004 enables users to select ultrasound data, images and/or video for display in the image display window 4002. The menu bar may include components for selecting one or more files in a patient folder directly and an image folder directory.

The image control bar 4006 includes touch controls that may be operated by touch and touch gestures applied by the user directly to the surface of the display. Exemplary touch controls may include, but are not limited to a depth control touch controls 4008, a 2-dimensional gain touch control 4010, a full screen touch control 4012, a text touch control 4014, a split screen touch control 4016, a ENV touch control 4018, a CD touch control 4020, a PWD touch control 4022, a freeze touch control 4024, a store touch control 4026, and a optimize touch control 4028.

Figure 41:
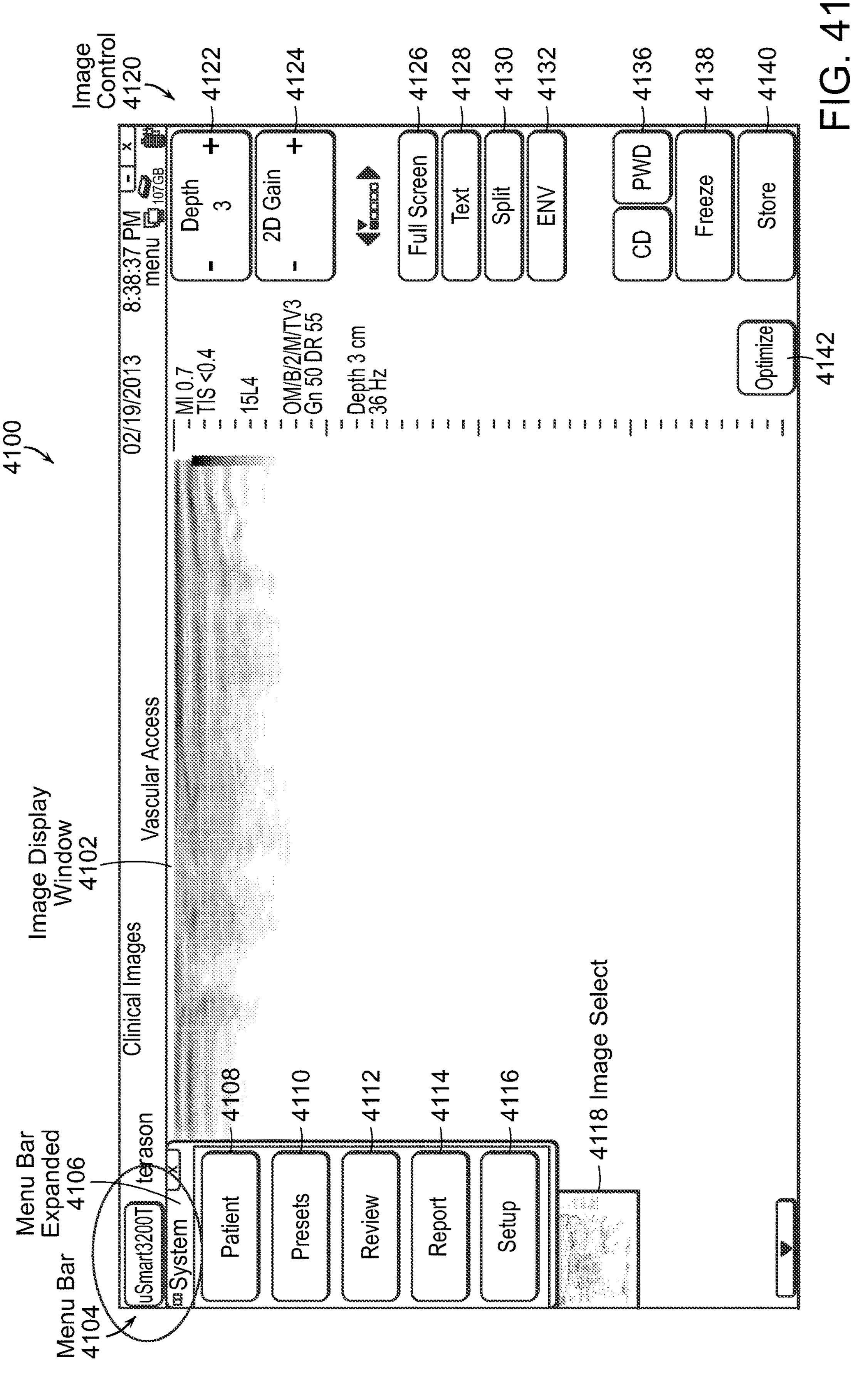
FIG. 41 illustrates a GUI Menu Screen Interface for a user mode of operation with a modular ultrasound imaging system in accordance with another embodiment of the invention.

FIG. 41 illustrates a GUI menu screen interface 4100, for a user mode of operation, with a modular ultrasound imaging system in accordance with one embodiment of the invention. The screen interface for a user mode of operation 4100 may be displayed when the menu selection mode is triggered from the menu bar 4104 thereby initiating operation of the ultrasound system. To assist a user in navigating the GUI home screen 4100, the home screen may be considered as including three exemplary work areas: a menu bar 4104, an image display window 4102, and an image control bar 4120. Additional GUI components may be provided on the main GUI menu screen 4100 to enable a user to close, resize and exit the GUI menu screen and/or windows in the GUI menu screen, for example.

The menu bar 4104 enables users to select ultrasound data, images and/or video for display in the image display window 4102. The menu bar 4104 may include touch control components for selecting one or more files in a patient folder directory and an image folder directory. Depicted in an expanded format, the menu bar may include exemplary touch control such as, a patient touch control 4108, a pre-sets touch control 4110, a review touch control 4112, a report touch control 4114, and a setup touch control 4116.

The image control bar 4120 includes touch controls that may be operated by touch and touch gestures applied by the user directly to the surface of the display. Exemplary touch controls may include, but are not limited to depth control touch controls 4122, a 2-dimensional gain touch control 4124, a full screen touch control 4126, a text touch control 4128, a split screen touch control 4130, a needle visualization ENV touch control 4132, a CD touch control 4134, a PWD touch control 4136, a freeze touch control 4138, a store touch control 4140, and a optimize touch control 4142.

Figure 42:
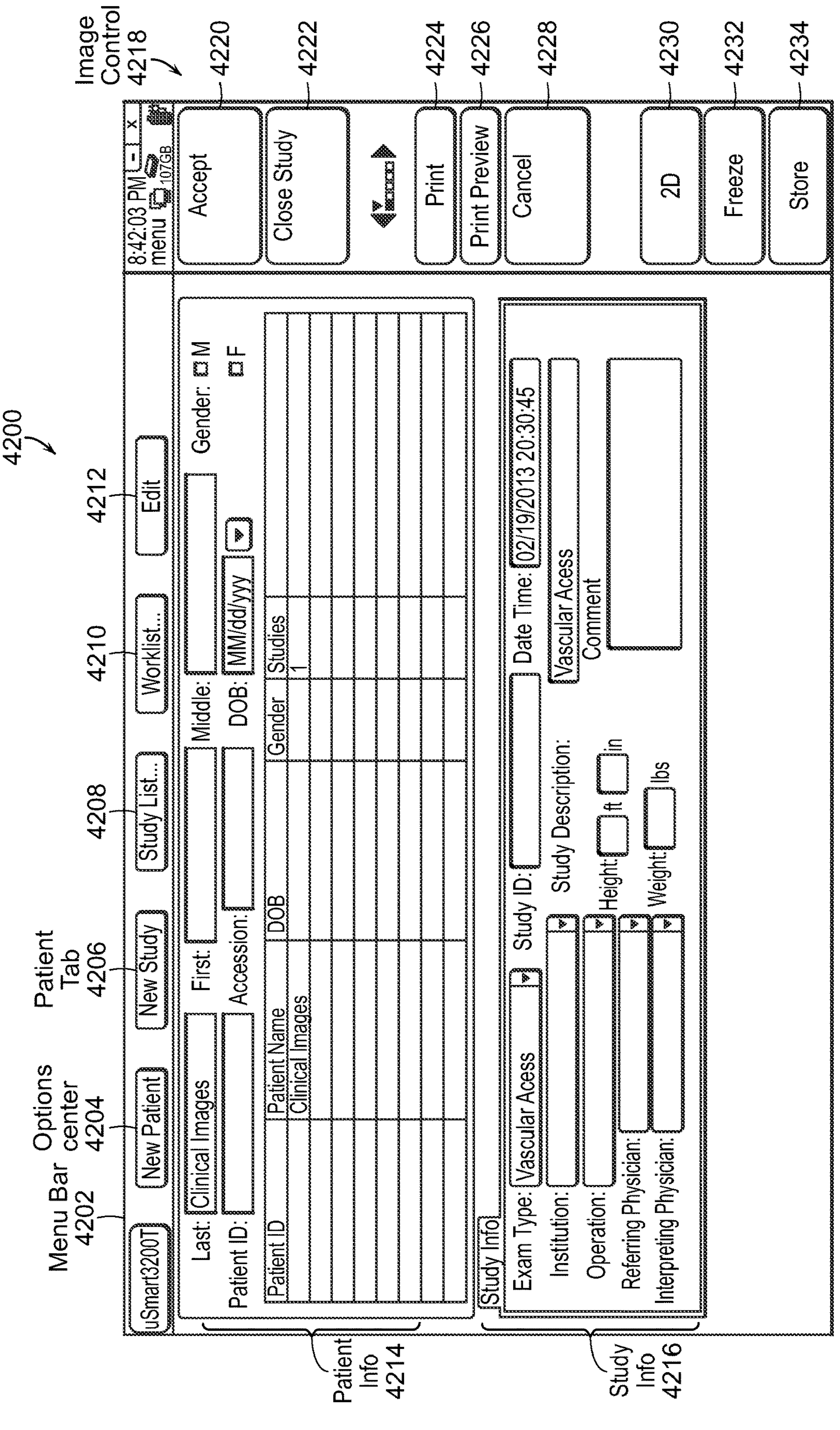
FIG. 42 illustrates a GUI Patient Data Screen Interface for a user mode of operation with a modular ultrasound imaging system in accordance with one embodiment of the invention.

FIG. 42 illustrates a GUI patient data screen interface 4200, for a user mode of operation, with a modular ultrasound imaging system in accordance with one embodiment of the invention. The screen interface for a user mode of operation 4200, may be displayed when the patient selection mode is triggered from the menu bar 4202, when the ultrasound system is started. To assist a user in navigating the GUI patient data screen 4200, the patient data screen may be considered as including five exemplary work areas: a new patient touchscreen control 4204, a new study touchscreen control 4206, a study list touchscreen control 4208, a work list touchscreen control 4210, and an edit touchscreen control 4212. Within each touchscreen control, further information entry fields are available 4214, 4216. For example, patient information section 4214, and study information section 4216, may be used to record data.

Within the patient data screen 4200, the image control bar 4218, includes touch controls that may be operated by touch and touch gestures applied by the user directly to the surface of the display. Exemplary touch controls may include, but are not limited to accept study touch control 4220, close study touch control 4222, print touch control 4224, print preview touch control 4226, cancel touch control 4228, a 2-dimensional touch control 4230, freeze touch control 4232, and a store touch control 4234.

Figure 43:
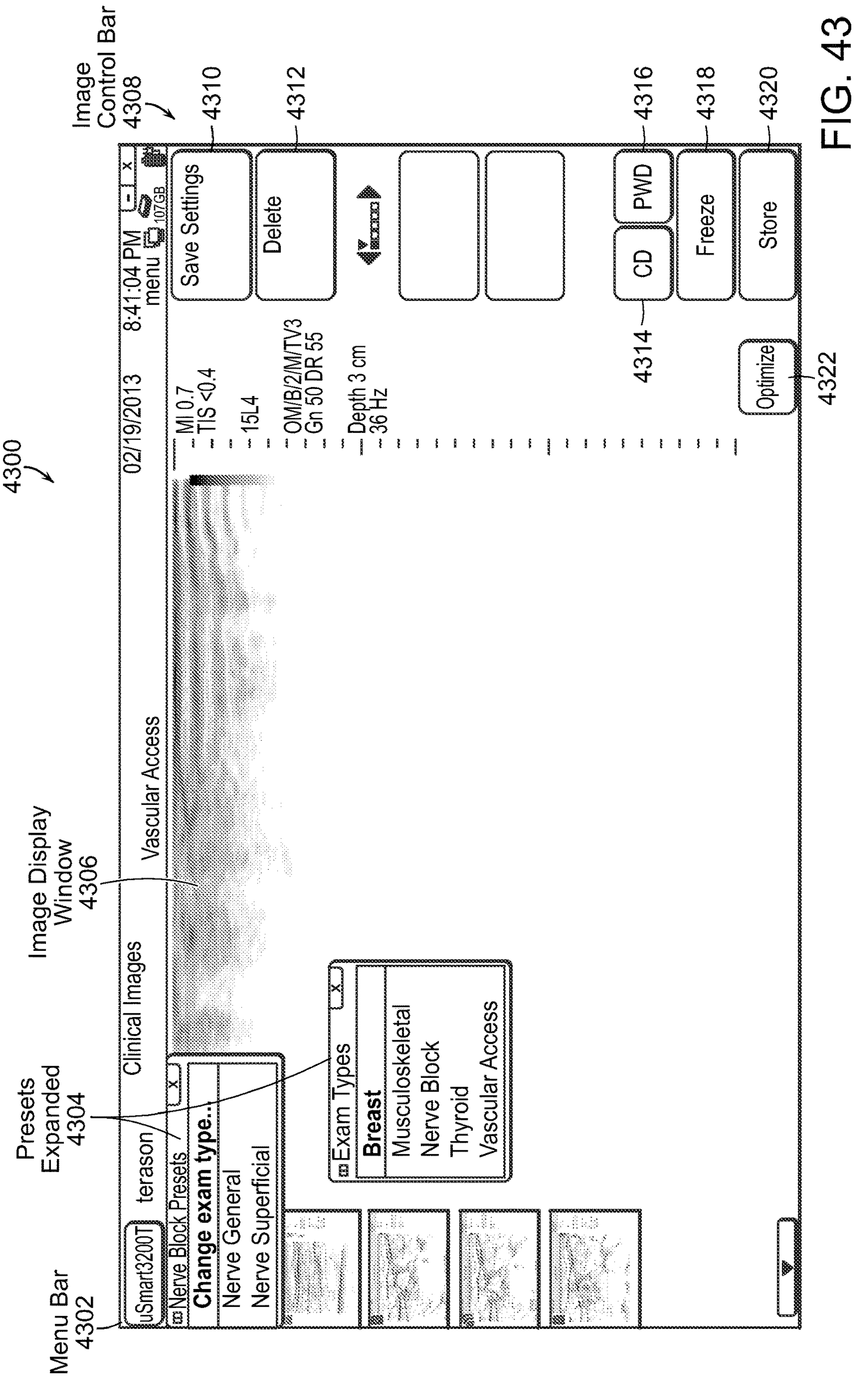
FIG. 43 illustrates a GUI Pre-sets Screen Interface for a user mode of operation with a modular ultrasound imaging system in accordance with one embodiment of the invention.

FIG. 43 illustrates a GUI patient data screen interface 4300, such as preset parameters for a user mode of operation with a modular ultrasound imaging system in accordance with one embodiment of the invention. The screen interface for a user mode of operation 4300, may be displayed when the pre-sets selection mode 4304, is triggered from the menu bar 4302, when the ultrasound system is started.

Within the pre-sets screen 4300, the image control bar 4308, includes touch controls that may be operated by touch and touch gestures applied by the user directly to the surface of the display. Exemplary touch controls may include, but are not limited to a save settings touch control 4310, a delete touch control 4312, CD touch control 4314, PWD touch control 4316, a freeze touch control 4318, a store touch control 4320, and a optimize touch control 4322.

Figure 44:
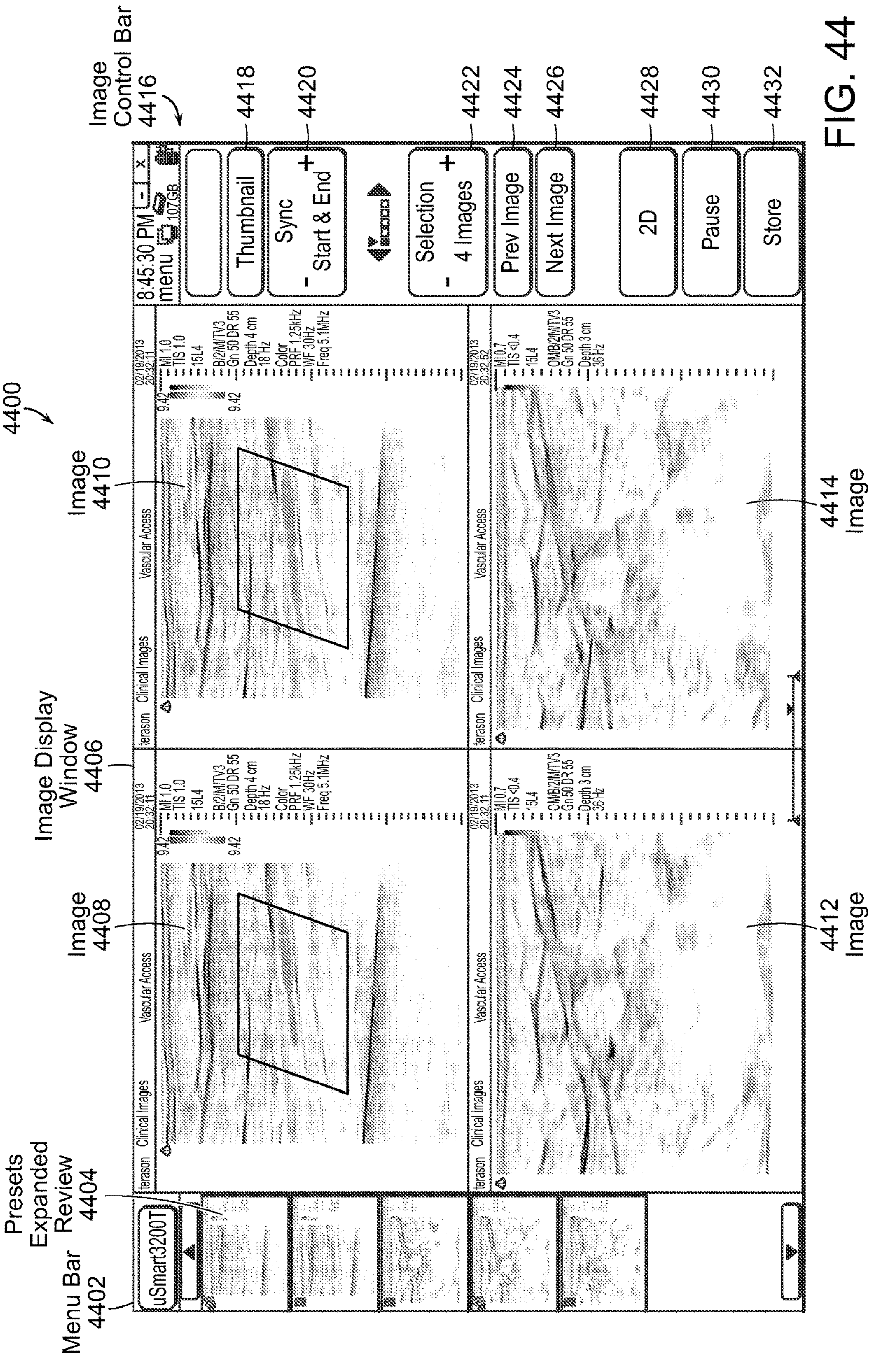
FIG. 44 illustrates a GUI Review Screen Interface for a user mode of operation with a modular ultrasound imaging system in accordance with one embodiment of the invention.

FIG. 44 illustrates a GUI review screen interface 4400, for a user mode of operation, with a modular ultrasound imaging system in accordance with one embodiment of the invention. The screen interface for a user mode of operation 4400, may be displayed when the pre-sets expanded review 4404, selection mode 4304, is triggered from the menu bar 4402, when the ultrasound system is started.

Within the review screen 4400, the image control bar 4416, includes touch controls that may be operated by touch and touch gestures applied by the user directly to the surface of the display. Exemplary touch controls may include, but are not limited to a thumbnail settings touch control 4418, sync touch control 4420, selection touch control 4422, a previous image touch control 4424, a next image touch control 4426, a 2-dimensional image touch control 4428, a pause image touch control 4430, and a store image touch control 4432.

A image display window 4406, may allow the user to review images in a plurality of formats. Image display window 4406, may allow a user to view images 4408, 4410, 4412, 4414, in combination or subset or allow any image 4408, 4410, 4412, 4414, to be viewed individually. The image display window 4406, may be configured to display up to four images 4408, 4410, 4412, 4414, to be viewed simultaneously.

Figure 45:
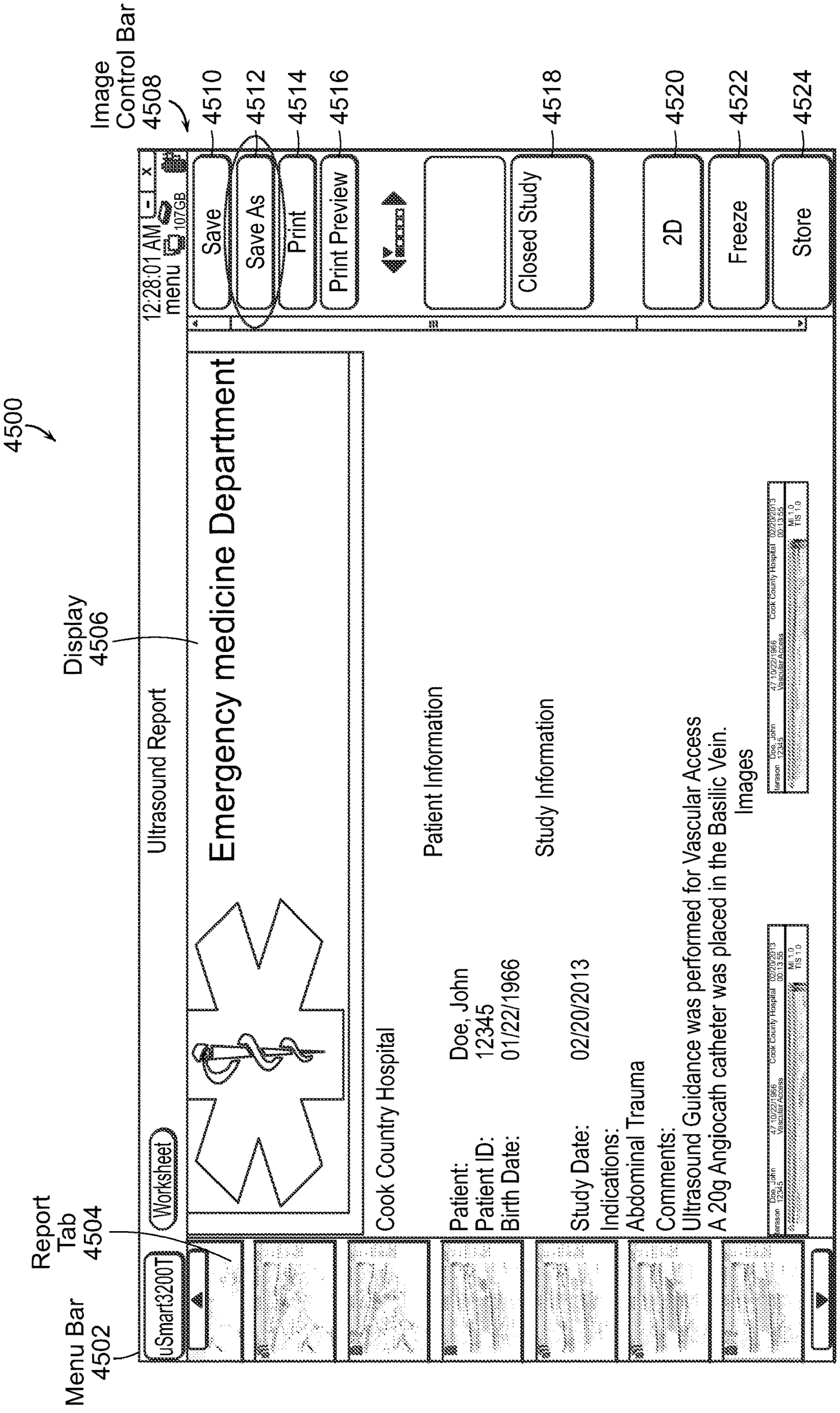
FIG. 45 illustrates a GUI Report Screen Interface for a user mode of operation with a modular ultrasound imaging system in accordance with one embodiment of the invention.

FIG. 45 illustrates a GUI Report Screen Interface for a user mode of operation with a modular ultrasound imaging system in accordance with one embodiment of the invention. The screen interface for a user mode of operation 4500, may be displayed when the report expanded review 4504, is triggered from the menu bar 4502, when the ultrasound system is started. The display screen 4506, contains the ultrasound report information 4526. The user may use the worksheet section within the ultrasound report 4526, to enter in comments, patient information and study information.

Within the report screen 4500, the image control bar 4508, includes touch controls that may be operated by touch and touch gestures applied by the user directly to the surface of the display. Exemplary touch controls may include, but are not limited to a save touch control 4510, a save as touch control 4512, a print touch control 4514, a print preview touch control 4516, a close study touch control 4518, a 2-dimensional image touch control 4520, a freeze image touch control 4522, and a store image touch control 4524.

Figure 46A:
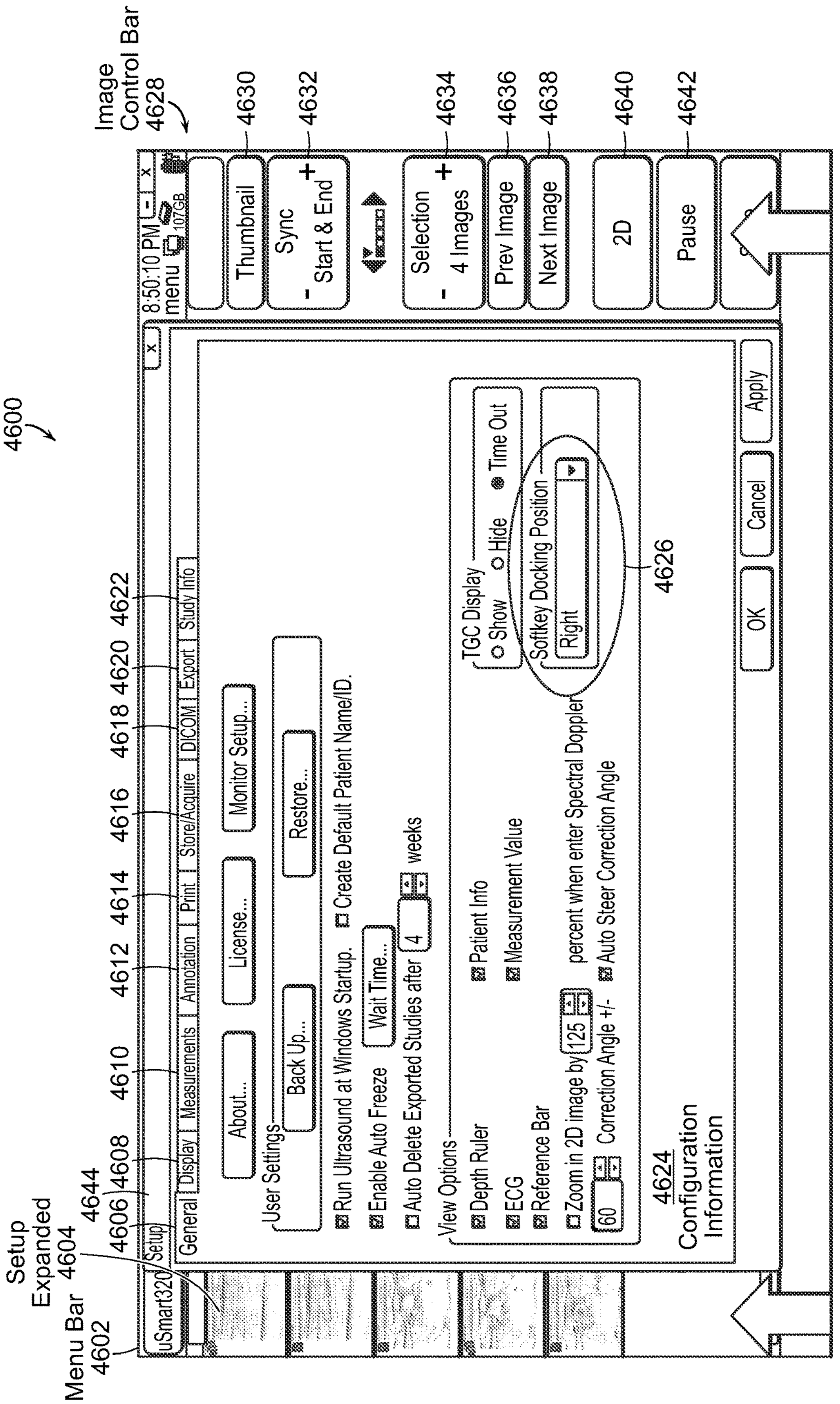
FIGS. 46A-46C illustrate a GUI Setup Display Screen Interface for a user mode of operation with a modular ultrasound imaging system in accordance with one embodiment of the invention.

FIG. 46A illustrates a GUI Setup Screen Interface for a user mode of operation with a modular ultrasound imaging system in accordance with one embodiment of the invention. The screen interface for a user mode of operation 4600, may be displayed when the report expanded review 4604, is triggered from the menu bar 4602, when the ultrasound system is started.

Figure 46B:
Figure 46C:
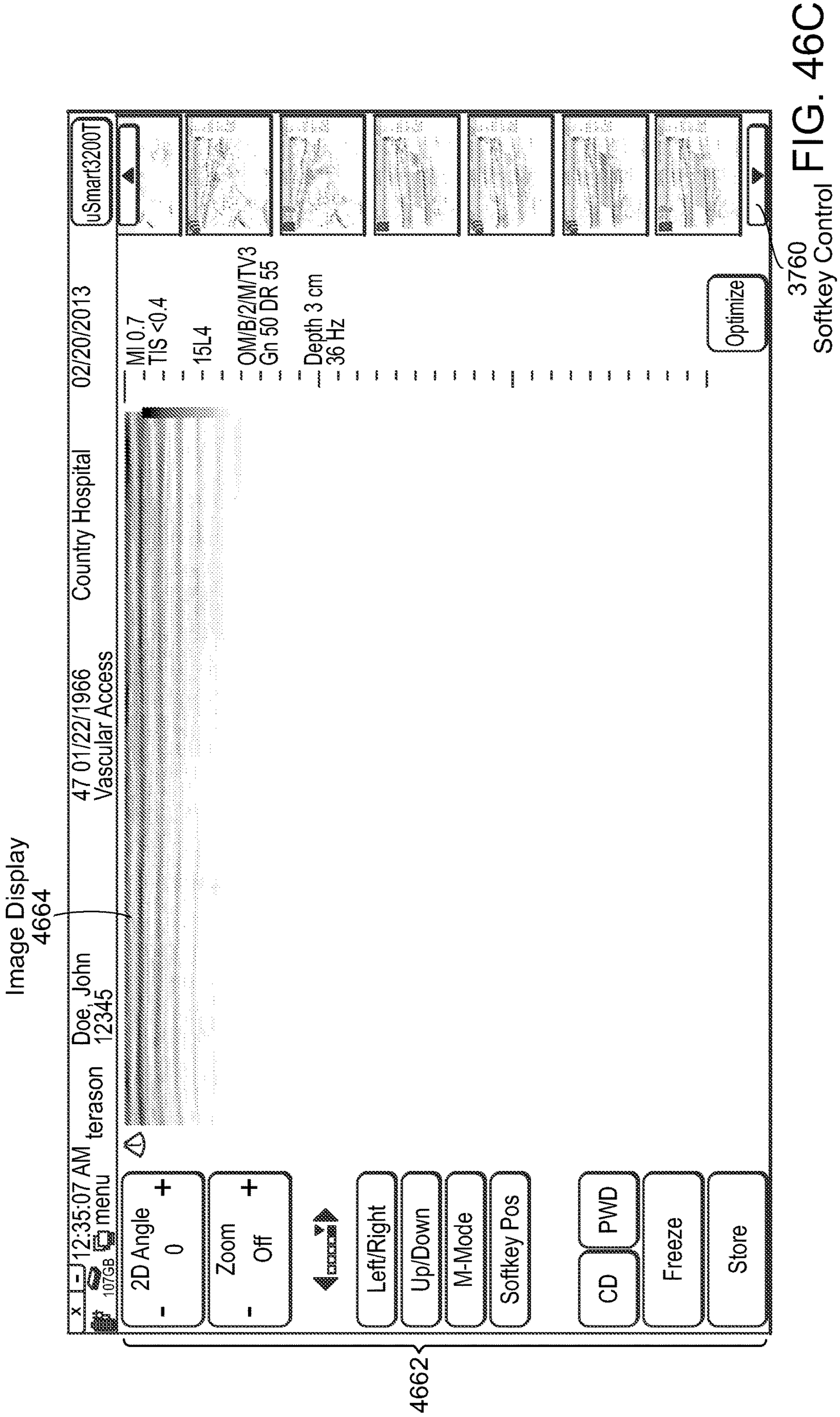

Within the setup expanded screen 4604, the setup control bar 4644, includes touch controls that may be operated by touch and touch gestures, applied by the user directly to the surface of the display. Exemplary touch controls may include, but are not limited to a general touch control 4606, a display touch control 4608, a measurements touch control 4610, annotation touch control 4612, a print touch control 4614, a store/acquire touch control 4616, a DICOM touch control 4618, an export touch control 4620, and a study information image touch control 4622. The touch controls may contain a display screen that allow the user to enter configuration information. For example, the general touch control 4606, contains a configuration screen 4624, wherein the user may enter configuration information. Additionally, the general touch control 4606, contains a section allowing user configuration of the soft key docking position 4626. FIG. 46B depicts the soft key controls 4652, with a right side alignment. FIG. 46B further illustrates that activation of the soft key control arrow 4650, will change the key alignment to the opposite side, in this case, left side alignment. FIG. 46C depicts left side alignment of the soft key controls 4662, the user may activate an orientation change by using the soft key control arrow 4660, to change the position to right side alignment.

Within the review screen 4600, the image control bar 4628, includes touch controls that may be operated by touch and touch gestures applied by the user directly to the surface of the display. Exemplary touch controls may include but are not limited to, a thumbnail settings touch control 4630, sync touch control 4632, selection touch control 4634, a previous image touch control 4636, a next image touch control 4638, a 2-dimensional image touch control 46 40, and a pause image touch control 4642.

Figure 47:
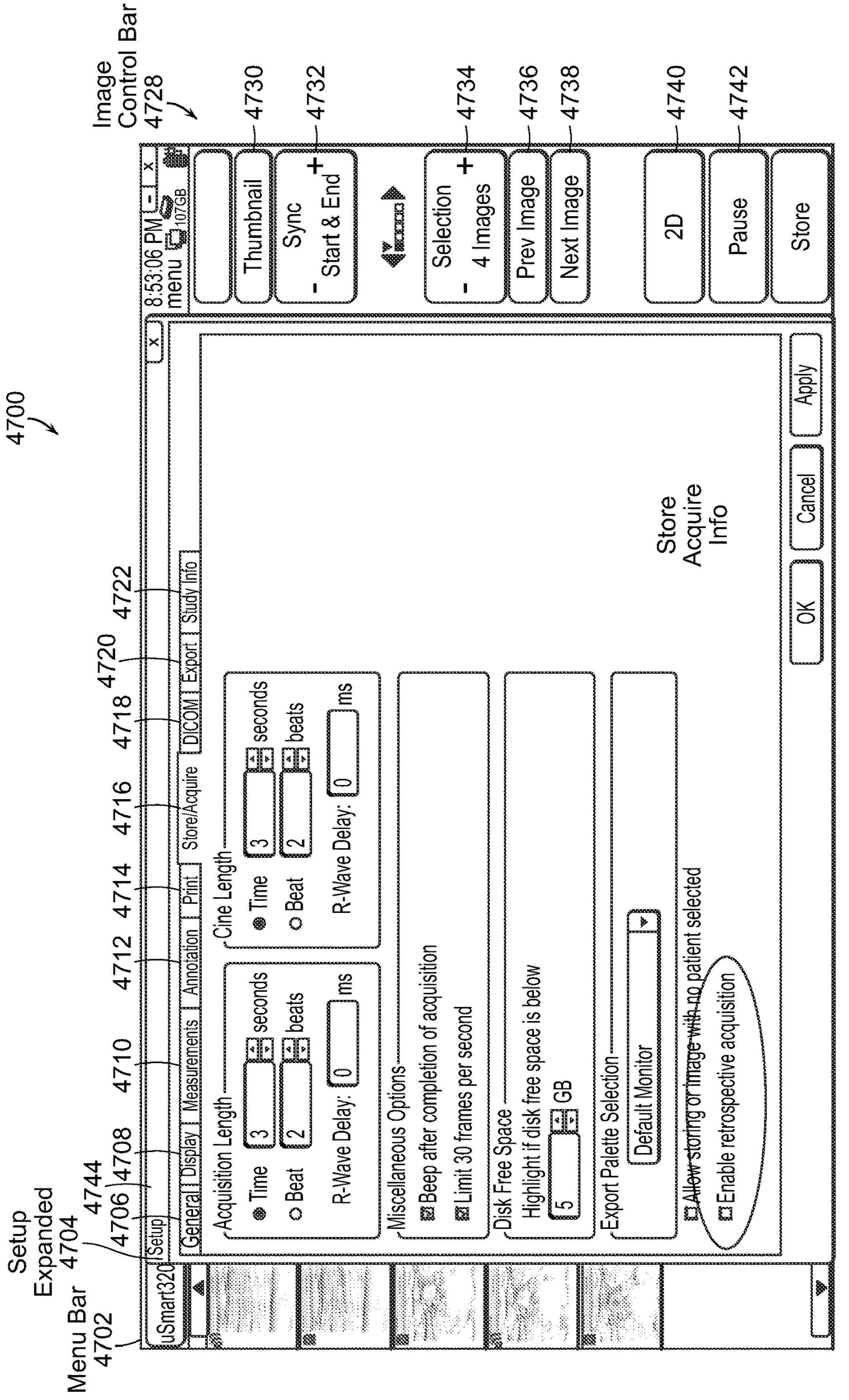
FIG. 47 illustrates a GUI Setup Store/Acquire Screen Interface for a user mode of operation with a modular ultrasound imaging system in accordance with one embodiment of the invention.

FIG. 47 illustrates a GUI Setup Screen Interface for a user mode of operation with a modular ultrasound imaging system in accordance with one embodiment of the invention. The screen interface for a user mode of operation 4700, may be displayed when the report expanded review 4704, is triggered from the menu bar 4702, when the ultrasound system is started.

Within the setup expanded screen 4704, the setup control bar 4744, includes touch controls that may be operated by touch and touch gestures applied by the user directly to the surface of the display. Exemplary touch controls may include, but are not limited to a plurality of icons such as a general touch control 4706, a display touch control 4708, a measurements touch control 4710, annotation touch control 4712, a print touch control 4714, a store/acquire touch control 4716, a DICOM touch control 4718, an export touch control 4720, and a study information image touch control 4722. The touch controls can contain a display screen that allow the user to enter store/acquire information. For example, the store/acquire touch control 4716, contains a configuration screen 4702, wherein the user may enter configuration information. The user can actuate a virtual keyboard allowing the user to enter alphanumeric characters in different touch activated fields. Additionally, the store/acquire touch control 4702, contains a section allowing user enablement of retrospective acquisition 4704. When the user enables the store function, the system is defaulted to store prospective cine loops. If the user enables the enable retrospective capture, the store function may collect the cine loop retrospectively.

Within the setup screen 4700, the image control bar 4728, includes touch controls that may be operated by touch and touch gestures applied by the user directly to the surface of the display. Exemplary touch controls may include, but are not limited to a thumbnail settings touch control 4730, synchronize touch control 4732, selection touch control 4734, a previous image touch control 4736, a next image touch control 4738, a 2-dimensional image touch control 4740, and a pause image touch control 4742.

A preferred embodiment of the microminiaturized PC enabled ultrasound imaging system runs on an industry standard PC and Windows® 2000 operating system (OS). It is therefore network ready which makes it ideal for telemedicine solutions while being cost efficient. It provides open architecture support embedded and thus integrated with third party applications. The preferred embodiment includes an enhanced Application Programming Interface (API), common interface, export support for third party applications, such as, but not limited to, for example, radiation therapy planning, image guided surgery, integrated solutions, for example, calculations, three-dimensional and reporting packages. The API provides a set of software interrupts, calls, and data formats that application programs use to initiate contact with network services, mainframe communication programs, telephone equipment or program-to-program communications. Software based feature enhancements reduce hardware obsolescence and provide efficient upgrades.

Further, the preferred embodiment includes system-on-chip integrated circuits (ICs) which run on PCs and have a large channel count, large dynamic range, high image quality, full feature sets, broad diagnostic coverage, minimal supply chain requirements, simplified design for easy testing and high reliability, and very low maintenance costs.

As previously described herein, the preferred embodiment includes a PC based design which is intuitive, has a simple graphical user interface, is easy to use and train with, which leverages PC industry know-how, robust electronics, high quality displays and low manufacturing costs. It also provides support of software controlled communications with other applications, which are embedded applications that allows patient data, scanner image, Current Procedural Terminology (CPT) code management, which is a numeric coding system by which physicians record their procedures and services, physician's plan, outcome assessment reports, all on an integrated PC. The reforms to the health care system have been applying pressure to lower costs, highlight the need for first visit/in-field diagnosis, data storage and retrieval solutions which when combined with technology innovations such as, for example, data storage and retrieval based on the Digital Imaging and Communications in Medicine (DICOM) standard, broadband and Picture Archiving and Communications Systems (PACS) drives, changes in patient record storage and retrieval and transmission, innovations in lower cost/handheld devices for ultrasound data acquisition, all which enable the preferred embodiment of the present invention. The DICOM standard aids the distribution and viewing of medical images such as, for example, ultrasound, Magnetic Resonance Images (MRIs), and CT scans. Broadband is a wide area network term that refers to a transmission facility providing bandwidth greater than 45 Mbps. Broadband systems are generally fiber optic in nature.

A preferred embodiment of the present invention provides image acquisition and end-user application, for example, radiation therapy, surgery, angiography, all applications executed on the same platform. This provides low cost, user friendly controls through a common software interface. The ultrasound system has scalable user interfaces for advanced users and has an intuitive Windows® based PC interface. A preferred embodiment of the ultrasound system also provides an enhanced diagnostic ability due to the features of one-stop image capture, analysis, storage, retrieval and transmittal capability for the data and images. A high image quality is provided by a 128 channel bandwidth. Besides ease of use, the ultrasound system also provides patient access at any time, any location and using any tool. Point of care imaging is provided with a 10 ounce probe in accordance with a preferred embodiment of the present invention. The data storage and retrieval abilities are based on the DICOM standard and are compatible with off-the-shelf third party analytical and patient record systems. The ultrasound system in accordance with a preferred embodiment also provides immediate image transfer ability using, but not limited to, for example, electronic mail, LAN/WAN, DICOM and Digital Imaging Network-Picture Archiving and Communications Systems (DINPACs). The choices to display the images captured include, but are not limited to, a desktop computer, a laptop computer, wearable personal computers and handheld devices such as personal digital assistants.

As described hereinbefore, the ultrasound systems of the present invention are used in minimally invasive surgery and robotic surgery methods including biopsy procedures, catheter introduction for diagnostic and therapeutic angiography, fetal imaging, cardiac imaging, vascular imaging, imaging during endoscopic procedures, imaging for telemedicine applications and imaging for veterinary applications, radiation therapy, and cryotherapy, without limitation. The embodiments use computer based tracking systems and CT and MR images to pinpoint the precise location of the target areas. Alternative preferred embodiments of ultrasound systems can at lower cost and using smaller footprint devices provide images just prior, during, and just after the procedure. Preferred embodiments overcome the need of requiring a separate ultrasound appliance to be wheeled into the procedure room and a method to move images from the ultrasound to the device that is tracking position and registering targets against previously captured CT and MR images. A preferred embodiment of the ultrasound system provides a fully integrated solution, since it can run its' ultrasound application on the same platform as any third party application that is processing the images. The system includes a streaming video interface, an interface between a third party application and the system's ultrasound application. A key component of this system allows the two applications to run on the same computer platform (using the same operating system (OS)) such as, for example, Windows® based platform, other platforms such as Linux can also be used and thus providing a seamless integration of the two applications. The details of the software interface to move images from the system's ultrasound application to another application are described herein below.

Preferred embodiments include control and data transfer methods that allow a third party Windows® based application to control, for example, a portable Windows® based ultrasound system by running the ultrasound application as a background task, sending control commands to the ultrasound application and receiving images (data) in return. Further, the embodiment configures a portable ultrasound Windows® based application as a server of live ultrasound image frames supplying another Windows® based application that acts as a client. This client application receives these ultrasound image frames and processes them further. In addition, an alternate embodiment configures the portable ultrasound Windows® based application as a server, interacting with a third party client application via two communication mechanisms, for example a component object model (COM) automation interface used by third party, hereinafter referred to interchangeably as external or a client to startup and control the portable ultrasound Windows® based application and a high-speed shared memory interface to deliver live ultrasound images.

A preferred embodiment includes and configures a shared memory interface to act as a streaming video interface between a portable Windows® based Ultrasound application and another third party Windows® based application. This streaming video interface is designed to provide ultrasound images to a third party client in real-time.

A preferred embodiment allows the third party Windows® based application to control the flow rate of images from the portable ultrasound Windows® based application through the shared memory interface within the same PC platform and the amount of memory required to implement this interface. These controls consist of a way to set the number of image buffers, the size of each buffer and the rate of image transfer. This flow rate control can be set for zero data loss thus ensuring that every frame is delivered to the third party Windows® based application from the ultrasound system, or minimum latency thus delivering the latest frame generated by ultrasound system to the third party Windows® based application first.

A preferred embodiment formats the ultrasound image frame such that probe, spatial, and temporal information can be interpreted by the third party Windows® based application as it retrieves the images (generated by the portable ultrasound Windows® based application) from the shared memory interface. The actual image data passed between the server (i.e. portable ultrasound application) and the client application (third party Windows® based application) is a Microsoft device independent bitmap (DIB) with 8 bit pixels and a 256 entry color table. The image frame also contains a header that provides the following additional information, for example, but not limited to, Probe Type, Probe Serial Number, Frame Sequence Number, Frame Rate, Frame Timestamp, Frame Trigger Timestamp, Image Width (in pixels), Image Height (in pixels), Pixel Size (in X and Y), Pixel Origin (x, y location of the first pixel in image relative to the Transducer Head, and Direction (spatial direction along or across each line of the image).

Further, the preferred embodiment controls the shared memory interface used to transfer ultrasound images between a Windows® based portable ultrasound system and a third party Windows® based system through the use of ActiveX controls. The Windows® based portable ultrasound application contains an ActiveX control that transfers a frame into the shared memory and sends out a Windows® Event (that includes a pointer to the frame just written) to the third party Windows® based application. This third party application has a similar ActiveX control that receives this Event and pulls the image frame out of shared memory.

The graphical user interface includes one or more control programs, each of which is preferably a self-contained, for example, client-side script. The control programs are independently configured for, among other functions, generating graphical or text-based user controls in the user interface, for generating a display area in the user interface as directed by the user controls, or for displaying the processed streaming media. The control programs can be implemented as ActiveX controls, as Java applets, or as any other self-contained and/or self-executing application, or portion thereof, operable within a media gateway container environment and controllable through the web page.

Ultrasonic content can be displayed within a frame in the graphical user interface. In an embodiment, the program generates an instance of an ActiveX control. ActiveX refers to a set of object-oriented programming technologies and tools provided by Microsoft® Corporation of Redmond, Washington. The core part of the ActiveX technology is the component object model (COM). A program run in accordance with the ActiveX environment is known as "component," a self-sufficient program that can be run anywhere in the network, as long as the program is supported. This component is commonly known as an "ActiveX control." Thus, an ActiveX control is a component program object that can be re-used by many application programs within a computer or among computers in a network, regardless of the programming language with which it was created. An ActiveX control runs in what is known as a container, which is an application program utilizing the COM program interfaces.

One advantage of using a component is that it can be re-used by many applications, which are known as "component containers." Another advantage is that an ActiveX control can be created using one of several well-known languages or development tools, including C++, Visual Basic, or PowerBuilder, or with scripting tools such as VBScript. ActiveX controls can be downloaded as small executable programs, or as self-executable code for Web pages animation, for example. Similar to ActiveX controls, and suitable for the client-side scripts, are applets. An applet is typically a self-contained, self-executing computer program written in Java™, a web-based, object-oriented programming language promulgated by SUN Microsystems Corporation of Sunnyvale, Calif.

The control programs can be stored and accessed locally at the client system, or downloaded from the network. Downloading is typically done by encapsulating a control program in one or more markup language-based files. The control programs can also be used for any commonly-needed task by an application program running in one of several operating system environments. Windows®, Linux and Macintosh are examples of operating system environments that can be used in preferred embodiments.

A preferred embodiment of the Ultrasound Imaging System has specific software architecture for the image streaming capabilities. This Ultrasound Imaging System is an application that controls the Ultrasound Probe of a preferred embodiment and allows to obtain and display visual images for medical purposes. The Imaging System has its own graphical user interface. This interface has reach in features and is conveniently organized to provide maximum flexibility working with the separate images as well as streams of images. Some of the possible medical applications require developing of graphical user interfaces with significantly different features. This involves integration of the Imaging System into other more complicated medical system. The preferred embodiment allows exporting imaging data in a highly effective and convenient fashion for original equipment manufacturers (OEMs) to have direct access to imaging data.

The quality of the Image Streaming solution in accordance with a preferred embodiment is measured by the following criteria such as, data transfer performance. Imaging data consumes a significant amount of memory and processor power. Large numbers of separate image frames are required to produce live medical video patient examination. It becomes very important to minimize data coping operations in a process of transferring data from one process generating video data to a process consuming video data. The second criteria includes industry standard imaging format. Since applications consuming video imaging data are intended to be developed by third party companies data can be represented in industry standard formats. A third criteria is convenience. Imaging data may be presented by means of a programming interface that is convenient to use and does not require additional learning.

Further, the criteria includes scalability and extendibility. A streaming data architecture may be easily extendable to accommodate new data types. It may provide a basic framework for future multiplication of video streams targeting more than one data receiving process.

The image streaming architecture of the preferred embodiment provides methods of data transportation between two processes. The image streaming architecture defines operational parameters regulating data transferring process, and describes the mechanism of transferring parameters between processes. One of the methods to transfer operational parameters from a third party client application to the imaging system of a preferred embodiment is by using existing COM interface.

In a preferred embodiment, the image transferring architecture intensively uses the object-oriented programming methodology and inter-processing capabilities of the Microsoft Windows® operating system. The object-oriented methodology provides a necessary foundation allowing an architectural solution that satisfies the necessary requirements. It also lays a groundwork for future enhancements and extensions making modification relatively simple and backward compatible.

Video imaging data represents complicated data structures with mutual interferences between different data elements. It also permits and often requires different interpretation of the same data elements. The preferred embodiment of the following image transferring architecture includes a shared memory for physical data exchange. For example, Windows® shared memory is a fast and economical way to exchange data between processes. Further, the shared memory can be subdivided into separate sections of a fixed size in certain embodiments. Each section can then be at a minimum a controllable unit. In addition, the imaging data can be abstracted as objects. Each frame of the imaging data can be represented by a separate object. The objects can then be mapped to the sections of the shared memory.

Preferred embodiments can include the locking-unlocking of a section-object. The programming API notification mechanism used is an event-driven mechanism. Event-driven mechanisms are implementation based on C++ pure-virtual functions.

In a preferred embodiment, the image transferring architecture consists of three layers: an application programming interface (API) layer, a programming interface implementation and shared memory access layer, and a physical shared memory layer. The application programming interface layer provides two different C++ class library interfaces to applications on a client and server side. All the associated sequence of instructions that belongs to the application itself is part of this layer as well. Application derived classes and their implementation are the key elements of application programming interface layer. The server which is the imaging data provider side uses, for example, Object Transmitter class and related derived and base classes. The client which is the imaging data consumer side uses an Object Factory class, for example, and related derived and base classes.

The programming interface implementation layer provides two different Dynamic Link Libraries (DLLs) implementing classes for the applications. This layer maps objects of the classes associated with the application to an internal implementation of objects accessing the shared memory physical system object. This layer allows the hiding of all implementation specific member variables and functions from the scope of the application. Thus, the application programming interface layers become uncluttered, easy to understand and use. The server side application can use, for example, Object-Xmitter.DLL, while the client side application can use, for example, ObjectFactory.DLL.

The physical shared memory layer represents the operating system object implementing shared memory functionality. It also describes the structure of the shared memory, it's segmentation, and memory controlling blocks.

With respect to the organization of the shared memory since shared memory is intended to be used for interprocess communications the operating system specifies a unique name at the time of it's creation. In order to manage the shared memory, other interprocess communications (IPC) system objects are required. They need to have unique names as well. To simplify a unique name generation process only one base is required. All other names are derived from the base one by an implementation code. Thus, the application programming interface requires the specification of only one base name for the logical shared memory object. The same unique name can be used by both the server side of the application and the client side of the application.

The server side of the application is responsible for the creation of shared memory creation. In a process of creation, it has to specify not only unique name of the shared memory but other configuration parameters. These parameters include, but are not limited to, segments count which specifies the number of segments to be allocated, segment size and operational flags. There are three such flags in a preferred embodiment. The first one specifies the segment submission and retrieval order. It can be one of, Last In First Out (LIFO), First In First Out (FIFO), or Last In Out (LIO). LIO is a modification of the usual LIFO in such a way that whenever at the time when a new frame arrives, if it finds frames that were ready for retrieval, but yet not locked for retrieval, they are erased. The second flag specifies shared memory implementation behavior under a condition when a new segment allocation is requested but there is no segment available. Typically it may happen when receiving application process data slower than submitting the application. This flag may allow deleting one of the previously allocated segments. If it does not allow deleting one of the previously allocated segments, it reports an exceptional condition back to the application. Using this flag application may automatically select overwriting of data in a shared memory or it may control the data overwrite process itself. The third flag can be used only when the second one allows overwriting segments in a shared memory. It specifies how to select a segment to be overwritten. By default, shared memory implementation deletes the youngest or the most recently submitted data segment. Alternatively, the oldest segment can be selected for overwrite process.

Figure 48:
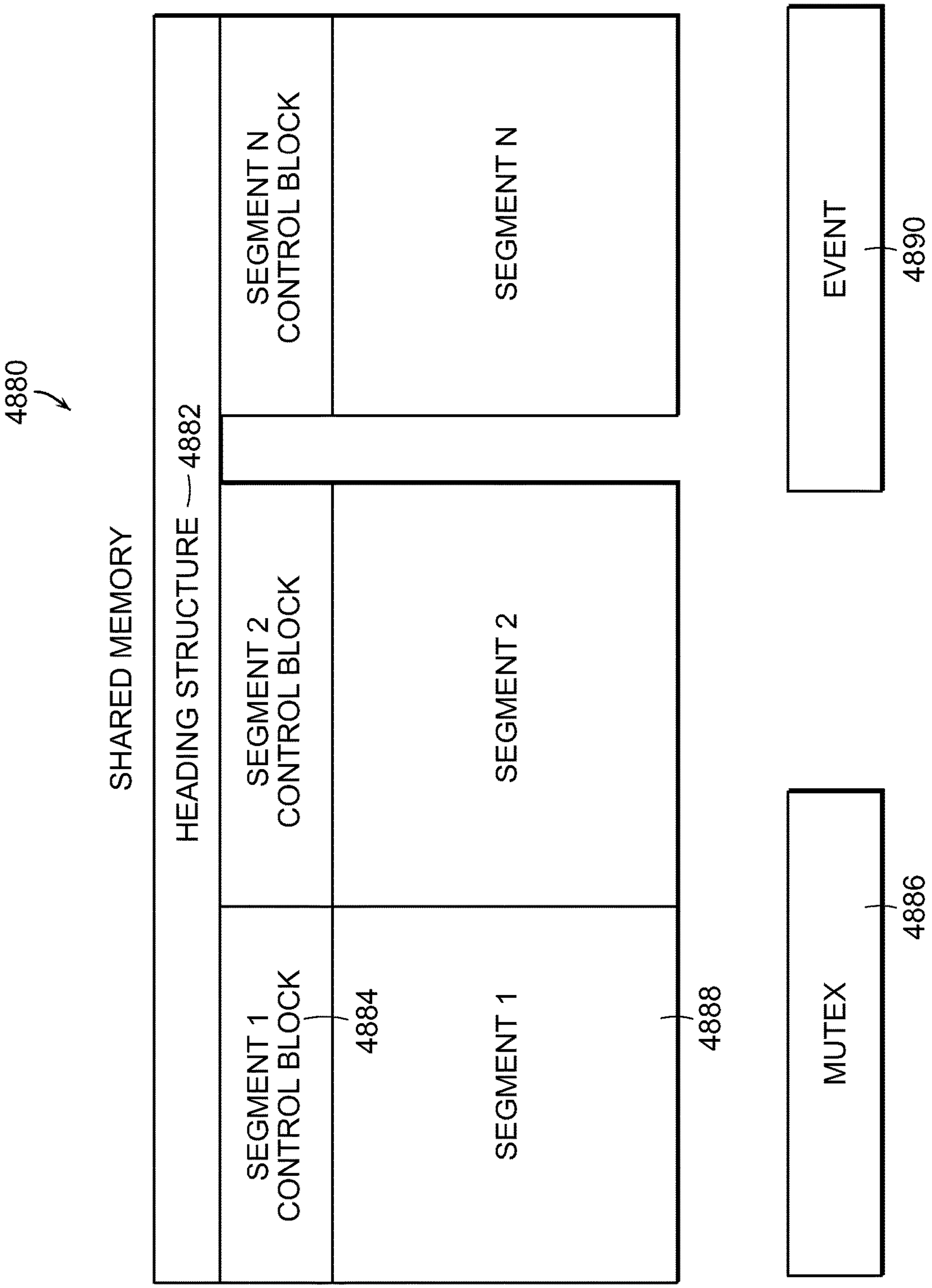
FIG. 48 is a block diagram illustrating the structure of the physical

At the time of the creation of the shared memory it's physical layout is initialized. Since the operating system does not allow address calculation in a physical shared memory data pointers are not used within shared memory. All addressing within the shared memory controlling blocks and segments is implemented in terms of relative offsets from the Virtual Origin (VO). With the offset zero from the VO, the shared memory heading structure is allocated. It contains all the parameters listed herein above. FIG. 48 is a block diagram illustrating the structure of the physical shared memory 4880.

Immediately after the allocation of the shared memory heading structure 4882 follows the creation of array of headers 4884 for every memory segment. The memory segment header contains the occupied size of the segment, unique tag of the class of the object mapped to the segment, and the segment state. Each segment can be in one of four states: unused where the segment is available for allocation, locked for write where the segment is mapped to an object of a specific class and currently is being formed, written, wherein the segment is mapped to an object of a specific class and available for retrieval, and locked for read, wherein the segment is mapped to an object of a specific class and currently is in a process on data retrieval. Since every segment has its own state it is possible for the application to lock more than one segment for object forming and object retrieval. This allows the system to have flexible multithreaded architecture on both the server and client sides of the application. Further, the ability to have more than one segment in a "written" state provides a "buffering" mechanism nullifying or minimizing performance difference of the applications on the server and client sides.

The last element in a physical shared memory layout contains memory segments 4886. The logical shared memory besides physical shared memory contains a physical system mutex 4888 and system event 4890. The physical mutex provides mutual exclusive access to physical shared memory. The physical event is of a manual control type. It stays at the level "high" all the time when at least one of the segments has a "written" state. It goes to the level "low" only when there is no single segment in a "written" state. This mechanism allows to retrieve "written" objects from the shared memory without passing control to an operating system within the same time-slice allocation for the thread.

In a preferred embodiment, the object transmitting programming interface consists of three classes: namely, AObjectXmitter, USFrame, and BModeFrame. The AObjectXmitter class allows the initiation of an object transferring service specifying desired operational parameters. Once the AObjectXmitter class object is instantiated the initialized objects of USFrame and BModeFrame classes can be created. The USFrame class constructor requires a reference to an object of the AObjectXmitter class. The first action that has to be accomplished upon instantiation of the USFrame object is to establish association of the object with one of the segments in the shared memory. The function Allocateo maps an object to an unused shared memory segment and locks this segment for the current object usage. At the time of mapping an object a bitmap size may be provided by an application. The provided size represents only the size required for bitmap data not including the memory size required for other data elements of the object.

The BModeFrame class is a class derived from the USFrame class. It inherits all the methods and functionality that the base class has. The only additional functionality provided by BModeFrame class is additional methods allowing to provide information related specifically to the BMode operation.

After the USFrame or BModeFrame class object has been instantiated and mapped to the shared memory segment the application can fill all desired data elements of the object. It is not necessary to provide a value for every data element. At the time when an object is being mapped to the shared memory segment, all data elements of the object are being initialized with default values. The only data elements that are not initialized upon mapping are bitmap data elements. When the server side of the application has provided all desired data elements it can hand over the object to the client side of the application by calling a method, for example, Submit( ).

The USFrame or BModeFrame object can be reused by means of subsequent remapping and resubmitting. Alternatively, it can be deleted and a new one can be created when it is appropriate for an application. Since object instantiation does not require any interprocess-communicatio-n mechanisms, it is as simple as memory allocation for an ordinary variable.

There are at least two advantages of the architecture of the preferred embodiment. Since the ObjectXmitter class does have knowledge about the USFrame or BModeFrame class, it is very easy to introduce additional classes similar or directly or indirectly derived from the USFrame class. This allows to produce future versions of Object Transmitting Programming Interface without requiring any modifications to the code or sequence of instructions that was developed for existing embodiments. Further, Object Transmitting Programming Interface classes do not have any member variables. This provides two more benefits of the interface. The first one is that these classes are COM object interface oriented and can be directly used for the COM object interface specification and implementation. The second benefit is that these classes effectively hide all implementation specific details making the interface very clear, easy to understand and use.

The Object Transmitting Programming Interface is implemented by the ObjectXmitter.DLL. For every object created by the application there is a mirroring implementation object being created by the code residing in the ObjectXmitter.DLL. Since every programming interface class has corresponding mirroring class in implementation modifications are facilitated and extend currently to specified image types. This can be accomplished by the creation of the corresponding mirroring classes in the implementation DLL. Implementation objects are responsible for handling of the shared memory and the mapping of programming interface objects. An embodiment of the present invention includes the DLL allowing instantiate of only one ObjectXmitter class object using only one communication channel with the one client application. Object Transmitting implementation transmits not only object data but provides additional information describing the object type transferred.

The Object Factory Programming Interface consists of three classes: AObjectFactory, USFrame, and BModeFrame. The class AObjectFactory contains three pure virtual member functions. This makes this class an abstract class that cannot be instantiated by an application. It is required from the application to define its own class derived from the AObjectFactory class. There is no need to define any "special" class derived from the AObjectFactory class. Since the application intends to process images that would be received, the chances that it will have a class processing images are very high. An image processing class can very well be derived from AObjectFactory class.

The class derived from an AObjectFactory class has to define and implement only pure virtual functions such as, for example, OnFrameOverrun( ), OnUSFrame( ), and OnBModeFrame( ). For instance, a derived class can be defined as follows:

```
Class ImageProcessor: public AObjectFactory {
public:
ImageProcessor(void);
~ImageProcessor(void);
virtual unsigned long OnFrameOverrun(void);
virtual unsigned long OnBModeFrame(const BModeFrame * frame);
virtual unsigned long OnUSFrame(const USFrame * frame);
};
```

Upon instantiation of an object of the class ImageProcessor base class member function Open( ) can be called. This function provides a shared memory name that matches to the shared memory name being used by the server side of application. Function Open( ) connects the client application to the server application via a specified shared memory.

At any moment after opening the shared memory, the application can expect a call on a virtual function OnFrameOverrun( ), OnUSFrame( ), and OnBModeFrame( ). Every invocation of OnUSFrame( ) function carries as an argument an object of USFrame class type. Every invocation of OnBModeFrame( ) function carries as an argument an object of BModeFrame class type. There is no need for an application to instantiate an object of USFrame or BModeFrame class. USFrame and BModeFrame objects are "given" to an application by underlying implementation on an AObjectFactory class.

The only action that application needs to accomplish is to process received frame and to release the "given" object. The application does not attempt to delete a frame object, as deletion is done by an underlying implementation. Member function Release( ) of USFrame object is called only when all data processing is done by the application and USFrame object or object of the derived class is no longer needed by the application.

Once the application has received an object of a class USFrame or BModeFrame it can retrieve imaging data and process them appropriately. The application needs to be aware that it does processing of the frame object data in a separate thread and make sure that processing function is written using a thread-safe programming technique. Since any of the pure virtual functions are being called within a separate thread created by the implementation DLL none of the subsequent calls are possible before virtual function returns control back to the calling thread. This means that as long as the application has not returned control to implementation created thread any new frames cannot be received by the application. Meanwhile the server side of the application can continue to submit extra frames. This eventually causes the shared memory to overflow and prevents any new frame transmission.

All the time when the application processes frame data it keeps shared memory resources locked from subsequent remapping. The more frames not released by the application the less shared memory segments are available for Object Transmitting Interface on the server side of the application. If framing objects are not being released with an appropriate speed ratio eventually all memory segments of the shared memory are locked by the client application. At that time the image transmitting application stops sending new frames or overwrites frames that are not locked yet by the receiving application. If all the segments were locked by the receiving application the transmitting application does not even have an option to overwrite existing frames.

The function OnFrameOverrun( ) is called when the Frame Overrun is raised by the servicing application. This condition is raised any time when the servicing application makes an attempt to submit a new frame and there is not any available shared segments to map an object to. This condition can be cleared only by the client side of application by means of calling function ResetFrameOverrun( ). If this function is not called by the client application the Frame Overrun condition is raised and OnFrameOverrun( ) pure virtual function is called again.

The Object Factory Interface has the same advantages that were outlined herein above in describing the Object Transmitting Interface. In addition to these advantages, it implements an event-driven programming method that minimizes programming effort and maximizes execution performance. At the same time there are functions such as, for example, USFrames( ), BModeFrames( ), GetUSFrame( ), and GetBModeFrame( ). These functions can be used to implement less efficient “polling” programming methods.

The Object Factory Programming Interface is implemented by the ObjectFactory.DLL. This DLL retrieves an object class type information as well as object related data from the shared memory. It creates an object of the type that is used by the transmitter. The Object factory implementation maps newly created objects to the corresponding data. Object factory implementation has a separate thread that fires newly generated and mapped object via pure virtual function event. The application “owns” this object for the duration of processing and by calling Releaseo function indicates that the object is no longer needed by the application. The factory implementation releases resources allocated for the object locally as well as shared memory resources.

Figure 49:
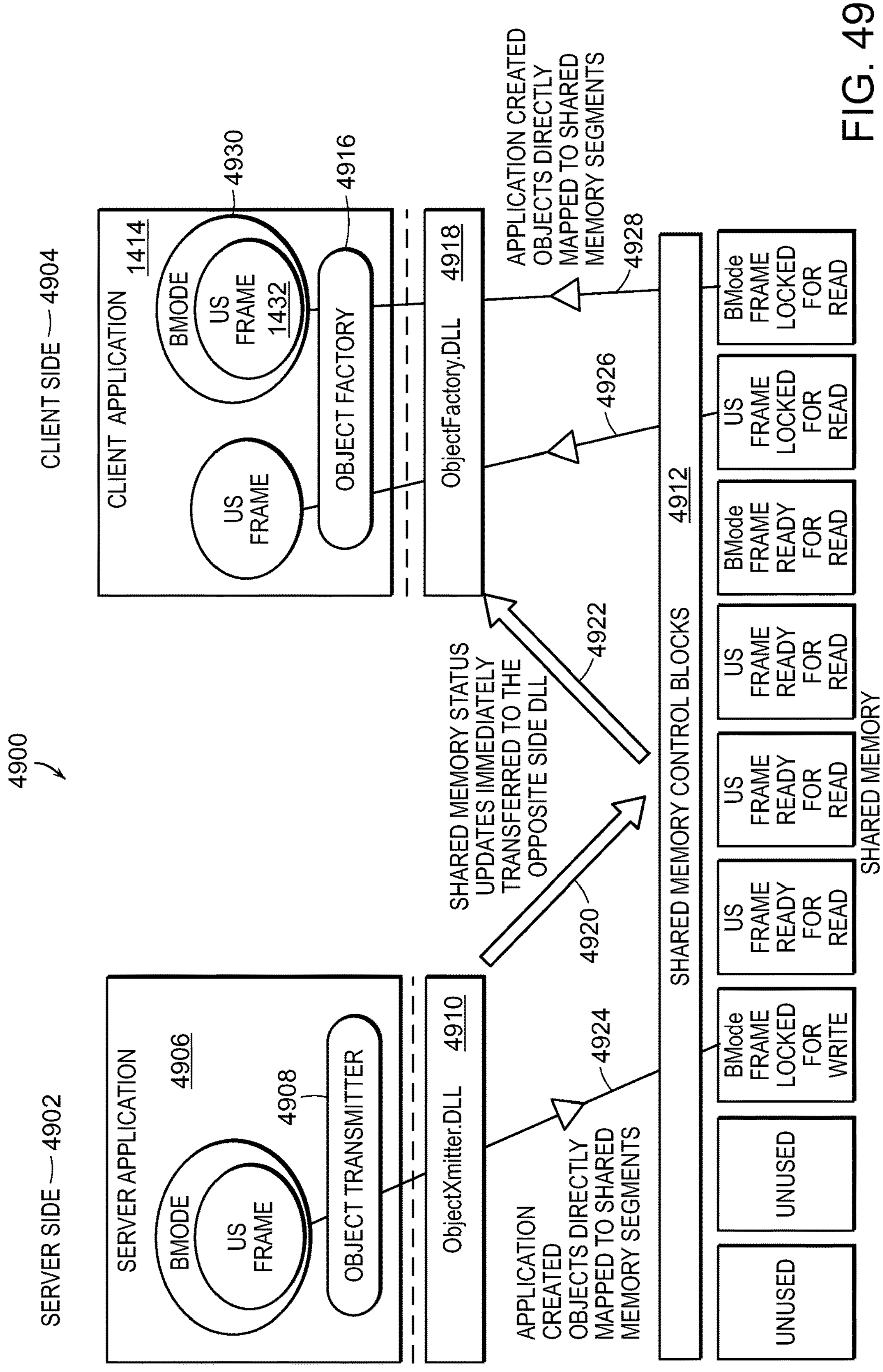
FIG. 49 illustrates a shared memory system to enable communication between ultrasound and non-ultrasound operations.

The processing flow described herein above is pictorially represented in the block diagram FIG. 49. Preferred embodiments, include the ease of code maintenance and feature enhancement for the image transferring mechanism. The Object Transferring 4908 and Object Factory 4916 Interfaces as well as their implementations allow such modifications to be made at a relatively low development cost. With respect to Object Modification, the shared memory implementation is completely independent from the transferred data types. Thus, any type modification does not require making any changes to the underlying code controlling shared memory. Since transferred data is encapsulated within classes of a particular type the only action that is needed to modify transferring an object is to modify the corresponding class defining such object. Since objects represent a class derivation tree any modification of the base class causes appropriate change of every object of the derived classes. Such modifications of the object types do not affect application code not related to modified object classes.

The new types of objects can be introduced by deriving a new class from one of the existing classes. A newly derived class can be derived from the appropriate level of the base classes. An alternative way to create a new object type is by the creation of a new base class. This method may have the advantage in the case when a newly defined class differs from existing ones significantly.

With respect to multiple Object Transferring Channels, alternate preferred embodiments, can support more than one AObjectXmitter class object and more than one corresponding communication channel. It also can be extended in such a way that it allows communication channels transmitting objects in opposite directions. This allows the application to distribute imaging data to more than one client application. It can accept incoming communication controlling image creation and probe operation.

Further, wireless and remote image streaming channels can be accommodated in preferred embodiments. A same Object Transmitting Programming Interface can be implemented to transfer images not via the shared memory but via the high-speed wireless communication network such as, for example, ISO 802.11a. It also can be used to transfer images across a wired Ethernet connection. Remote and wireless image streaming assumes that the recipient computing system can differ in performance. This makes the selection of a model of the recipient's device one of the important factors for the successful implementation.

The streamed imaging included in preferred embodiments thus utilizes a shared-memory client-server architecture that provides high bandwidth with low overhead.

The Ultrasound Imaging System software application of a preferred embodiment is used as a server of live ultrasound image frames by a client application. This client-server relationship is supported by two communications mechanisms as described hereinabove. A COM automation interface is used by the client application to start-up and control the ultrasound imaging system application. A high-speed shared-memory interface delivers live ultrasound images with probe identification, spatial and temporal information from the application to the client application.

Complexities of the shared-memory implementation are encapsulated for the client application in a simple ActiveX COM API (TTFrameReceiver). The shared-memory communications have flexible parameters that are specified by the client application. Queue order, number of buffers, buffer size and overwrite permission are all specified by the client when opening the image-frame stream. The queue order mode can be specified as First-In-First-Out (FIFO), Last-In-First-Out (LIFO) and Last-In-Out (LIO). In general, the FIFO mode is preferred when zero data loss is more important than minimum latency. The LIO mode delivers only the most recent image frames and is preferred when minimum latency is more important than data loss. The LIFO mode can be used when minimum latency and minimum data loss are both important. However, in the LIFO mode, frames might not always be delivered in sequential order and a more complicated client application is required to sort them after they are received. Overwrite permission, when all of the shared-memory buffers are full, is specified as not allowed, overwrite oldest and overwrite newest.

Each image frame contains a single ultrasound image, probe identification information, pixel spatial information and temporal information. The image format is a standard Microsoft device independent bitmap (DIB) with 8-bit pixels and a 256-entry color table.

The TTFrameReceiver ActiveX control provides two schemes for receiving frames. The first scheme is event driven. A COM event, FrameReady, is fired when a frame has been received. Following the FrameReady event, the image and associated data can be read using the data access methods of the interface. After image and other data have been copied, the client releases the frame by calling the ReleaseFrame method. The next FrameReady event does not occur until after the previous frame is released. In another embodiment, the client can poll for the next available frame using the WaitForFrame method.

In a preferred embodiment, both the client application and the server application are executed on the same computer. The computer can be running the Microsoft® Windows® 2000/XP operating system, for example, without limitation. The client application (USAutoView) can be developed using Microsoft® Visual C++6.0 and MFC. The source code can be-compiled, for example, in Visual Studio 6.0. The server side COM Automation interface and the TTFrameReceiver ActiveX control may be compatible with other MS Windows® software development environments and languages.

In an embodiment of the present invention, the name of the server side COM automation interface (ProgfD) is, for example, “Ultrasound.Document” and the interface is registered on the computer the first time the application is run. The dispatch interface can be imported into a client application from a type library.

In a preferred embodiment, automation interface is extended to support frame streaming with the addition of different methods such as void OpenFrameStream (BSTR* queueName, short numBuffers, long bufferSize, BSTR* queueOrder, short overwritepermission). The Opens frame stream transmitter on the server side; opens the shared-memory interface to the client application, queueNam,e is a unique name of the shared-memory "file" and is the same name that is used when opening the receiver, numBuffers is the number of buffers in the shared-memory queue, bufferSize is the size of each buffer in the shared-memory queue in bytes wherein the buffer size is 5120 bytes larger than the largest image that can be transmitted, queueOrder "LIO", "FIFO", or "LIFO", overwritePermission is 0 for overwrite not allowed, 1 for overwrite oldest, or 2 for overwrite newest. Note, OpenFrameStream must be called before opening the TTFrameReceiver control.

The next additional methods include void CloseFrameStream( ) which closes the frame stream transmitter on the server side, void StartTransmitting( ), which tells the server side to start transmitting ultrasound frames, void StopTransmitting( ), which tells the server side to stop transmitting ultrasound frames, and short GetFrameStreamStatus( ), which gets the status of the frame stream transmitter. It is important to check that the stream transmitter is open before opening the TTFrameReceiver. The COM automation interface is non-blocking and the OpenFrameStream call cannot occur at the instant it is called from the client application.

In a preferred embodiment, the TTFrameReceiver ActiveX Control is the client application's interface to the live ultrasound frame stream. Frame Stream Control Methods include boolean Open(BSTR name), which opens the frame stream receiver. The frame stream receiver cannot be opened until after the frame stream transmitter on the server has been opened. It also includes boolean Close( ), which closes the frame stream receiver, long WaitForFrame(long timeoutms), which wait for a frame to be ready or until end of timeout period, and boolean ReleaseFrame( ), which release the current image frame. The current frame can be released as soon as all of the desired data has been copied. The next frame cannot be received until the current frame is released. The return values of the other data access functions are not valid after the current frame is released until the next FrameReady event.

Data Access Methods in a preferred embodiment for the image includes long GetPtrBitmapinfo( ), which gets a pointer to the header (with color table) of the DIB that contain the image. The ultrasound image is stored as a standard Microsoft device independent bitmap (DIB). BITMAPINFO and BITMAPINFOHEADER structures can be cast to the returned pointer as needed. Memory for the BITMAPINFO structure is allocated in shared-memory and may not be de-allocated; instead, ReleaseFrame( ) can be called to return the memory to the shared-memory mechanism. Further methods include long GetPtrBitmapBits( ), which gets a pointer to the image pixels. The returned pointer can be cast as needed for use with the Microsoft DIB API. Memory for the bitmap pixels is allocated in shared-memory and may not be de-allocated; instead, ReleaseFrame( ) is called to return the memory to the shared-memory mechanism.

The methods related to probe identification include short GetProbeType( ), which gets the defined ultrasound probe type.being used, BSTR GetProbeType( ), which gets the defined probe name, long GetProbeSN( ), which gets the serial number of the probe being used.

With respect to temporal information, the methods include short GetSequenceNum( ), which gets the sequence number of the current frame. The sequence number is derived from an 8-bit counter and thus repeats every 256 frames. It is useful for determining gaps in the frame sequence and for re-ordering frames received when using the LIFO buffer order mode. Further, double GetRate( ), gets the frame rate when combined with the sequence number, provides precise relative timing for the received frames, BSTR GetTimestamp( ), which gets a timestamp for the current frame which provides an absolute time for the current frame that may be useful when synchronizing to external events. The resolution is approximately milliseconds. Timestamps can be averaged and used in conjunction with rate and sequence number to achieve higher precision. Lastly, with respect to temporal information, the methods include BSTR GetTriggerTimestamp( ), which gets a timestamp for the start of ultrasound scanning wherein the ultrasound probe is stopped when "freezing" the image. The trigger timestamp is recorded when live imaging is resumed.

Spatial Information in preferred embodiments has the following methods, short GetXPixels( ), which get the width of the image in pixels; short GetYPixels( ), which gets the height of the image in pixels; double GetXPixelSize( ), which gets the size of each pixel in the x-direction, (x-direction is defined to be horizontal and parallel to each image line); and double GetYPixelSize( ), which gets the size of each pixel in the y-direction. The y-direction is defined to be vertical and perpendicular to each image line. Further, double GetXOrigin( ), which get the x-location of the first pixel in the image relative to the transducer head and double GetYOrigin( ), which gets the x-location of the first pixel in the image relative to the transducer head. The positive y-direction is defined to be away from the transducer head into the patient. Another method includes short GetXDirection( ), which gets the spatial direction along each line of the image. The positive x-direction is defined to be away from the probe marker. The short GetYDirection( ), gets the spatial direction across each line of the image. The positive y-direction is defined to be away from the transducer head into the patient.

The spatial position of any pixel in the image relative to the transducer head can easily be calculated as follows:

$$PX=OX+NX*SX*DX$$

$$PY=OY+NY*SY*DY$$

wherein,

P=the position of the pixel relative to the transducer head,

O=the origin,

N=the index of the pixel in the image,

S=the pixel size,

D=the direction of the pixel.

Further, events in a preferred embodiment, void FrameReady( ) is used when a frame is ready and data can be read. The handler copies data from the data access methods and then calls ReleaseFrame( ). It is recommended that any kind of indefinite processing, for example, function that invokes message loops be avoided in the handler. Further, void FrameOverrun( ) is used when the server is unable to send a frame or a frame has to be overwritten in the buffers because the buffers are full. This only applies to the FIFO and LIFO modes, since the LIO automatically releases old buffers. This event is usefully for determining whether the client application is reading frames quickly enough and whether the number of buffers allocated is sufficient for the latency of the client.

In a preferred embodiment, USAutoView is a sample client application that automates the server side and displays live ultrasound image frames. It has functions to demonstrate starting and stopping the server side, hiding and showing the server side, toggling between showing and not showing graphics on the image, freezing and resuming the ultrasound acquisition, loading a preset exam, changing the designated patient size, changing the image size, spatial information, and inverting the image.

Figure 50:
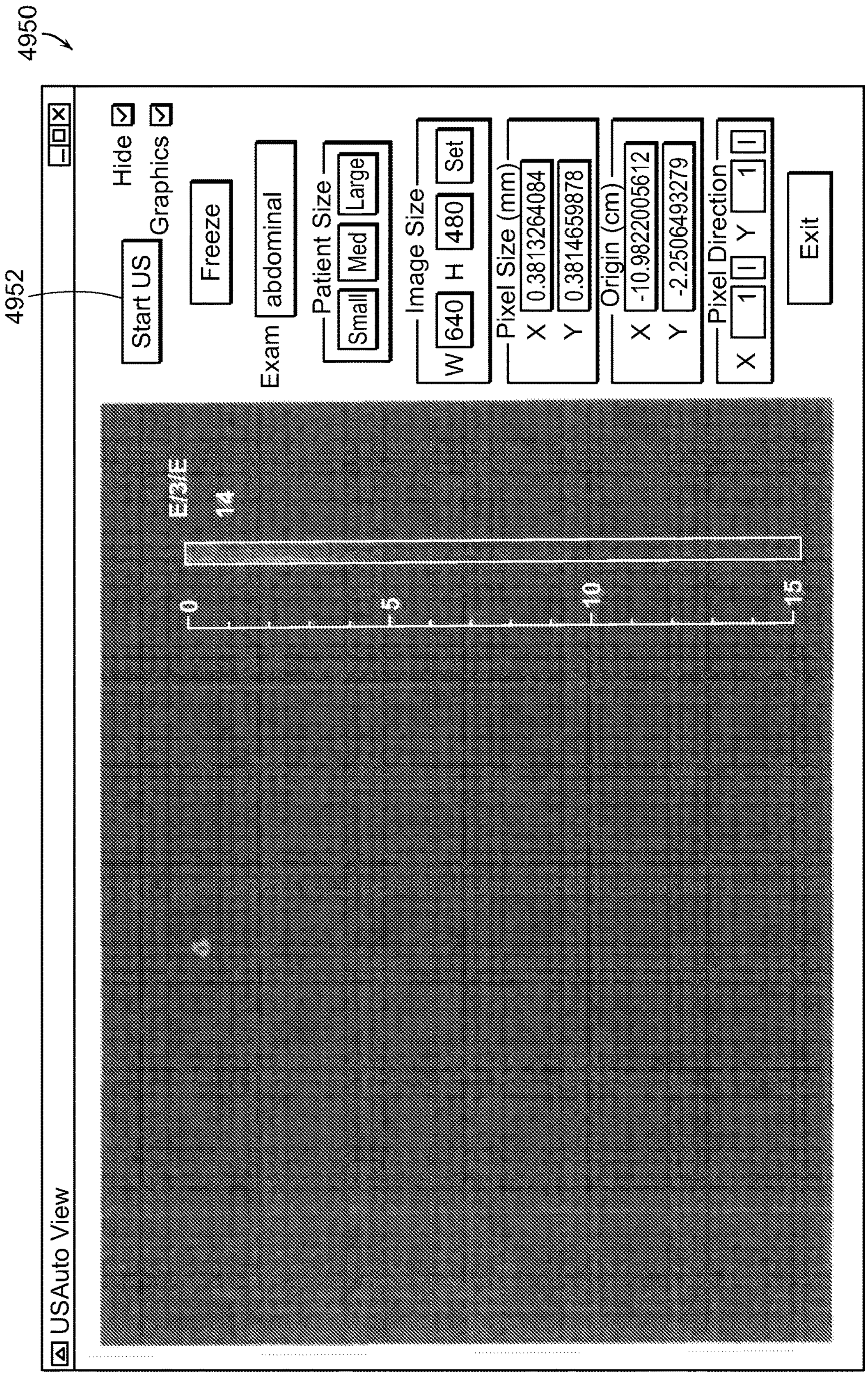
FIG. 50 is a view of a graphical user interface configured in accordance with one embodiment of the present invention.

FIG. 50 is a view of a graphical user interface used for a USAutoView UI in accordance with a preferred embodiment of the present invention. The USAutoView program is a Windows® dialog application with three ActiveX components. TTFrameReceiver which supplies ActiveX interface to receive ultrasound frames, TTAutomate which encapsulates automation of the server side and TTSimpleImageWnd which is the image display window. CUSAutoViewDlg is the main dialog. It manages the automation of the server side through the TTAutomate control, receiving ultrasound frames through TTFrameReceiver and image display through TTSimplelinageWnd. The OnStartUS( )method of CUSAutoViewDlg calls the TTAutomate and TTFrameReceiver methods needed to start or stop automation and data transmission from the server side.

The method OnFramReady( ) handles the FrameReady event from TTFrameReciever. It copies the desired data from TTFrameReceiver and then releases the frame with TTFrameReceiver's ReleaseFrame( ) method. It avoids any functions that perform indeterminate processing, such as functions that invoke message loops.

TTAutomate is an ActiveX control that encapsulates automation functions for the server side. The native COM Automation interface of the server side is non-blocking and requires waiting with GetStatusFlags to coordinate functions. TTAutomate wraps each function in the required wait loops. The wait loops allow Windows® messages to be processed so that the client application's user interface thread does not become blocked while waiting. Although automation methods in TTAutomate cannot return until the function has been completed, other Windows® messages are still processed before the function is completed. It is recommended to prevent multiple concurrent calls from message handlers to TTAutomate methods, as coordination with the server side is generally non-reentrant. Source code for this control is included in the USAutoView workspace. It may be reused or modified as desired.

TTSimpleImageWnd is an ActiveX control that provides a display window for device independent bitmaps (DIB's). The two properties of the display interface are long DIBitmapInfo and long DIBits. DIBitmapInfo corresponds to a pointer to a block of memory that contains the BITMAPINFO structure for the DIB. DIBits corresponds to a pointer to a block of memory that contains the image pixels. To load a new image, the DIBitmapInfo is set to the pointer to the bitmap info of the DIB. Then DIBits is set to the pointer to the bitmap bits. When DIBits is set, the pointer that was set for DIBitmapInfo is expected to still be valid and both the bitmap info and bitmap bits are copied internally for display on the screen. Both DIBitmapInfo and DIBits are set to zero to clear the image. Source code for this control is included in the USAutoView workspace. It may be reused or modified as desired.

The preferred embodiments of the present invention include a plurality of probe types. For example, the probes include, but are not limited to, a convex-linear transducer array operating between, 2-4 MHz, a phased-linear transducer array operating between 2-4 MHz, a convex-linear endocavity transducer array operating between 4-8 MHz, a linear transducer array operating between 4-8 MHz and a linear transducer array operating between 5-10 MHz.

Preferred embodiments of the portable ultrasound system of the present invention provide high resolution images such as the following during an examination: B-mode, M-mode, Color Doppler (CD), Pulsed Wave Doppler (PWD), Directional Power Doppler (DirPwr) and Power Doppler (PWR). Once the system software is installed the probe device is connected into a desktop or laptop. The probe can be an industry standard transducer connected to a 28 oz. case that contains the system's beamforming hardware. If the probe is connected to a laptop, then a 4-pin FireWire cable is connected to a IEEE 1394 serial connection located on a built-in MediaBay. However, if the probe is connected to a desktop, the computer may not be equipped with a MediaBay. One can connect the probe using an External DC Module (EDCM) connector. Before connecting the probe, one needs to make sure that the FireWire is connected on both the right and left sides of the computer.

In an embodiment, the EDCM is designed to accept a 6-pin IEEE 1394 (also referred to as FireWire) cable at one end and a Lemo connector from the probe at the other end. The EDCM accepts an input DC voltage from +10 to +40 Volts. Further, the system, in an embodiment, can be connected to a host computer with IEEE 1394. The 6-pin IEEE 1394 input to the EDCM can originate from any IEEE 1394 equipped host computer running, for example, the Windows® 2000 operating system. An external IEEE 1394 hub may also be necessary to provide the requisite DC voltage to the EDCM. In a host computer equipped with IEEE 1394, there are one of two types of IEEE 1394 connectors; a 4-pin or a 6-pin. The 6-pin connector is most often found in PC-based workstations that use internal PCI-bus cards. Typically, the 6-pin connector provides the necessary DC voltage to the EDCM. A 6-pin-male to 6-pin-male IEEE 1394 cable is used to connect the host computer to the EDCM.

The 4-pin connector is found in laptop computers that do not contain a MediaBay in accordance with a preferred embodiment or provide a DC voltage output. When using this connector type, an external IEEE-1394 hub can be used to power the EDCM and the probe.

When power is not provided from the host computer, an external IEEE-1394 hub can be used between the host computer and the EDCM. The hub derives its power from a wall outlet and is connected using a medical-grade power supply that conforms to the IEC 60601-1 electrical safety standard.

To connect the hub to the host computer, a 4-pin-male to 6-pin-male or 6-pin-male to 6-pin-male IEEE cable is required. The appropriate connector (4-pin or 6-pin) is inserted into the host computer and the 6-pin connector into the hub. The hub is then connected to the EDCM using a 6-pin-male to 6-pin-male IEEE 1394 cable. An IEEE 1394 hub is only necessary when the host computer cannot supply at least +10 to +40 DC volts and 10 watts power to the EDCM. If the host computer can supply adequate voltage and power, a 6-pin-male to 6-pin-male IEEE 1394 cable can be used to connect the computer directly to the EDCM.

Figure 51:
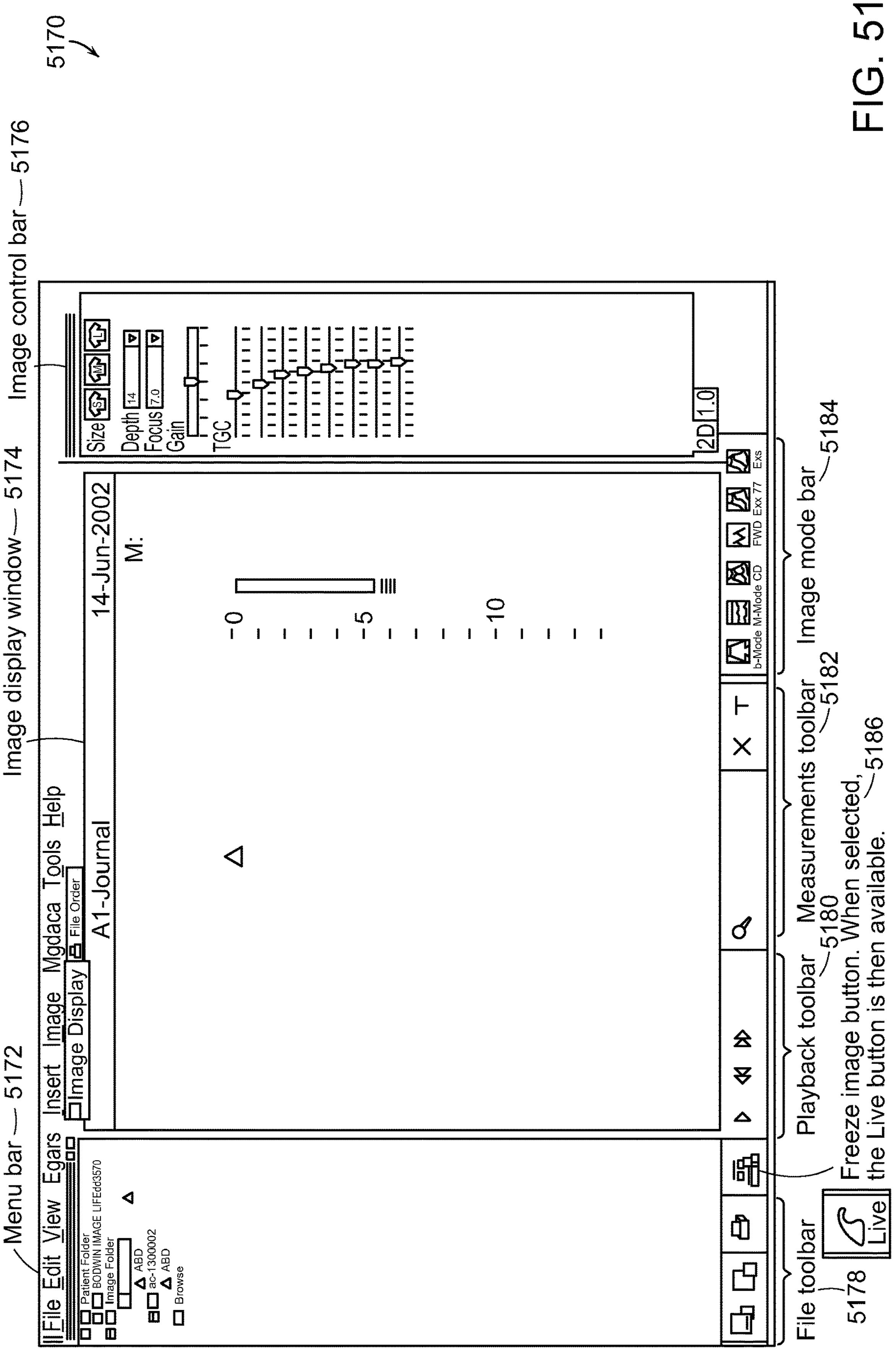
FIG. 51 illustrates a main screen display of a graphical user interface in accordance with one embodiment of the present invention shared memory, according to one embodiment of the present invention.

FIG. 51 illustrates a view of a main screen display of a graphical user interface in accordance with a preferred embodiment of the present invention. When the user starts the system in accordance with the present invention the main screen 5170 displays. To help the user navigate, the main screen can be considered as four separate work areas that provide information to help one perform tasks. These include a menu bar 5172, an image display window 5174, an image control bar 5176, and a tool bar 5178-5186.

In order to resize windows and regions the user can click the small buttons in the upper right of the window to close, resize, and exit the program. A user interface or button closes the window but leaves the program running (minimizing the window). A system button appears at the bottom of the screen, in the area called the taskbar. By clicking the system button in the taskbar the window re-opens. Another interface button enlarges the window to fill the entire screen (called maximizing), however, when the window is at its largest, the frame rates may decrease. Another interface button returns the window to the size that it was before being enlarged. The system program can be closed by another interface button.

Figure 52A:
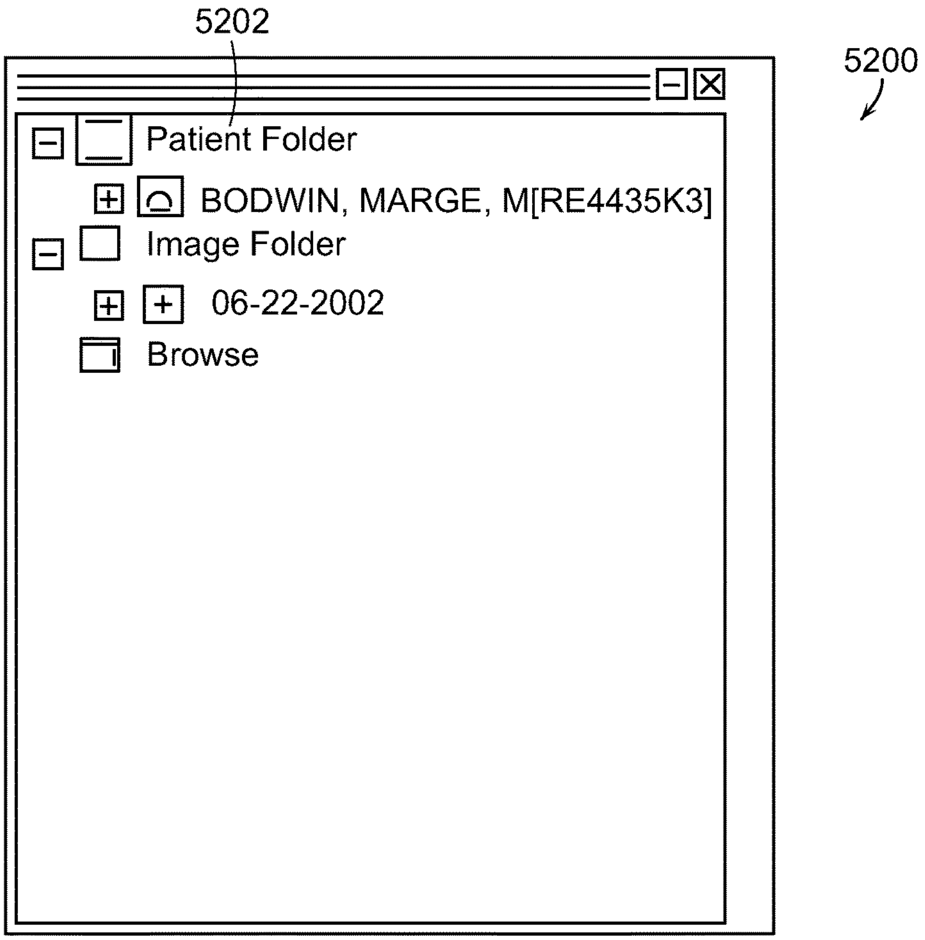
FIGS. 52A-52C show an alternate display of a graphical user interface, in accordance with another embodiment of the present invention.
Figure 52B:
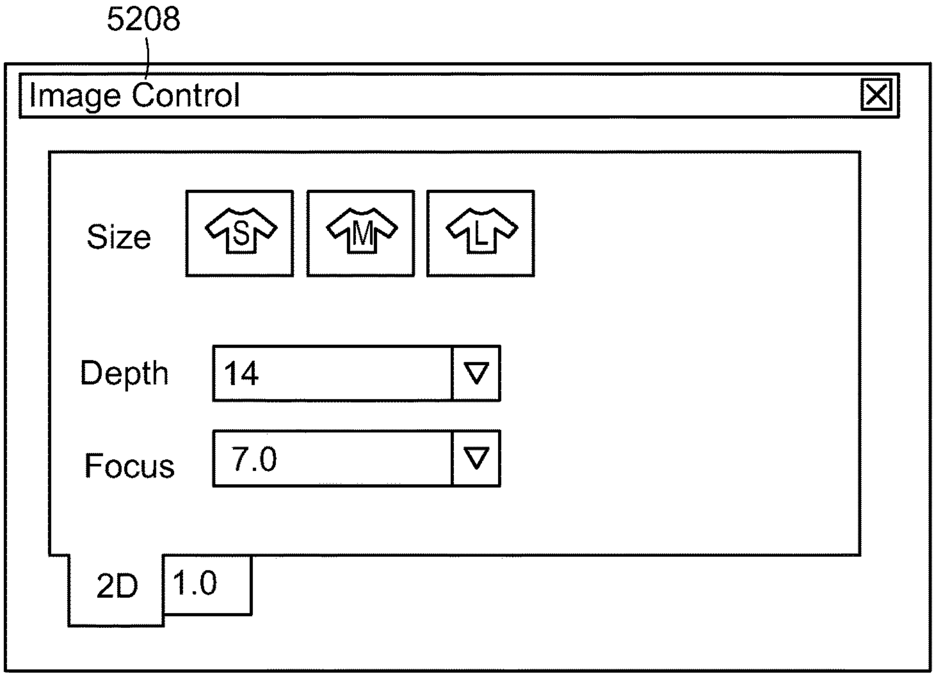
Figure 52C:
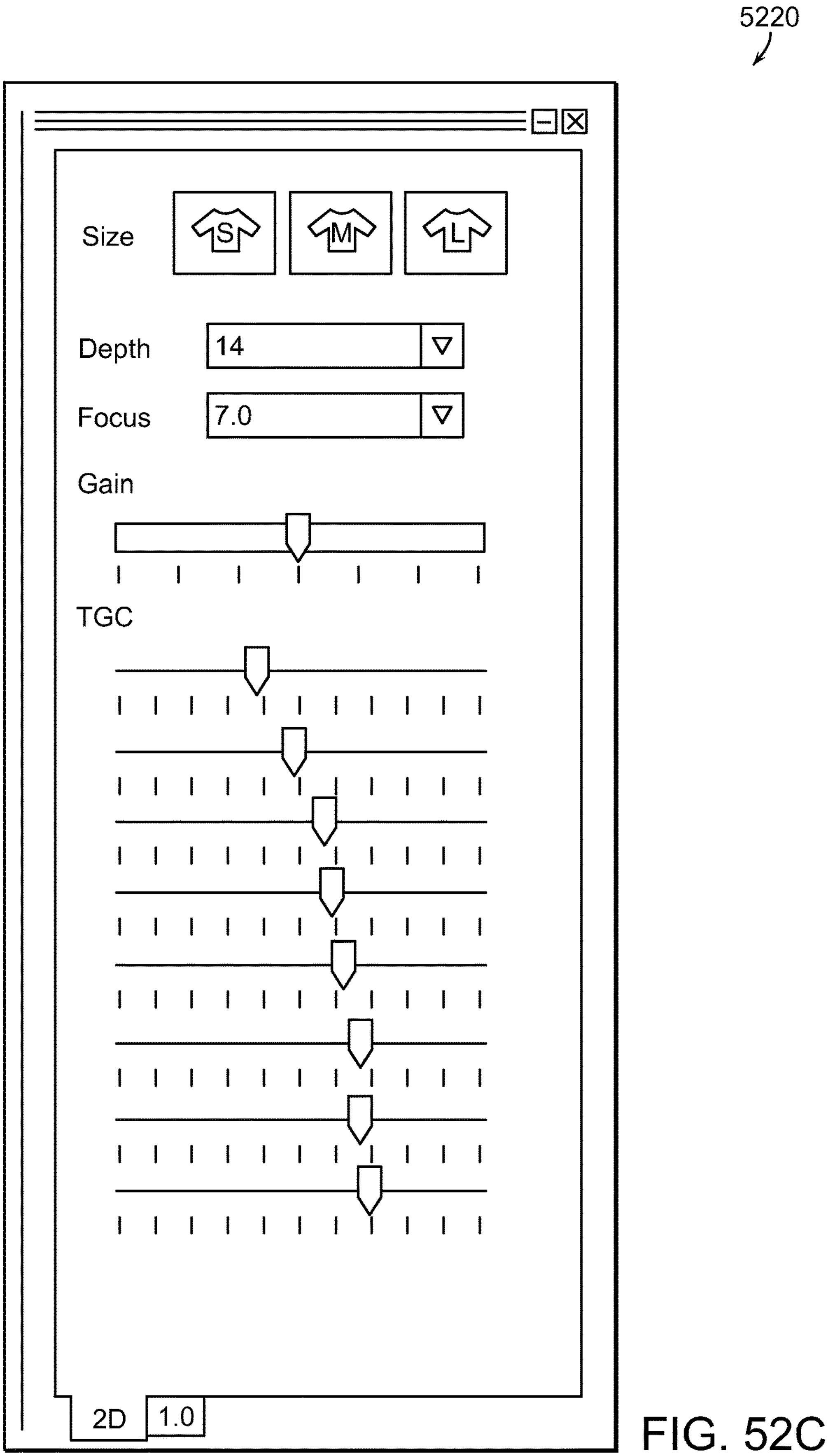

The user can increase or decrease the width of each region of the application to meet one's needs. For example, to make the Explorer window more narrow, the cursor is placed at either end of the region and by clicking and dragging the new desired size is obtained. One can re-position the size and location of each region so that they become floating windows. To create floating windows, the user simply clicks one's mouse on the double-edged border of the specific region and drags it until it appears as a floating window. To restore the floating window back to original form, one double-clicks in the window. These functionalities are depicted in FIGS. 52A-52C which are views in a graphical user interface in accordance with a preferred embodiment of the present invention.

Figure 53A:
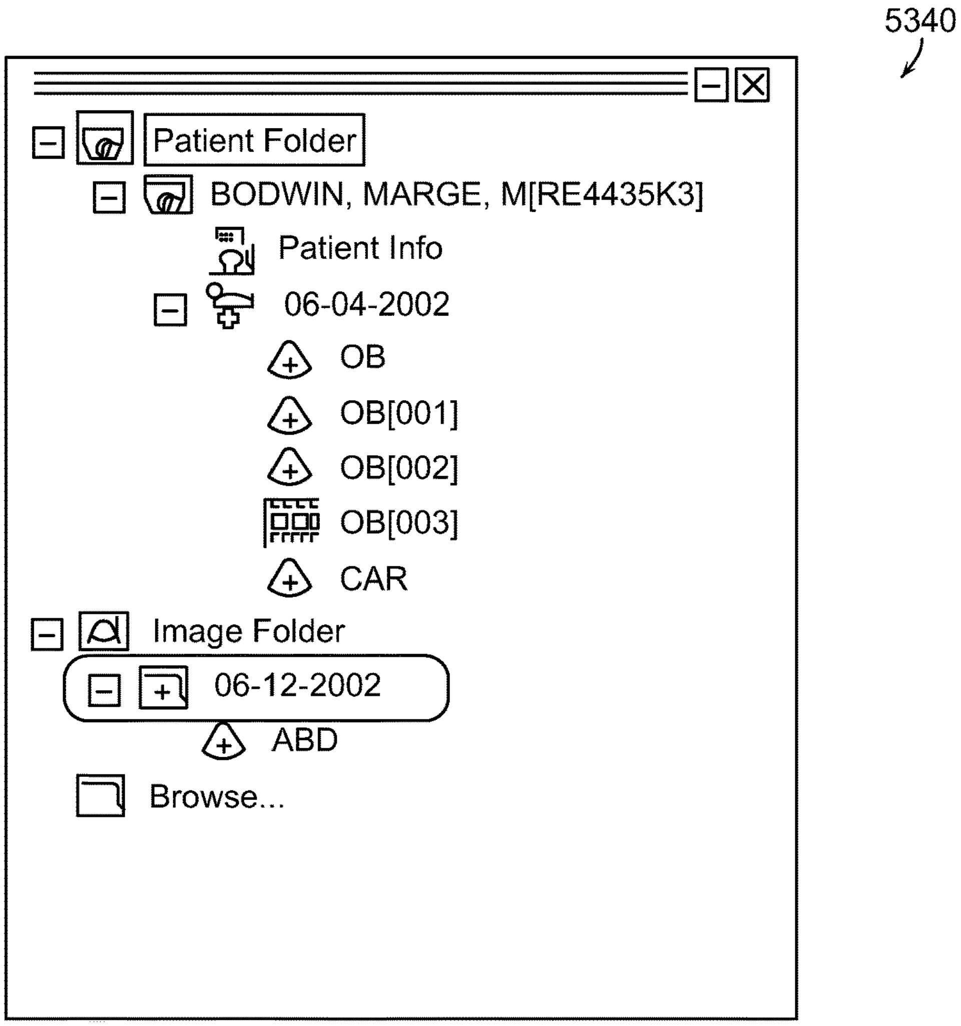
FIGS. 53A-53B illustrate a patient folder and image folder of a graphical user interface, in accordance with one embodiment of the present invention.
Figure 53B:
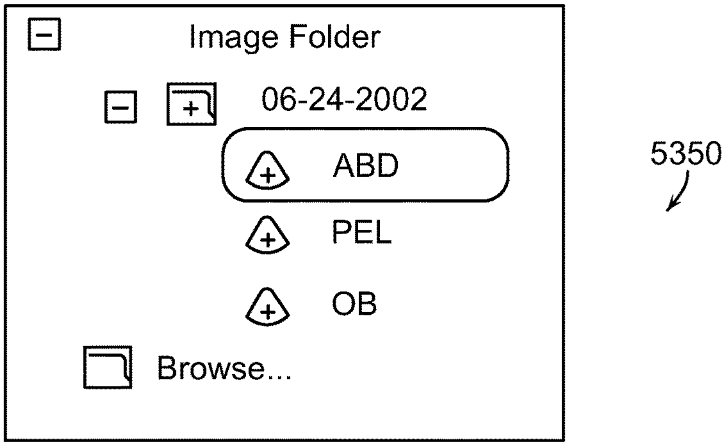

The Explorer window provides the nested level file directory 5202 for all patient folders the user creates images that are created and saved. The folder directory structure includes the following, but is not limited to, patient folder, and an image folder. The patient folder directory is where patient information files are stored along with any associated images. The image folder directory contains images by date and exam type. The images in this directory are not associated with a patient and are created without patient information. FIGS. 53A-53B illustrate the patient folder 5240 and image folder 5250 in accordance with a preferred embodiment of the present invention. The menu bar at the top of the screen provides nine options one can use to perform basic tasks. To access a menu option simply click the menu name to display the drop-down menu options. The user can also access any menu by using its shortcut key combination.

The Image display window provides two tabs: Image Display and Patient Information. The user clicks on the Image Display tab to view the ultrasound image. The image is displayed in the window according to the control settings that are defined. Once the image is saved, when the user retrieves it again, the category, date and time of the image is also shown in the Image Display window. The Patient Info tab is used to enter new patient information which is later stored in a patient folder. The user can access this tab to also make modifications and updates to the patient information.

Figure 54A:
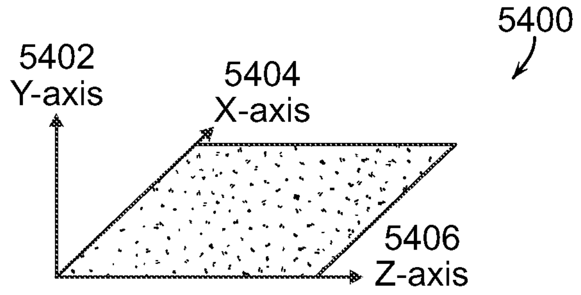
FIGS. 54A-54C illustrate XY bi-plane probe comprising a two one-dimensional, ID multi-element arrays in accordance with a preferred embodiment of the invention.
Figure 54B:
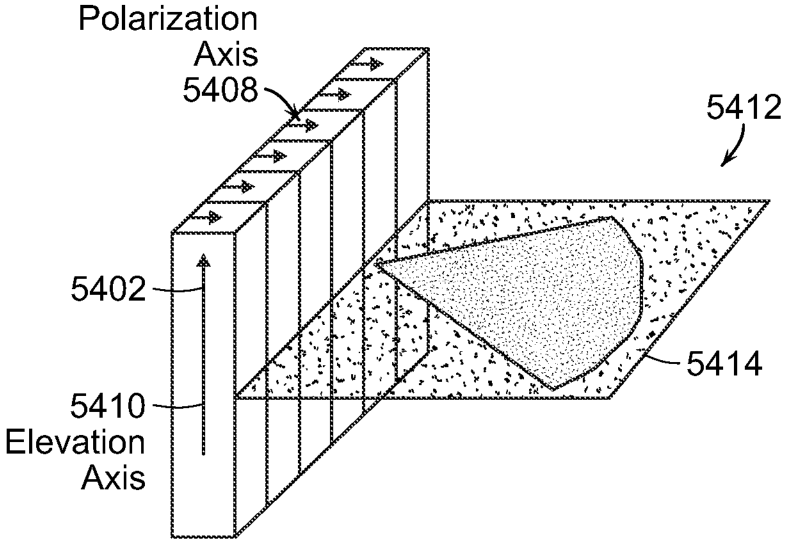
Figure 54C:
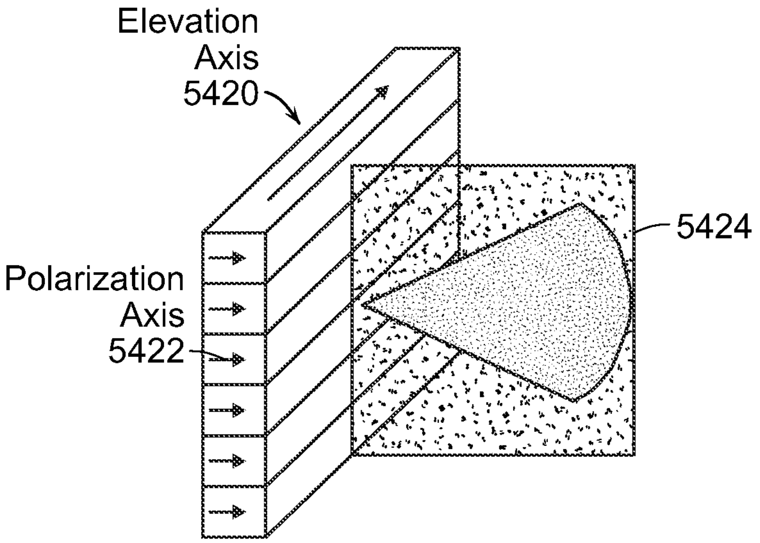

FIGS. 54A and 54C illustrate an XY bi-plane probe consisting of two one dimensional, multi-element arrays. The arrays may be constructed where one array is on top of the other with a polarization axis of each array being aligned in the same direction. The elevation axis of the two arrays can be at a right angle or orthogonal to one another. Exemplary embodiments can employ transducer assemblies such as those described in U.S. Pat. No. 7,066,887, the entire contents of which is incorporated herein by reference, or transducers sold by Vernon of Tours Cedex, France, for example. Illustrated by FIG. 54A, the array orientation is represented by arrangement 5400. The polarization axis 3908, of both arrays are pointed in the z-axis 5406. The elevation axis of the bottom array, is pointed in y-direction 5402, and the elevation axis of the top array, is in the x-direction 5404.

Further illustrated by FIG. 54B, a one dimensional multi-element array forms an image as depicted in arrangement 5412. A one-dimensional array with an elevation axis 3910, in a y-direction 5414, forms the ultrasound image 5414, on the x-axis 5404, z-axis 5406, plane. A one-dimensional array with the elevation axis 5410, in the x-direction 5404, forms the ultrasound image 5414, on the y-axis 5402, z-axis 5406. A one dimensional transducer array with elevation axis 5410, along a y-axis 5402, and polarization axis 5408, along a z-axis 5406, will result in a ultrasound image 5414, formed along the x 5404 and the z 5406 plane. An alternate embodiment illustrated by FIG. 54C depicts a one-dimensional transducer array with an elevation axis 5420, in a x-axis 5404, and a polarization axis 5422, in the z-axis 5406, direction. The ultrasound image 5424, is formed on the y 5402 and the z 5406 plane.

Figure 55:
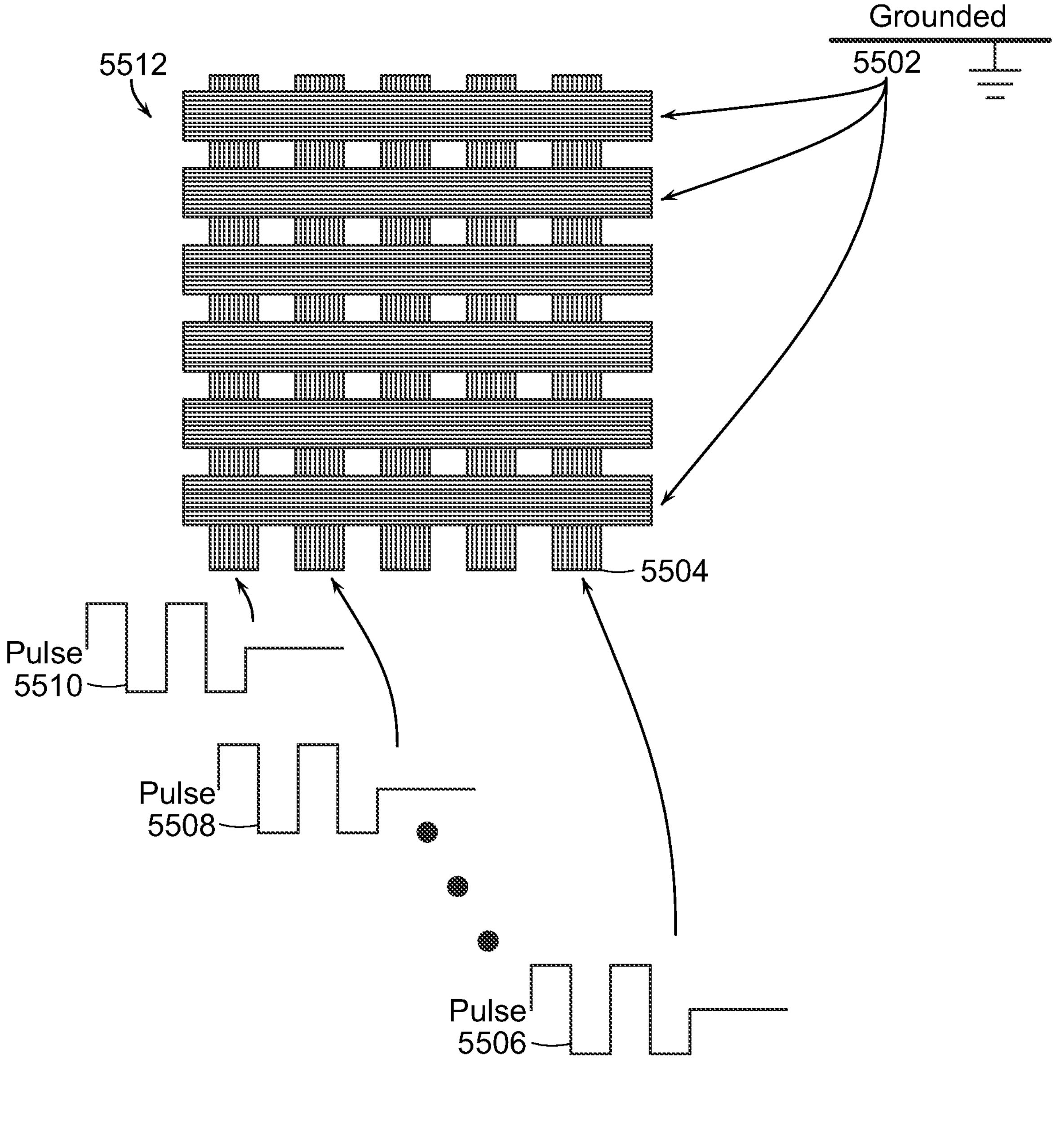
FIG. 55 illustrates the operation of a bi-plane image forming xy-probe, in accordance with one embodiment of the present invention.

FIG. 55 illustrates the operation of a bi-plane image forming xy-probe where array 5512 has a high voltage applied for forming images. High voltage driving pulses 5506, 5508, 5510, may be applied to the bottom array 5504, with a y-axis elevation. This application may result in generation of transmission pulses for forming the received image on the XZ plane, while keeping the elements of the top array 5502 at a grounded level. Such probes enable a 3D imaging mode using simpler electronics than a full 2D transducer array. A touchscreen activated user interface as described herein can employ screen icons and gestures to actuate 3D imaging operations. Such imaging operations can be augmented by software running on the tablet data processor that processes the image data into 3D ultrasound images. This image processing software can employ filtering smoothing and/or interpolation operations known in the art. Beamsteering can also be used to enable 3D imaging operations. A preferred embodiment uses a plurality of 1D sub-array transducers arranged for bi plane imaging.

Figure 56:
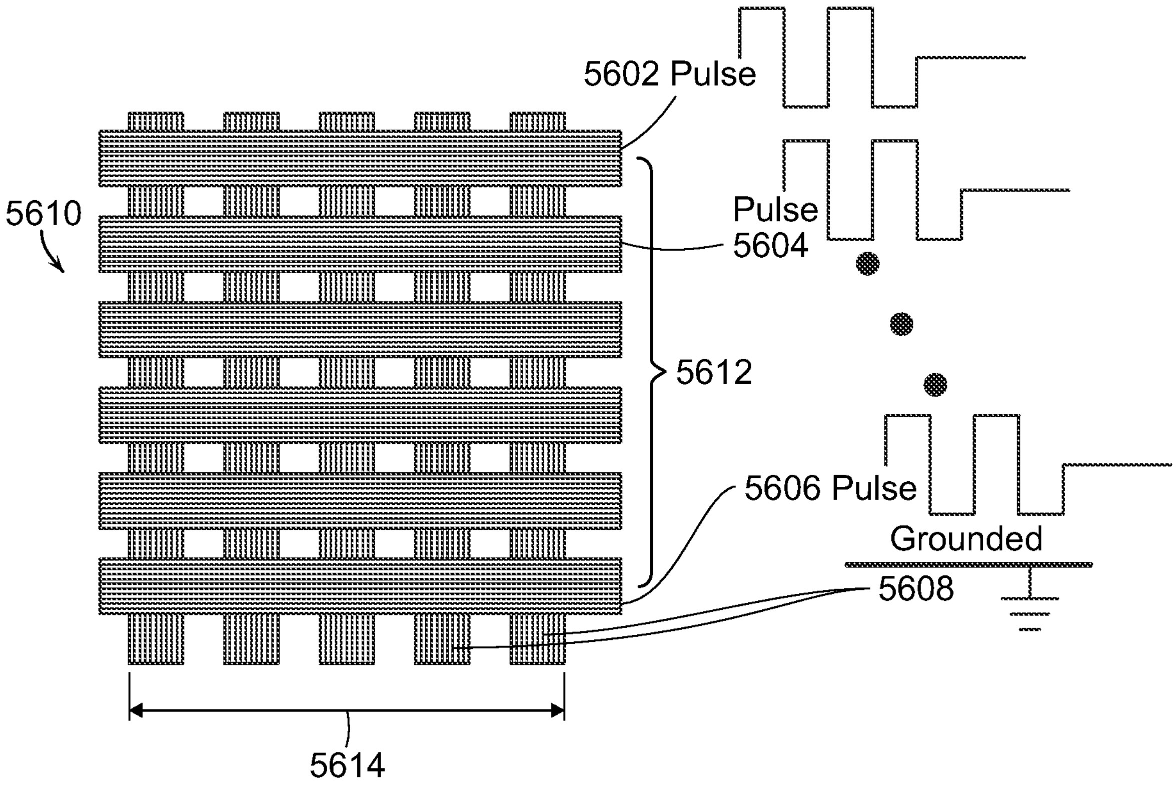
FIG. 56 illustrates the operation of a bi-plane image forming xy-probe, in accordance with another embodiment of the present invention.

FIG. 56 illustrates the operation of a bi-plane image forming xy-probe. FIG. 56 illustrates a array 5610, that has a high voltage applied to it for forming images. High voltage pulses 5602, 5604, 5606, may be applied to the top array 5612, with elevation in the x-axis, generating transmission pulses for forming the received image on the yz-plane, while keeping the elements of the bottom array 5614, grounded 4108. This embodiment can also utilize orthogonal 1D transducer arrays operated using sub-array beamforming as described herein.

Figure 57:
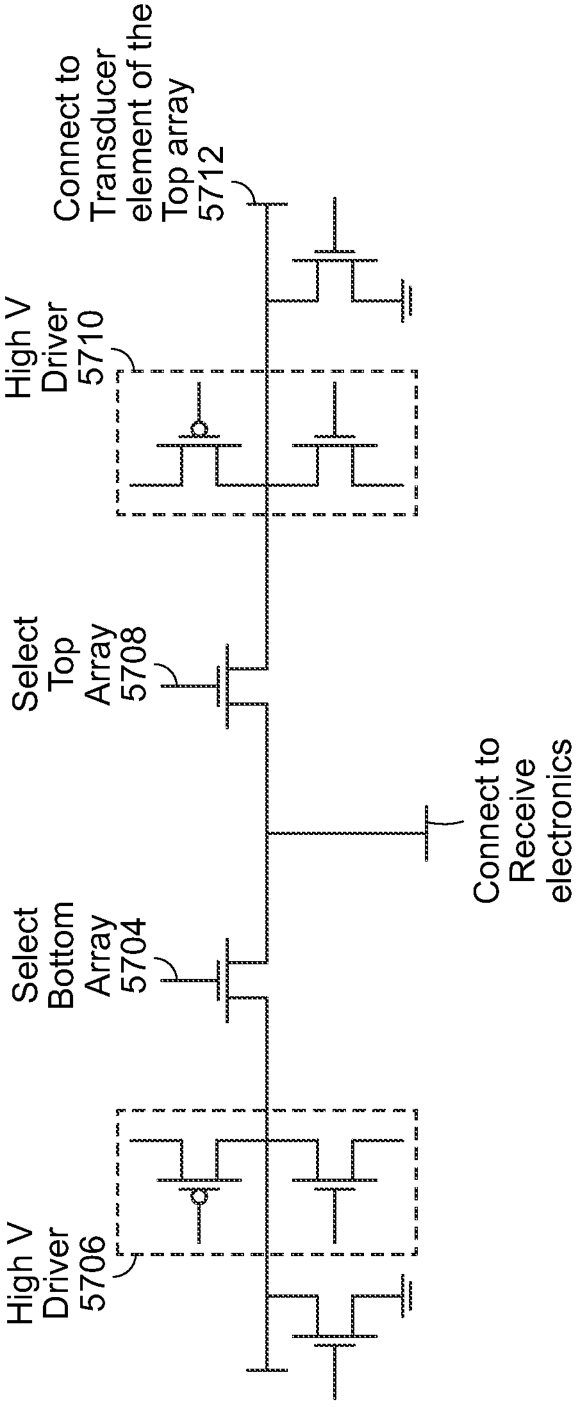
FIG. 57 illustrates a high voltage driver circuit for a bi-plane image forming xy-probe, in accordance with one embodiment of the present invention.

FIG. 57 illustrates the circuit requirements of a bi-plane image forming xy-probe. The receive beamforming requirements are depicted for a bi-plane probe. A connection to receive the electronics 5702, is made. Then elements from the select bottom array 5704, and select top array 5708, are connected to share one connect to the receive electronics 5702 channel. A two to one mux circuit can be integrated on the high voltage driver 5706, 5710. The two to one multiplexor circuit can be integrated into high voltage driver 5706, 5712. One receive beam is formed for each transmit beam. The bi-plane system requires a total of 256 transmit beams for which 128 transmit beams are used for forming a XZ-plane image and the other 128 transmit beams are used for forming a YZ-plane image. A multiple-received beam forming technique can be used to improve the frame rate. An ultrasound system with dual received beam capabilities for each transmit beam provides a system in which two received beams can be formed. The bi-plane probe only needs a total of 128 transmit beams for forming the two orthogonal plane images, in which 64 transmit beams are used to form a XZ-plane image with the other 64 transmit beams for the YZ-plane image. Similarly, for an ultrasound system with a quad or 4 receive beam capability, the probe requires 64 transmit beams to form two orthogonal-plane images.

Figure 58A:
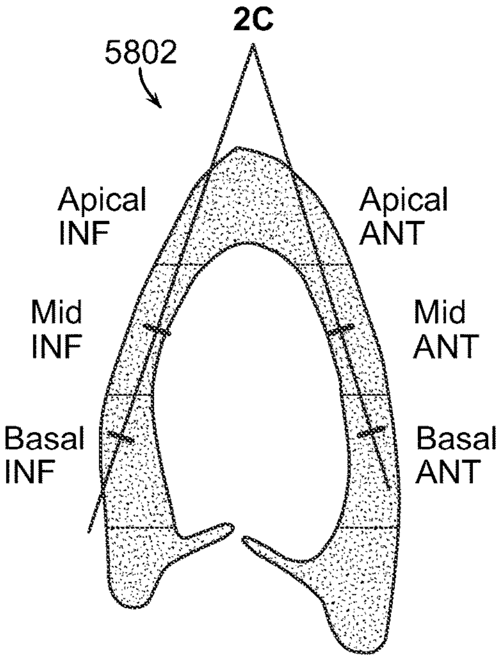
FIGS. 58A-58B illustrate simultaneous bi-plane evaluation of left ventricular condition, according to an embodiment of the present invention.
Figure 58B:
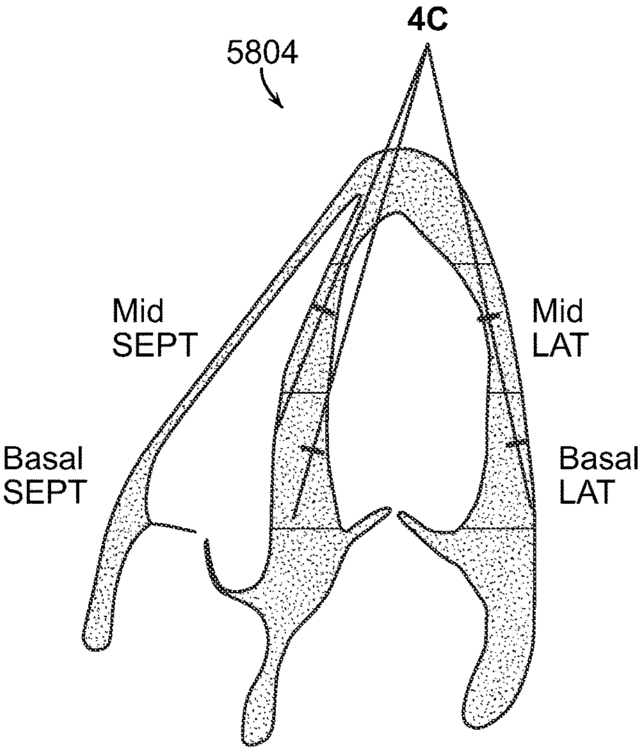

FIGS. 58A-58B illustrate an application for simultaneous bi-plane evaluation. The ability to measure the LV mechanical dyssynchrony with echocardiograph can help identify patients that are more likely to benefit from Cardiac Resynchronization Therapy. LV parameters needed to be quantified are Ts-(lateral-septal), Ts-SD, Ts-peak, etc. The Ts-(lateral-septal) can be measured on a 2D apical 4-chamber view Echo image, while the Ts-SD, Ts-peak (medial), Ts-onset(medial), Ts-peak(basal), Ts-onset (basal) can be obtained on two separated parasternal short-axis views with 6 segments at the level of mitral valve and at the papillary muscle level, respectively, providing a total of 12 segments. FIG. 58A-58B depict an xy-probe providing apical four chamber 5804, and apicial two chamber 5802 images, to be viewed simultaneously.

Figure 59A:
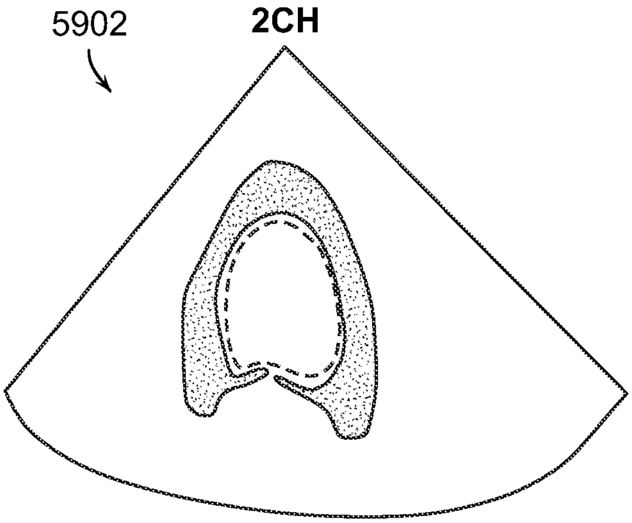
FIGS. 59A-59B illustrate ejection fraction probe measurement techniques in accordance with preferred embodiments of the invention.
Figure 59B:
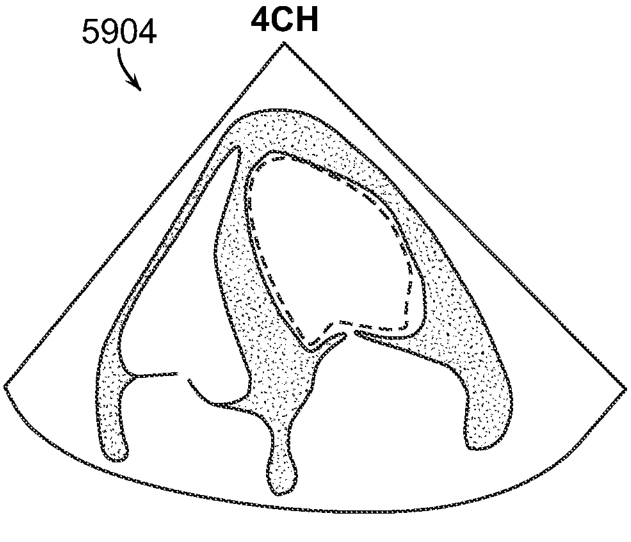

FIGS. 59A-59B illustrate ejection fraction probe measurement techniques. The biplane-probe provides for EF measurement, as visualization of two orthogonal planes ensure on-axis views are obtained. Auto-border detection algorithm, provides quantitative Echo results to select implant responders and guide the AV delay parameter setting. As depicted in FIG. 59A XY probe acquires real-time simultaneous images from two orthogonal planes and the images 5902, 5904 are displayed on a split screen. A manual contour tracing or automatic boarder tracing technique can be used to trace the endocardial boarder at both end-systole and end-diastolic time from which the EF is calculated. The LV areas in the apical 2CH 5902, and 4CH 5904, views, A1 and A2 respectively, are measured at the end of diastole and the end of systole. The LVEDV, left ventricular end-diastolic volume, and LVESV, left ventricular the end-systole volume, are calculated using the formula:

$$V = \frac{8}{3\pi}\frac{A_1 A_2}{L}.$$

And the ejection fraction is calculated by $$EF = \frac{LVDEV - LVESD}{LVEDV}.$$

Figure 60:
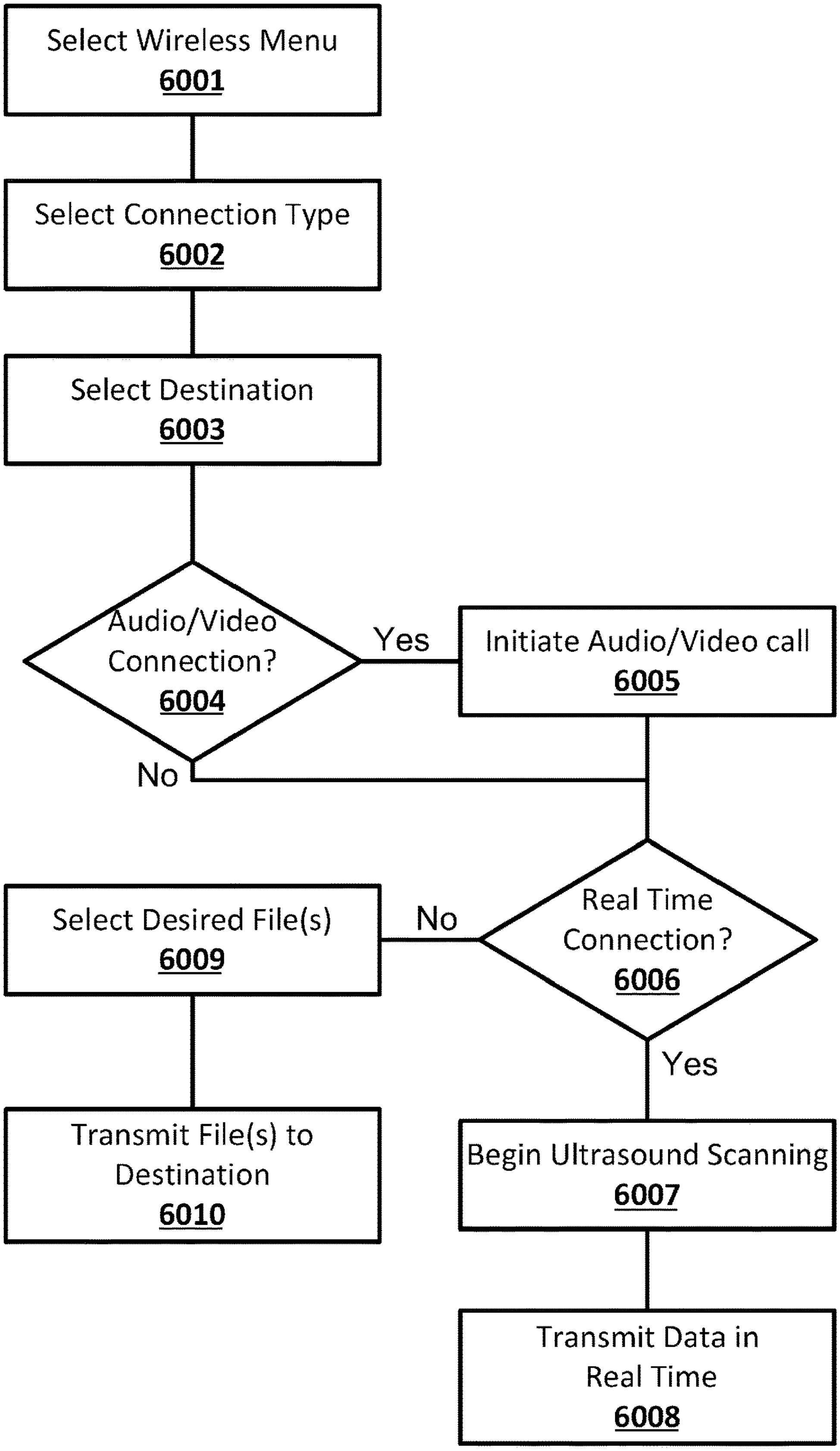
FIG. 60 illustrates an exemplary method for wirelessly communicating data to and from a portable ultrasound imaging device, according to an embodiment of the present invention.

FIG. 60 illustrates an exemplary method for wirelessly communicating data to and from a portable ultrasound imaging device, according to an embodiment of the present invention. The method may begin with selecting 6071 a wireless communication menu option which presents various wireless connections available to the user. For example, a user may wish to connect to a WiFi network, a 3G or 4G cellular network, or some other wireless network. The method may continue with selecting 6002 a desired wireless connection. The method may further include selecting 6003 one or more destinations where the ultrasound data is to be transmitted. In some embodiments, this selection may be performed by selecting one or more hospitals, doctors, clinics, etc. using the touchscreen UI, similar to how one selects a contact from a phone contact list. The method may further include determining 6004 whether an audio and/or video connection is desired. In some embodiments, in addition to transmitting ultrasound and other medical data between the portable ultrasound device and a remote hospital or clinic, the user may also establish an audio and/or video connection via the same wireless network. This function allows the user of the ultrasound imaging device to, for example, remotely perform and transmit ultrasound data while being in direct audio and/or video contact with a hospital or medical professional. In one example, initiating an audio and/or video call with a hospital may allow the user of the portable ultrasound imaging device to receive direction and/or advice from a doctor while performing an ultrasound procedure. If an audio and/or video call is desired, the method may further include initiating 6005 the audio/video call with the desired destination.

If no audio/video connection is desired, or after an audio/video call is initiated, the method may further include determining 6006 whether ultrasound imaging data is intended to be transmitted in real time, or whether the user merely wishes to transmit ultrasound data that has already been generated. If a real time connection is desired, the method may further include beginning 6007 the ultrasound scanning and transmitting 6008 the ultrasound data to the desired destination or destinations in real time. If no real time ultrasound data transmission is required, the method may continue with selecting 6009 the desired file or files and transmitting 6010 the selected file or files to the desired destination or destinations.

In some embodiments, a user may carry out the methods described above by navigating through the various windows, folders, sub-folders, menus, and/or sub-menus presented via the touch sensitive UI. The various UI commands used to select a menu option, destination, file, etc. may be performed with a touchscreen gesture performed over an icon, by dragging and dropping an icon from one location to another, selecting or deselecting one or more check boxes, or performing any other sufficiently unique or distinguishable touchscreen command. In some embodiments, the various touchscreen commands described herein may be user configurable, while in other embodiments they are hard-coded. As will be appreciated, the various elements of the methods described herein may be performed in any desired order. For example, in some embodiments a user may select 6003 one or more destinations prior to selecting 6009 the file or files which are to be transmitted, while in other embodiments a user may select 6009 one or more files prior to selecting 6003 the desired destination. Similarly, other elements of the method described above may be performed in various sequences, or simultaneously, and the methods described herein are not intended to be limited to any particular sequence unless specifically stated.

It is noted that the operations described herein are purely exemplary, and imply no particular order. Further, the operations can be used in any sequence, when appropriate, and/or can be partially used. Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified.

With the above illustrative embodiments in mind, it should be understood that such embodiments can employ various computer-implemented operations involving data transferred or stored in computer systems. Such operations are those requiring physical manipulation of physical quantities. Typically, though not necessarily, such quantities take the form of electrical, magnetic, and/or optical signals capable of being stored, transferred, combined, compared, and/or otherwise manipulated.

Further, any of the operations described herein that form part of the illustrative embodiments are useful machine operations. The illustrative embodiments also relate to a device or an apparatus for performing such operations. The apparatus can be specially constructed for the required purpose, or can incorporate general-purpose computer devices selectively activated or configured by a computer program stored in the computer. In particular, various general-purpose machines employing one or more processors coupled to one or more computer readable media can be used with computer programs written in accordance with the teachings disclosed herein, or it may be more convenient to construct a more specialized apparatus to perform the required operations.

The foregoing description has been directed to particular illustrative embodiments of this disclosure. It will be apparent, however, that other variations and modifications may be made to the described embodiments, with the attainment of some or all of their associated advantages. Moreover, the procedures, processes, and/or modules described herein may be implemented in hardware, software, embodied as a computer-readable medium having program instructions, firmware, or a combination thereof. For example, one or more of the functions described herein may be performed by a processor executing program instructions out of a memory or other storage device.

It will be appreciated by those skilled in the art that modifications to and variations of the above-described systems and methods may be made without departing from the inventive concepts disclosed herein. Accordingly, the disclosure should not be viewed as limited except as by the scope and spirit of the appended claims.

The invention claimed is:

1. A portable medical ultrasound imaging system including:

an ultrasound display tablet, a tablet housing of the ultrasound display tablet being mounted on a cart and having a front panel operable by a user during a medical ultrasound imaging procedure;

a multi-port transducer connector that is connectable to a plurality of transducer probes including at least one transducer probe that communicates with the ultrasound display tablet;

a complex programmable logic device (CPLD) that clocks an ultrasound scan by at least one transducer probe connected to the multi-port transducer connector;

a touch screen display disposed on the front panel wherein a first touch actuated gesture controls focus and a second touch actuated gesture controls gain during the medical ultrasound imaging procedure; and a computer disposed in the tablet housing, the computer being connected to a beamformer device that generates beamformed image data and including at least one processor and at least one memory powered by a battery on the cart, wherein the computer controls selection of an imaging mode from at least one selected from B-mode imaging, M-mode imaging, an elastography imaging mode or a color Doppler imaging mode in response to touch actuation of the touch screen display, the at least one processor configured to operate a graphical user interface (GUI) on the touch screen display using battery power to perform an ultrasound imaging sequence using at least one imaging mode, the GUI including a plurality of work areas including:

a first work area including a touch actuatable menu window having one or more selectable touch actuated control icons, wherein at least one control icon is configured to operate an ultrasound image display that displays an ultrasound image obtained from the ultrasound scan by the at least one connected transducer probe, and a second touch actuated selectable work area to display a list of anatomic regions, each anatomic region having touch actuated image presets for ultrasound imaging of the anatomic region.

2. The system of claim 1, wherein the touch screen display is configured to receive one or more user inputs including at least two user inputs for placing a first cursor and a second cursor with respect to the ultrasound image, and wherein the computer is further configured to perform a caliper measurement based at least in part on a distance between the first cursor and the second cursor.

3. The system of claim 1, wherein the ultrasound image is generated by a connected transducer probe selected by a touch actuated switch.

4. The system of claim 1, wherein the touch screen display is configured to receive one or more user inputs including a tracing gesture performed on the image display area to trace a feature displayed on the ultrasound image.

5. The system of claim 4, wherein the tracing gesture is configured to trace an image of a liver displayed with the touch screen display.

6. The system of claim 4, wherein the tracing gesture is configured to trace an image of a waveform displayed with the touch screen display.

7. The system of claim 4, wherein the computer is further configured to measure an area or a volume associated with the traced feature in response to the tracing gesture.

8. The system of claim 1, wherein the touch screen display is configured to receive one or more user inputs including a first user input configured to place a first cursor at a first location with respect to the ultrasound image and a second user input configured to fix the first cursor at the first location.

9. The system of claim 1, wherein the touch screen display is configured to receive one or more user inputs including a user input configured to select an area of the ultrasound image associated with an anatomic feature shown in the ultrasound image.

10. The system of claim 1, wherein the portable medical ultrasound imaging system is configured to perform at least one of: abdominal imaging, biopsy procedures, catheter introduction, fetal imaging, cardiac imaging, vascular imaging, imaging during endoscopic procedures, radiation therapy, cryotherapy, imaging for telemedicine applications, or imaging for veterinary applications.

11. The system of claim 1, wherein the touch screen display is configured to receive one or more user inputs including at least one of: a tap gesture, a double tap gesture, a drag gesture, a press gesture, or a press-and-drag gesture performed on the touch screen display.

12. The system of claim 1, wherein a transducer probe housing includes a transducer array that comprises a biplane transducer array such that orthogonal images are simultaneously displayed on the touch screen display.

13. The system of claim 1, wherein the touch actuatable image control window includes at least one of: a 2D touch control, a Doppler beam steering control, a color touch control, a storage touch control, a split screen touch control, a PW imaging touch control, an annotation touch control, or a dynamic range touch control.

14. The system of claim 1, wherein the processor is further configured to superimpose an image associated with the touch actuatable image control window over the ultrasound image.

15. The system of claim 1, wherein an image display area is rendered on the touch screen display between a touch actuatable image control window and the touch actuatable menu window and wherein the GUI operating on the touch screen display further simultaneously displays an additional work area having a plurality of touch actuated controls.

16. The system of claim 1, wherein the one or more selectable components of the touch actuatable menu window include selectable components for selecting one or more files in a patient folder directory or an image folder directory.

17. The system of claim 1 wherein the beamformer device comprises an integrated circuit that is within a transducer probe housing.

18. The system of claim 1 wherein the beamformer device comprises an integrated circuit that is within the tablet housing.

19. The system of claim 1 further comprising a transducer probe housing connection cable.

20. The system of claim 1 further comprising a touch actuated imaging depth control icon in a touch actuated image control window.

21. The system of claim 1 further comprising a touch actuated liver imaging procedure.

22. The system of claim 1 wherein at least one of the plurality of transducer probes obtains measurements used to calculate an ejection fraction.

23. The system of claim 1 wherein cardiac imaging provides a plurality of different views of the heart.

24. A portable medical ultrasound imaging system including:

an ultrasound display tablet, a tablet housing of the ultrasound display tablet having a front panel operable by a user during a medical ultrasound imaging procedure including at least one of a B mode imaging procedure, an M mode imaging procedure, color doppler imaging or an elastography imaging procedure selectable by the user;

a multiport transducer connector that is connectable to a plurality of transducer probes including at least one transducer probe that communicates with the ultrasound display tablet;

a complex programmable logic device (CPLD) that clocks an ultrasound scan by at least one or more-transducer probe connected to the multi-port transducer connector;

a touch screen display disposed on the front panel wherein a first touch actuated focus control gesture controls a focus and a second touch actuated gain control gesture controls gain during the imaging procedure and wherein a number of focal zones can be selected; and a computer disposed in the tablet housing, the computer being connected to a beamformer circuit that generates beamformed image data, the computer, including at least one processor and at least one memory powered by a battery wherein the computer controls selection of an imaging mode from at least one selected from B-mode imaging, M-mode imaging, a color Doppler imaging mode, or an elastography imaging mode in response to touch actuation of the touch screen display, at least one imaging mode configured to perform a liver imaging procedure, the at least one processor configured to operate a graphical user interface (GUI) on the touch screen display using battery power to perform an ultrasound imaging sequence using at least one imaging mode, the GUI including a plurality of work areas including:

a first work area including a touch actuatable menu window having one or more selectable touch actuated controls wherein at least one control icon is configured to operate an ultrasound image display area that displays an ultrasound image obtained from the ultrasound scan by the at least one connected ultrasound transducer probe, and a second touch actuated selectable work area to display a list of anatomic regions, each anatomic region having touch actuated image presets for ultrasound imaging of the anatomic region.

25. The system of claim 24 wherein a touch actuated input on the displayed ultrasound image includes a tracing gesture performed on a lesion of the liver on a display work area of the touch screen display.

26. The system of claim 24 wherein the beamformer circuit is within a transducer probe housing.

27. The system of claim 24 wherein the at least one transducer probe connected to the multiport transducer is selected for an elastography imaging procedure with a touch actuated switch on the touch screen display wherein the selected transducer probe applies a pressure to a region to be imaged.

28. The system of claim 24 wherein the beamformer circuit is within the tablet housing.

29. The system of claim 24 wherein at least one of the plurality of transducer probes obtains measurements used to calculate an ejection fraction.

30. The system of claim 24 wherein cardiac imaging provides a plurality of different views of the heart.

31. A portable medical ultrasound imaging system including:

an ultrasound display having a tablet housing in a tablet form factor, the tablet housing having a front panel operable by a user during a medical ultrasound imaging procedure including at least one of a B mode imaging procedure, an M mode imaging procedure, color doppler imaging mode or an elastography imaging mode selectable by the user;

a multiport transducer connector that is connectable to a plurality of transducer probes including at least one transducer probe that communicates with the ultrasound display;

a complex programmable logic device (CPLD) that clocks an ultrasound scan by at least one or more transducer probes connected to the multi-port transducer connector;

a touch screen display disposed on the front panel wherein a first touch actuated focus control gesture controls a focus and a second touch actuated gain control gesture controls gain during the medical imaging procedure and wherein a number of focal zones can be selected;

a keyboard on an operator console that is mounted on the cart to control one or more operations of the medical ultrasound imaging procedure; and a computer mounted on the cart, the computer being connected to a beamformer circuit that generates beamformed image data and including at least one processor and at least one memory powered by a battery wherein the computer controls selection of an imaging mode selected from at least one of the B-mode imaging, M-mode imaging, color Doppler imaging mode, or elastography imaging mode in response to touch actuation of the touch screen display, the at least one processor configured to operate a graphical user interface (GUI) on the touch screen display using battery power to perform an ultrasound imaging sequence using at least one imaging mode, the GUI being configured to selectively actuate a plurality of touch actuated windows on the touch screen display including:

a touch actuated expandable menu window having one or more selectable touch actuated controls;

a touch actuated expandable setup window that displays a plurality of touch actuated configuration options for controlling setup and display of ultrasound images obtained from the ultrasound scan and configured to receive at least one touch actuated input within the setup window on the touch screen display; and a touch actuated patient data entry window including patient identification and ultrasound examination type wherein data is entered using at least one of the touch screen display or the keyboard.

32. The system of claim 31 wherein the touch actuated input received in the expandable setup window is a tracing gesture performed on a lesion of a liver.

33. The system of claim 31 wherein the beamformer circuit is within a transducer probe housing.

34. The system of claim 31 wherein the transducer applies a pressure to a region to be imaged.

35. The system of claim 31 wherein the beamformer circuit is within the tablet housing.

36. The system of claim 31 wherein the GUI is configured to select at least one of a bi-plane transducer and a second transducer that is actuated with a touch actuated switch that selects one of a connected plurality of transducer probes that are attached to the multiport connector to perform an imaging operation.

37. The system of claim 31 wherein the GUI is configured to select an annotation icon to enter annotations for an ultrasound scan, to select a DICOM touch control.

38. The system of claim 31 wherein the GUI is configured to select an expanded ultrasound report window to enter patient information, study information and date of the study.

39. The system of claim 31 wherein the GUI is configured to select a measurement of an anatomical feature.

40. The system of claim 31 wherein the GUI is configured to select split screen format.

41. The system of claim 31 wherein the GUI is configured to transfer ultrasound images to a separate display for viewing.

42. The system of claim 31 wherein at least one of the plurality of transducer probes obtains measurements used to calculate an ejection fraction.

43. The system of claim 31 wherein cardiac imaging provides a plurality of different views of the heart.

* * * * *